United States Patent
Sengun et al.

(10) Patent No.: US 12,376,843 B2
(45) Date of Patent: Aug. 5, 2025

(54) TISSUE AUGMENTATION TACKS FOR USE WITH SOFT TISSUE FIXATION REPAIR SYSTEMS AND METHODS

(71) Applicant: Medos International Sárl, Le Locle (CH)

(72) Inventors: Mehmet Ziya Sengun, Canton, MA (US); Benjamin Cleveland, Milford, MA (US); Reagan A. Theis, Marshfield, MA (US); Gerome O. Miller, Randolph, MA (US)

(73) Assignee: Medos International Sàrl, Le Locle (CH)

( * ) Notice: Subject to any disclaimer, the term of this patent is extended or adjusted under 35 U.S.C. 154(b) by 258 days.

(21) Appl. No.: 17/824,307

(22) Filed: May 25, 2022

(65) Prior Publication Data

US 2022/0287705 A1 Sep. 15, 2022

Related U.S. Application Data

(63) Continuation of application No. 15/618,984, filed on Jun. 9, 2017, now abandoned, which is a
(Continued)

(51) Int. Cl.
*A61B 17/04* (2006.01)
*A61B 17/06* (2006.01)
(Continued)

(52) U.S. Cl.
CPC ...... *A61B 17/0401* (2013.01); *A61B 17/0483* (2013.01); *A61B 17/0485* (2013.01);
(Continued)

(58) Field of Classification Search
CPC ............ A61B 17/0401; A61B 17/1712; A61B 2017/0404; A61B 2017/0406;
(Continued)

(56) References Cited

U.S. PATENT DOCUMENTS

| 4,034,850 A | 7/1977 | Mandel et al. |
| 4,164,046 A | 8/1979 | Cooley |

(Continued)

FOREIGN PATENT DOCUMENTS

| AU | 2015308795 A1 | 4/2017 |
| BR | PI0814523 A2 | 2/2015 |

(Continued)

OTHER PUBLICATIONS

U.S. Appl. No. 15/419,330, filed Jan. 30, 2017, Tissue Augmentation Constructs for Use With Soft Tissue Fixation Repair Systems and Methods.
(Continued)

*Primary Examiner* — Diane D Yabut
*Assistant Examiner* — Christian D Knauss
(74) *Attorney, Agent, or Firm* — Barnes & Thornburg LLP

(57) ABSTRACT

Devices, systems, and methods to improve both the reliability of soft tissue repair procedures and the speed at which the procedures are completed are provided. The devices and systems include one or more tissue augmentation constructs, which include constructs that are configured to increase a footprint across which suture applied force to tissue when the suture is tied down onto the tissue. The tissue augmentation constructs can be quickly and easily associated with the repair suture, and can be useful in many different tissue repair procedures that are disclosed in the application. In one exemplary embodiment, one or more constructs are disposed on a suture threader, which can be used to associate the construct(s) with a repair suture(s) being used to repair the soft tissue. Tissue augmentation constructs can include various blocks and patches, among other formations. Exemplary methods for manufacturing the tissue augmentation constructs are also provided.

23 Claims, 106 Drawing Sheets

Related U.S. Application Data continuation-in-part of application No. 15/419,330, filed on Jan. 30, 2017, now abandoned.

(60) Provisional application No. 62/393,277, filed on Sep. 12, 2016, provisional application No. 62/348,548, filed on Jun. 10, 2016, provisional application No. 62/289,702, filed on Feb. 1, 2016.

(51) Int. Cl.

| | |
|---|---|
| *A61B 17/16* | (2006.01) |
| *A61B 17/17* | (2006.01) |
| *A61B 50/30* | (2016.01) |
| *A61F 2/08* | (2006.01) |
| *A61L 31/04* | (2006.01) |
| *A61L 31/14* | (2006.01) |
| *A61B 17/00* | (2006.01) |
| *A61B 50/20* | (2016.01) |

(52) U.S. Cl.
CPC .... *A61B 17/06166* (2013.01); *A61B 17/1604* (2013.01); *A61B 17/1714* (2013.01); *A61B 17/1796* (2013.01); *A61B 50/30* (2016.02); *A61F 2/0811* (2013.01); *A61L 31/044* (2013.01); *A61L 31/148* (2013.01); *A61B 2017/00526* (2013.01); *A61B 2017/0053* (2013.01); *A61B 2017/0404* (2013.01); *A61B 2017/0406* (2013.01); *A61B 2017/0409* (2013.01); *A61B 2017/0417* (2013.01); *A61B 2017/0495* (2013.01); *A61B 50/20* (2016.02); *A61L 2430/34* (2013.01)

(58) Field of Classification Search
CPC .... A61B 2017/0409; A61B 2017/0411; A61B 2017/0446; A61B 2017/0462; A61B 2017/0475; A61B 2017/0403; A61F 2/0811; A61F 2002/0841; A61F 2002/0858; A61F 2002/0864; A61F 2002/0888

See application file for complete search history.

(56) References Cited

U.S. PATENT DOCUMENTS

| | | | |
|---|---|---|---|
| 4,210,148 | A | 7/1980 | Stivala |
| 4,454,875 | A | 6/1984 | Pratt et al. |
| 4,516,584 | A | 5/1985 | Garcia |
| 4,549,545 | A | 10/1985 | Levy |
| 4,585,458 | A | 4/1986 | Kurland |
| 4,720,218 | A | 1/1988 | DeFries et al. |
| 4,723,540 | A | 2/1988 | Gilmer, Jr. |
| 4,932,960 | A | 6/1990 | Green et al. |
| 5,116,357 | A | 5/1992 | Eberbach |
| 5,209,756 | A | 5/1993 | Seedhom et al. |
| 5,219,359 | A | 6/1993 | McQuilkin et al. |
| 5,290,217 | A | 3/1994 | Campos |
| 5,306,290 | A | 4/1994 | Martins et al. |
| 5,318,575 | A | 6/1994 | Chesterfield et al. |
| 5,336,616 | A | 8/1994 | Livesey et al. |
| 5,366,460 | A | 11/1994 | Eberbach |
| 5,370,650 | A | 12/1994 | Tovey et al. |
| 5,374,268 | A | 12/1994 | Sander |
| 5,383,904 | A | 1/1995 | Totakura et al. |
| 5,397,352 | A | 3/1995 | Burres |
| 5,425,766 | A | 6/1995 | Bowald |
| 5,464,426 | A | 11/1995 | Bonutti |
| 5,500,000 | A | 3/1996 | Feagin et al. |
| 5,503,638 | A | 4/1996 | Cooper et al. |
| 5,514,378 | A | 5/1996 | Mikos et al. |
| 5,522,831 | A | 6/1996 | Sleister et al. |
| 5,549,628 | A | 8/1996 | Cooper et al. |
| 5,575,803 | A | 11/1996 | Cooper et al. |
| 5,582,288 | A | 12/1996 | Zatarga |
| 5,630,844 | A | 5/1997 | Dogan et al. |
| 5,645,547 | A | 7/1997 | Coleman |
| 5,645,568 | A | 7/1997 | Chervitz et al. |
| 5,658,313 | A | 8/1997 | Thal |
| 5,700,277 | A | 12/1997 | Nash et al. |
| 5,713,374 | A | 2/1998 | Pachence et al. |
| 5,720,765 | A | 2/1998 | Thal |
| 5,769,214 | A | 6/1998 | Zatarga |
| 5,800,447 | A | 9/1998 | Wenstrom, Jr. |
| 5,810,848 | A | 9/1998 | Hayhurst |
| 5,961,521 | A | 10/1999 | Roger |
| 6,027,523 | A | 2/2000 | Schmieding |
| 6,059,818 | A | 5/2000 | Johnson et al. |
| 6,080,192 | A | 6/2000 | Demopulos et al. |
| 6,152,949 | A | 11/2000 | Bonutti |
| 6,156,056 | A | 12/2000 | Kearns et al. |
| 6,171,317 | B1 | 1/2001 | Jackson et al. |
| 6,171,318 | B1 | 1/2001 | Kugel et al. |
| 6,245,081 | B1 | 6/2001 | Bowman et al. |
| 6,293,794 | B1 | 9/2001 | McSpadden |
| 6,425,924 | B1 | 7/2002 | Rousseau |
| 6,436,068 | B1 | 8/2002 | Bardy |
| 6,464,706 | B1 | 10/2002 | Winters |
| 6,491,714 | B1 | 12/2002 | Bennett |
| 6,497,687 | B1 | 12/2002 | Blanco |
| 6,514,274 | B1 | 2/2003 | Boucher et al. |
| 6,746,458 | B1 | 6/2004 | Cloud |
| 6,755,867 | B2 | 6/2004 | Rousseau |
| 6,814,741 | B2 | 11/2004 | Bowman et al. |
| 6,960,164 | B2 | 11/2005 | O'Heeron |
| 6,964,685 | B2 | 11/2005 | Murray et al. |
| 7,078,615 | B2 | 7/2006 | Gladfelter et al. |
| 7,082,337 | B2 | 7/2006 | Sommer et al. |
| 7,087,073 | B2 | 8/2006 | Bonutti |
| 7,218,972 | B2 | 5/2007 | Rodriguez |
| 7,303,577 | B1 | 12/2007 | Dean |
| 7,357,810 | B2 | 4/2008 | Koyfman et al. |
| 7,368,124 | B2 | 5/2008 | Chun et al. |
| 7,442,202 | B2 | 10/2008 | Dreyfuss |
| 7,488,347 | B1 | 2/2009 | Goble et al. |
| 7,559,937 | B2 | 7/2009 | de la Torre et al. |
| 7,572,275 | B2 | 8/2009 | Fallin et al. |
| 7,615,061 | B2 | 11/2009 | White et al. |
| 7,641,688 | B2 | 1/2010 | Lesh |
| 7,677,296 | B2 | 3/2010 | Mason |
| 7,717,710 | B2 | 5/2010 | Danger et al. |
| 7,736,330 | B2 | 6/2010 | Bardy |
| 7,780,625 | B2 | 8/2010 | Bardy |
| 7,785,334 | B2 | 8/2010 | Ford et al. |
| 7,795,027 | B2 | 9/2010 | Hiles |
| 7,806,905 | B2 | 10/2010 | Ford et al. |
| 7,824,414 | B2 | 11/2010 | Evans |
| 7,833,244 | B2 | 11/2010 | Cerundolo |
| 7,887,551 | B2 | 2/2011 | Bojarski et al. |
| 7,892,256 | B2 | 2/2011 | Grafton et al. |
| 7,905,903 | B2 | 3/2011 | Stone et al. |
| 7,914,808 | B2 | 3/2011 | Malaviya et al. |
| 7,981,092 | B2 | 7/2011 | Duke |
| 8,012,174 | B2 | 9/2011 | ElAttrache et al. |
| 8,016,883 | B2 | 9/2011 | Coleman et al. |
| 8,067,149 | B2 | 11/2011 | Livesey et al. |
| 8,080,260 | B2 | 12/2011 | Derwin et al. |
| 8,105,384 | B2 | 1/2012 | Lambrecht et al. |
| 8,109,936 | B2 | 2/2012 | Tipirneni |
| 8,114,161 | B2 | 2/2012 | Evans et al. |
| 8,118,836 | B2 | 2/2012 | Denham et al. |
| 8,133,258 | B2 | 3/2012 | Foerster et al. |
| 8,133,500 | B2 | 3/2012 | Ringeisen et al. |
| 8,133,501 | B2 | 3/2012 | Li et al. |
| 8,137,381 | B2 | 3/2012 | Foerster et al. |
| 8,197,837 | B2 | 6/2012 | Jamiolkowski et al. |
| 8,226,715 | B2 | 7/2012 | Hwang et al. |
| 8,231,653 | B2 | 7/2012 | Dreyfuss |
| 8,277,458 | B2 | 10/2012 | Schneider |
| 8,298,262 | B2 | 10/2012 | Stone et al. |
| 8,317,825 | B2 | 11/2012 | Stone |
| 8,333,803 | B2 | 12/2012 | Park et al. |
| 8,361,113 | B2 | 1/2013 | Stone et al. |

(56) References Cited

U.S. PATENT DOCUMENTS

| | | |
|---|---|---|
| 8,366,787 B2 | 2/2013 | Brown et al. |
| 8,419,794 B2 | 4/2013 | ElAttrache et al. |
| 8,435,264 B2 | 5/2013 | Sojka et al. |
| 8,568,362 B2 | 10/2013 | Moreno, Jr. et al. |
| 8,579,807 B2 | 11/2013 | Moreno, Jr. et al. |
| 8,585,773 B1 | 11/2013 | Kucklick |
| 8,597,352 B2 | 12/2013 | Schwartz |
| 8,636,686 B2 | 1/2014 | Minnelli et al. |
| 8,636,780 B2 | 1/2014 | Goble et al. |
| 8,637,066 B2 | 1/2014 | Binnette et al. |
| 8,649,881 B2 | 2/2014 | Helgesson |
| 8,672,969 B2 | 3/2014 | Stone et al. |
| 8,690,831 B2 | 4/2014 | Duke |
| 8,690,960 B2 | 4/2014 | Hotter et al. |
| 8,740,913 B2 | 6/2014 | Schneider |
| 8,758,351 B2 | 6/2014 | Evans et al. |
| 8,758,437 B2 | 6/2014 | Laurencin et al. |
| 8,771,351 B2 | 7/2014 | ElAttrache et al. |
| 8,795,364 B2 | 8/2014 | Evans et al. |
| 8,821,536 B2 | 9/2014 | Euteneuer et al. |
| 8,821,544 B2 | 9/2014 | Sengun et al. |
| 8,828,448 B2 | 9/2014 | Korossis et al. |
| 8,834,350 B2 | 9/2014 | Chapman et al. |
| 8,834,521 B2 | 9/2014 | Pinto et al. |
| 8,858,560 B2 | 10/2014 | Bradley et al. |
| 8,870,915 B2 | 10/2014 | Mayer et al. |
| 8,876,864 B2 | 11/2014 | Spedden et al. |
| 8,895,045 B2 | 11/2014 | Jamiolkowski et al. |
| 8,936,622 B2 | 1/2015 | Wales et al. |
| 8,986,377 B2 | 3/2015 | Richter et al. |
| 8,986,378 B2 | 3/2015 | Koob |
| 9,005,250 B2 | 4/2015 | Evans |
| 9,060,763 B2 | 6/2015 | Sengun |
| 9,089,357 B2 | 7/2015 | Huddleston |
| 9,125,717 B2 | 9/2015 | Alexander |
| 9,173,647 B2 | 11/2015 | Bonutti et al. |
| 9,180,143 B2 | 11/2015 | Bolland et al. |
| 9,180,144 B2 | 11/2015 | Bolland et al. |
| 9,186,435 B2 | 11/2015 | Hiles |
| 9,226,756 B2 | 1/2016 | Teisen et al. |
| 9,226,828 B2 | 1/2016 | Bonutti |
| 9,271,750 B2 | 3/2016 | Arthur et al. |
| 9,271,766 B2 | 3/2016 | Bonutti |
| 9,339,369 B2 | 5/2016 | McQuillan et al. |
| 9,345,567 B2 | 5/2016 | Sengun |
| 9,381,013 B2 | 7/2016 | Norton |
| 9,387,280 B2 | 7/2016 | Brunelle et al. |
| 9,463,012 B2 | 10/2016 | Bonutti et al. |
| 9,545,268 B2 | 1/2017 | Bonutti |
| 9,579,129 B2 | 2/2017 | Bonutti |
| 9,585,654 B2 | 3/2017 | Dean et al. |
| 9,642,891 B2 | 5/2017 | Hart et al. |
| 9,801,978 B2 | 10/2017 | Paulos et al. |
| 9,814,453 B2 | 11/2017 | Bonutti et al. |
| 9,867,706 B2 | 1/2018 | Bonutti |
| 9,888,999 B2 | 2/2018 | Forsell et al. |
| 9,918,827 B2 | 3/2018 | Berelsman et al. |
| 9,980,761 B2 | 5/2018 | Bonutti et al. |
| 9,999,449 B2 | 6/2018 | Bonutti |
| 10,028,814 B2 | 7/2018 | Levin et al. |
| 10,076,543 B2 | 9/2018 | Wilhelmi et al. |
| 10,159,722 B2 | 12/2018 | Sun et al. |
| 10,172,607 B2 | 1/2019 | Burkhart |
| 10,172,703 B2 | 1/2019 | Adams et al. |
| 10,238,378 B2 | 3/2019 | Bonutti et al. |
| 10,265,155 B2 | 4/2019 | Lu et al. |
| 10,286,119 B2 | 5/2019 | Badylak et al. |
| 10,314,688 B2 | 6/2019 | Shepard et al. |
| 10,350,049 B2 | 7/2019 | Morse et al. |
| 10,376,259 B2 | 8/2019 | Bonutti et al. |
| 10,702,260 B2 | 7/2020 | Sengun et al. |
| 11,484,401 B2 | 11/2022 | Whittaker et al. |
| 11,523,812 B2 | 12/2022 | Sengun et al. |
| 11,937,803 B2 | 3/2024 | Sengun et al. |
| 11,938,017 B2 | 3/2024 | Whittaker et al. |
| 2001/0041916 A1* | 11/2001 | Bonutti ............ A61B 17/0401 606/232 |
| 2001/0051815 A1 | 12/2001 | Esplin |
| 2001/0053913 A1 | 12/2001 | Freedland |
| 2002/0019649 A1 | 2/2002 | Sikora et al. |
| 2002/0133236 A1 | 9/2002 | Rousseau |
| 2003/0023316 A1 | 1/2003 | Brown et al. |
| 2003/0032961 A1 | 2/2003 | Pelo et al. |
| 2003/0105519 A1 | 6/2003 | Fasol et al. |
| 2003/0130694 A1 | 7/2003 | Bojarski et al. |
| 2004/0048796 A1 | 3/2004 | Hariri et al. |
| 2004/0116963 A1 | 6/2004 | Lattouf |
| 2004/0133238 A1 | 7/2004 | Cerier |
| 2004/0260344 A1 | 12/2004 | Lyons et al. |
| 2004/0267362 A1 | 12/2004 | Hwang et al. |
| 2005/0010178 A1 | 1/2005 | Katz |
| 2005/0209705 A1 | 9/2005 | Niederauer et al. |
| 2005/0220842 A1 | 10/2005 | DeWitt et al. |
| 2005/0288710 A1 | 12/2005 | Fallin et al. |
| 2005/0288711 A1 | 12/2005 | Fallin et al. |
| 2006/0004364 A1 | 1/2006 | Green et al. |
| 2006/0029633 A1 | 2/2006 | Kaiser et al. |
| 2006/0079904 A1 | 4/2006 | Thal |
| 2006/0089646 A1 | 4/2006 | Bonutti |
| 2006/0149266 A1 | 7/2006 | Cordasco |
| 2006/0190041 A1 | 8/2006 | Fallin et al. |
| 2006/0247776 A1 | 11/2006 | Kim |
| 2006/0286144 A1 | 12/2006 | Yang et al. |
| 2007/0010829 A1 | 1/2007 | Nobles et al. |
| 2007/0034669 A1 | 2/2007 | de la Torre et al. |
| 2007/0088391 A1 | 4/2007 | McAlexander et al. |
| 2007/0168021 A1 | 7/2007 | Holmes, Jr. et al. |
| 2007/0185532 A1 | 8/2007 | Stone et al. |
| 2007/0191849 A1 | 8/2007 | ElAttrache et al. |
| 2007/0219558 A1 | 9/2007 | Deutsch |
| 2007/0288023 A1 | 12/2007 | Pellegrino et al. |
| 2007/0288040 A1 | 12/2007 | Ferree |
| 2008/0065114 A1 | 3/2008 | Stone et al. |
| 2008/0125815 A1 | 5/2008 | Heaven et al. |
| 2008/0167519 A1 | 7/2008 | St-Germain |
| 2008/0188933 A1 | 8/2008 | Koob et al. |
| 2008/0188936 A1 | 8/2008 | Ball et al. |
| 2008/0195205 A1 | 8/2008 | Schwartz |
| 2008/0275476 A1 | 11/2008 | Cropper et al. |
| 2008/0281355 A1 | 11/2008 | Mayer et al. |
| 2008/0281422 A1 | 11/2008 | Schmieding |
| 2008/0294256 A1 | 11/2008 | Hagan et al. |
| 2009/0018655 A1 | 1/2009 | Brunelle et al. |
| 2009/0082805 A1 | 3/2009 | Kaiser et al. |
| 2009/0156986 A1 | 6/2009 | Trenhaile |
| 2009/0156997 A1 | 6/2009 | Trenhaile |
| 2009/0222039 A1 | 9/2009 | Dreyfuss et al. |
| 2009/0306711 A1 | 12/2009 | Stone et al. |
| 2009/0312776 A1 | 12/2009 | Kaiser et al. |
| 2009/0312782 A1* | 12/2009 | Park ................ A61F 2/0811 606/184 |
| 2009/0318960 A1 | 12/2009 | Burkhart |
| 2009/0318961 A1 | 12/2009 | Stone et al. |
| 2010/0016889 A1 | 1/2010 | Ferree |
| 2010/0063599 A1 | 3/2010 | Brunelle et al. |
| 2010/0106194 A1 | 4/2010 | Bonutti et al. |
| 2010/0168864 A1 | 7/2010 | White et al. |
| 2010/0179591 A1 | 7/2010 | Saltzman et al. |
| 2010/0185219 A1 | 7/2010 | Gertzman et al. |
| 2010/0198258 A1 | 8/2010 | Heaven et al. |
| 2010/0204775 A1 | 8/2010 | Edwin |
| 2010/0249696 A1 | 9/2010 | Bardy |
| 2010/0249805 A1 | 9/2010 | Olson et al. |
| 2010/0249834 A1 | 9/2010 | Dreyfuss |
| 2010/0256677 A1 | 10/2010 | Albertorio et al. |
| 2010/0262184 A1 | 10/2010 | Dreyfuss |
| 2010/0280428 A1 | 11/2010 | Widgerow et al. |
| 2011/0046669 A1 | 2/2011 | Goraltchouk et al. |
| 2011/0060375 A1 | 3/2011 | Bonutti |
| 2011/0071551 A1 | 3/2011 | Singhatat et al. |
| 2011/0184441 A1 | 7/2011 | St-Germain |
| 2011/0208240 A1* | 8/2011 | Stone ............. A61B 17/06166 606/232 |
| 2011/0238179 A1 | 9/2011 | Laurencin et al. |

(56) References Cited

U.S. PATENT DOCUMENTS

| | | | |
|---|---|---|---|
| 2011/0301638 A1 | 12/2011 | Walters | |
| 2011/0319895 A1 | 12/2011 | Gamache | |
| 2012/0071959 A1 | 3/2012 | Helgesson | |
| 2012/0095470 A1 | 4/2012 | Kaiser et al. | |
| 2012/0109156 A1* | 5/2012 | Overes | A61B 17/0483 606/139 |
| 2012/0130422 A1 | 5/2012 | Hootstein | |
| 2012/0150226 A1 | 6/2012 | Burkhart et al. | |
| 2012/0158053 A1 | 6/2012 | Paulos | |
| 2012/0165864 A1 | 6/2012 | Hernandez et al. | |
| 2012/0189707 A1 | 7/2012 | Chun et al. | |
| 2012/0265219 A1 | 10/2012 | Rushdy et al. | |
| 2012/0271323 A1 | 10/2012 | Fan et al. | |
| 2012/0283831 A1 | 11/2012 | Murray | |
| 2013/0023929 A1* | 1/2013 | Sullivan | A61B 17/0487 606/232 |
| 2013/0066371 A1 | 3/2013 | Rogers et al. | |
| 2013/0090521 A1 | 4/2013 | Lau et al. | |
| 2013/0096612 A1 | 4/2013 | Zajac et al. | |
| 2013/0096678 A1 | 4/2013 | Denham | |
| 2013/0116710 A1 | 5/2013 | Ziniti et al. | |
| 2013/0116730 A1 | 5/2013 | Denham et al. | |
| 2013/0131733 A1* | 5/2013 | Chien | A61B 17/866 606/104 |
| 2013/0165972 A1 | 6/2013 | Sullivan | |
| 2013/0178898 A1 | 7/2013 | Arnett et al. | |
| 2013/0197574 A1 | 8/2013 | Mayer et al. | |
| 2013/0226204 A1 | 8/2013 | Kumar | |
| 2013/0237997 A1 | 9/2013 | Arai et al. | |
| 2013/0261662 A1 | 10/2013 | Mayer et al. | |
| 2013/0296893 A1 | 11/2013 | Dean et al. | |
| 2013/0296895 A1 | 11/2013 | Sengun | |
| 2013/0296934 A1 | 11/2013 | Sengun | |
| 2013/0317527 A1 | 11/2013 | Jacinto et al. | |
| 2013/0345747 A1* | 12/2013 | Dreyfuss | A61B 17/0401 606/232 |
| 2013/0345749 A1 | 12/2013 | Sullivan et al. | |
| 2014/0039503 A1 | 2/2014 | Pilgeram | |
| 2014/0058371 A1 | 2/2014 | Krishnan | |
| 2014/0066959 A1 | 3/2014 | Bonutti | |
| 2014/0067058 A1 | 3/2014 | Koob et al. | |
| 2014/0081285 A1 | 3/2014 | Kucklick | |
| 2014/0155938 A1 | 6/2014 | Anderson | |
| 2014/0172096 A1 | 6/2014 | Koob et al. | |
| 2014/0222038 A1 | 8/2014 | Seedhom et al. | |
| 2014/0243891 A1 | 8/2014 | Schmieding et al. | |
| 2014/0243893 A1 | 8/2014 | Santangelo et al. | |
| 2014/0343604 A1 | 11/2014 | Frank | |
| 2015/0025552 A1 | 1/2015 | Stoll | |
| 2015/0032157 A1 | 1/2015 | Dooney, Jr. et al. | |
| 2015/0038793 A1 | 2/2015 | Prior et al. | |
| 2015/0038994 A1 | 2/2015 | Prior et al. | |
| 2015/0045887 A1 | 2/2015 | Mathies | |
| 2015/0066079 A1 | 3/2015 | Schmieding | |
| 2015/0157449 A1 | 6/2015 | Gustafson et al. | |
| 2015/0164498 A1 | 6/2015 | Dreyfuss et al. | |
| 2015/0173742 A1 | 6/2015 | Palese et al. | |
| 2015/0173754 A1* | 6/2015 | Norton | A61B 17/0401 606/228 |
| 2015/0201929 A1 | 7/2015 | Dooney, Jr. et al. | |
| 2015/0230913 A1 | 8/2015 | Derwin et al. | |
| 2015/0327972 A1 | 11/2015 | Horne et al. | |
| 2015/0342587 A1* | 12/2015 | Norton | A61B 17/0218 600/204 |
| 2015/0352257 A1 | 12/2015 | Early | |
| 2015/0359530 A1 | 12/2015 | Moore | |
| 2016/0030148 A1 | 2/2016 | Cossa | |
| 2016/0032239 A1 | 2/2016 | Livermore-Clifford et al. | |
| 2016/0045196 A1 | 2/2016 | Sengun et al. | |
| 2016/0106441 A1 | 4/2016 | Teisen et al. | |
| 2016/0120631 A1 | 5/2016 | Murphy | |
| 2016/0374795 A1 | 12/2016 | Dougherty et al. | |
| 2017/0035552 A1 | 2/2017 | Fallin et al. | |
| 2017/0095324 A1 | 4/2017 | Adams et al. | |
| 2017/0119366 A1 | 5/2017 | Benavitz et al. |
| 2017/0143551 A1 | 5/2017 | Coleman |
| 2017/0150963 A1 | 6/2017 | Coleman |
| 2017/0215864 A1 | 8/2017 | Sengun et al. |
| 2017/0215865 A1 | 8/2017 | Sengun et al. |
| 2017/0216015 A1 | 8/2017 | Sengun et al. |
| 2017/0216016 A1 | 8/2017 | Sengun et al. |
| 2017/0273680 A1 | 9/2017 | Sengun et al. |
| 2017/0340437 A1 | 11/2017 | Bowley et al. |
| 2018/0161141 A1 | 6/2018 | Priewe et al. |
| 2018/0228596 A1 | 8/2018 | Wyland |
| 2018/0311411 A9 | 11/2018 | Derwin et al. |
| 2018/0360914 A1 | 12/2018 | Hart et al. |
| 2018/0360915 A1 | 12/2018 | Hart et al. |
| 2019/0015548 A1 | 1/2019 | Harrell |
| 2019/0038395 A1 | 2/2019 | Van Kampen |
| 2019/0053834 A1 | 2/2019 | Bonutti |
| 2019/0054205 A1 | 2/2019 | Francis et al. |
| 2019/0091006 A1 | 3/2019 | Adams et al. |
| 2019/0133655 A1 | 5/2019 | Bonutti et al. |
| 2019/0134269 A1 | 5/2019 | Murray et al. |
| 2019/0142411 A1 | 5/2019 | Bonutti et al. |
| 2019/0209163 A1 | 7/2019 | Coleman |
| 2019/0255217 A1 | 8/2019 | Early |
| 2019/0274675 A1 | 9/2019 | Coleman |
| 2020/0000573 A1 | 1/2020 | Whittaker et al. |
| 2023/0065869 A1 | 3/2023 | Whittaker et al. |
| 2023/0149010 A1 | 5/2023 | Sengun et al. |

FOREIGN PATENT DOCUMENTS

| | | |
|---|---|---|
| CN | 102014807 A | 4/2011 |
| CN | 102341047 A | 2/2012 |
| CN | 103037778 A | 4/2013 |
| CN | 103269647 A | 8/2013 |
| CN | 103654927 A | 3/2014 |
| CN | 104053406 A | 9/2014 |
| CN | 104394777 A | 3/2015 |
| CN | 105120774 A | 12/2015 |
| CN | 105142540 A | 12/2015 |
| CN | 105208970 A | 12/2015 |
| CN | 103385742 B | 6/2017 |
| CN | 104939876 B | 7/2019 |
| CN | 104706393 B | 11/2019 |
| EP | 0464163 B1 | 4/1995 |
| EP | 1964520 A2 | 9/2008 |
| EP | 2389204 A1 | 11/2011 |
| EP | 2590691 A1 | 5/2013 |
| EP | 2700309 A1 | 2/2014 |
| EP | 2774545 A2 | 9/2014 |
| EP | 2968646 A1 | 1/2016 |
| EP | 3410952 B1 | 4/2020 |
| FR | 2959408 B1 | 11/2012 |
| JP | 2004522555 A | 7/2004 |
| JP | 2004536659 A | 12/2004 |
| JP | 2008539842 A | 11/2008 |
| JP | 2010227578 A | 10/2010 |
| JP | 2015112492 A | 6/2015 |
| JP | 2016507346 A | 3/2016 |
| JP | 2017192729 A1 | 10/2017 |
| JP | 2019000637 A | 1/2019 |
| KR | 20190025492 A | 3/2019 |
| WO | 2000054666 A1 | 9/2000 |
| WO | 2002007609 A2 | 1/2002 |
| WO | 2009059293 A2 | 5/2009 |
| WO | 2012121986 A2 | 9/2012 |
| WO | 2013054216 A1 | 4/2013 |
| WO | 2014100109 A1 | 6/2014 |
| WO | 2015031654 A2 | 3/2015 |
| WO | 2018135568 A1 | 7/2018 |

OTHER PUBLICATIONS

U.S. Appl. No. 15/419,342, filed Jan. 30, 2017, Soft Tissue Fixation Repair Methods Using Tissue Augmentation Constructs.

U.S. Appl. No. 15/419,360, filed Jan. 30, 2017, Tissue Augmentation Scaffolds for Use With Soft Tissue Fixation Repair Systems and Methods.

(56) References Cited

OTHER PUBLICATIONS

U.S. Appl. No. 15/419,373, filed Jan. 30, 2017, Soft Tissue Fixation Repair Methods Using Tissue Augmentation Scaffolds.
U.S. Appl. No. 15/618,984, filed Jun. 9, 2017, Tissue Augmentation Tacks for Use With Soft Tissue Fixation Repair Systems and Methods.
U.S. Appl. No. 16/445,930, filed Jun. 19, 2019, Tissue Augmentation Scaffolds for Use in Soft Tissue Fixation Repair.
U.S. Appl. No. 17/976,550, filed Oct. 28, 2022, Tissue Augmentation Scaffolds for Use in Soft Tissue Fixation Repair.
U.S. Appl. No. 17/987,512, filed Nov. 15, 2022, Soft Tissue Fixation Repair Methods Using Tissue Augmentation Constructs.
[No Author Listed] BioKnotless™ Anchor, product brochure, Mitek Products, Ethicon, <https://www.shoulderdoc.co.uk/documents/mitek_bioknotless.pdf> P/N 900541 Rev. A Feb. 2001. (2 pages) Retrieved Jun. 8, 2017
[No Author Listed] Fastin® RC Dual Channeled Anchor, DePuy Synthes, Mitek Sports Medicine, online product listing; <https://www.depuysynthes.com/hcp/mitek-sports-medicine/products/qs/Fastin-RC>, © DePuy Synthes 2014-2017 (1 page) Retrieved Jun. 8, 2017.
[No Author Listed] Gryphon® Suture Anchor, DePuy Synthes, online product listing, <https://www.depuysynthes.com/hcp/mitek-sports-medicine/products/qs/GRYPHON-Suture-Anchor>, © DePuy Synthes 2014-2017 (1 page) Retrieved Jun. 8, 2017.
[No Author Listed] Healix Advance™ Anchor (online product listing) <https://www.depuysynthes.com/hcp/mitek-sports-medicine/products/qs/HEALIX-ADVANCE> © DePuy Synthes 2014-2017 (1 page) Retrieved Jun. 8, 2017.
[No Author Listed] Healix Advance™ Knotless Anchor, product brochure, <http://synthes.vo.llnwd.net/o16/LLNWMB8/INT%20Mobile/Synthes%20International/Product%20Support%20Material/legacy_DePuy_Mitek_PDFs/DSEM-MTK-0414-0053_LR.pdf>, 2015 (4 pages) Retrieved Jun. 8, 2017.
[No Author Listed] Healix BR™ Dual Threaded Suture Anchor (online product listing), <https://www.depuysynthes.com/hcp/shoulder/products/qs/HEALIX-BR-Dual-Threaded-Suture-Anchor> © DePuy Synthes 2014-2017 (2 pages) Retrieved Jun. 8, 2017.
[No Author Listed] Healix Peek™ Dual Threaded Suture Anchor (online product listing) https://www.depuysynthes.com/hcp/mitek-sports-medicine/products/qs/HEALIX-PEEK-Dual-Threaded-Suture-Anchor, © DePuy Synthes 2014-2017 (1 page) Retrieved Jun. 8, 2017.
[No Author Listed] Healix Ti™ Dual Threaded Suture Anchor with Titanium, product brochure, © 2009, DePuy Mitek Inc. (4 pages).
[No Author Listed] Healix Transtend™ Implant System brochure, DePuy Synthes, Mitek Sports Medicine, 2016. (12 pages).
[No Author Listed] Micro Quickanchor® Suture Anchors, Depuy Synthes, Mitek Sports Medicine, online product listing, <https://www.depuysynthes.com/hcp/mitek-sports-medicine/products/qs/Micro-QUICKANCHOR>, © DePuy Synthes 2014-2017 (1 page) Retrieved Jun. 8, 2017.
[No Author Listed] Microfix® Absorbable Anchor Quickanchor® Suture Anchors, DePuy Synthes, online product listing, <https://www.depuysynthes.com/hcp/mitek-sports-medicine/products/qs/MICROFIX-Absorbable-Anchor>, © DePuy Synthes 2014-2017 (1 page) Retrieved Jun. 8, 2017.
[No Author Listed] Minilok™ Quickanchor® Suture Anchors, DePuy Synthes, Mitek Sports Medicine, online product listing, <https://www.depuysynthes.com/hcp/mitek-sports-medicine/products/qs/MINILOK-Absorbable-Anchor>, © DePuy Synthes 2014-2017 (1 page) Retrieved Jun. 8, 2017.
[No Author Listed] Tacit® Threaded Anchors, DePuy Synthes, Mitek Sports Medicine, online product listing, <https://www.depuysynthes.com/hcp/mitek-sports-medicine/products/qs/TACIT-Threaded-Anchors>, © DePuy Synthes 2014-2017 (1 page) Retrieved Jun. 8, 2017.
[No Author Listed] Versalok® Suture Anchor, DePuy Synthes, online product listing; <https://www.depuysynthes.com/hcp/shoulder/products/qs/VERSALOK-Suture-Anchor>, © 2007 (1 page) Retrieved Jun. 8, 2017.
Beimers, L., et al., The biomechanical effects of polytetrafluoroethylene suture augmentations in lateral-row rotator cuff repairs in an ovine model. J Shoulder Elbow Surg. Oct. 2014;23(10):1545-52. doi: 10.1016/j.jse.2014.02.003. Epub Apr. 22, 2014.
European Office Action for Application No. 18177019.9, issued Feb. 14, 2020 (7 pages).
Extended European Search Report issued Nov. 6, 2018, in Application No. 18177019.9 (10 pages).
European Search Report for Application No. 20180748.4, issued Oct. 22, 2020 (13 pages).
Japanese Office Action for Japanese Application No. 2018-540045, mailed Mar. 2, 2021 (16 pages).
Japanese Office Action for Japanese Application No. 2018-539932, mailed Mar. 2, 2021 (13 pages).
Invitation to Pay Additional Fees for Application No. PCT/US2017/015950, mailed May 12, 2017 (13 pages).
International Search Report and Written Opinion for Application No. PCT/US2017/015950, mailed Jul. 18, 2017 (17 pages).
Invitation to Pay Additional Fees issued for Application No. PCT/US2017/015954, mailed Apr. 28, 2017. (16 pages).
International Search Report and Written Opinion for Application No. PCT/US2017/015954, mailed Jul. 24, 2017 (19 pages).
Springer, S., A new procedure could revolutionize ACL repairs. Boston Globe, Mar. 23, 2016, 10 pages. Retrieved from <https://www.bostonglobe.com/sports/2016/03/23/new-surgery-could-revolutionize-knee-repairs/BJISuh60AYKYTKWPwaYFWP/story.html> on Feb. 26, 2017.
Young, A.T., Microcellular foams via phase separation. Journal of Vacuum Science & Technology A: Vacuum, Surfaces, and Films, vol. 4, Issue 3, May 1986, pp. 1128-1133.
Japanese Search Report for Japanese Application No. 2020-105206, issued Jan. 5, 2024 (10 pages).
Japanese Notice of Reason for Refusal for Japanese Application No. 2020-105206, issued Jan. 16, 2024 (6 pages).

\* cited by examiner

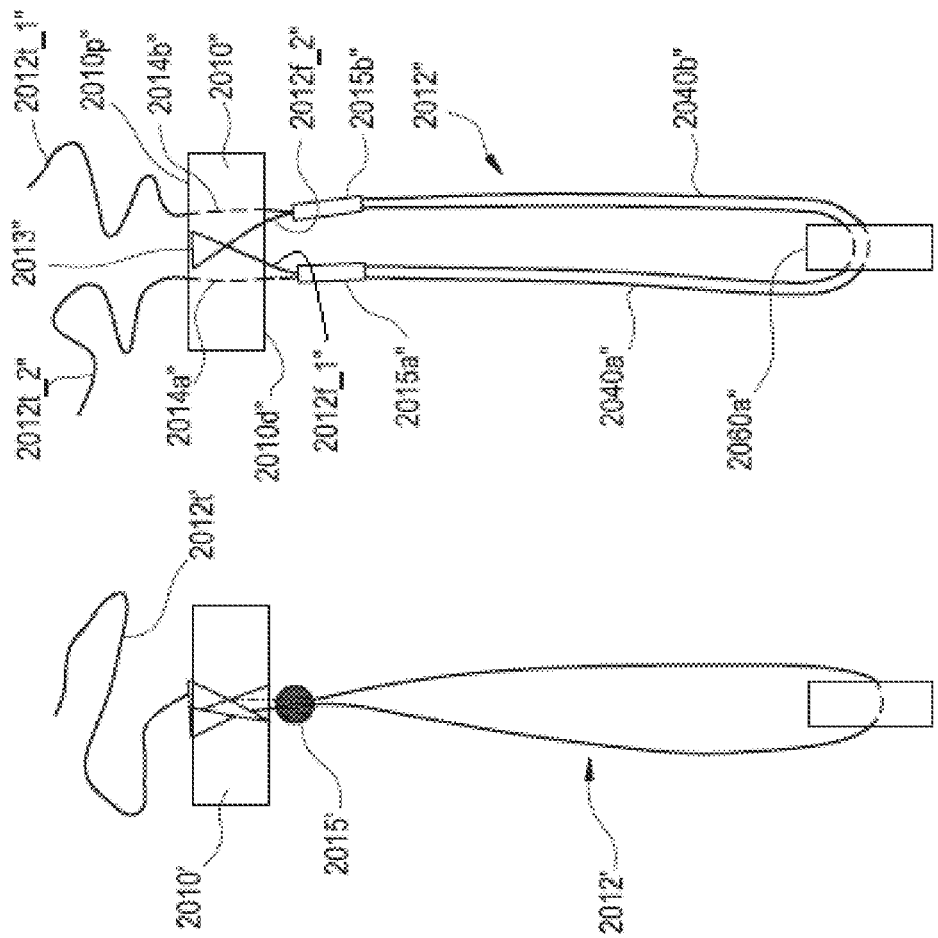

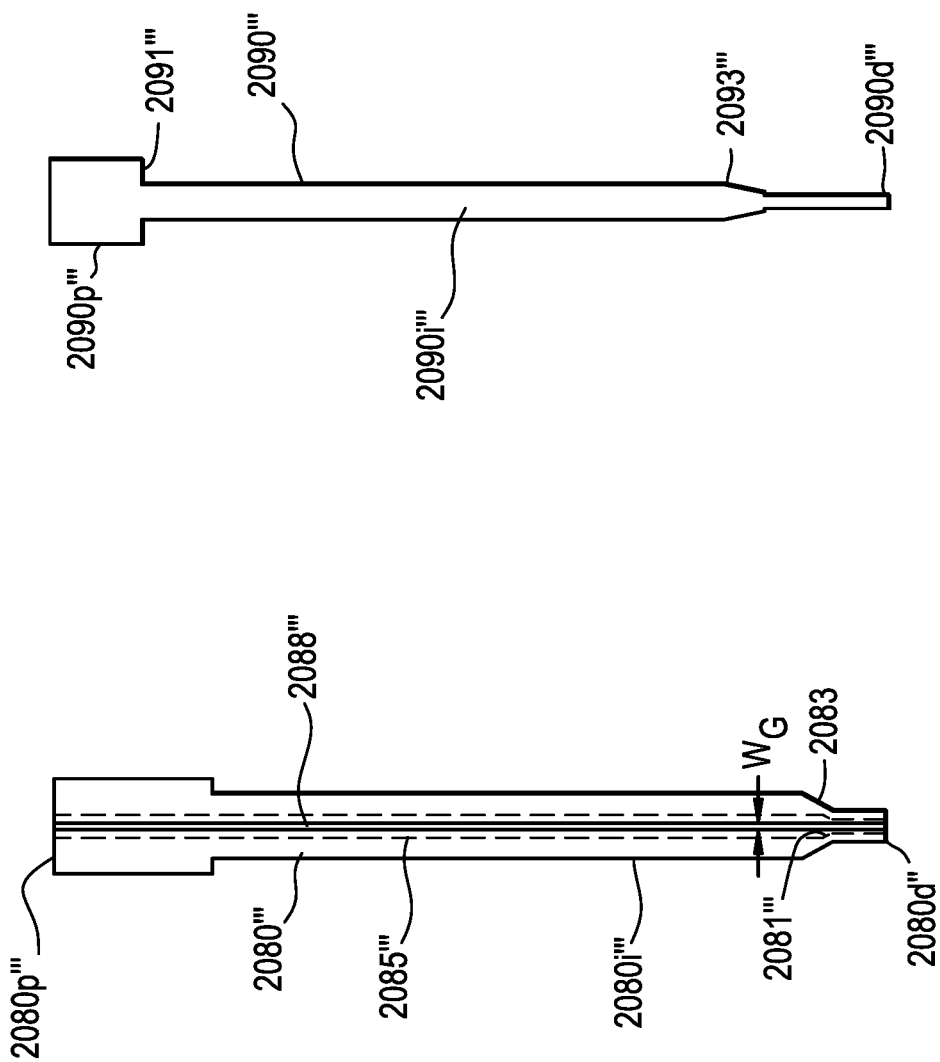

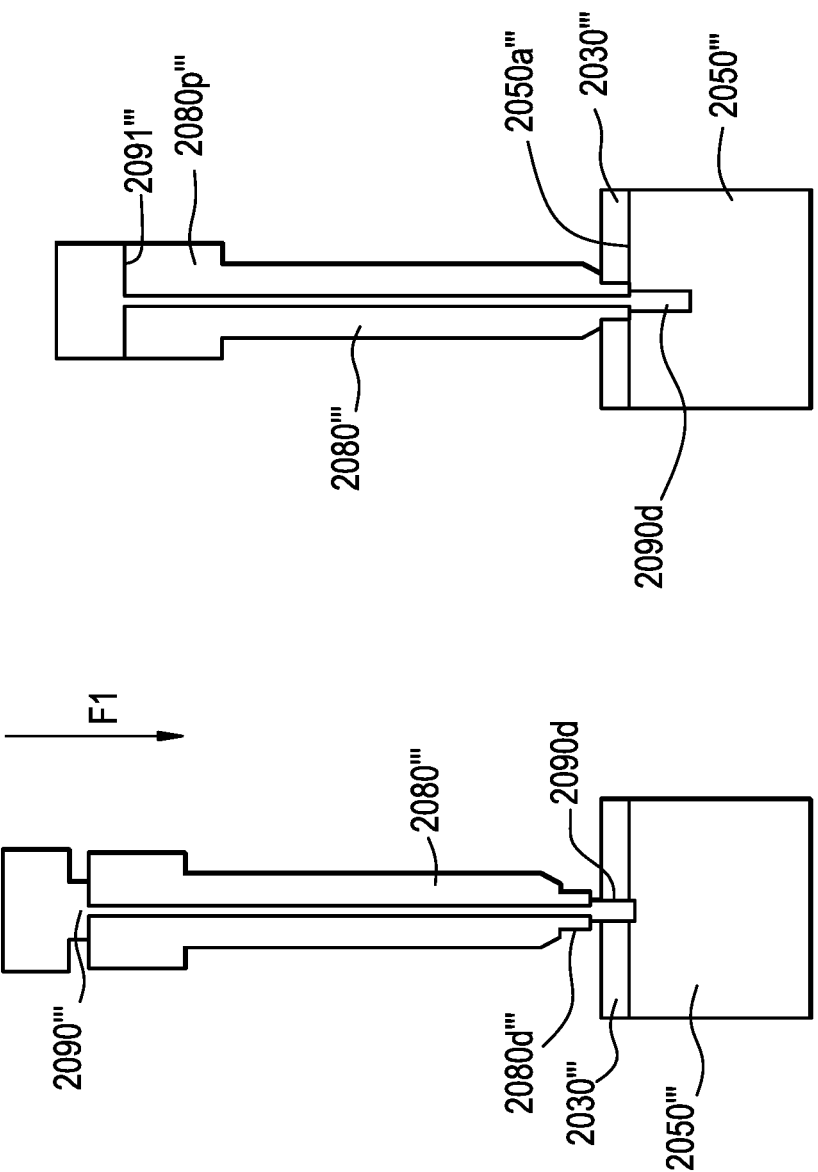

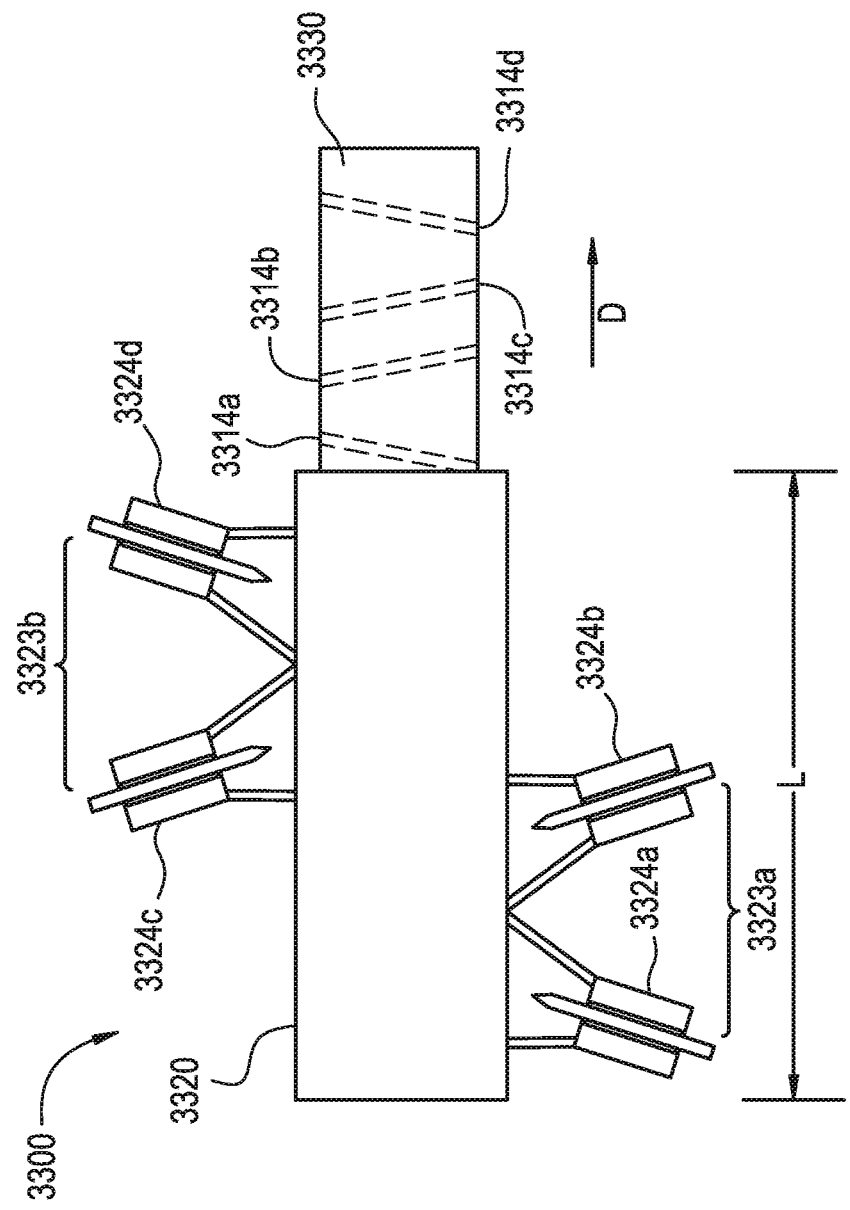

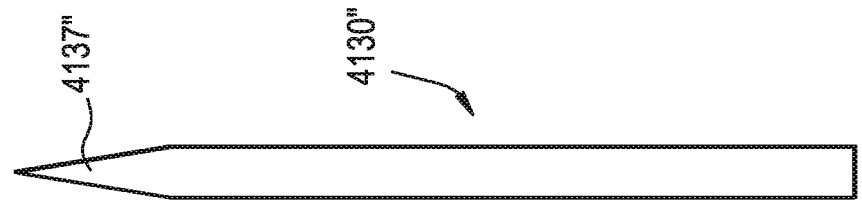
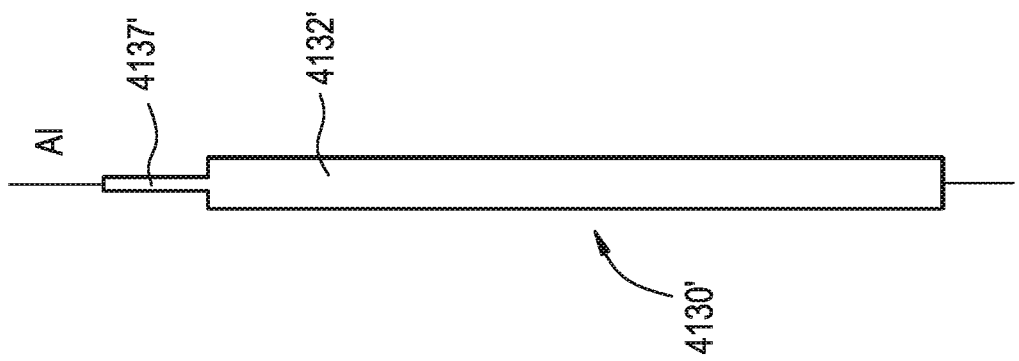
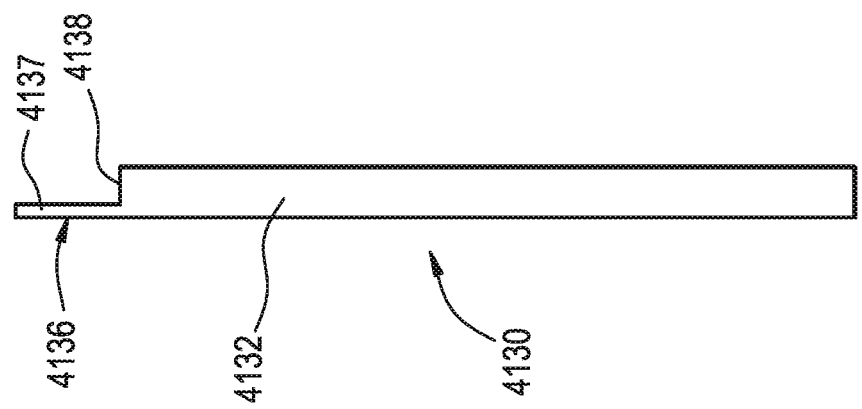

TISSUE AUGMENTATION TACKS FOR USE WITH SOFT TISSUE FIXATION REPAIR SYSTEMS AND METHODS

CROSS REFERENCE TO RELATED APPLICATIONS

The present application is a continuation of and claims priority to U.S. patent application Ser. No. 15/618,984, filed Jun. 9, 2017, and entitled "TISSUE AUGMENTATION TACKS FOR USE WITH SOFT TISSUE FIXATION REPAIR SYSTEMS AND METHODS," which is a continuation-in-part of and claims priority to U.S. patent application Ser. No. 15/419,330, filed Jan. 30, 2017, and entitled "TISSUE AUGMENTATION CONSTRUCTS FOR USE WITH SOFT TISSUE FIXATION REPAIR SYSTEMS AND METHODS," which claims priority to each of U.S. Provisional Patent Application Ser. No. 62/289,702, filed Feb. 1, 2016, and entitled "COMPRESSION STRIPS AND SCAFFOLDS FOR USE IN SOFT TISSUE FIXATION," U.S. Provisional Patent Application Ser. No. 62/348,548, filed Jun. 10, 2016, and entitled "COMPRESSION CONSTRUCTS AND RELATED METHODS FOR USE IN SOFT TISSUE FIXATION," and U.S. Provisional Patent Application Ser. No. 62/393,277, filed Sep. 12, 2016, and entitled "TISSUE AUGMENTATION CONSTRUCTS AND RELATED METHODS FOR USE IN SOFT TISSUE FIXATION," all of which are incorporated by reference herein in their entireties.

FIELD

The present disclosure relates to systems, devices, and methods for securing soft tissue to bone, and more particularly relates to systems, devices, and methods that increase the area of coverage and/or compression between suture filament and tissue during procedures like rotator cuff repairs.

BACKGROUND

A common injury, especially among athletes and people of advancing age, is the complete or partial detachment of tendons, ligaments, or other soft tissues from bone. Tissue detachment may occur during a fall, by overexertion, or for a variety of other reasons. Surgical intervention is often needed, particularly when tissue is completely detached from its associated bone. Currently available devices for tissue attachment include screws, staples, suture anchors, and tacks. Currently available devices for patients of advancing age can be particularly insufficient due to degenerated tissue leading to inadequate suture-to-anchor fixation and further damage to the soft tissue.

Repair constructs made from one or more surgical filaments are typically used in soft tissue repair procedures, e.g., rotator cuff fixations, to secure the tissue in a desired location. The repair constructs are typically disposed through one or more portions of the tissue to be repaired, which can cause trauma to the tissue, and are often coupled to anchors disposed in bone to which the tissue is to be approximated. Further, in situations where the soft tissue has already begun to degenerate, the added pressure applied by the sutures can cause further damage to the tissue, for instance by causing abrasion of the tissue or "cheese-wiring," which refers to one or more strings of tissue peeling away from the main tissue like a string of cheese peels away from a cheese block when a wire cheese slicer is used to separate cheese from the block. In other words, because the suture has a small surface area, and a significant amount of force is being applied to the soft tissue over the small surface area of the tissue, the suture may have a tendency to cut into the already compromised tissue, thus causing further damage. Currently available solutions to this problem include the application of a relatively large formation of allograft or xenograft, typically about 3 centimeters by about 3 centimeters, to the soft tissue after the repair has been performed but prior to tightening the soft tissue down with the suture. The application of the formation, however, is often expensive, necessitates many sutures, and requires a high skill level to operate and is thus used by only a select few surgeons. Further, the application of the relatively large formation can add a significant amount of time to a surgical procedure, on the order of an additional half hour to one hour per allograft or xenograft formation applied.

It is therefore desirable to provide systems, devices, and methods for use in soft tissue repair that are robust, strong, and promote healing, yet minimize the costs and time of the procedure.

SUMMARY

Systems, devices, and methods are generally provided for performing surgical procedures involving sutures, such as rotator cuff repairs, among other suture repair procedures. More specifically, the systems, devices, and methods are designed to allow a user to quickly add one or more tissue augmentation constructs or matrices onto suture being used to perform the tissue repair. The tissue augmentation constructs, which come in a variety of configurations, including but not limited to tapes, tubes, blocks, rings, tacks, washers, and patches, can expand a footprint of the sutures with which they are associated. The expanded footprint helps distribute force applied by the suture on the tissue across a greater surface area, can protect aspects of the system and/or tissue, provide bulk to otherwise compromised or degenerate tissue and/or tendon, and can help promote tissue growth and repair at the surgical site.

The tissue augmentation constructs can be associated with the suture(s) in an on-demand fashion so that a surgeon can quickly and easily expand the footprint of the sutures, or similarly purposed materials such as suture tape, being used based on the needs presented during the procedure. The constructs can be associated with suture using a variety of techniques, including disposing the constructs on the suture and threading the suture through the constructs, among other techniques. In some exemplary embodiments, a tissue augmentation construct is predisposed on a threader, and the threader is operable to associate a suture being used in the soft tissue repair with the tissue augmentation construct. Surgical procedures that utilize the tissue augmentation constructs provided for in the present disclosure are also provided, as are various manufacturing techniques and methods for forming tissue augmentation constructs.

In one exemplary embodiment, a surgical soft tissue repair system includes a first suture limb and a first tissue augmentation block. The tissue augmentation block is disposed on the first suture limb such that the first tissue augmentation block extends along a first length of the first suture limb. As a result, a tissue engaging surface area of the system along the first length is increased. The system can additionally include a second suture limb and a second tissue augmentation block. The second tissue augmentation block can be disposed on the second suture limb such that the second tissue augmentation block extends along a second length of the second suture limb. The second tissue augmentation block can further increase a second tissue engaging surface area of the system along the second length. The first suture limb and the second suture limb can be formed from a single suture. Alternatively, the first suture limb and the second suture limb can be formed from different sutures.

The first tissue augmentation block can have a number of different configurations. In one configuration, the first tissue augmentation block includes an opening that extends through the first tissue augmentation block with the first suture limb being disposed through the opening of the first tissue augmentation block such that the first tissue augmentation block freely passes along a length of the first suture limb in an unrestricted manner. In a second configuration, the first tissue augmentation block includes a tape having a substantially flat tissue-engaging surface with a width that is at least two times as large as a diameter of the first suture limb and a length that is substantially greater than the width of the tape. The first suture limb on which the tape is disposed extends through the substantially flat tissue-engaging surface of the tape at a plurality of locations along the length of the substantially flat tissue-engaging surface. Other configurations of tissue augmentation blocks are also provided for, including but not limited to bars and washers. In configurations where the system includes first and second tissue augmentation blocks, the first and second tissue augmentation blocks can have the same or different configurations. Further, in some embodiments, the first tissue augmentation block can include at least one of: fabric, plastic, synthetic polymer, natural polymer, collagen, collagen scaffold, reconstituted collagen, a biological autograft, allograft, allogenic, xenogeneic, or xenograft, connective tissue including human dermal matrix, acellular porcine dermal matrix, acellular bovine dermal matrix, periosteal tissue, pericardial tissue, and/or fascia, and combinations thereof. In some embodiments, the first tissue augmentation block includes collagen. The blocks can be woven, nonwoven, knitted, or manufactured using a variety of techniques known to those skill in the art or otherwise provided for herein.

In some embodiments, at least one additional tissue augmentation block can be disposed on the first suture limb. For example, each of an additional tissue augmentation block of the at least one additional tissue augmentation block and the first tissue augmentation block disposed on the first suture limb can include a washer. The washer can have an opening that extends through a thickness of the washer, and the first suture limb on which the washer is disposed can extend through the washer opening. The washer can be sized such that the thickness of the washer is substantially less than a length of the first suture limb on which the washer is disposed.

The system can also include a threader on which the first tissue augmentation block is disposed. The threader can include a distal end that is configured to receive the first suture limb and dispose the first tissue augmentation block onto the first suture limb as the threader is moved with respect to the first tissue augmentation block. The threader can more specifically include a collapsible opening at the distal end that is configured to receive the first suture limb, a proximal handle portion, and an elongate intermediate portion that extends between the collapsible opening and the proximal handle portion. The elongate intermediate portion can have the first tissue augmentation block disposed on it. The threader can be configured such that applying a force to the proximal handle portion advances the elongate intermediate portion and the collapsible opening in the direction of the applied force such that when the first suture limb is disposed within the collapsible opening, the applied force disposes the first tissue augmentation block onto the first suture limb. The system can further include an installation tool that has a handle portion and a cartridge. The cartridge can have a length and a width that is sized to receive and retain the first tissue augmentation block disposed on the threader, with the threader extending through the entire length of the cartridge.

In another exemplary embodiment, a soft tissue suture repair system includes a tissue augmentation block and a threader. The threader has a proximal handle, a distal receiving end, and an intermediate portion extending between the proximal handle and the distal receiving end. The intermediate portion of the threader has the tissue augmentation block disposed on it. Further, the threader is configured to dispose the tissue augmentation block onto a suture by associating a suture with the distal receiving end and applying a force to the proximal handle to advance the distal receiving end towards the tissue augmentation block.

In some embodiments the threader can be configured such that the distal receiving end, and thus a suture associated therewith, passes through the tissue augmentation block in response to the application of the force to the proximal handle. Sometimes, the intermediate portion is a filament portion, a fiber, a thread, a wire, a cord, and/or some other flexible structure. Further, the system can include a suture that can be configured to be associated with the distal receiving end of the threader and can be configured to have the tissue augmentation block disposed on it.

The tissue augmentation block can have various configurations. In one configuration, the tissue augmentation block includes an opening that extends through the block and the intermediate portion of the threader can be disposed through the opening. In a second configuration, the tissue augmentation block includes a tape having a substantially flat tissue-engaging surface with a width that is at least two times as large as a diameter of the suture on which the tape is disposed, and a length that is substantially greater than the width of the tape. The intermediate portion of the threader on which the tape is disposed can extend through the substantially flat tissue-engaging surface of the tape at a plurality of locations along the length of the substantially flat tissue-engaging surface. Other configurations are also provided for, including but not limited to the tissue augmentation block including a bar or a washer.

The system can include an installation tool for disposing the tissue augmentation block on a suture. The installation tool can include a handle portion and a cartridge. The cartridge can have a length and a width that is sized to receive and retain the tissue augmentation block. Further, in some embodiments, the tissue augmentation block can include at least one of: fabric, plastic, synthetic polymer, natural polymer, collagen, collagen scaffold, reconstituted collagen, biological autograft connective tissue, biological allograft connective tissue, biological xenograft connective tissue, human dermal matrix, porcine dermal matrix, bovine dermal matrix, periosteal tissue, pericardial tissue, and fascia, and in some embodiments, the tissue augmentation block include collagen.

In still another exemplary embodiment, a surgical kit for soft tissue repair includes one or more bone anchors, one or more sutures, one or more tissue augmentation blocks, and one or more threaders. Each tissue augmentation block is configured to be disposed on a suture limb of a suture of the one or more sutures. Further, at least one of the threaders is configured to dispose a tissue augmentation block of the one or more tissue augmentation blocks onto a suture of the one or more sutures.

In some embodiments the surgical kit can also include a drill for drilling a bone hole sized to receive a bone anchor of the one or more bone anchors. In various embodiments, the one or more tissue augmentation blocks can include a plurality of tissue augmentation blocks, and/or the one or more sutures can include a plurality of sutures, and/or the one or more bone anchors can include a plurality of bone anchors.

One of the one or more tissue augmentation blocks can include an opening extending through the block. The opening can be configured to have the suture limb extending through the tissue augmentation block when the tissue augmentation block is disposed on the suture limb such that the tissue augmentation block freely passes along a length of the suture limb in an unrestricted manner. Alternatively, one of the one or more tissue augmentation blocks can include a tape having a substantially flat tissue-engaging surface with a width that is at least two times as large as a diameter of the suture limb on which the tissue augmentation block is disposed and a length that is substantially greater than the width of the tape. The substantially flat tissue-engaging surface can be configured to have the suture limb extend through it at a plurality of locations along the length of the substantially flat tissue-engaging surface when the tissue augmentation block is disposed on the suture limb. Other configurations of the one or more tissue augmentation blocks are also provided for, including but not limited to bars and washers. The washers can be sized such that a thickness of the washer is substantially less than a length of a suture limb on which the washer is to be disposed. Further, in some embodiments, a tissue augmentation block of the one or more tissue augmentation blocks can include at least one of: fabric, plastic, synthetic polymer, natural polymer, collagen, collagen scaffold, reconstituted collagen, a biological autograft, allograft, allogenic, xenogeneic, or xenograft, connective tissue including human dermal matrix, acellular porcine dermal matrix, acellular bovine dermal matrix, periosteal tissue, pericardial tissue, and/or fascia, and combinations thereof. In some embodiments, one or both of the first and second augmentation blocks includes collagen. The blocks can be woven, non-woven, knitted, or manufactured using a variety of techniques known to those skill in the art or otherwise provided for herein.

One or more of the threaders can include a proximal handle, a distal receiving end, and an intermediate portion extending between the proximal handle and the distal receiving end. The threader can be configured to dispose one or more tissue augmentation blocks onto one or more sutures by associating one or more sutures with the distal receiving end and applying a force to the proximal handle to advance the distal receiving end towards the one or more tissue augmentation blocks. The distal receiving end can be configured such that the distal receiving end, and thus one or more sutures associated therewith, passes through one or more tissue augmentation blocks in response to the application of the force to the proximal handle.

In an exemplary method of soft tissue repair, the method includes attaching a first suture to soft tissue such that two suture limbs of the first suture extend from the soft tissue, disposing at least one tissue augmentation block on at least one of the first and second suture limbs, coupling the two suture limbs with at least one suture anchor disposed in bone, and tightening the suture limbs such that the tissue augmentation block(s) is directed towards the soft tissue. By disposing a tissue augmentation block on at least one of the two suture limbs, a surface area for engaging tissue associated with the respective suture limb is increased. One or more tissue augmentation blocks can be disposed on both suture limbs if desired.

In some embodiments the step of attaching a first suture to soft tissue such that two suture limbs of the suture extend from the soft tissue further comprises installing a medial row stitch. In such embodiments, the step of coupling the two suture limbs with at least one suture anchor disposed in bone can include installing a lateral row fixation.

In some embodiments the step of disposing at least one tissue augmentation block on at least one of the first and second limbs can include coupling a first limb of the two suture limbs to a threader associated with a first tissue augmentation block and applying a force to the threader associated with the first tissue augmentation block to dispose the first tissue augmentation block on the first limb. The method can further include coupling a second limb of the two suture limbs to a threader associated with a second tissue augmentation block and applying a force to the threader associated with the second tissue augmentation block on the second limb.

The tissue augmentation block(s) used in the methods can have a variety of configurations. For example, in some instances, one or more of the tissue augmentation blocks can include an opening extending through the block, and the opening can be configured to have one of the suture limbs extending therethrough when the tissue augmentation block is disposed on the respective suture limb such that the tissue augmentation block freely passes along a length of the suture limb in an unrestricted manner. By way of further non-limiting example, in some instances, one or more of the tissue augmentation blocks can include a tape having a substantially flat tissue-engaging surface with a width that is at least two times greater than a diameter of the suture limb on which the block is disposed, and a length that is substantially greater than the width of the tape. The substantially flat tissue-engaging surface can be configured to have the suture limb extend through it at a plurality of locations along the length of the substantially flat tissue-engaging surface when the tissue augmentation block is disposed on the suture limb. Other configurations of tissue augmentation blocks are also provided for, including but not limited to bars and washers. The washers can be sized such that a thickness of the washer is substantially less than a length of a suture limb on which the washer is to be disposed. Further, in some embodiments, one or more of the tissue augmentation blocks can include at least one of: fabric, plastic, synthetic polymer, natural polymer, collagen, collagen scaffold, reconstituted collagen, a biological autograft, allograft, allogenic, xenogeneic, or xenograft, connective tissue including human dermal matrix, acellular porcine dermal matrix, acellular bovine dermal matrix, periosteal tissue, pericardial tissue, and/or fascia, and combinations thereof. In some embodiments, one or both of the first and second augmentation blocks includes collagen. The blocks can be woven, non-woven, knitted, or manufactured using a variety of techniques known to those skill in the art or otherwise provided for herein.

In some embodiments that include a second suture, the step of coupling the two suture limbs with at least one suture anchor disposed in bone can include coupling the two suture limbs with a first suture anchor of the at least one suture anchor. The method can additionally include attaching a second suture to the soft tissue such that a third suture limb and a fourth suture limb extend from the soft tissue. At least one second tissue augmentation block can be can be disposed on at least one of the third and fourth suture limbs, and the third and fourth suture limbs can be coupled with a second anchor of the at least one suture anchor disposed in bone. The method can further include tightening the third and fourth suture limbs such that the second tissue augmentation block is directed towards the soft tissue. By disposing a tissue augmentation block on at least one of the third and fourth suture limbs, a surface area for engaging tissue associated with at least one of the third and fourth suture limbs is increased. One or more tissue augmentation blocks can be disposed on both suture limbs if desired.

The step of disposing at least one tissue augmentation block on at least one of the first and second suture limbs can include disposing a first tissue augmentation block on the first suture limb and a second tissue augmentation block on the second suture limb in some instances. In some of those instances, the first and second suture limbs can be coupled together to form a mattress stitch.

In yet other embodiments the method can further include attaching a second suture to the soft tissue such that a third suture limb and a fourth suture limb extend from the soft tissue, disposing at least one second tissue augmentation block on at least one of the third and fourth suture limbs, and disposing at least one tissue augmentation block on each of the first and second suture limbs of the first suture. By disposing tissue augmentation blocks on the first, second, and at least one of the third and fourth suture limbs, a surface area for engaging tissue associated with the respective suture limbs are increased. The method can further include coupling the first and third suture limbs with a first suture anchor disposed in the bone, and coupling the second and fourth suture limbs with a second suture anchor disposed in the bone. In some embodiments, the second and third limbs can cross over each other. The method can further include tightening the first, second, third, and fourth suture limbs such that the tissue augmentation blocks are directed towards the soft tissue.

In still other embodiments, the method can further include attaching a second suture to the soft tissue such that a third suture limb and a fourth suture limb extend from the soft tissue. The first and second limbs of the first suture can be coupled together, for instance by using a first knot to tie them together. The at least one tissue augmentation block that is disposed on at least one of the first and second suture limbs can be slid over the first knot. The third and fourth suture limbs also can be coupled together, for instance by using a second knot to tie them together. At least one of the third and fourth suture limbs can extend above the at least one tissue augmentation block to help maintain a location of the at least one tissue augmentation block with respect to the soft tissue.

Sometimes the method can include attaching a second suture to the soft tissue at a location that is laterally displaced from a location of the first suture such that a third suture limb and a fourth suture limb extend from the soft tissue. Further, a tissue augmentation block of the at least one tissue augmentation block can be disposed on the first suture limb. The first and third suture limbs can be coupled together to form a mattress stitch, for instance by using a first knot to tie them together, and the tissue augmentation block of the at least one tissue augmentation block can be slid over the first knot. The second and fourth suture limbs also can be coupled together, for instance by using a second knot to tie them together. At least one of the second and fourth suture limbs can extend above the tissue augmentation block to help maintain a location of the tissue augmentation block with respect to the soft tissue.

In other embodiments, the first tissue augmentation block of the at least one tissue augmentation block can be disposed on the first suture limb. In some such embodiments, the method can include attaching a second suture to the soft tissue such that a third suture limb and a fourth suture limb extend from the soft tissue. A second tissue augmentation block of the at least one tissue augmentation block can be disposed on the fourth suture limb, thereby increasing a surface area for engaging tissue associated with the fourth suture limb. Further, a third tissue augmentation block of the at least one tissue augmentation block can be disposed on each of the second and third suture limbs. The first and second suture limbs can be coupled with a first suture anchor disposed in the bone, and the third and fourth suture limbs can be coupled with a second suture anchor disposed in the bone. The first, second, third, and fourth suture limbs can be tightened such that the first, second, and third tissue augmentation blocks can be directed towards the soft tissue.

Another exemplary method of soft tissue repair includes coupling a first suture limb of a first suture to a first threader having a first tissue augmentation block disposed thereon, the first suture being attached to a first suture implant disposed in bone in a body, and the first suture limb being coupled to tissue, and applying a force to the first threader to move the first threader with respect to the first tissue augmentation block such that the first suture limb is passed into the first tissue augmentation block to dispose the first tissue augmentation block onto a portion of the first suture limb. The first suture limb and the first tissue augmentation block are then disassociated from the first threader, and the first tissue augmentation block is advanced towards the first suture implant. A portion of the first suture limb is secured at a surgical site, and a location of the first tissue augmentation block and/or the first suture limb is adjusted with respect to the tissue.

In some embodiments, the first suture can be coupled to the tissue by forming a medial row stitch with the first suture. Further, in some instances the method can include coupling a second suture limb of the first suture to a second threader having a second tissue augmentation block disposed thereon, the second suture limb being coupled to tissue, and applying a force to the second threader to move the second threader with respect to the second tissue augmentation block such that the second suture limb is passed into the second tissue augmentation block to dispose the second tissue augmentation block onto a portion of the second limb. The second suture limb and the second tissue augmentation block can be disassociated from the second threader. The second tissue augmentation block can be advanced towards the first suture implant, and a portion of the second suture limb can be secured at the surgical site. In some embodiments in which the first suture includes both a first suture limb and second suture limb, the first and second suture limbs can be coupled together by way of a mattress stitch.

Various methods provided for can also include a second suture associated with a second suture implant. More specifically, a third suture limb of a second suture can be coupled to a third threader having a third tissue augmentation block disposed on it. The second suture can be attached to a second suture implant disposed in bone in a body, and the third suture limb can be coupled to tissue. A force can be applied to the third threader to move the threader with respect to the third tissue augmentation block. As a result, the third suture limb can be passed into the third tissue augmentation block to dispose the third tissue augmentation block onto a portion of the third suture limb. The third suture limb and the third tissue augmentation block can be disassociated from the third threader, and a portion of the third suture limb can be secured at the surgical site. A portion of the first suture limb of the first suture can be secured at the surgical site by coupling the first suture limb to a first lateral anchor, a portion of the second suture limb of the first suture can be secured at the surgical site by coupling the second suture limb to a second lateral anchor, and a portion of the third suture limb of the second suture can be secured at the surgical site by coupling the third suture limb to the second lateral anchor. Further, a portion of a fourth suture limb of the second suture can be secured at the surgical site by coupling the fourth suture limb to the first lateral anchor.

In some embodiments, the step of securing a portion of the first suture limb at the surgical site can include coupling a second suture limb of the first suture with the first suture limb using a first knot. Further, the step of adjusting a location of at least one of the first tissue augmentation block and first suture limb with respect to the tissue can include sliding the first tissue augmentation block over the first knot. In such embodiments, the method can also include coupling a third suture limb and a fourth suture limb of a second suture that extend from the tissue with a second knot. Further, at least one of the third and fourth suture limbs can extend above the first tissue augmentation block to help maintain a location of the first tissue augmentation block with respect to the tissue.

In some other embodiments, the step of securing a portion of the first suture limb at the surgical site can include coupling a third suture limb of a second suture that extends from the tissue with a first knot to form a mattress stitch. Further, the step of adjusting a location of at least one of the first tissue augmentation block and first suture limb with respect to the tissue can include sliding the first tissue augmentation block over the first knot. In such embodiments, the method can also include coupling the second suture limb of the first suture and a fourth suture limb of the second suture with a second knot. Further, at least one of the second and fourth suture limbs can extend above the first tissue augmentation block to help maintain a location of the first tissue augmentation block with respect to the tissue. Still further, a location of the second suture can be laterally displaced with respect to a location of the first suture.

In still some other embodiments, the method can include coupling a fourth suture limb of a second suture to a third threader having a third tissue augmentation block disposed on it. The fourth suture limb can be coupled to tissue. A force can be applied to the second threader to move the second threader with respect to the second tissue augmentation block so that the fourth suture limb is passed into the third tissue augmentation block. As a result, the third tissue augmentation block is disposed onto a portion of the fourth suture limb. The fourth suture limb and the third tissue augmentation block can be disassociated from the third threader. A portion of a third suture limb, which is also from the second suture, can be secured within the body by coupling the portion to a first suture anchor that is disposed in bone. A portion of the fourth suture limb can also be secured within the body by coupling it to the first suture anchor. The second tissue augmentation block can be disposed on the third suture limb, in addition to being disposed on the second suture limb. Further, securing portions of the first and second suture limbs at the surgical site can include coupling a portion of the respective first and second suture limbs to a second suture anchor disposed in bone.

The first tissue augmentation block, or any tissue augmentation block for that matter, can have a variety of configurations. For example, in some instances the first tissue augmentation block can have an opening extending through the block, and the opening can be configured to have one of the suture limbs extending therethrough when the first tissue augmentation block is disposed on the respective suture limb such that the first tissue augmentation block freely passes along a length of the suture limb in an unrestricted manner. By way of further non-limiting example, in some instances the first tissue augmentation block can include a tape having a substantially flat tissue-engaging surface with a width that is at least two times greater than a diameter of the suture limb on which the block is disposed, and a length that is substantially greater than the width of the tape. The substantially flat tissue-engaging surface can be configured to have the suture limb extend through it at a plurality of locations along the length of the substantially flat tissue-engaging surface when the tissue augmentation block is disposed on the suture limb. Other configurations of tissue augmentation blocks are also provided for, including but not limited to bars and washers. The washers can be sized such that a thickness of the washer is substantially less than a length of a suture limb on which the washer is to be disposed. Further, in some embodiments, the first tissue augmentation block, or again any tissue augmentation block for that matter, can include at least one of: fabric, plastic, synthetic polymer, natural polymer, collagen, collagen scaffold, reconstituted collagen, a biological autograft, allograft, allogenic, xenogeneic, or xenograft, connective tissue including human dermal matrix, acellular porcine dermal matrix, acellular bovine dermal matrix, periosteal tissue, pericardial tissue, and/or fascia, and combinations thereof. In some embodiments, one or both of the first and second augmentation blocks includes collagen. The blocks can be woven, non-woven, knitted, or manufactured using a variety of techniques known to those skill in the art or otherwise provided for herein.

In one exemplary embodiment of a soft tissue repair system that includes a patch or scaffold, the system has a scaffold, a first threader, and a second threader. Each of the first and second threaders include a proximal handle, a distal receiving end, and an intermediate portion extending between the proximal handle and the distal receiving end, and the intermediate portion of each threader has the scaffold disposed on it. The first and second threaders are configured to dispose the scaffold onto sutures by associating respective sutures with the respective distal receiving ends and applying a force to the respective proximal handles to advance the respective distal receiving ends towards the scaffold.

The first and second threaders can be configured so that their respective distal receiving ends, and thus suture(s) associated therewith, pass through the scaffold in response to the application of the force to the proximal handles. In some embodiments, the intermediate portion of each of the first and second threaders can include a filament portion, a fiber, a thread, a wire, a cord, and/or some other flexible structure. The proximal handles of the first and second suture threaders can be disposed on a first side of the scaffold, the distal receiving ends of the first and second threaders can be disposed on a second side of the scaffold, and the intermediate portions of the first and second threaders can extend from the first side to the second side in a pre-installation configuration.

In some embodiments, the intermediate portion of the first threader can be disposed more proximate to a first side of the scaffold than a second, opposite side of the scaffold, and the intermediate portion of the second threader can be disposed more proximate to the second, opposite side of the scaffold than the first side. Further, a third threader and a fourth threader can also be provided, with each including a proximal handle, a distal receiving end, and an intermediate portion extending between the proximal handle and the distal receiving end. The intermediate portion of each of the third and fourth threaders can have the scaffold disposed on it. Further, the third and fourth threaders can be configured to dispose the scaffold onto sutures by associating respective sutures with the respective distal receiving ends and applying a force to the respective proximal handles to advance the respective distal receiving ends towards the scaffold. In some embodiments, the intermediate portion of the third threader can be disposed diagonally with respect to the scaffold such that the distal receiving end of the third threader is proximate to the distal receiving end of the first threader and the proximal handle of the third threader is proximate to the proximal handle of the second threader, and the intermediate portion of the fourth threader can be disposed diagonally with respect to the scaffold such that the distal receiving end of the fourth threader is proximate to the distal receiving end of the second threader and the proximal handle of the fourth threader is proximate to the proximal handle of the first threader.

The system can also include multiple sutures. For example, a first suture can be configured to be associated with the distal receiving end of the first threader and configured to have the scaffold disposed on it, and a second suture can similarly be configured to be associated with the distal receiving end of the second threader and configured to have the scaffold disposed on it. In some embodiments, the suture(s) can be coupled to the scaffold in a pre-installation configuration. By way of example, a first suture can be coupled to the scaffold at a first medial location on the scaffold and a second suture can be coupled to the scaffold at a second medial location on the scaffold. Each of the first and second sutures can include a hollow self-locking mechanism, and the intermediate portion of the first and second threaders can be disposed in the hollow self-locking mechanisms of the first and second sutures, respectively. Such a scaffold can include a flexible zone that is located at the first and second medial locations, with the flexible zone being configured to allow the scaffold to stretch.

In embodiments having the first and second sutures coupled to the first and second medial locations as described, a leading tail can extend from each of the hollow self-locking mechanisms of the first and second sutures, towards a first side of the scaffold. The leading tails can be configured to be coupled to the distal receiving ends of the first and second threaders disposed within the respective hollow self-locking mechanisms of the first and second sutures. In some embodiments, a trailing tail can extend from each of the hollow self-locking mechanisms of the first and second sutures, towards a second, opposite side of the scaffold. Each of the trailing tails can be configured to be coupled to a suture anchor, whether the same anchor or different anchors. In some other embodiments, the system can include trailing tails that are separate sutures than the first and second sutures. For example, a first trailing tail can be disposed more proximate to a second, opposite side of the scaffold than the first side of the scaffold, and can also be disposed more proximate to the hollow self-locking mechanism of the first suture than the hollow self-locking mechanism of the second suture. Similarly, a second trailing tail can be disposed more proximate to the second, opposite end of the scaffold than the first side of the scaffold, and can also be disposed more proximate to the hollow self-locking mechanism of the second suture than the hollow self-locking mechanism of the first suture. Each of the trailing tails can be configured to be coupled to a suture anchor, whether the same anchor or different anchors.

In some embodiments having the first and second sutures coupled to the first and second medial locations as described, third and fourth threaders and third and fourth sutures can also be provided. The third and fourth threaders can each include a proximal handle, a distal receiving end, and an intermediate portion extending between the proximal handle and the distal receiving end. The intermediate portion of each of the third and fourth threaders can have the scaffold disposed on it, with the intermediate portion being associated with the third and fourth sutures. More specifically, the third and fourth sutures can be coupled to the scaffold proximate to the first and second medial locations, respectively. Each of the third and fourth sutures can include a hollow self-locking mechanism, and the intermediate portions of the third and fourth threaders can be disposed in the hollow self-locking mechanisms of the third and fourth sutures, respectively. Further, the third and fourth threaders can be configured to dispose the scaffold onto sutures by associating respective sutures with the respective distal receiving ends and applying a force to the respective proximal handles to advance the respective distal receiving ends towards the scaffold. In some embodiments, a leading tail can extend from each of the hollow self-locking mechanisms of the first, second, third, and fourth sutures. The leading tails of the first and second sutures can extend towards a first side of the scaffold, and the leading tails of the third and fourth sutures can extend towards a second, opposite side of the scaffold. The leading tails can be configured to be coupled to the distal receiving ends of the first, second, third, and fourth threaders disposed within the respective hollow self-locking mechanisms of the first, second, third, and fourth sutures.

In some embodiments that include a scaffold and first and second threaders, one or more additional threaders can be provided. For example, a third threader and a fourth threader can be provided. Each of the third and fourth threaders can include a proximal handle, a distal receiving end, and an intermediate portion extending between the proximal handle and the distal receiving end. The intermediate portion of each of the third and fourth threaders can have the scaffold disposed on it, with the third threader being configured to dispose the scaffold onto the same suture as the first threader and the fourth threader being configured to dispose the scaffold onto the same suture as the second threader. More particularly, the association of the third and fourth threaders with the same suture as the first and second threaders, respectively, can be configured to be achieved by associating the respective suture with the distal receiving end of the respective third and fourth threaders and applying a force to the proximal handle of the respective third and fourth threaders to advance the respective distal receiving end towards the scaffold. The third and fourth threaders can be disposed in the scaffold such that the distal receiving ends of the third and fourth threaders are disposed on a tissue-engaging face of the scaffold and the proximal handles of the third and fourth threaders are disposed on a face of the scaffold that is opposite of the tissue-engaging face.

A limb of the suture onto which the scaffold is disposed by the first and third threaders can include a first loop that extends from the tissue-engaging face, around an edge of the scaffold to the face of the scaffold that is opposed to the tissue-engaging face, and into the scaffold at a first location on the scaffold, and a limb of the suture onto which the scaffold is disposed by the second and fourth threaders can include a second loop that extends from the tissue-engaging face, around the edge of the scaffold to the face of the scaffold that is opposed to the tissue-engaging face, and into the scaffold at a second location on the scaffold in a post-installation configuration of the system. Alternatively, a limb of the suture onto which the scaffold is disposed by the first and third threaders can include a first loop that extends from the tissue-engaging face of the scaffold, to the face of the scaffold that is opposed to the tissue-engaging face, and into the scaffold at a first location on the scaffold that is offset from an edge of the scaffold, and a limb of the suture onto which the scaffold is disposed by the second and fourth threaders can include a second loop that extends from the tissue-engaging face of the scaffold, to the face of the scaffold that is opposed to the tissue-engaging face, and into the scaffold at a second location that is offset from the edge of the scaffold in a post-installation configuration of the system.

The scaffold can have a variety of configurations, shapes, and sizes, and can be made of a variety of materials. In some embodiments, the scaffold can include at least one of: fabric, plastic, synthetic polymer, natural polymer, collagen, collagen scaffold, reconstituted collagen, a biological autograft, allograft, allogenic, xenogeneic, or xenograft, connective tissue including human dermal matrix, acellular porcine dermal matrix, acellular bovine dermal matrix, periosteal tissue, pericardial tissue, and/or fascia, and combinations thereof. In some embodiments, the scaffold includes collagen. The scaffold can be woven, non-woven, knitted, or manufactured using a variety of techniques known to those skill in the art or otherwise provided for herein. Still further, in some embodiments a first layer of the scaffold can include a biodegradable polymer, and a second layer of the scaffold can include an extracellular matrix. A thickness of the first layer can be greater than a thickness of the second layer. Further, in some embodiments, the scaffold can include one or more adjustable suture loops disposed on an edge of the scaffold, the adjustable suture loop(s) being configured to prevent the scaffold from unintentionally sliding with respect to a suture limb passed through the respective adjustable suture loop(s).

In another exemplary embodiment of a soft tissue repair system, the system includes a scaffold and two sets of suture limbs. The scaffold has a first layer of material, and includes a tissue-facing surface and a second surface that is opposed to the tissue-facing surface, as well as a medial edge and an opposed lateral edge. The first set of suture limbs includes a first suture limb and a second suture limb that are disposed through the scaffold between the tissue-facing surface and the second surface along a length of the scaffold that extends substantially between the medial and opposed lateral edges. The second set of suture limbs includes a third suture limb and a fourth suture limb that are disposed above the tissue-facing surface of the scaffold. The system is configured such that a terminal lateral end of one of the first and second suture limbs and a terminal lateral end of one or the third and fourth suture limbs are disposed proximate to each other on a first side of the scaffold, and a terminal lateral end of the other of the first and second suture limbs and a terminal lateral end of the other of the third and fourth suture limbs are disposed proximate to each other on a second side of the scaffold. The first and second sides of the scaffold are distinguished by being on opposite sides of a central longitudinal axis of the scaffold that extends between the medial and lateral edges. Further, at least one of the first and second suture limbs extends through the scaffold from the tissue-facing surface to the second surface and then, for that suture limb, forms at least one stitch that passes a terminal lateral end of the suture limb through the scaffold to and through the lateral edge. Optionally, a stitch of that nature, or similar to that nature, can also be formed with at least one of the third and fourth suture limbs.

The scaffold can include a second layer of material disposed above the first layer of material such that the second layer of material is disposed above the tissue-facing surface of the scaffold and the second layer of material includes the second surface of the scaffold. In such embodiments, the first suture limb and the second suture limb can be disposed between a top-most surface of the first layer of material that is opposed to the tissue-facing surface of the scaffold and a tissue-facing surface of the second layer of material that is opposed to the second surface of the scaffold.

In some embodiments, the first and second suture limbs can be disposed on opposite sides of the central longitudinal axis of the scaffold such that the first and second suture limbs do not intersect at locations at which the first and second suture limbs are disposed through the scaffold between the tissue-facing surface and the second surface. In some such embodiments, the third and fourth suture limbs can be disposed with respect to the central longitudinal axis of the scaffold such that the third and fourth suture limbs cross over the central longitudinal axis at least once and intersect each other at least once at a location at which the third and fourth suture limbs are disposed above each of the tissue-facing surface and the second surface. In some other such embodiments, the third and fourth suture limbs can be disposed on opposite sides of the central longitudinal axis of the scaffold such that the first and fourth suture limbs do not intersect at location at which the third and fourth suture limbs are disposed above each of the tissue-facing surface and the second surface and are in contact with the second surface. The first set of the suture limbs can be disposed further from the central longitudinal axis than the second set of the suture limbs for portions of the limbs that extend between the medial and lateral edges. Alternatively, the second set of the suture limbs can be disposed further from the central longitudinal axis than the first set of the suture limbs for portions of the limbs that extend between the medial and lateral edges.

In some other embodiments, the first and second suture limbs can be disposed with respect to the central longitudinal axis of the scaffold such that the first and second suture limbs cross over the central longitudinal axis at least once and intersect each other at least once at a location at which the first and second suture limbs are disposed through the scaffold between the tissue-facing surface and the second surface. In some such embodiments, the third and fourth suture limbs can be disposed with respect to the central longitudinal axis of the scaffold such that the third and fourth suture limbs also cross over the central longitudinal axis at least once and intersect each other at least once at a location at which the third and fourth suture limbs are disposed above each of the tissue-facing surface and the second surface. In some other such embodiments, the third and fourth suture limbs can be disposed on opposite sides of the central longitudinal axis of the scaffold such that the first and fourth suture limbs do not intersect at location at which the third and fourth suture limbs are disposed above each of the tissue-facing surface and the second surface and are in contact with the second surface.

The third and fourth suture limbs can be disposed above the second surface of the scaffold. Further, in some embodiments, the third and fourth suture limbs can be in contact with the second surface of the scaffold. Alternatively, the third and fourth suture limbs can be disposed through the scaffold between the tissue-facing surface and the second surface along a portion of a length of the scaffold that extends between the medial and opposed lateral edges. Further alternatively, the third and fourth suture limbs can partially extend above the second surface of the scaffold and partially through the scaffold. For instance, a portion of the third and fourth suture limbs extending between the medial and opposed lateral edges can be disposed above the second surface of the scaffold and another portion of the third and fourth suture limbs can be disposed through the scaffold between the tissue-facing surface and the second surface along the portion of the length of the scaffold that extends between the medial and opposed lateral edges.

The at least one stitch can include a loop in which the suture limb forming the loop passes around the medial edge and into the scaffold such that the terminal lateral end of the suture limb passes through the scaffold from the medial edge to and through the lateral edge. Alternatively, the at least one stitch can include a jog in which the suture limb forming the jog passes into the scaffold at an entry location on the second surface that is more proximate to the medial edge than the lateral edge along a longitudinal axis extending substantially parallel to the central longitudinal axis of the scaffold such that the terminal end of the suture limb passes through the scaffold approximately from the entry location to and through the lateral edge. At least one of the third and fourth suture limbs can also extend through the scaffold from the tissue-facing surface to the second surface and then, for that suture limb, form at least one stitch that passes a terminal lateral end of the suture limb through the scaffold to and through the lateral edge. The stitch can likewise be a loop or jog.

The first set of suture limbs can extend from a first mattress stitch and a second set of suture limbs can extend from a second mattress stitch. The system can further include at least one additional suture having a fifth suture limb and a sixth suture limb. In some embodiments, the fifth and sixth suture limbs can extend from a central medial mattress stitch, while in some other embodiments the fifth and sixth suture limbs can extend from a central lateral mattress stitch. In still further embodiments, suture limbs can extend from each of a central medial mattress stitch and a central lateral mattress stitch. Whether a central medial or lateral mattress stitch, the system can be configured such that a terminal lateral end of one of the fifth and sixth suture limbs can be disposed proximate to the terminal lateral ends of the respective first, second, third, and fourth suture limbs that are disposed on the first side of the scaffold, and a terminal lateral end of the other of the fifth and sixth suture limbs can be disposed proximate to the terminal lateral ends of the respective first, second, third, and fourth suture limbs that are disposed on the second side of the scaffold.

Exemplary methods of soft tissue repair that include using a patch or scaffold are also disclosed. One exemplary method includes passing each of a first suture limb and a second suture limb through soft tissue and attaching a scaffold to each of the first and second suture limbs. This results in a surface area for engaging tissue associated with each of the first and second suture limbs being increased. A first end of the scaffold is advanced to a location that is proximate to locations through which the first and second suture limbs pass through the soft tissue, and one or more suture tails are coupled to at least one suture anchor that is disposed in the bone to which the soft tissue is being attached. In some embodiments, the one or more suture tails are part of suture from which the first and second limbs are formed, while in other embodiments the one or more suture tails are separate sutures from sutures that form the first and second suture limbs.

The step of advancing a first end of the scaffold to a location that is proximate to locations through which the first and second suture passes through the soft tissue can included disposing a second, opposite end of the scaffold beyond the soft tissue such that it extends over bone to which the soft tissue is being attached. In some embodiments, the step of attaching a scaffold to each of the first and second suture limbs can include threading each of the first and second suture limbs from the first end of the scaffold to the second, opposite end of the scaffold, with the first suture limb being thread at a location that is more proximate to a first side of the scaffold than a second, opposite side of the scaffold and the second suture limb being thread at a location that is more proximate to the second, opposite side of the scaffold than the first side of the scaffold. In such embodiments, the step of coupling one or more suture tails with at least one suture anchor disposed in the bone to which the soft tissue is being attached can include coupling a first tail of the one or more suture tails with a first suture anchor disposed in the bone to which the soft tissue is being attached and coupling a second tail of the one or more suture tails with a second suture anchor disposed in the bone to which the soft tissue is being attached. The first suture limb can be of a first suture and the second suture limb can be of a second suture. In some embodiments, the step of attaching a scaffold to each of the first and second suture limbs can include disposing at least one of the first and second suture limbs through an opening of a loop disposed on an edge of the scaffold and collapsing the opening of the loop through which the first and/or second suture limbs are disposed around the respective limb(s) to prevent the scaffold from unintentionally sliding with respect to the limb(s) disposed through the opening.

In embodiments having the first suture and the second suture, threading the first suture limb from the first end of the scaffold to the second, opposite end of the scaffold can include coupling the first suture limb to a threader disposed in the scaffold and applying a force to the threader to dispose the scaffold onto the first suture limb. Similarly, threading the second suture limb from the first end of the scaffold to the second, opposite end of the scaffold can include coupling the second suture limb to a threader disposed in the scaffold and applying a force to the threader to dispose the scaffold onto the second suture limb.

In embodiments having the first suture and the second suture, the method can include installing a first medial row stitch using the first suture, and installing a second medial row stitch using the second suture. Further, the step of coupling one or more suture tails with at least one suture anchor disposed in the bone to which the soft tissue is being attached can include installing a lateral row fixation.

The step of attaching a scaffold to each of the first and second suture limbs can include disposing the first suture limb through the scaffold from a tissue-engaging face of the scaffold to a face of the scaffold that is opposed to the tissue-engaging face, with the disposing of the first suture limb occurring at a first location on the scaffold that is proximate to a proximal edge of the scaffold. The attachment step can further include passing the first suture limb around the proximal edge of the scaffold and into the scaffold through the proximal edge to form a first loop, and passing the first suture limb through the scaffold from the proximal edge to a distal edge of the scaffold. The step can also include disposing the second suture limb through the scaffold from the tissue-engaging face of the scaffold to the face of the scaffold that is opposed to the tissue-engaging face, with the disposing of the second suture limb occurring at a second location on the scaffold that is proximate to the proximal edge of the scaffold. The attachment step can still further include passing the second suture limb around the proximal edge of the scaffold and into the scaffold through the proximal edge to form a second loop, and passing the second suture limb through the scaffold from the proximal edge to the distal edge of the scaffold.

Alternatively, the step of attaching a scaffold to each of the first and second suture limbs can include disposing the first suture limb through the scaffold from a tissue-engaging face of the scaffold to a face of the scaffold that is opposed to the tissue-engaging face, with the disposing of the first suture limb occurring at a first location on the scaffold that is proximate to a proximal edge of the scaffold. The attachment step can further include passing the first suture limb back into the scaffold through the face of the scaffold that is opposed to the tissue-engaging face, with the passing of the first suture limb back into the scaffold occurring at a second location on the scaffold that is offset from the first location to form a first stitch. The attachment step can also include passing the first suture limb through the scaffold from the second location to a distal edge of the scaffold. The attachment step can still further include disposing the second suture limb through the scaffold from the tissue-engaging surface of the scaffold to the face of the scaffold that is opposed to the tissue-engaging face, with the disposing of the second suture limb occurring at a third location on the scaffold that is proximate to the proximal edge of the scaffold. The attachment step can also include passing the second suture limb back into the scaffold through the face of the scaffold that is opposed to the tissue-engaging face, with the passing of the second suture limb back into the scaffold occurring at a fourth location on the scaffold that is offset from the third location to form a second stitch. Still further, the attachment step can include passing the second suture limb through the scaffold from the fourth location to the distal edge of the scaffold.

The first suture can include a third suture limb and the second suture can include a fourth suture limb. In such embodiments, which also include the first and second suture anchors, the method can further include passing the third suture limb over the scaffold and coupling it to the second suture anchor, and passing the fourth suture limb over the scaffold and coupling it to the first suture anchor. Further, a first medial anchor to which the first suture is coupled and a second medial anchor to which the second suture is coupled can be installed such that the first and third suture limbs extend from the first medial anchor and the second and fourth suture limbs extend from the second medial anchor.

In other embodiments that include the third and fourth suture limbs, the method can include threading the third suture limb from the first end of the scaffold to the second, opposite end of the scaffold and coupling the third suture limb to the second suture anchor. Similarly, the fourth suture limb can be threaded from the first end of the scaffold to the second, opposite end of the scaffold and coupled to the first suture anchor. The resulting configuration can be a crossed configuration between the third and fourth suture limbs. Further, a first medial anchor to which the first suture is coupled and a second medial anchor to which the second suture is coupled can be installed such that the first and third suture limbs extend from the first medial anchor and the second and fourth suture limbs extend from the second medial anchor.

Carrying forward with some embodiments having four suture limbs, threading the first suture limb from the first end of the scaffold to the second, opposite end of the scaffold can include coupling the first suture limb to a threader disposed in the scaffold and applying a force to the threader to dispose the scaffold onto the first suture limb. Similarly, threading each of the second, third, and fourth suture limbs from the first end of the scaffold to the second, opposite end of the scaffold can include coupling the second, third, and fourth suture limbs to respective threaders disposed in the scaffold and applying a force to each of the threader to dispose the scaffold onto each of the second, third, and fourth suture limbs.

In some embodiments, the first suture limb can be coupled to a first medial location on the scaffold and can include a hollow self-locking mechanism with a first threader disposed in that hollow self-locking mechanism, and the second suture limb can be coupled to a second medial location on the scaffold and can include a hollow self-locking mechanism with a second threader disposed in that hollow self-locking mechanism. In such embodiments the method can include coupling a leading tail of the first suture limb to the soft tissue and subsequently to the first threader, and coupling a leading tail of the second suture limb to the soft tissue and subsequently to the second threader. The first and second threaders can be moved with respect to the hollow self-locking mechanisms of the respective first and second suture limbs to pass the leading tail of the first and second suture limbs through the hollow self-locking mechanisms of that same limb. The step of advancing a first end of the scaffold to a location that is proximate to locations through which the first and second limbs pass through the tissue can include applying a force to the leading tails for the first and second suture limbs after they have passed through the respective hollow self-locking mechanism to advance the first end of the scaffold. Further, the step of coupling the one or more suture tails with at least one suture anchor disposed in the bone to which the soft tissue is being attached can include coupling a first trailing tail of the one or more suture tails to one of a first and second suture anchor of the at least one suture anchor disposed in the bone to which the soft tissue is being attached, and coupling a second trailing tail of the one or more suture tails to the other of the first and second suture anchors of the at least one suture anchor disposed in the bone to which the soft tissue is being attached. In some embodiments, the first trailing tail is part of the first suture and the second trailing tail is part of the second suture. In some other embodiments, the first trailing tail and the second trailing tail are separate sutures than the first and second sutures.

In some other embodiments having four suture limbs, the first suture limb can be coupled to the scaffold at a first medial location on the scaffold and can include a hollow self-locking mechanism with a first threader disposed in that hollow self-locking mechanism, and the second suture limb can be coupled to the scaffold at a second medial location on the scaffold and can include a hollow self-locking mechanism with a second threader disposed in that hollow self-locking mechanism. Further, a third suture limb of a third suture can be coupled to the scaffold proximate to the first medial location on the scaffold and a fourth suture limb of a fourth suture can be coupled to the scaffold proximate to the second medial location on the scaffold. The third and fourth suture limbs can each include a hollow self-locking mechanism having third and fourth threaders disposed in the hollow self-locking mechanisms of the respective third and fourth limbs. In such embodiments the method can include coupling a leading tail of the first suture limb to the soft tissue and subsequently to the first threader, and coupling a leading tail of the second suture limb to the soft tissue and subsequently to the second threader. The first and second threaders can be moved with respect to the hollow self-locking mechanisms of the respective first and second suture limbs to pass the leading tail of the first and second suture limbs through the hollow self-locking mechanisms of that same limb. The step of advancing a first end of the scaffold to a location that is proximate to locations through which the first and second limbs pass through soft tissue can include applying a force to the leading tails for the first and second suture limbs after they have passed through the respective hollow self-locking mechanism to advance the first end of the scaffold. Further, the step of coupling the one or more suture tails with at least one suture anchor disposed in the bone to which the soft tissue is being attached can include coupling the leading tail of the third suture limb to a collapsible loop coupled to a first suture anchor of the at least one suture anchor disposed in the bone to which the soft tissue is being attached and subsequently to the third threader, and coupling the leading tail of the fourth suture limb to a collapsible loop coupled to a second suture anchor of the at least one suture anchor disposed in the bone to which the soft tissue is being attached and subsequently to the fourth threader. The third and fourth threaders can be moved with respect to the hollow self-locking mechanisms of the respective third and fourth suture limbs to pass the leading tail of the third and fourth suture limbs through the hollow self-locking mechanisms of that same limb. A force can be applied to the leading tails of the third and fourth suture limbs after they have passed through the respective hollow self-locking mechanism to advance the second, opposite end of the scaffold towards the bone to which the soft tissue is being attached.

In some embodiments, the scaffold can include at least one of: fabric, plastic, synthetic polymer, natural polymer, collagen, collagen scaffold, reconstituted collagen, a biological autograft, allograft, allogenic, xenogeneic, or xenograft, connective tissue including human dermal matrix, acellular porcine dermal matrix, acellular bovine dermal matrix, periosteal tissue, pericardial tissue, and/or fascia, and combinations thereof. In some embodiments, the scaffold includes collagen. The scaffold can be woven, non-woven, knitted, or manufactured using a variety of techniques known to those skilled in the art or otherwise provided for herein.

In yet another exemplary embodiment, a soft tissue suture repair system includes a suture filament and a tissue augmentation tack. The suture filament includes a collapsible loop defined by a self-locking mechanism configured to adjust a size of the collapsible loop by moving along a length of the suture filament. The suture filament further includes a first tail and a second tail, the first and second tails extending from an opposite side of the self-locking mechanism than the collapsible loop extends from the self-locking mechanism. At least one of the first and second tails is actuable to move the self-locking mechanism along a length of the suture filament to adjust the size of the collapsible loop. The tissue augmentation tack is coupled to the suture filament. The tissue augmentation tack has a diameter that is at least two times greater than a diameter of the suture filament.

The tissue augmentation tack can be coupled at least one of the first and second tails, and it can be disposed on the opposite side of the self-locking mechanism from the collapsible loop. In some embodiments, the system can further include a guide having a lumen extending from a proximal end of the guide to a distal end of the guide. The lumen can be configured to receive an inserter tool for inserting an anchor coupled to the collapsible loop to a surgical site. In some such embodiments, the guide can include a slot formed in an outer surface of the guide, with the slot being configured to receive the suture filament. Further, the slot can extend an entire length of guide, from the proximal end to the distal end.

The system can include an anchor coupled to the collapsible loop. The anchor can have many different configurations. For example, the anchor can be a toggle anchor. In a further example, the anchor can be a soft anchor formed of a flexible construct. The soft anchor can be actuable from an unstressed configuration, in which the soft anchor has a first length and a first diameter, to a stressed configuration, in which the soft anchor has a second length that is less than the first length and a second diameter that is greater than the first diameter. The first tail can be actuable to move the self-locking mechanism along a length of the suture filament to adjust the size of the collapsible loop, and a locking knot can be formed by part of the second tail to fix a location of the tissue augmentation tack with respect to the suture filament. In some embodiments, the diameter of the tissue augmentation tack can be at least three times greater than a diameter of the suture filament.

The tissue augmentation tack can include one or more materials, including at least one of: fabric, plastic, synthetic polymer, natural polymer, collagen, collagen scaffold, reconstituted collagen, biological autograft connective tissue, biological allograft connective tissue, biological xenograft connective tissue, human dermal matrix, porcine dermal matrix, bovine dermal matrix, periosteal tissue, pericardial tissue, and fascia. In some such embodiments, the tissue augmentation tack includes collagen.

Exemplary methods of soft tissue repair that include using a tissue augmentation tack are also disclosed. In one exemplary embodiment, the surgical method includes inserting an anchor coupled to a collapsible loop of a surgical filament into bone, disposing the collapsible loop through tissue adjacent to the bone, and applying tension to a first tail of the surgical filament to collapse the collapsible loop, thereby drawing a tissue augmentation tack coupled to the surgical filament towards the tissue and bone such that the tissue augmentation tack applies a force to the tissue to draw the tissue towards the bone. The tissue augmentation tack has a diameter that is at least two times greater than a diameter of the suture filament. The method further includes locking a location of the tissue augmentation tack with respect to the bone to set the location of the tissue with respect to the bone.

In some embodiments the method can further include positioning a distal end of a guide adjacent to the tissue. In such embodiments, inserting an anchor coupled to a collapsible loop of a surgical filament into bone can further include passing the anchor through the guide. Further, the method can include advancing a punch through the guide to form a hole in the tissue. In such embodiments, disposing the collapsible loop through tissue adjacent to the bone can further include passing the collapsible loop through the hole in the tissue. Still further, the punch can be advanced through the guide to form a hole in the bone. In such embodiments, inserting an anchor coupled to a collapsible loop of a surgical filament into bone can further include inserting the anchor into the hole in the bone.

In some embodiments, the method can include inserting a portion of the collapsible loop into a slot formed in an outer surface of the guide to assist in managing the suture filament during performance of the method. The slot can extend an entire length of the guide, between its proximal and distal ends. Further, the guide can be removed before applying tension to the first tail of the surgical filament to collapse the collapsible loop.

The surgical method can further include toggling the anchor to set a location of the anchor with respect to the bone. In some embodiments, the anchor can be a soft anchor formed of a flexible construct. In such instances, the method can include actuating the anchor from an unstressed configuration to a stressed configuration to set a location of the anchor with respect to the bone. In some embodiments, the diameter of the tissue augmentation tack can be at least three times greater than a diameter of the suture filament. Further, the tissue augmentation tack can include one or more materials, including at least one of: fabric, plastic, synthetic polymer, natural polymer, collagen, collagen scaffold, reconstituted collagen, biological autograft connective tissue, biological allograft connective tissue, biological xenograft connective tissue, human dermal matrix, porcine dermal matrix, bovine dermal matrix, periosteal tissue, pericardial tissue, and fascia. In some such embodiments, the tack can include collagen.

Unless otherwise specified, the steps of the methods provided for in the present disclosure can be performed in any order.

BRIEF DESCRIPTION OF DRAWINGS

FIG. 21H is a schematic view of an alternative exemplary embodiment of the tissue augmentation construct of FIG. 21A;

FIG. 21I is a schematic view of another alternative exemplary embodiment of the tissue augmentation construct of FIG. 21A;

FIG. 21K is a side view of one exemplary embodiment of a guide for use in conjunction with a tissue augmentation construct, such as the tissue augmentation construct of FIG. 21J;

FIG. 21L is a side view of one exemplary embodiment of a punch for use in conjunction with the guide of FIG. 21K;

FIGS. 21M-21R are schematic sequential views of one exemplary embodiment for installing the suture construct of FIG. 21J using the inserter of FIG. 21J, the guide of FIG. 21K, and the punch of FIG. 21L;

Figure 27A:
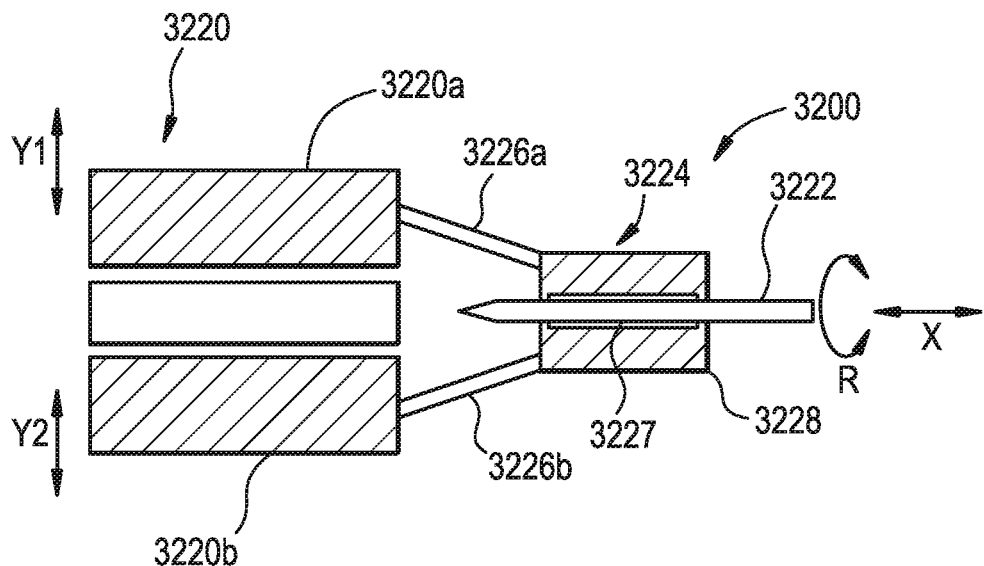
FIG. 27A is a schematic side view of one exemplary embodiment of a tunneling station for use in manufacturing a tissue augmentation construct.
Figure 27B:
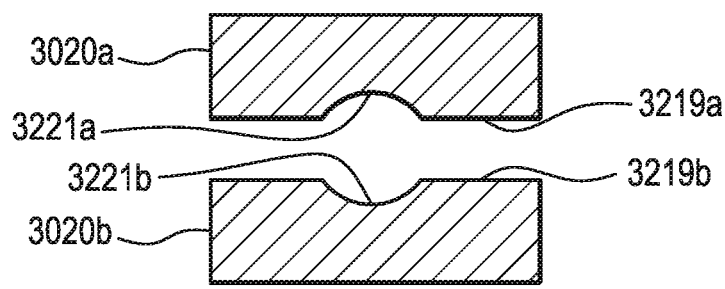
FIGS. 27B and 27C are side schematic views of a support of the tunneling station of FIG. 27A.
Figure 27C:
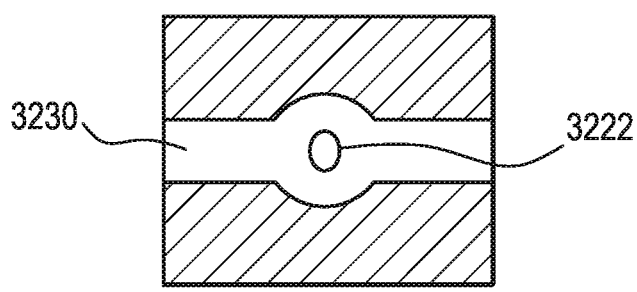
Figure 27D:
Figure 27E:
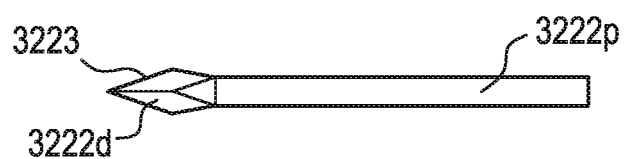
Figure 27F:
Figure 27G:
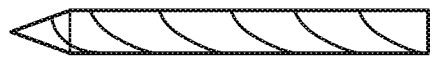
Figure 27H:
Figure 27I:
Figure 27J:
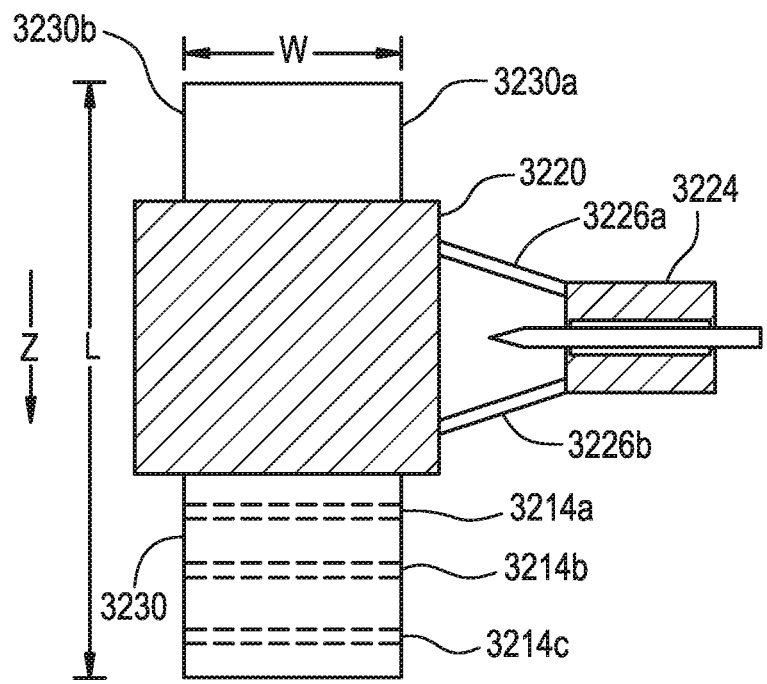
Figure 27K:
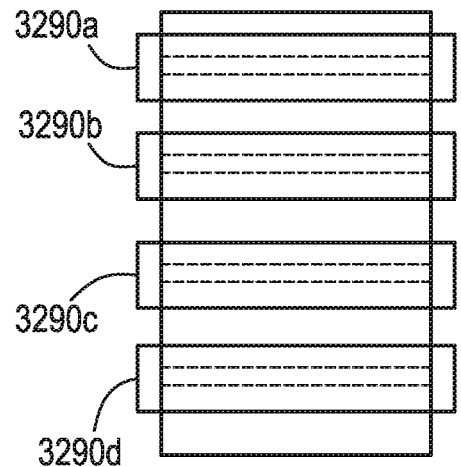
Figure 27L:
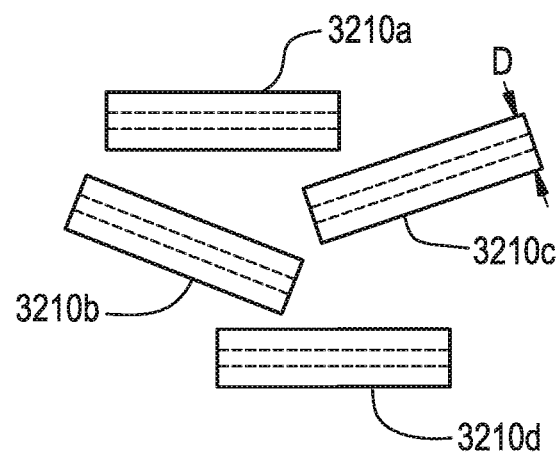
Figure 27M:
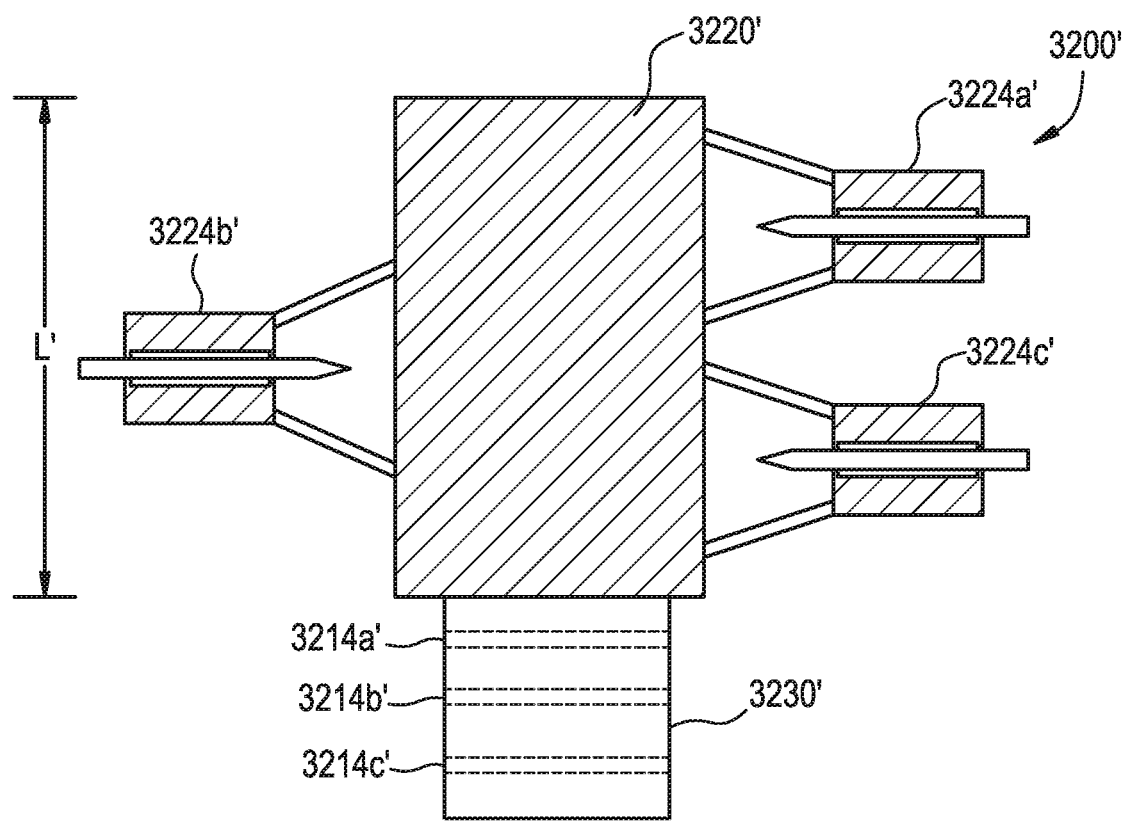
Figure 28:
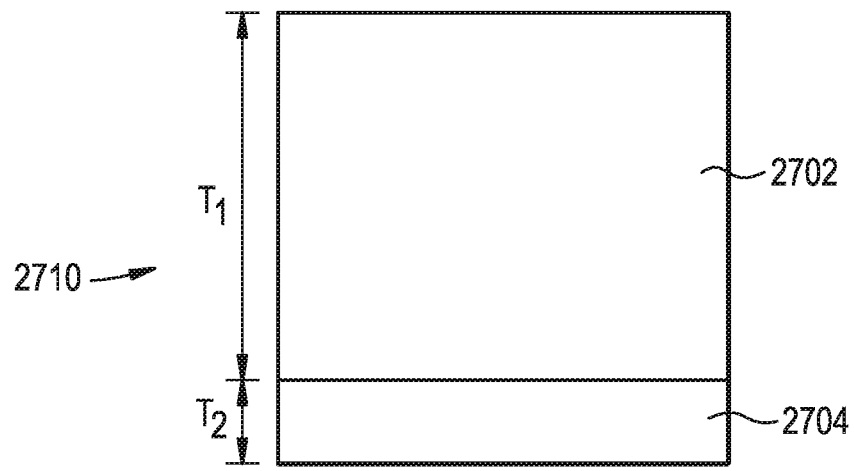
Figure 29A:
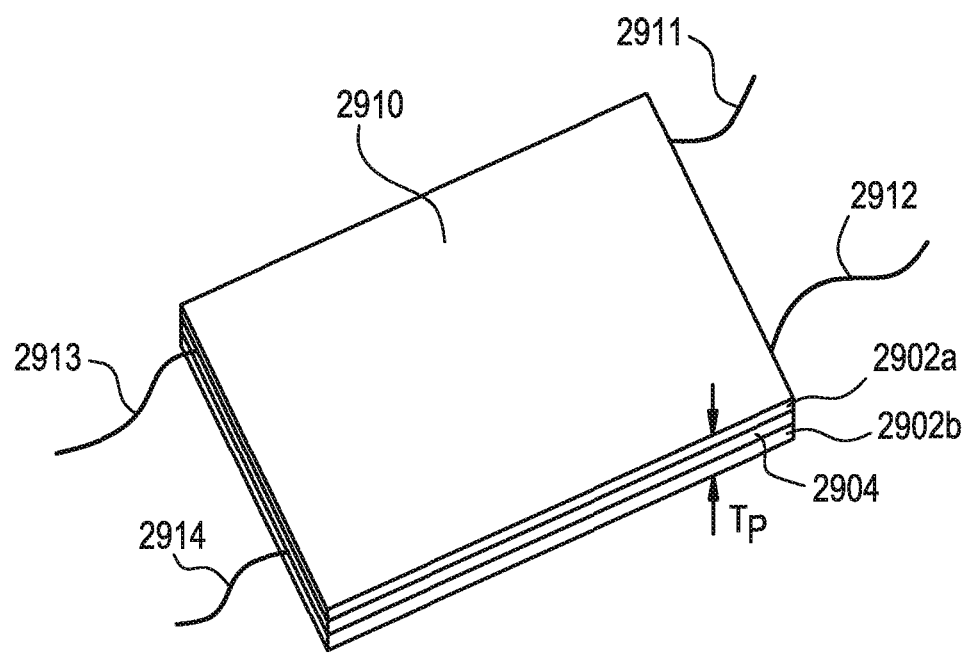
Figure 29B:
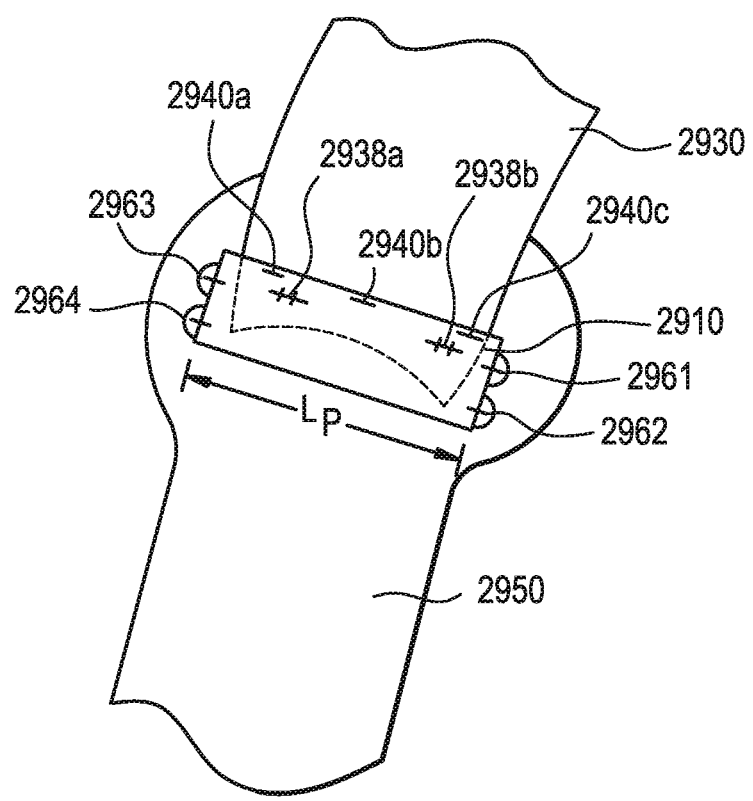
Figure 30A:
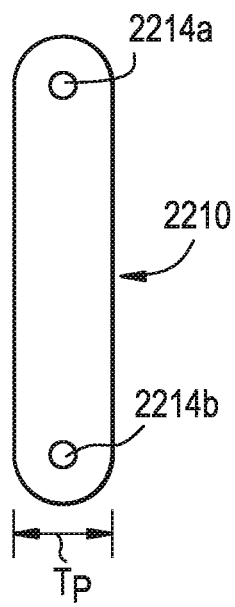
Figure 30B:
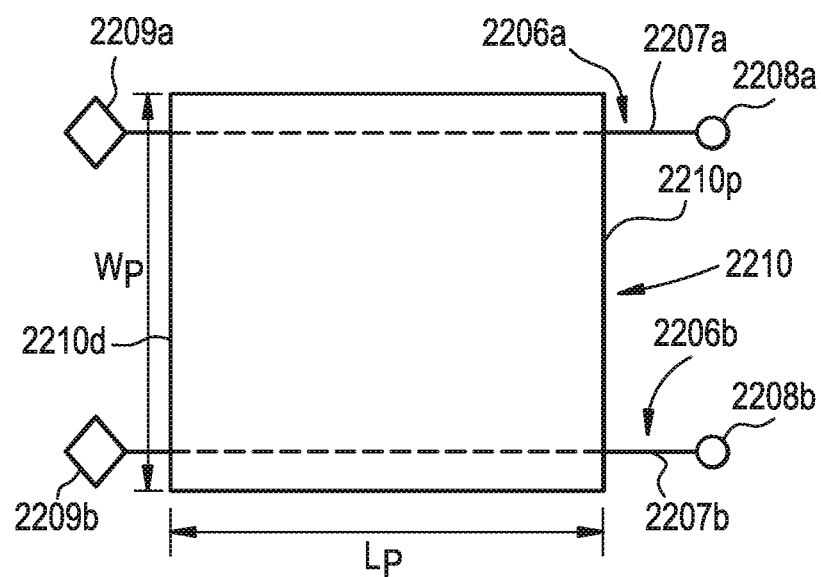
Figure 30C:
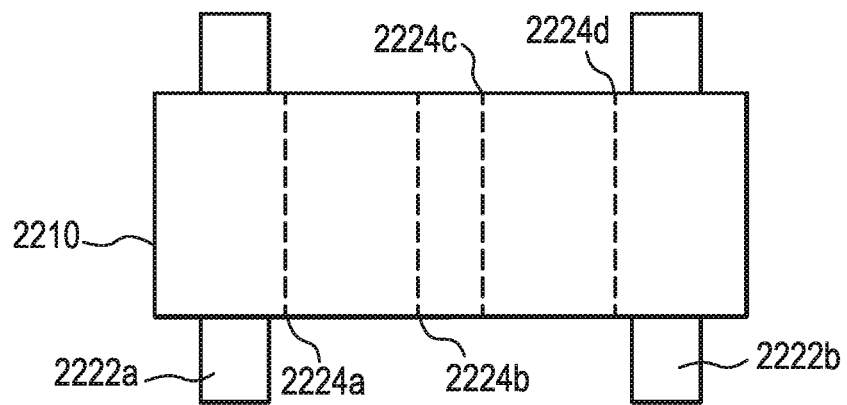
Figure 30D:
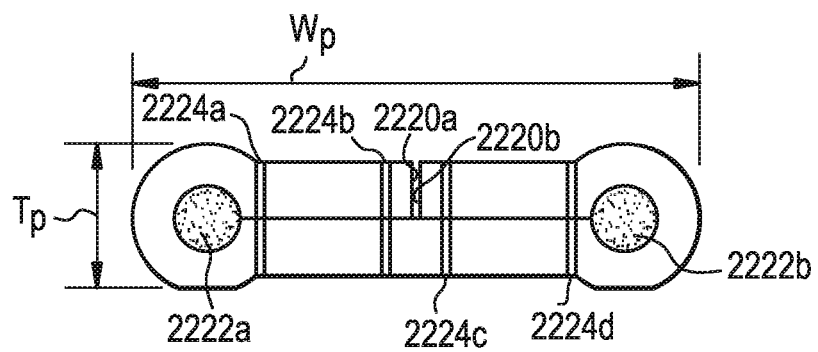
Figure 30E:
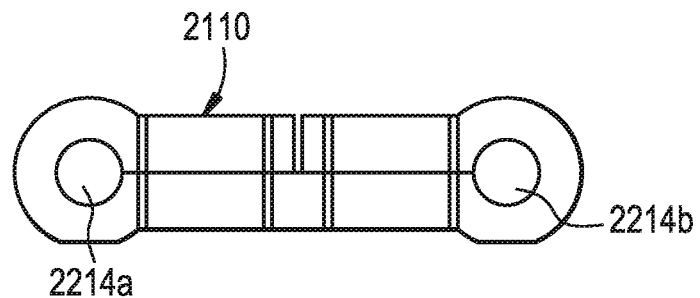
Figure 30F:
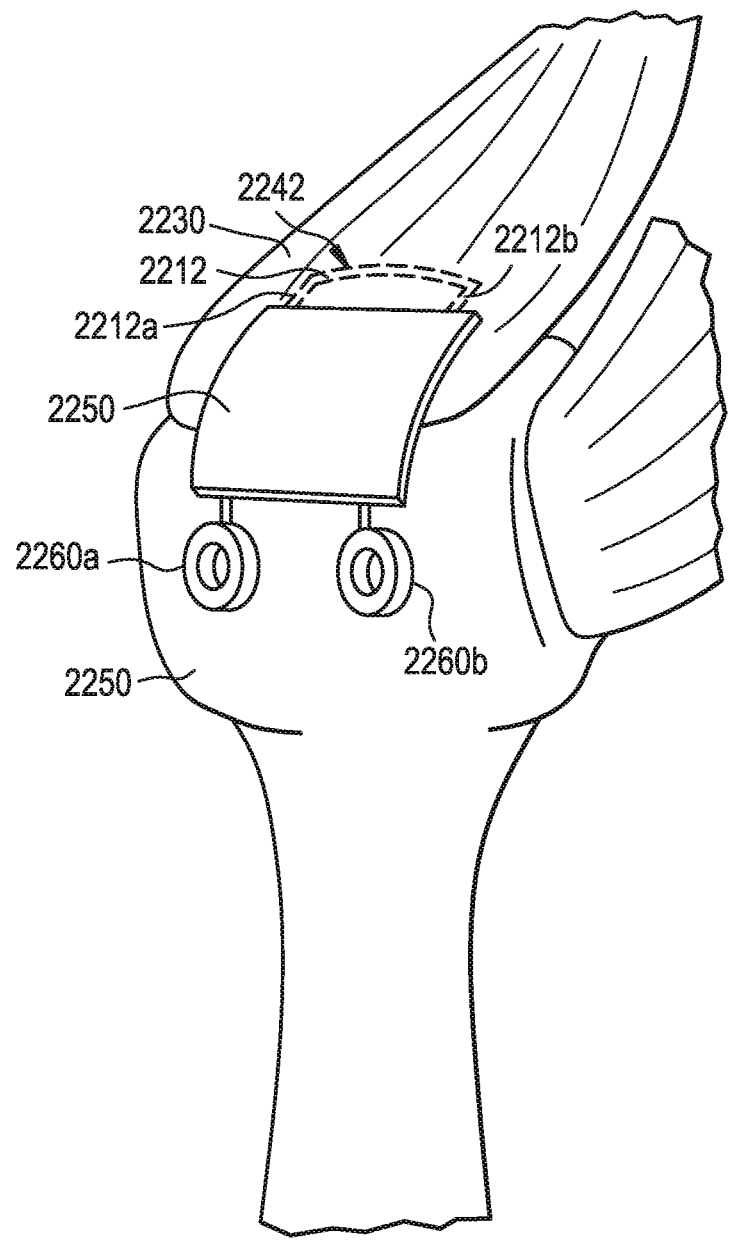
Figure 30G:
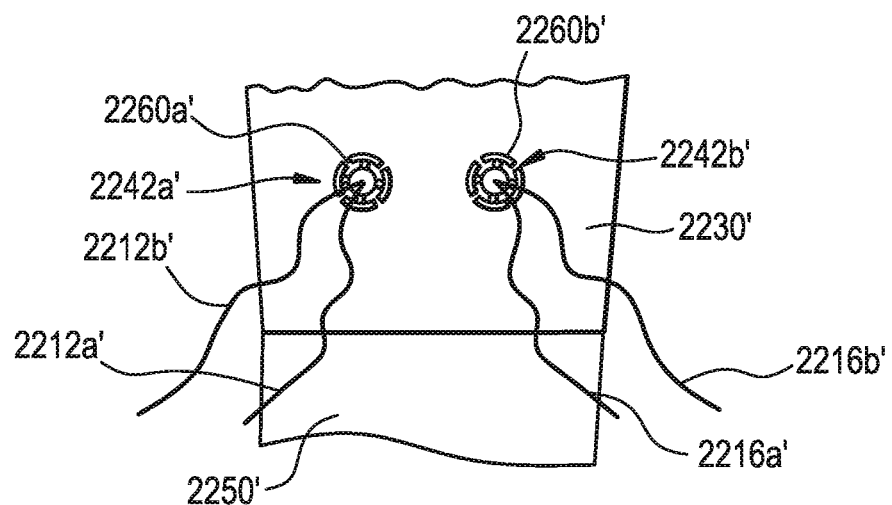
Figure 30H:
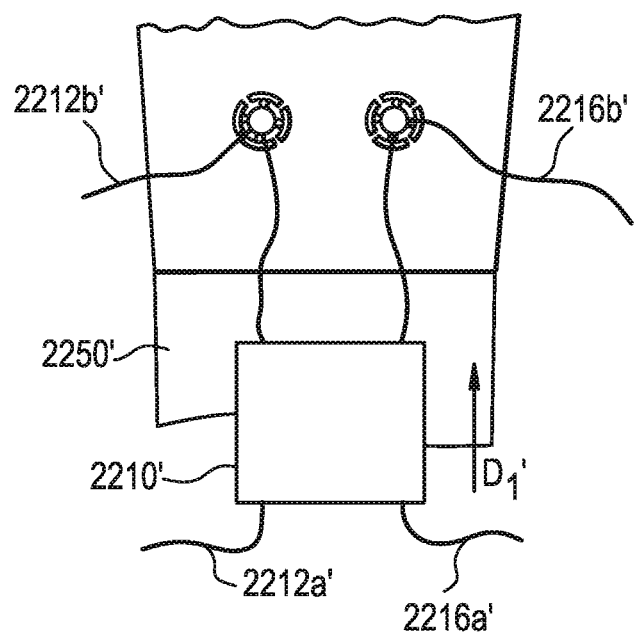
Figure 30I:
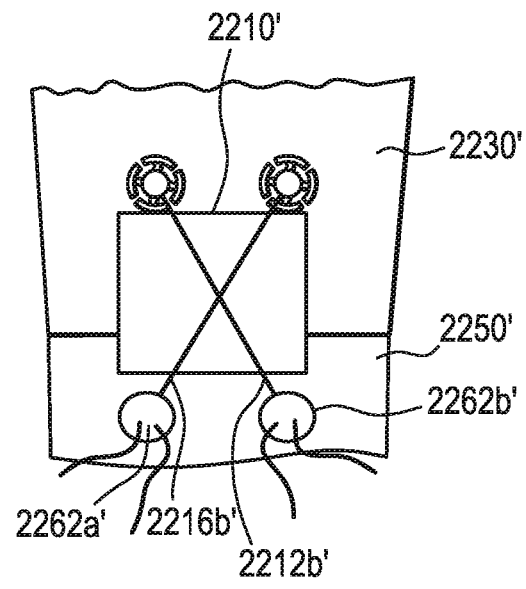
Figure 30J:
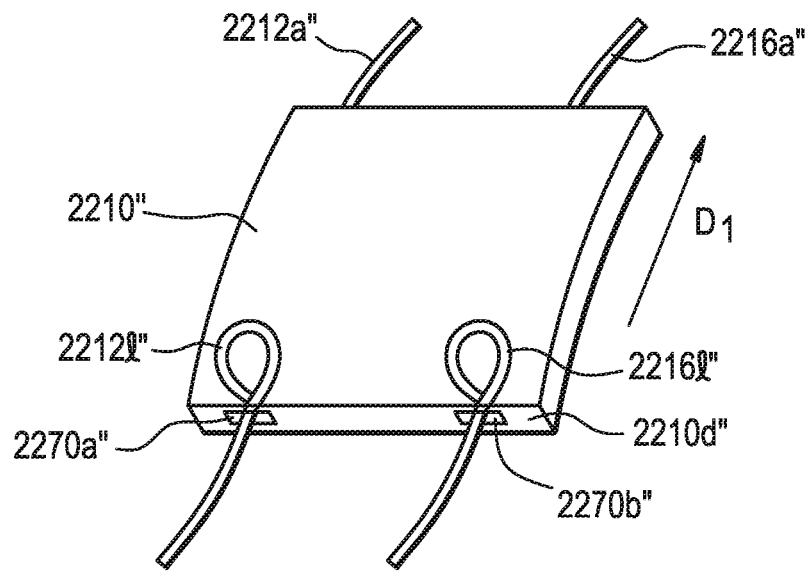
Figure 30K:
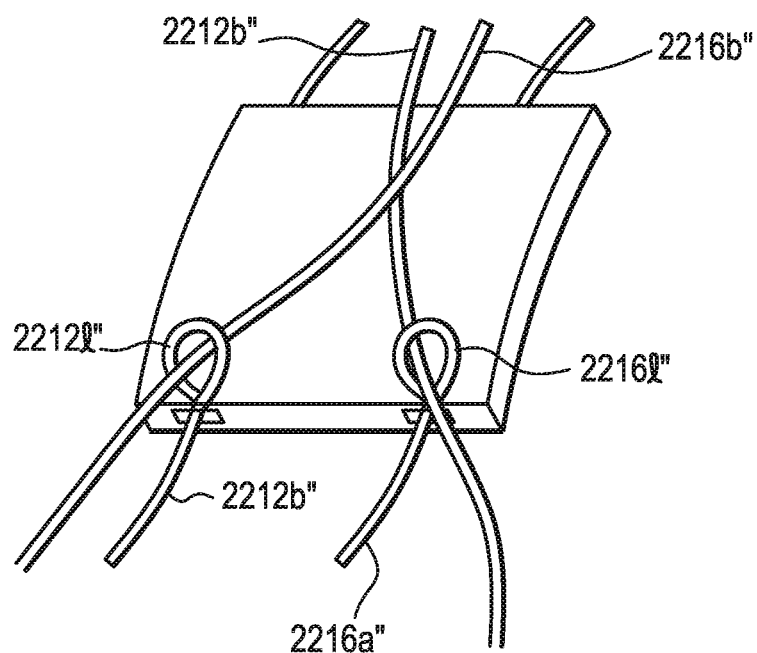
Figure 30L:
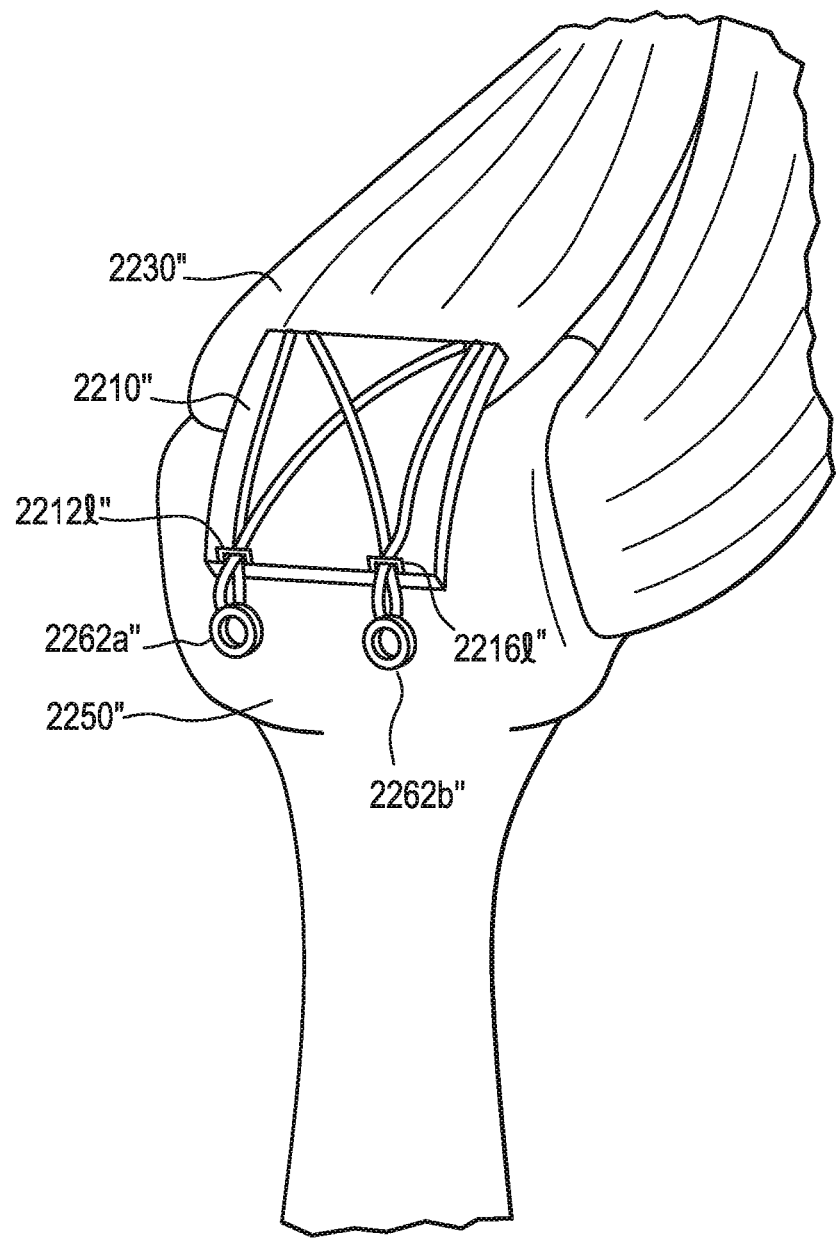
Figure 31B:
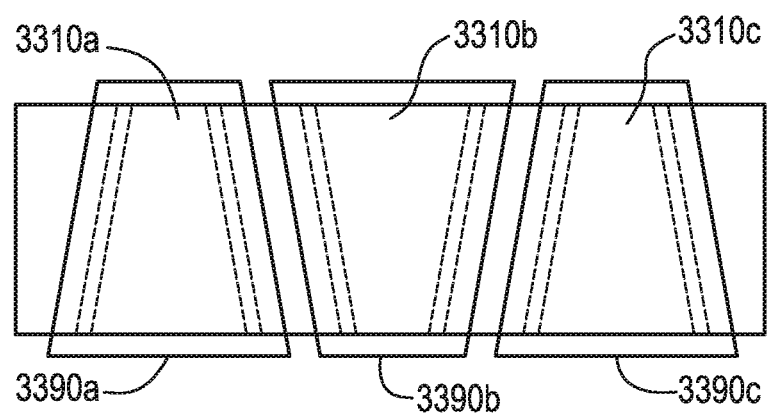
Figure 31C:
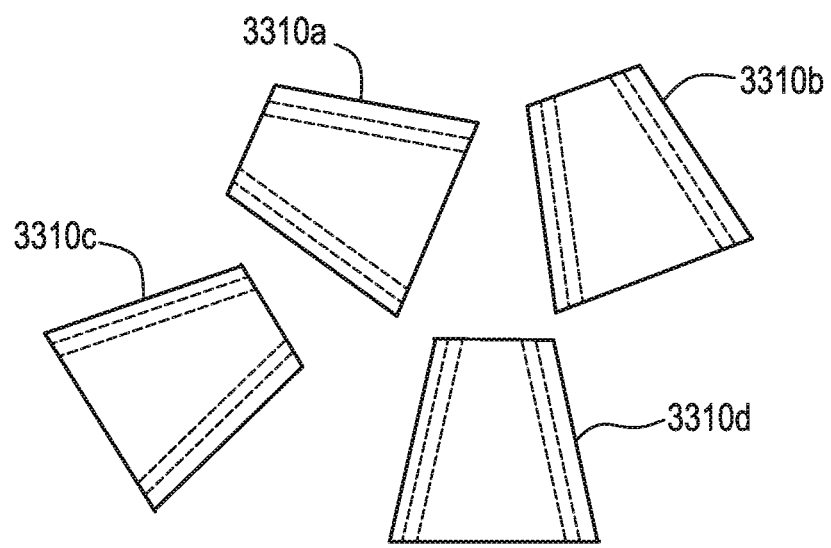
Figure 32A:
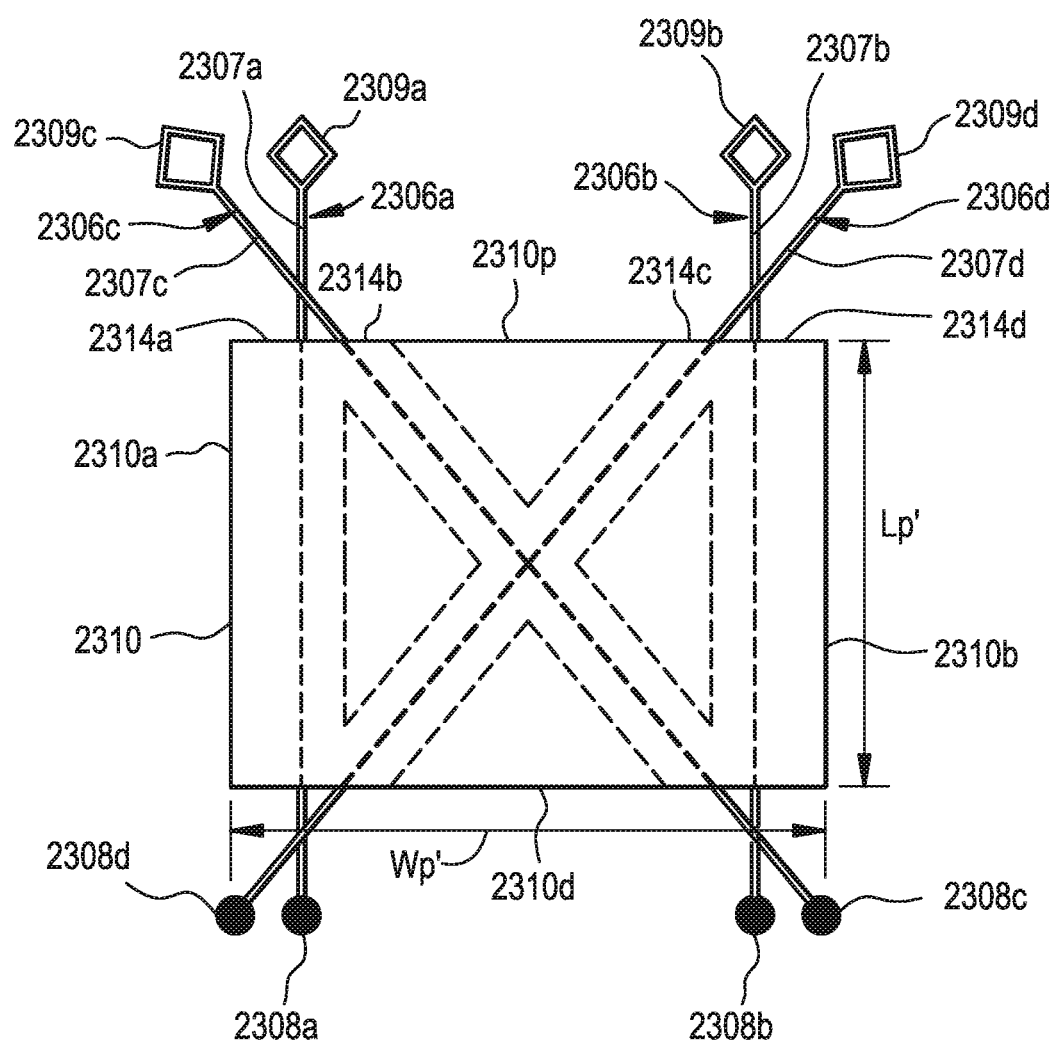
Figure 32B:
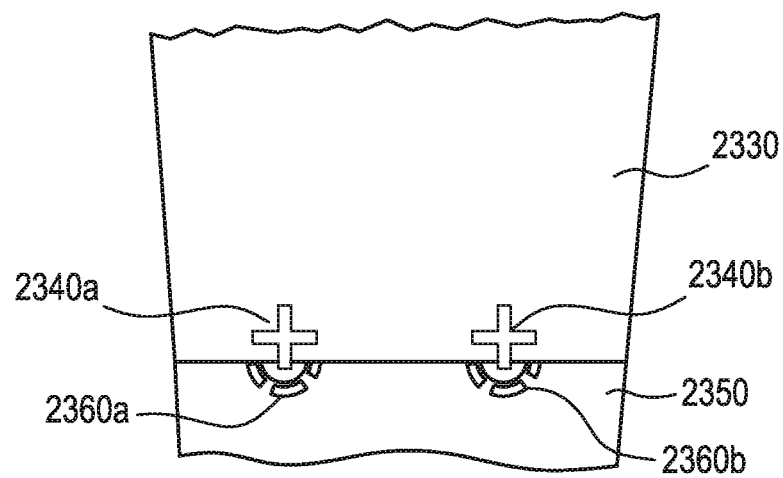
Figure 32C:
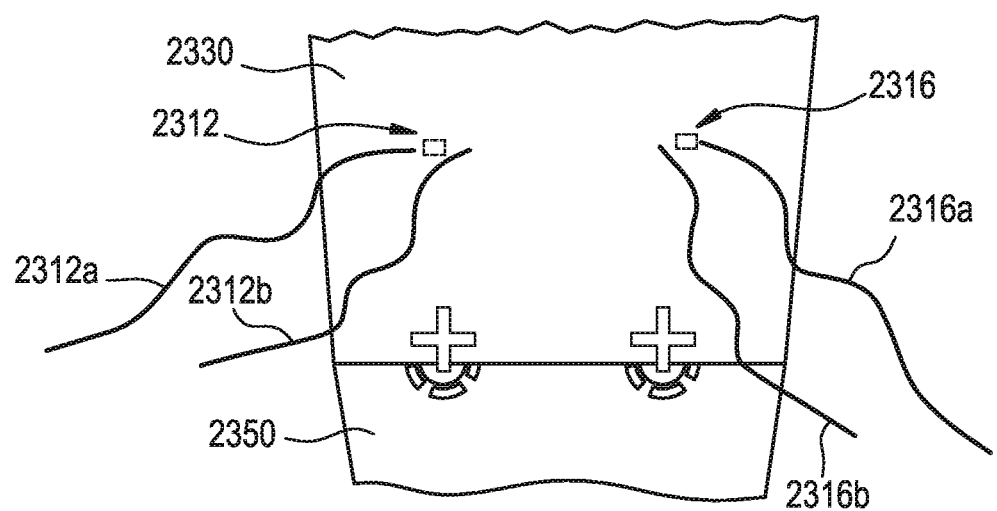
Figure 32D:
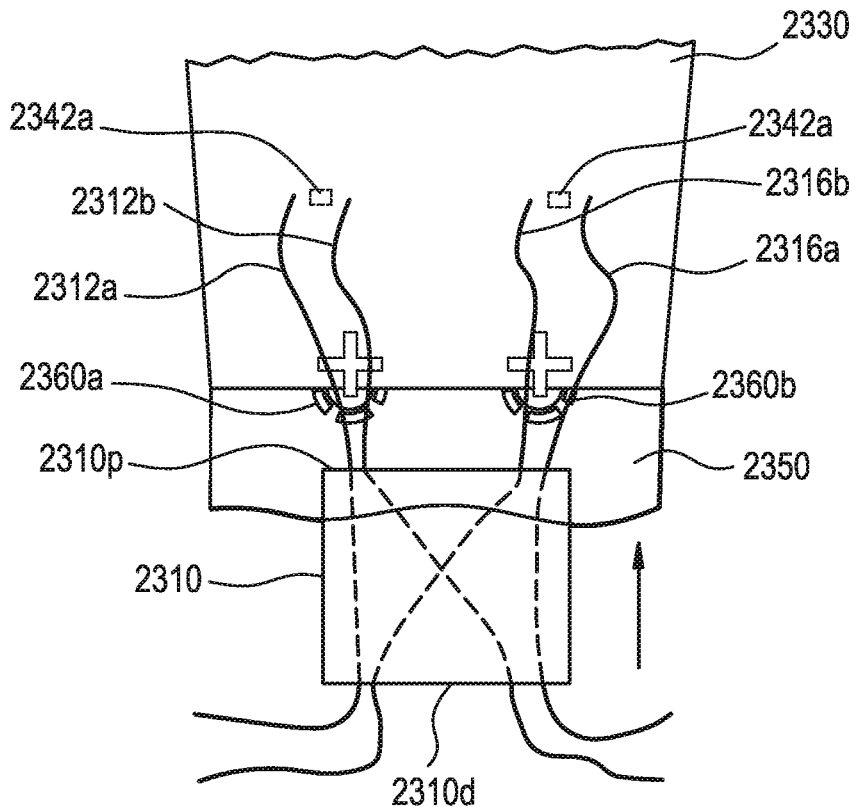
Figure 32E:
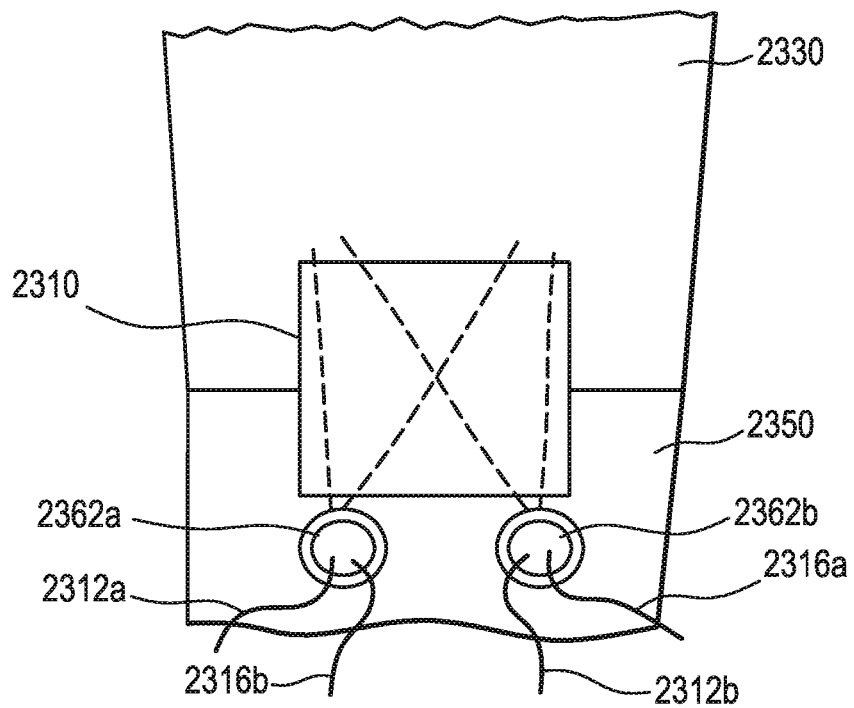
Figure 32F:
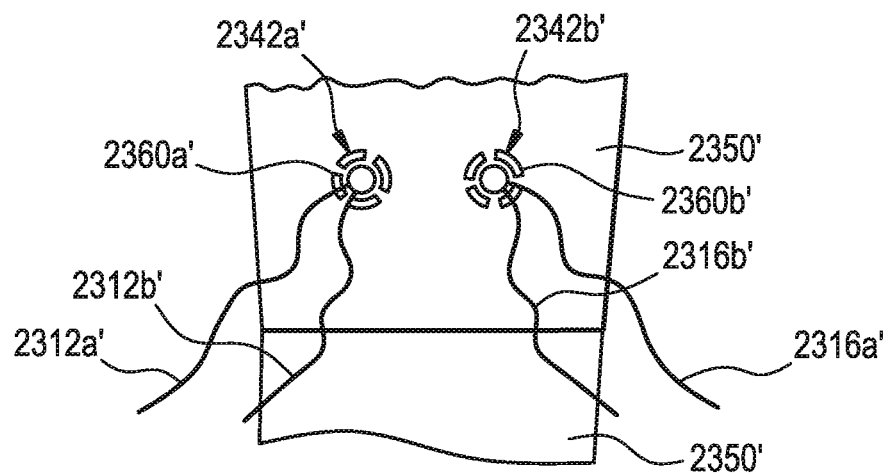
Figure 32G:
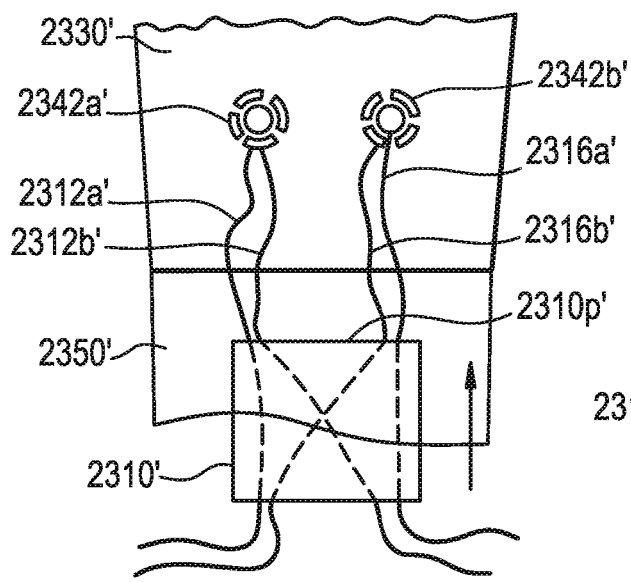
Figure 32H:
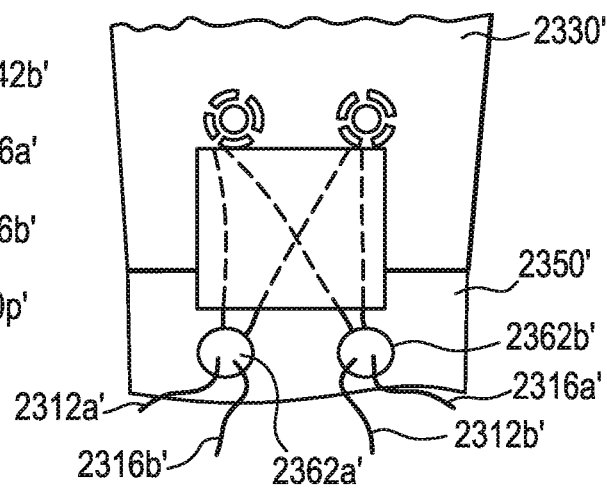
Figure 32I:
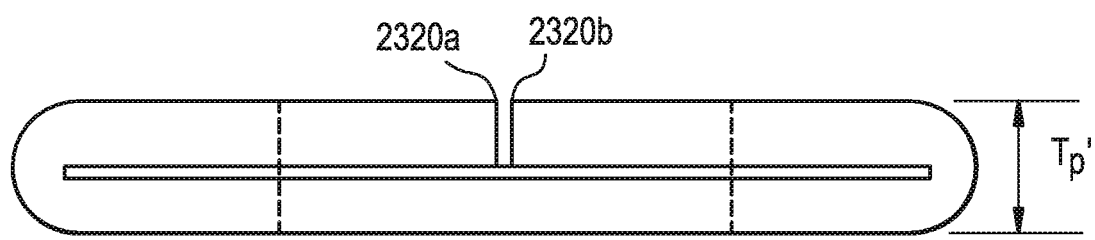
Figure 32J:
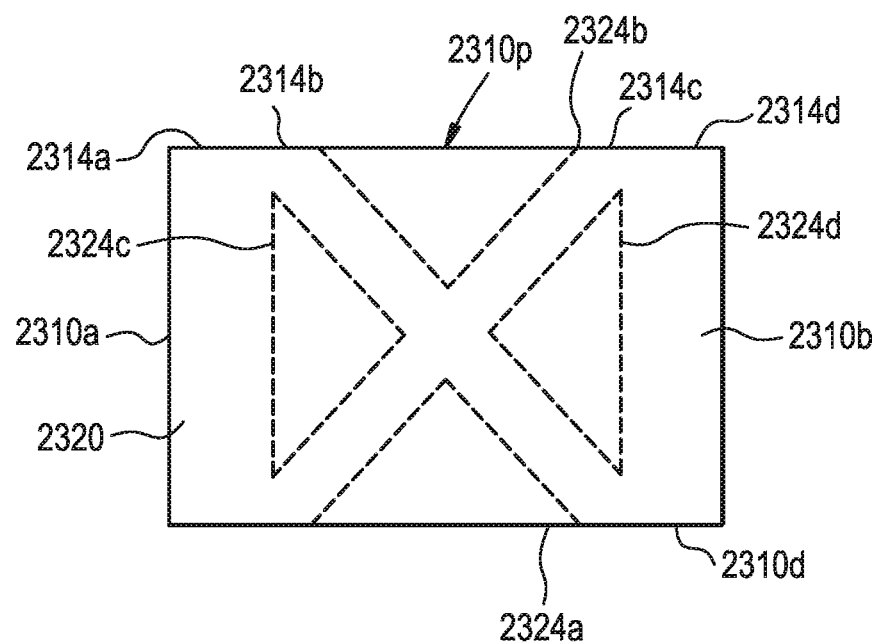
Figure 34A:
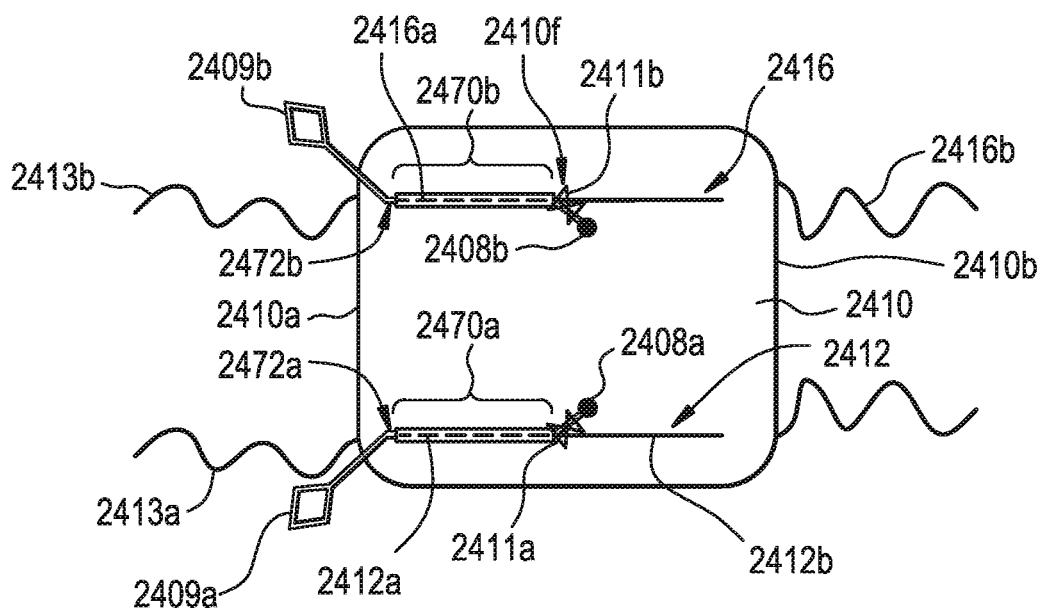
Figure 34B:
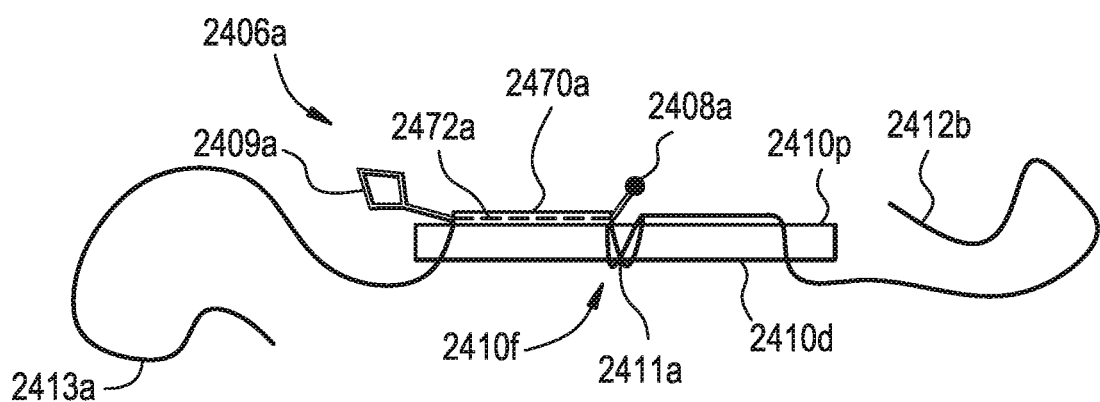
Figure 34C:
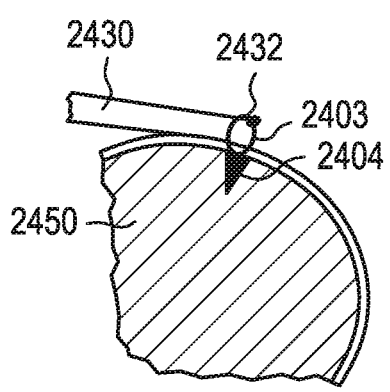
Figure 34D:
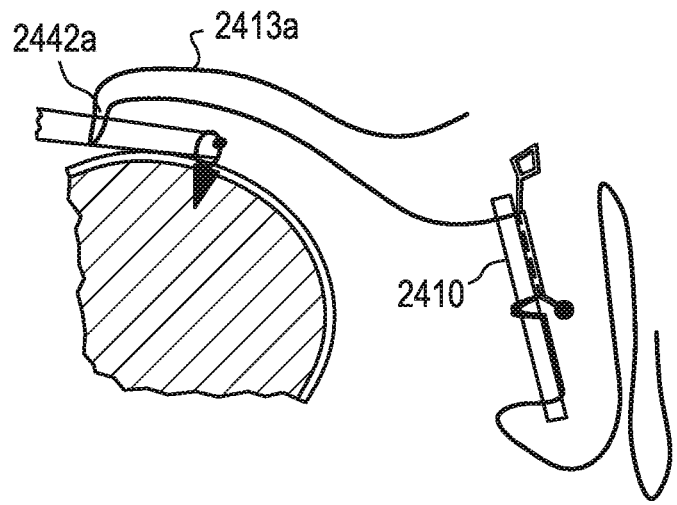
Figure 34E:
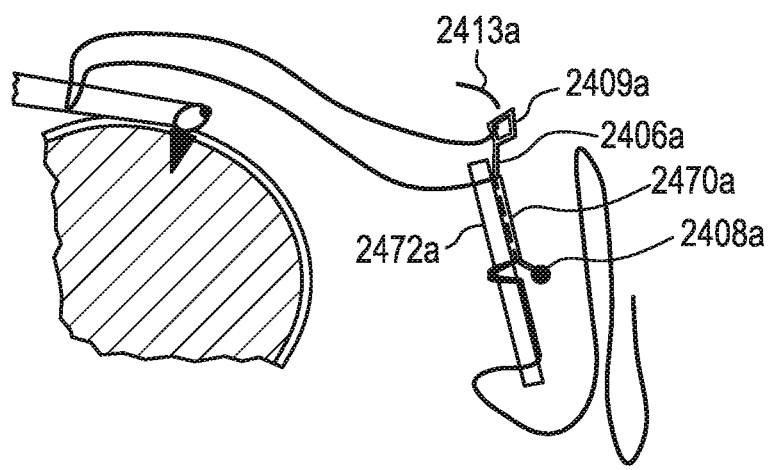
Figure 34F:
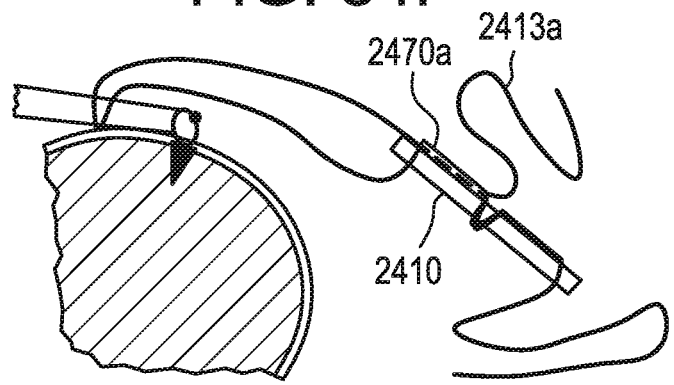
Figure 34G:
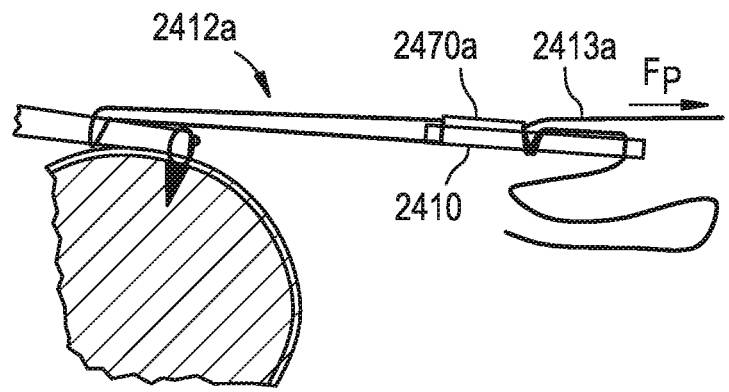
Figure 34H:
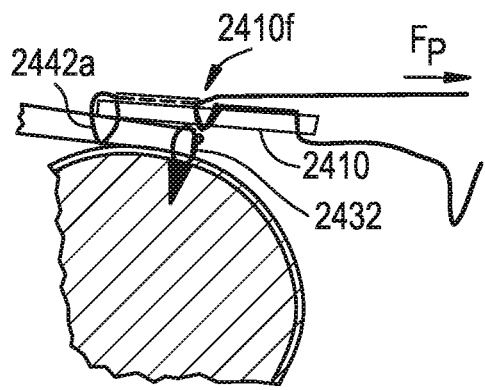
Figure 34I:
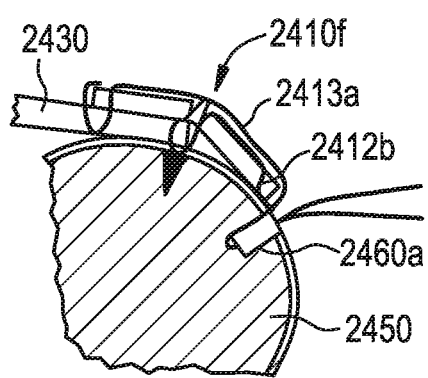
Figure 34J:
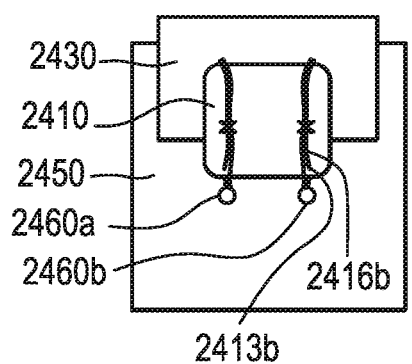
Figure 34K:
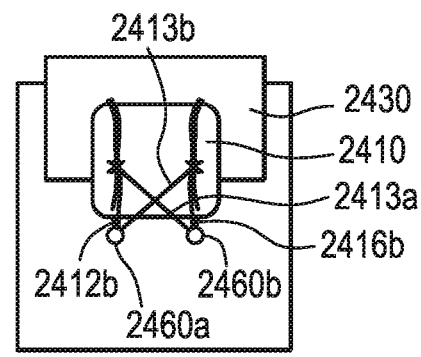
Figure 35A:
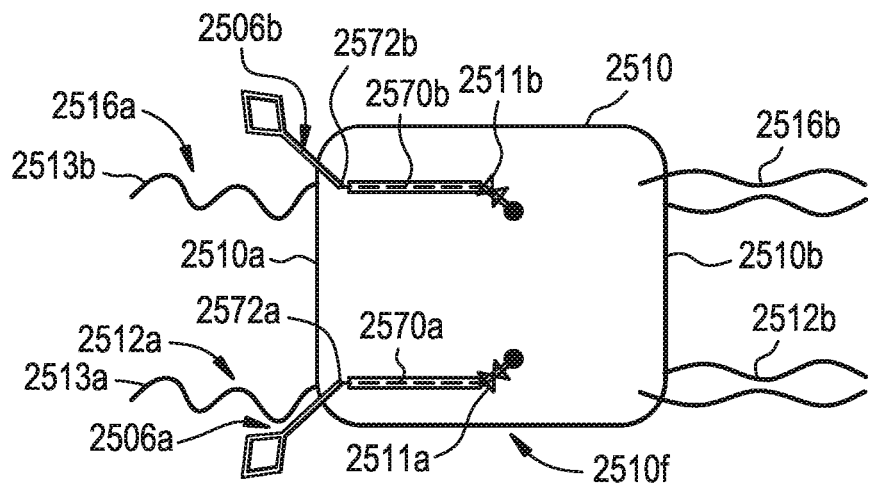
Figure 35B:
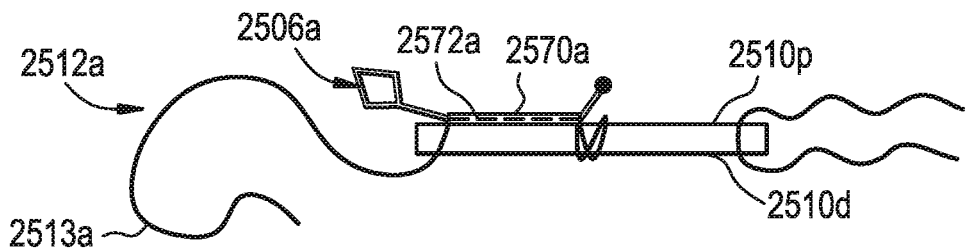
Figure 35C:
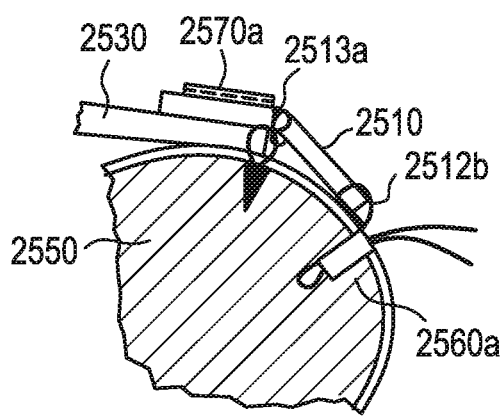
Figure 35D:
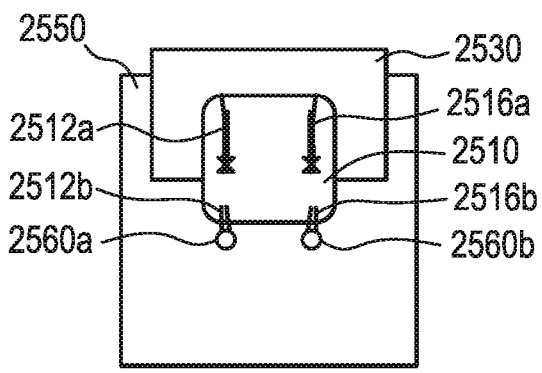
Figure 36A:
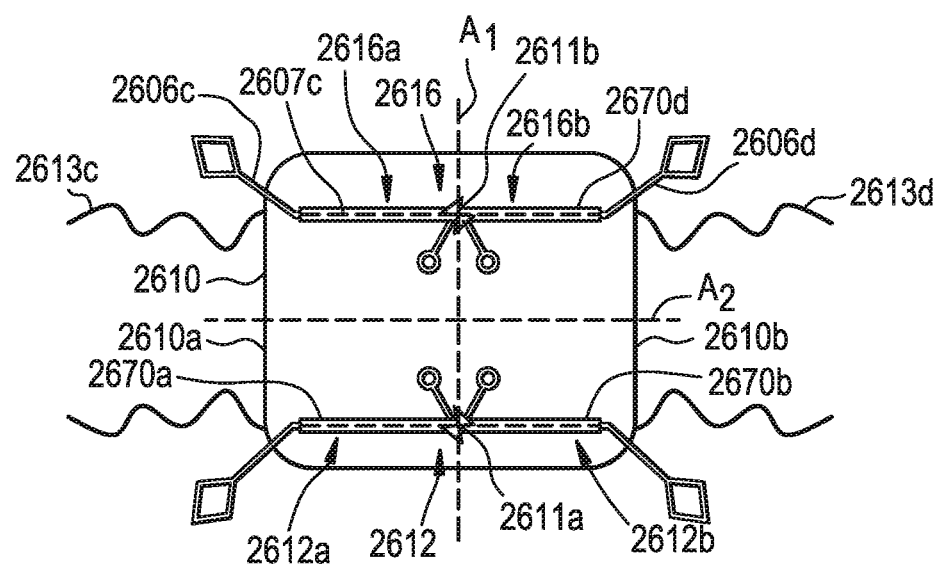
Figure 36B:
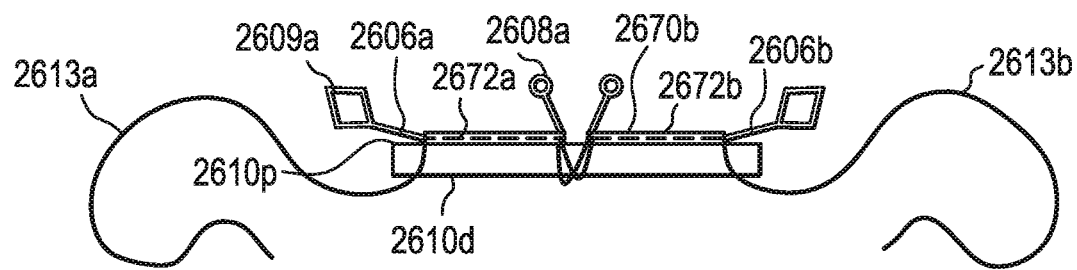
Figure 38A:
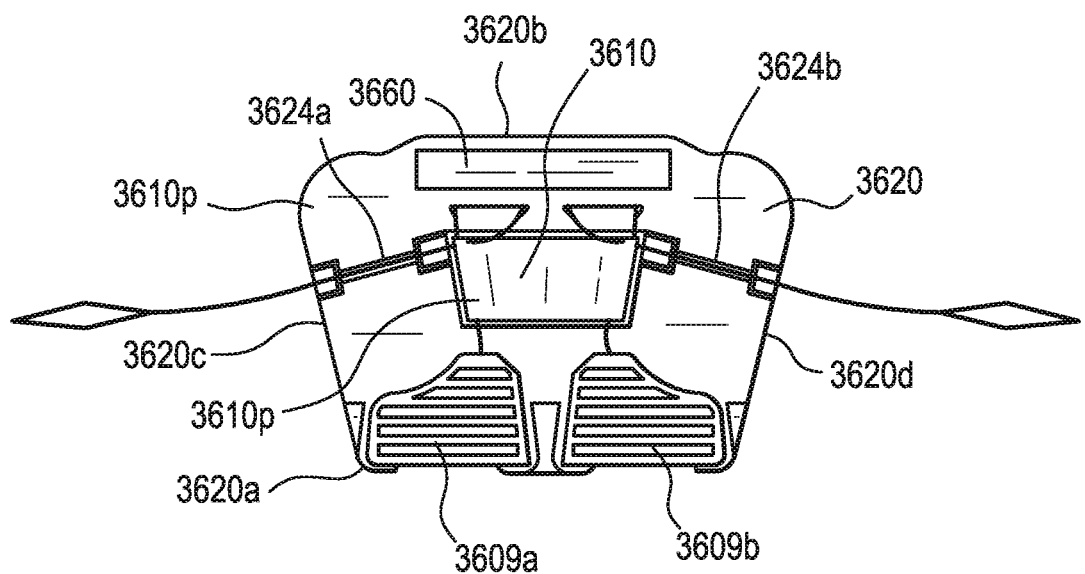
Figure 38B:
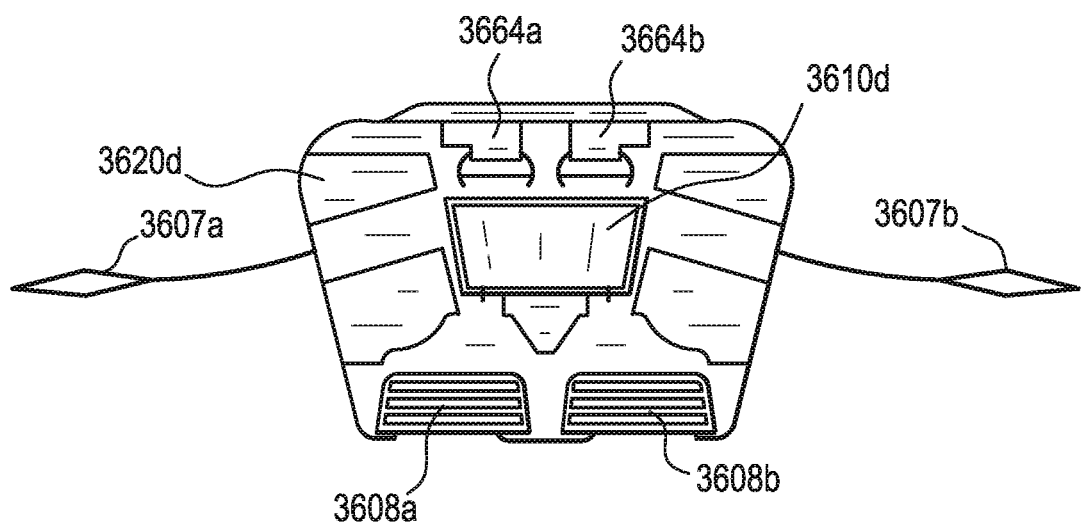
Figure 38C:
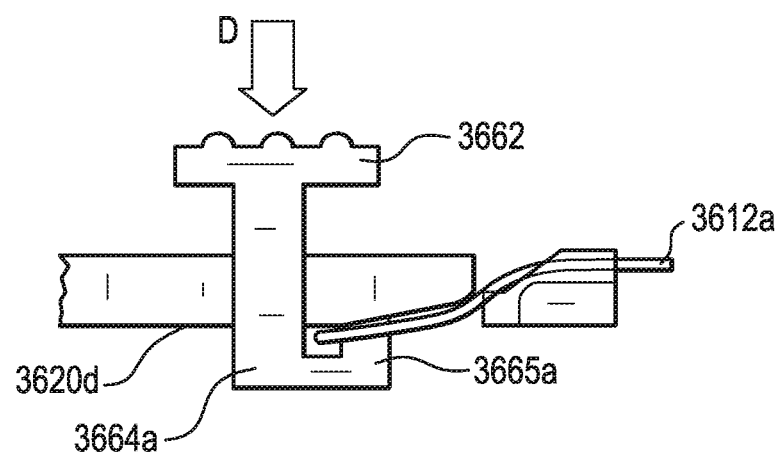
Figure 38D:
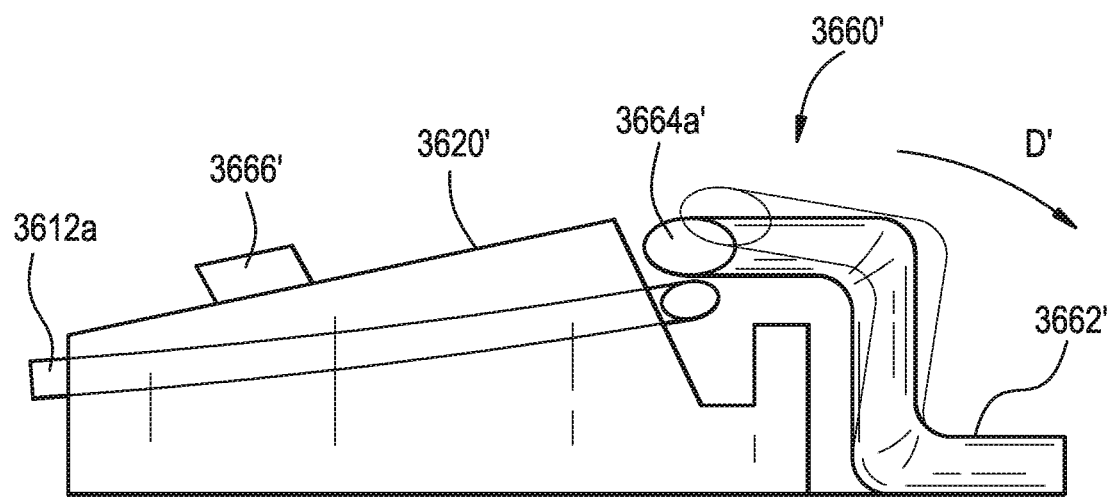
Figure 38E:
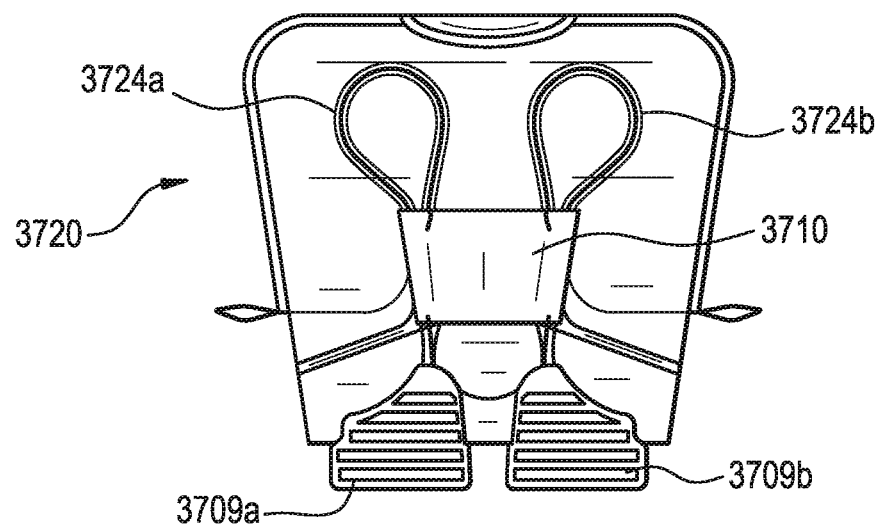
Figure 38F:
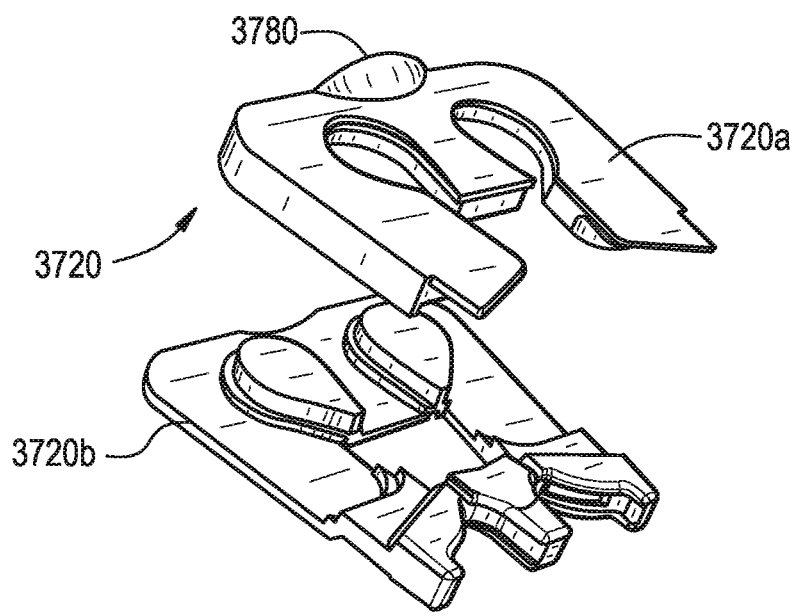
Figure 38G:
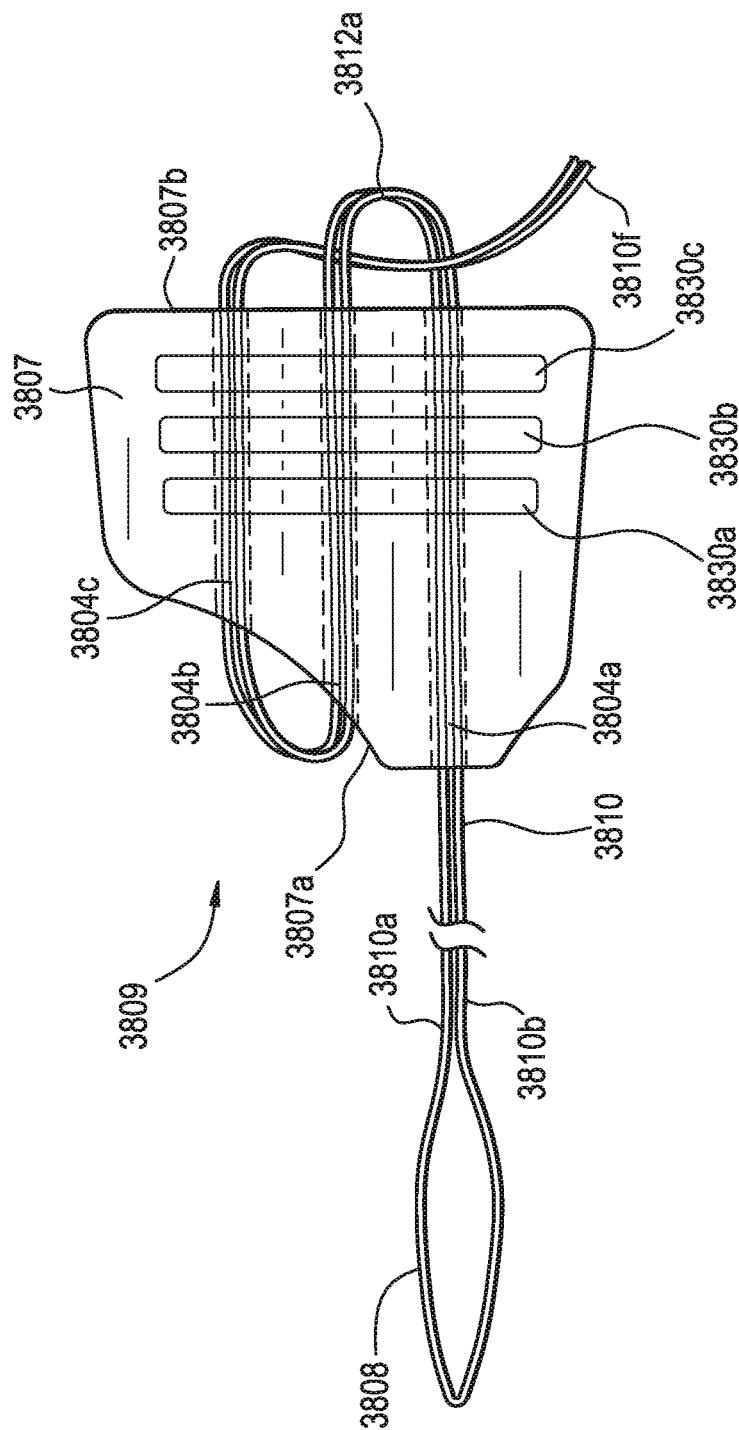
Figure 38H:
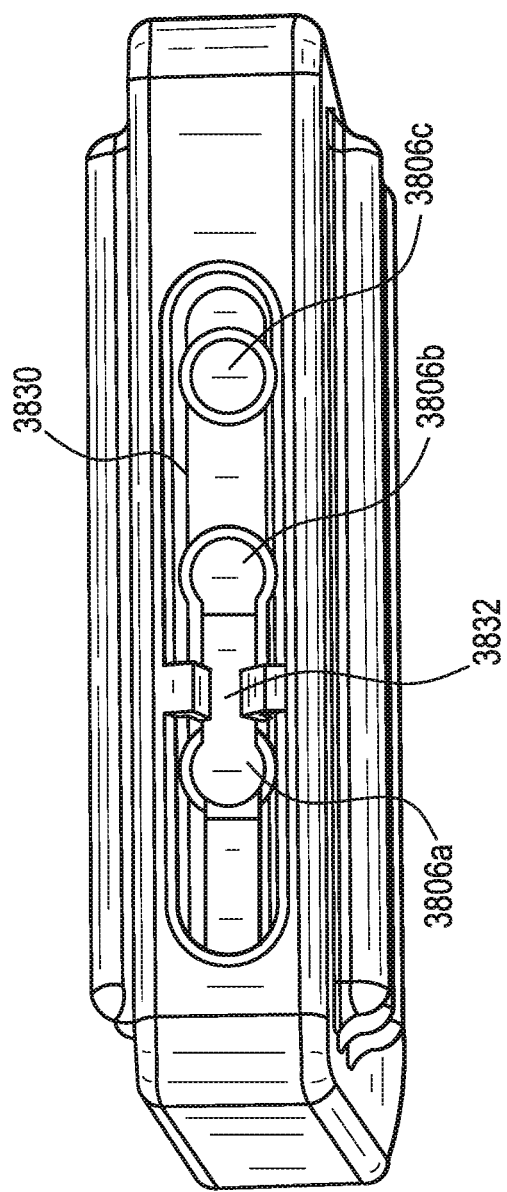
Figure 40:
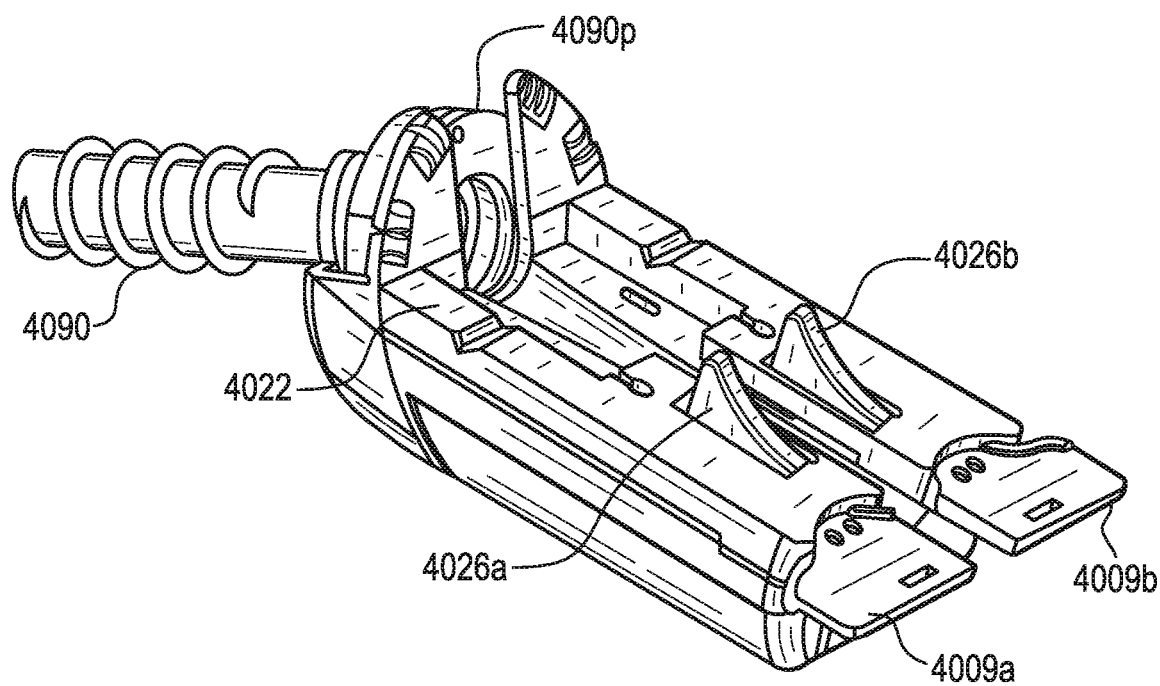
Figure 41A:
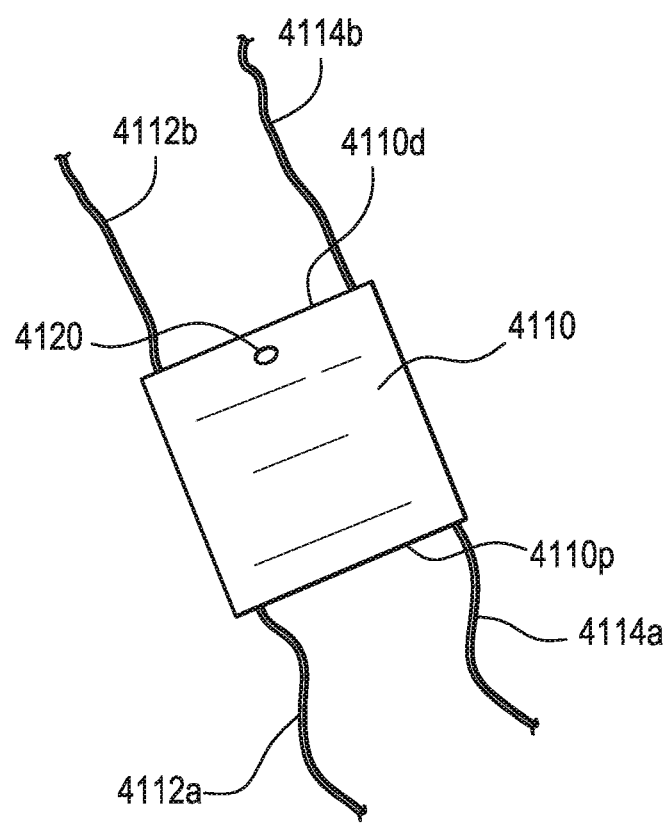
Figure 41E:
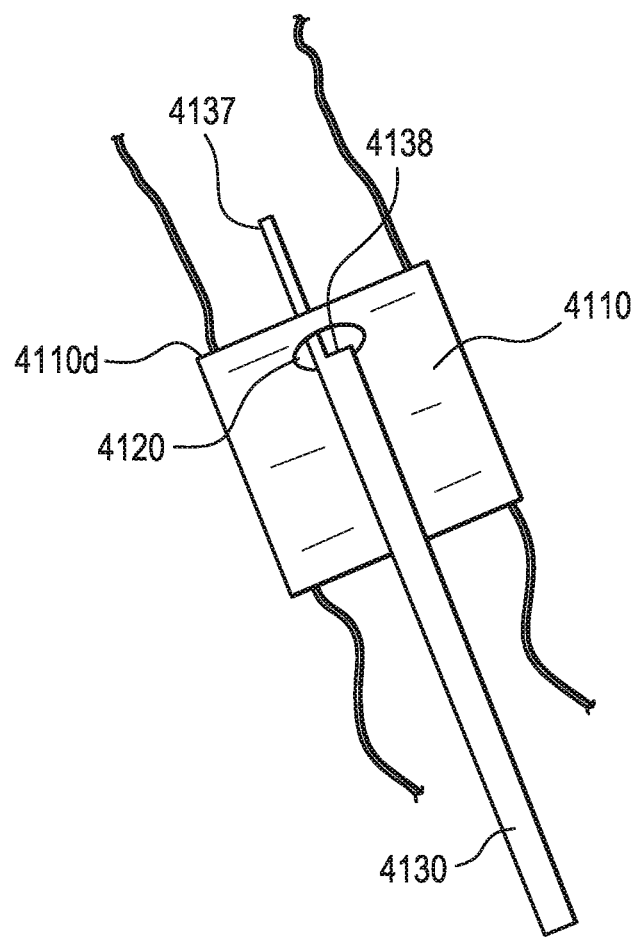
Figure 42A:
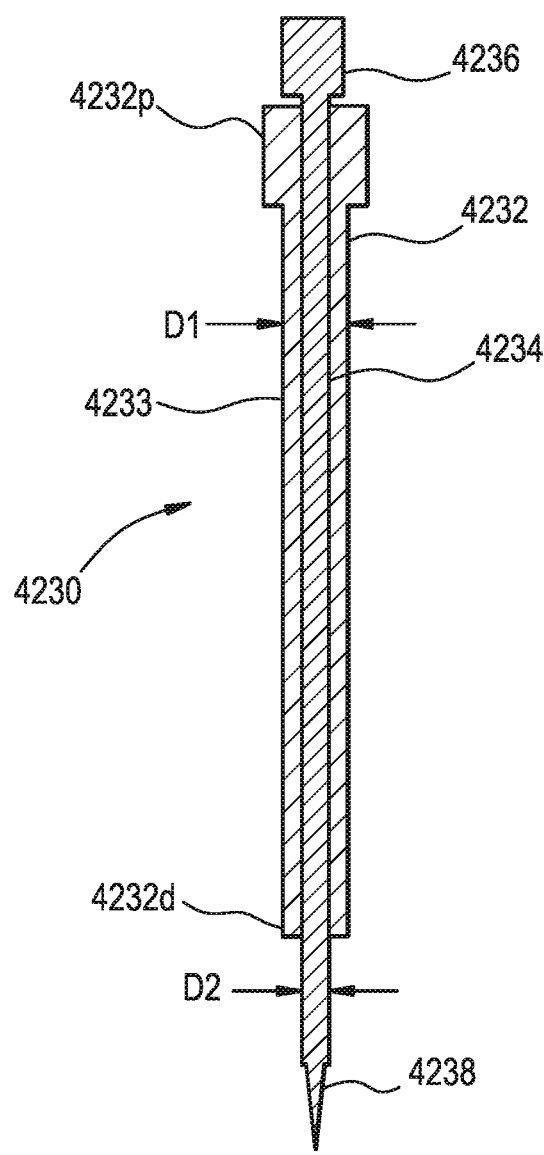
Figure 42B:
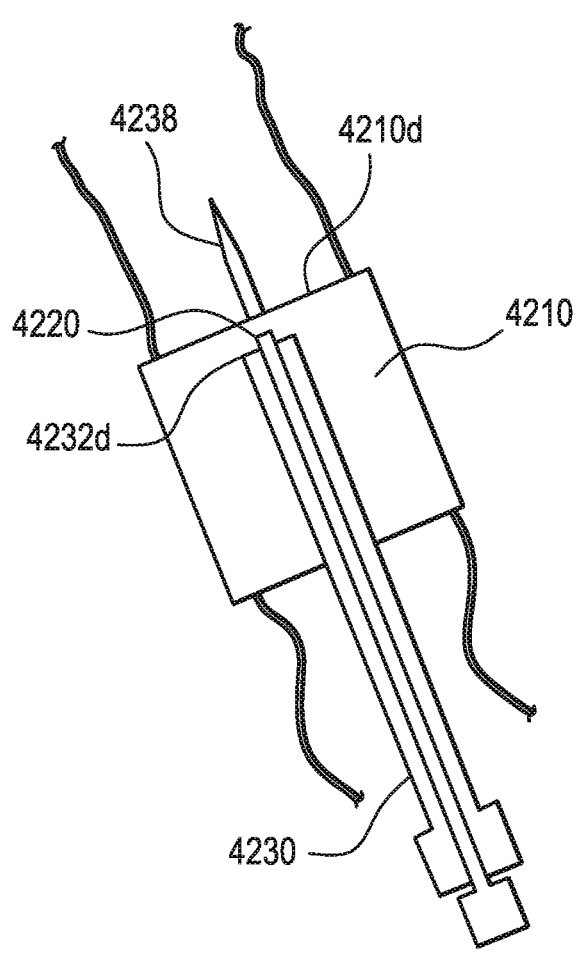
Figure 42C:
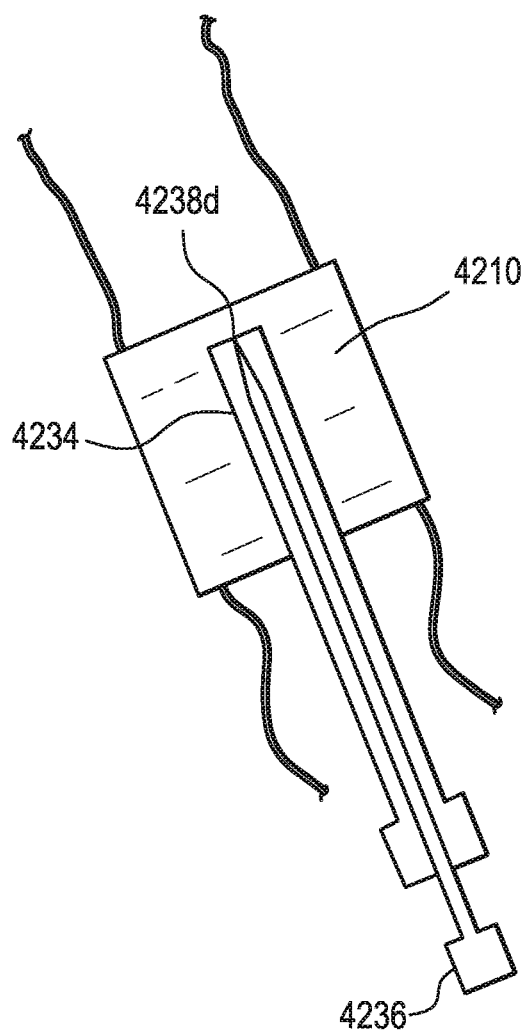
Figure 43:
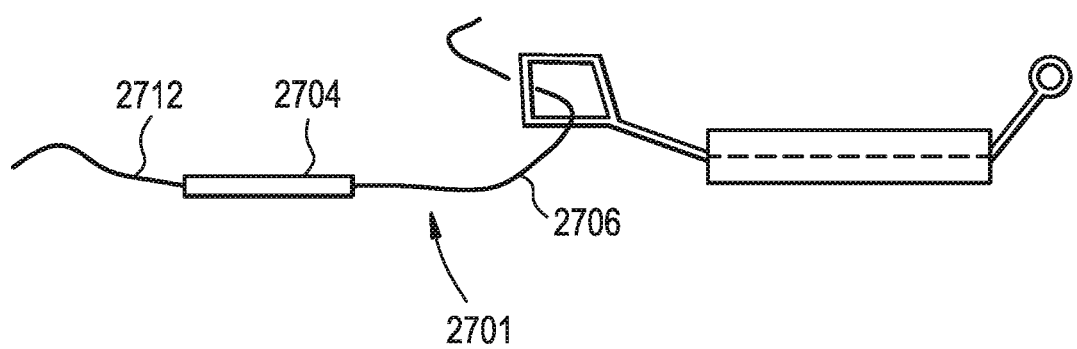

27D-27I are various exemplary embodiments of distal ends of lumen formation tools that can be used in conjunction with the tunneling station of FIG. 27A;

FIGS. 27J-27L are schematic sequential views of one exemplary embodiment for manufacturing a tissue augmentation construct using the tunneling station of FIG. 27A;

FIG. 27M is a schematic side view of another exemplary embodiment of a tunneling station for use in manufacturing a tissue augmentation construct;

FIG. 28 is a side view of one exemplary embodiment of a tissue augmentation construct;

FIG. 29A is a perspective view of another exemplary embodiment of a tissue augmentation construct;

FIG. 29B is a perspective view of the tissue augmentation construct of FIG. 29A installed at a surgical site;

FIG. 30A is a side view of another exemplary embodiment of a tissue augmentation construct;

FIG. 30B is a top view of the tissue augmentation construct of FIG. 30A;

FIGS. 30C-30E are schematic sequential views of an exemplary embodiment for manufacturing the tissue augmentation construct of FIG. 30A;

FIG. 30F is a schematic view of one exemplary embodiment for installing the tissue augmentation construct of FIG. 30A;

FIGS. 30G-30I are schematic sequential views of one exemplary embodiment for installing a tissue augmentation construct similar to that of FIG. 30A;

FIG. 30J is a perspective view of still another exemplary embodiment of a tissue augmentation construct, the tissue augmentation construct having collapsible loops disposed thereon;

FIG. 30K is a perspective view of the tissue augmentation construct of FIG. 30J having suture limbs passed through the collapsible loops;

FIG. 30L is a schematic view of one exemplary embodiment for installing the tissue augmentation construct of FIG. 30J;

FIG. 31A-31C are schematic sequential views of a further exemplary embodiment for manufacturing a tissue augmentation construct;

FIG. 32A is a top view of still another exemplary embodiment of a tissue augmentation construct;

FIGS. 32B-32E are schematic sequential views of one exemplary embodiment for installing the tissue augmentation construct of FIG. 32A;

FIGS. 32F-32H are schematic sequential views of one exemplary embodiment for installing a tissue augmentation construct similar to that of FIG. 32A;

FIGS. 32I-32J are schematic sequential views of one exemplary embodiment for manufacturing the tissue augmentation construct of FIG. 32A;

FIGS. 33A-33E are schematic top views of various exemplary embodiments of tissue augmentation constructs and suture configurations;

FIG. 34A is a top view of another exemplary embodiment of a tissue augmentation construct;

FIG. 34B is a side view of the tissue augmentation construct of FIG. 34A;

FIGS. 34C-34J are schematic sequential views of one exemplary embodiment for installing the tissue augmentation construct of FIG. 34A;

FIG. 34K is a schematic view of another exemplary embodiment for installing the tissue augmentation construct of FIG. 34A;

FIG. 35A is a top view of still another exemplary embodiment of a tissue augmentation construct;

FIG. 35B is a side view of the tissue augmentation construct of FIG. 35A;

FIGS. 35C and 35D are schematic sequential views of one exemplary embodiment for installing the tissue augmentation construct of FIG. 35A;

FIG. 36A is a top view of another exemplary embodiment of a tissue augmentation construct;

FIG. 36B is a side view of the tissue augmentation construct of FIG. 36A;

FIGS. 36C-36I are schematic sequential views of one exemplary embodiment for installing the tissue augmentation construct of FIG. 36A;

FIGS. 37A-37E are schematic sequential views of one exemplary embodiment for installing a tissue augmentation construct;

FIG. 38A is a top view of one exemplary embodiment of a tissue augmentation construct management device;

FIG. 38B is a bottom view of the tissue augmentation construct management device of FIG. 38A;

FIG. 38C is a schematic side view of a release mechanism of the tissue augmentation construct management device of FIG. 38A;

FIG. 38D is a schematic side view of an alternative exemplary release mechanism that can be used in conjunction with a tissue augmentation construct management device like the device of FIG. 38A;

FIG. 38E is a top view of another exemplary embodiment of a tissue augmentation construct management device;

FIG. 38F is a perspective exploded view of the tissue augmentation construct management device of FIG. 38E;

FIG. 38G is a top view of a threader of the tissue augmentation construct management device of FIG. 38A;

FIG. 38H is a rear perspective view of the threader of FIG. 38G;

FIGS. 39A-39F are schematic sequential views illustrating a method for using still another exemplary embodiment of a tissue augmentation construct management device;

FIG. 40 is a perspective view of another exemplary embodiment of a tissue augmentation construct management device;

FIG. 41A is a perspective view of another exemplary embodiment of a tissue augmentation construct;

FIGS. 41B-41D are various exemplary embodiments of distal ends of delivery tools that can be used with the tissue augmentation construct of FIG. 41A;

FIG. 41E is a perspective view of the delivery tool of FIG. 41B being used to deliver the tissue augmentation construct of FIG. 41A;

FIG. 42A is a side cross sectional view of yet another exemplary embodiment of a delivery tool for delivering a tissue augmentation construct;

FIGS. 42B and 42C are schematic sequential views of the delivery tool of FIG. 42A being used to deliver a tissue augmentation construct; and FIG. 43 is a schematic view of one exemplary embodiment of a suture leader.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure. Further, in the present disclosure, like-numbered components of the embodiments generally have similar features. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

The figures provided herein are not necessarily to scale. Still further, to the extent arrows are used to describe a direction of movement, these arrows are illustrative and in no way limit the direction the respective component can or should be moved. A person skilled in the art will recognize other ways and directions for creating the desired result in view of the present disclosure. Additionally, a number of terms may be used throughout the disclosure interchangeably but will be understood by a person skilled in the art. By way of non-limiting example, the terms suture, filament, and flexible members may be used interchangeably, and includes other similarly purposed materials, such as suture tape. Further, to the extent the term "block" is used to describe some of the constructs and matrices provided for herein, the constructs and matrices are not limited to a square or a rectangle, or any shape having flat surfaces for that matter. Still further, to the extent the term "thread" is used to describe associating one component with another, the term is not limited to mean actually passing filament through another material. It can also include passing it through an opening (e.g., an opening formed in a body, as described below at least with respect to some tissue augmentation blocks), and thus can more generally mean associating one component with another.

Systems, devices, and methods for soft tissue repair are generally provided, with such systems or devices including but not being limited to: one or more surgical repair filaments and/or flexible members; one or more tissue augmentation constructs or matrices, which include strips, tubes, bars, tacks, washers, and/or patches, each of which is described in greater detail below; and one or more suture implants or similarly configured or purposed devices. The terms "tissue augmentation construct" and "tissue augmentation matrix" may also be interchangeably used with the terms "suture augmentation construct" and "suture augmentation matrix," as well as more generally with the terms "augmentation construct" and "augmentation matrix," and the terms "construct" and "matrix." As described herein, the term "construct" refers to any implant associated with suture limbs to expand the footprint of the limb, the term "block" refers to a subset of constructs that includes strips or tapes, tubes, bars, washers, and other cannulated bodies, and the terms "tack" or "button," and "patches" or "scaffold" are described in greater detail below (as are the terms strips, tapes, tubes, bars, and washers, among others). Surgical repair filaments or flexible members can come in a variety of configurations including in typical suture configurations and tape forms, and can be used in connection with a variety of types of suture implants, e.g., filament anchors, suture anchors, or bone anchors, including hard and soft anchors, to attach or reattach soft tissue to bone. The repair filaments can pass through soft tissue so that the soft tissue can be positioned in a desired location. The repair filaments are secured to anchors which, in turn, are fixed in bone. The tissue augmentation construct(s) can be associated with the surgical repair filaments to increase coverage and bulk to compromised or degenerate soft tissue, to increase a surface area along which compression between the suture repair filament and tissue being repaired is applied, and to help promote tissue growth and repair. While each of the repair filament, tissue augmentation construct, and suture implant is described as being part of the systems or devices, any one component can be provided for separately for use with the other components or other implants and devices used in surgical procedures.

While many different repair procedures can be enhanced by the present disclosures, in some exemplary embodiments the soft tissue repair devices and systems provided for herein can be used for rotator cuff fixation procedures. In rotator cuff fixation procedures a surgeon can reattach the rotator cuff to the bone by first threading a suture through the soft tissue such that two suture limbs extend from the tissue. The surgeon can thread each of the suture limbs through respective tissue augmentation constructs, and subsequently fix the suture limbs to one or more bone anchors proximate to the tissue. The tissue augmentation constructs increase the surface area, or footprint, of the system that contacts the soft tissue. This enlarged footprint may disperse any loading forces on the soft tissue, and, as a result, the tensioned suture may be less likely to abrade or otherwise damage the soft tissue, for instance by "cheese wiring." Moreover, the tissue augmentation constructs can be easily and quickly threaded onto or otherwise associated with suture limbs during the procedure, which contrasts from existing systems that involved complicated, time-intensive approaches for associating xenograft or allograft formations with suture limbs. The resulting procedures thus allow for the tissue augmentation constructs to be added onto suture limbs in an on-demand fashion. Still further, the tissue augmentation constructs can be made from biocompatible materials (e.g., collagen), among other types of materials, such that during healing new bands of tissue growth can occur, further increasing the efficacy of the rotator cuff fixation procedure. In other non-limiting exemplary embodiments disclosed herein, the soft tissue repair devices and systems can be used in other soft tissue repair procedures for example, repair of torn anterior cruciate ligament (ACL), instability or glenoid procedures, meniscal repair, superior capsule reconstruction, and hip capsular closure, among others. Various methods of manufacturing the tissue augmentation constructs, as well as using installation tools and/or threaders to associate tissue augmentation constructs with operative sutures are also described.

Figure 1A:
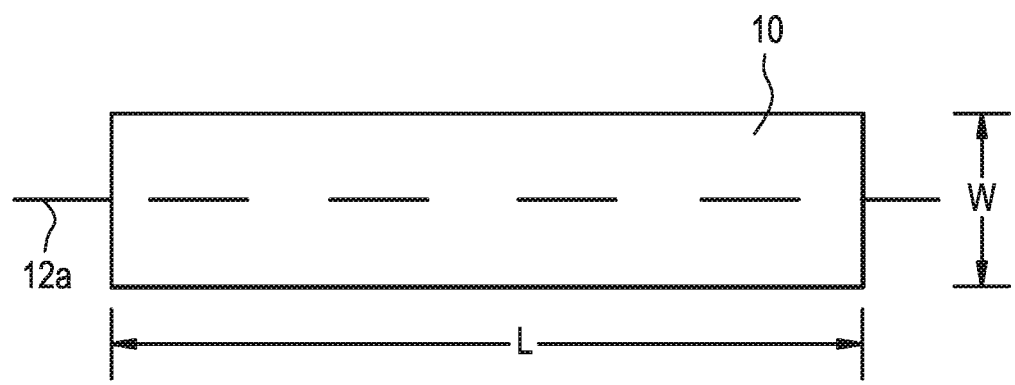
FIG. 1A is a top view of one exemplary embodiment of a tissue augmentation construct.
Figure 1B:
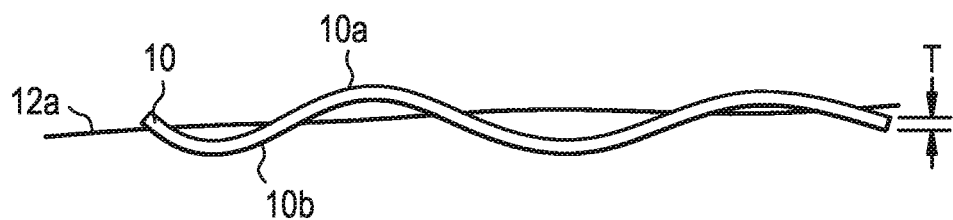
FIG. 1B is a side view of the tissue augmentation construct of FIG. 1A.

Tissue Augmentation Constructs—Tissue Augmentation Blocks Having a Strip or Tape Configuration One exemplary embodiment of a tissue augmentation construct, as shown a tissue augmentation block 10, is provided for in FIGS. 1A and 1B. In one exemplary embodiment, the tissue augmentation block 10 is a strip or tape configured to be threaded onto or otherwise associated with a suture limb 12a. More particularly, the tissue augmentation strip or tape 10 can have a substantially rectangular shape with a width W, length L, and thickness T, and includes a substantially flat, tissue-engaging surface 10a and/or 10b. As shown, the tape 10 is longer than it is wide and wider than it is thick. Typically the length L is substantially greater than the width W and the width W is substantially greater than the thickness T. Further, the width W can be greater than a diameter of a filament or suture with which the tissue augmentation tape 10 is associated, e.g., the suture limb 12a, thereby increasing the surface area of compression of the system or device used in the surgical repair.

A person skilled in the art will recognize that the dimensions of the length L, width W, and thickness T of the tissue augmentation strip 10 can depend on a variety of factors, including but not limited to the size of the filament with which it is to be associated, the anatomy of the patient, and the type of procedure being performed. In some embodiments a ratio of the width W of the strip 10 to a diameter of the suture limb 12a can be approximately in the range of about 2:1 to about 20:1, and more particularly the width W can be at least three times greater than the diameter of the filament or suture with which the tissue augmentation strip 10 is associated in some instances. In embodiments in which the suture limb 12a is a suture tape, the width W of the tissue augmentation strip 10 can be at least two times greater than the diameter of the suture tape with which the strip is associated in some instances. A person skilled in the art will recognize that the ratio of the width of a tissue augmentation strip to diameter of the filament or related structure with which the strip is used can be any suitable ratio, depending, at least in part, on the type of filament or related structure being used, the type of strip or other construct being used, and the type of procedure being performed, and thus a ratio of width to diameter may be smaller or larger than those provided for herein. Further, in some embodiments a ratio of the width L of the strip 10 to the width W of the strip 10 can be approximately in the range of about 2:1 to about 20:1, and more particularly the length L can be at least three times greater than the width W in some instances, at least five times greater in some other instances, and at least ten times greater in some instances, although other L-W ratios are possible. Still further, the strip 10 can be substantially flat and approximately uniform. In some embodiments a ratio of the width W of the strip 10 to the thickness T of the strip 10 can be approximately in the range of about 2:1 to about 20:1, and more particularly the width W can be at least three times greater than the thickness T in some instances, at least five times greater in some other instances, and at least ten times greater in some instances, although other W-T ratios are possible. A variety of other sizes and shapes of the tissue augmentation tape strip 10, including ratios of the dimensions of the tissue augmentation strip and associated components (e.g., the suture limb 12a) can be utilized without departing from the spirit of the present disclosure.

While ratios can be useful to help describe the relationship between the strip 10 and the filament limb 12a, and the relationship between the dimensions of the strip 10, some exemplary, non-limiting dimensions for a tissue augmentation strip can also be useful in understanding the present disclosure. As mentioned above, these dimensions can be dependent on a variety of factors. In some embodiments, the length L can cover a significant portion, to almost an entire portion, of a length of tissue extending between a stitch made in tissue and a bone anchor used to help secure the tissue. In some embodiments, the length L can be approximately in the range of about 5 millimeters to about 1 centimeter, the width W can be approximately in the range of about 1 millimeter to about 5 millimeters, and the thickness T can be approximately in the range of about 0.5 millimeter to about 3 centimeters. Further, while the strip 10 is described as having a length, width, and thickness, and it is shown as being substantially flat in FIG. 1A, FIG. 1B illustrates that the strip 10 can be relatively flexible, for instance it can be bunched in portions by the suture limb 12 passing therethrough. Materials used to form the strip 10 are described in a later section of the present disclosure.

A number of techniques can be used to associate the tissue augmentation strip 10 with the suture limb 12a. As shown in FIG. 1B, the suture limb 12a is threaded from a top side 10a to a bottom side 10b and back to the top side 10a of the tissue augmentation strip 10. The process of threading the suture limb 12a through the tissue augmentation strip 10 can be repeated as many times as desired. In some embodiments a suture threader can be threaded through the tissue augmentation strip 10 ahead of a procedure so that the operative suture can be threaded through the tissue augmentation strip in vivo during the procedure. Exemplary suture threaders are discussed below with regards to alternative tissue augmentation constructs.

While the tissue augmentation strip 10 of FIG. 1B is shown having an exaggerated, wave-like profile when engaged with the suture limb 12a, in practice the tissue augmentation strip 10 can conform to the geometry of the soft tissue that it is contacting. By including the tissue augmentation strip 10 on the suture limb 12a, the suture limb 12a has a broader foot print, thus covering more surface area of the tissue. Further the tissue augmentation strip 10 may allow force applied to the tissue by the suture limb 12a to be distributed over a larger amount of surface area. The larger amount can be dependent on the surface area of the tissue augmentation strip 10. Thus, in embodiments where the width of the tissue augmentation strip 10 is at least three times greater than the diameter of the suture limb 12a, the force of the suture limb 12a on the tissue may be distributed over an area that is at least three times greater than would otherwise be if no tissue augmentation strip 10 was associated with the suture limb 12a. The increased tissue surface area coverage and distributed force of the tissue augmentation strip 10 may result in a reduced pressure peak on the soft tissue. In use, it is either the surface 10a or the surface 10b that engages the tissue and may allow for the increased distribution. Where the soft tissue has become degenerated due to injury or age, a reduction in pressure can result in less chance of abrasion of the tissue. Further, the broader tissue coverage may enhance healing of otherwise compromised tissue.

The suture limb 12a used in conjunction with the tissue augmentation strip 10 can be any type of suture (e.g., braided filament, cannulated filament, mono filament, suture tape, etc.) and can have a size between about a #5 filament (about 20 gauge to about 21 gauge) and about a #3-0 filament (about 29 gauge to about 32 gauge). A person skilled in the art will recognize a variety of other filament types and sizes that can also be used in conjunction with the augmentation strip 10, such as, if a suture tape is used.

Tissue Augmentation Constructs—Tissue Augmentation Constructs Having a Cannulated Portion Another exemplary embodiment of a tissue augmentation construct, as shown a tissue augmentation block 110, is provided for in FIGS. 2A-2D. Alternatively, tissue augmentation constructs, like block 110, can be referred to generally as tissue augmentation constructs having a cannulated body. Tissue augmentation constructs having a cannulated body can include the tube 110, bars 3010, 3010', and washers 310, 410. In one exemplary embodiment of augmentation blocks, the blocks can be a cannulated tube configured to be disposed on or otherwise associated with a suture limb 112a. More particularly, the augmentation tube 110 can have a substantially cylindrical, or ovoid, body with a bore or lumen 114 extending therethrough from a proximal-most end 110p to a distal-most end 110d. To the extent the block 110 is described as a tube, such description in no way limits the configuration of the tissue augmentation blocks to being tubes or having a tubular construction. A tube-like configuration is one of a variety of configurations of blocks provided for herein or otherwise derivable herefrom. Other non-limiting embodiments of blocks include but are not limited to bars and washers, as further described below.

Turning back to the cannulated nature of the block 110, the bore 114 can be used, for example, to receive the suture limb 112a so that the block 110 and limb 112a can be associated with each other, as described in greater detail below. As shown, the block 110 has a length L' that is greater than a diameter D, and in many instances substantially greater. Further, the diameter D can be greater than a diameter of a filament or suture with which the tissue augmentation block 110 is associated, e.g., the suture limb 112a, thereby increasing the surface area of tissue augmentation of the system or device used in the surgical repair.

A person skilled in the art will recognize that the dimensions of the length L' and diameter D of the tissue augmentation tube 110, as well as a diameter d of the bore 114, can depend on a variety of factors, including but not limited to the size of the filament with which it is to be associated, the anatomy of the patient, and the type of procedure being performed. In some embodiments a ratio of the length L' and the diameter D can be approximately in the range of about 2:1 to about 20:1, and more particularly the length L' can be at least three times greater than the diameter D in some instances. Further, in some embodiments a ratio of the diameter D of the tube 110 to a diameter of the suture limb 112a can be approximately in the range of about 2:1 to about 20:1, and more particularly the diameter D can be at least three times greater than the diameter of the filament or suture with which the tissue augmentation tube 110 is associated in some instances. A variety of other sizes and shapes of the tissue augmentation tube 110, including ratios of the dimensions of the tissue augmentation block and associated components (e.g., the suture limb 112a) can be utilized without departing from the spirit of the present disclosure.

While ratios can be useful to help describe the relationship between the tube 110 and the filament limb 112a, and the relationship between the dimensions of the tube 110, some exemplary, non-limiting dimensions for a tissue augmentation tube can also be useful in understanding the present disclosure. As mentioned above, these dimensions can be dependent on a variety of factors. In some embodiments, the length L' can cover a significant portion, to almost an entire portion, of a length of tissue extending between a stitch made in tissue and a bone anchor used to help secure the tissue. In some embodiments, the length L' can be approximately in the range of about 5 millimeters to about 2 centimeter, and the diameter D can be approximately in the range of about 1 millimeter to about 5 millimeters. The size of the diameter d of the bore 114 can also depend on a variety of factors, including but not limited to the size of the limb to be passed therethrough. In some embodiments, the diameter d can be approximately in the range of about 0.75 millimeters to about 3 millimeters.

Alternative embodiments of tissue augmentation blocks 110 having cannulated portions are shown in FIGS. 2E, 2F, 2G, 2H, and 2I. Not all tissue augmentation blocks have cannulated portions, although that is a common feature of the blocks 110, 3010, 3110, tube, 2810', 2810" provided for in FIGS. 2A-2I. Other configurations of tissue augmentation blocks do not have cannulated portions, or cannulated portions through which sutures limbs are passed, and thus other configurations can be associated with limbs using other techniques provided for herein otherwise known to those skilled in the art.

As discussed above, and shown in FIGS. 2E and 2F, tissue augmentation bars 3010, 3110 can have a rectangular and/or square cross sectional shape. Other cross sectional shapes are possible and include, for example, triangular, quadrilaterals, pentagons, hexagons, octagons, etc. As shown in FIG.

2E, cannulated bar 3010 is configured to be disposed on or otherwise associated with a suture limb, as described above with respect to the cannulated tube 110. More particularly, the bar 3010 can have a substantially rectangular body with a rectangular bore or lumen 3014 extending therethrough from a proximal-most end 3010p to a distal-most end 3010d. The bore 3014 can be used, for example, to receive the suture limb so that the bar 3010 and suture limb can be associated with each other, as described in greater detail below. It is contemplated that bore 3014 can be created through manufacturing techniques discussed below with respect to augmentation block 110.

Figure 2A:
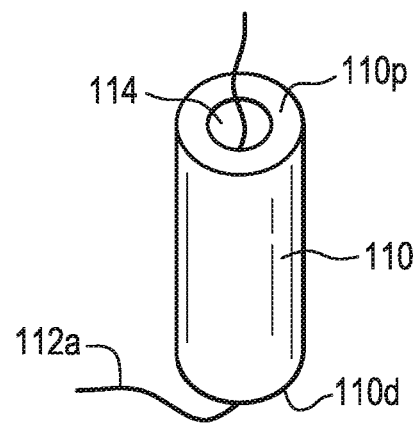
FIG. 2A is a perspective side view of another exemplary embodiment of a tissue augmentation construct.
Figure 2B:
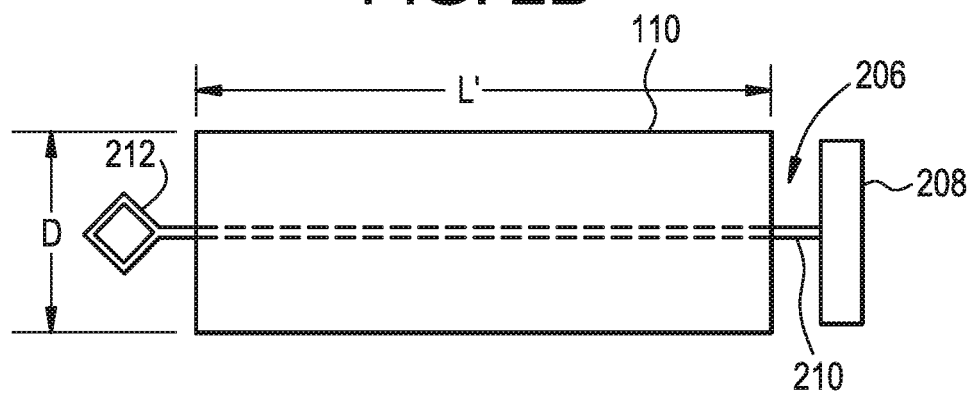
FIG. 2B is a side view of the tissue augmentation construct of FIG. 2A having a threader disposed therein.
Figure 2D:
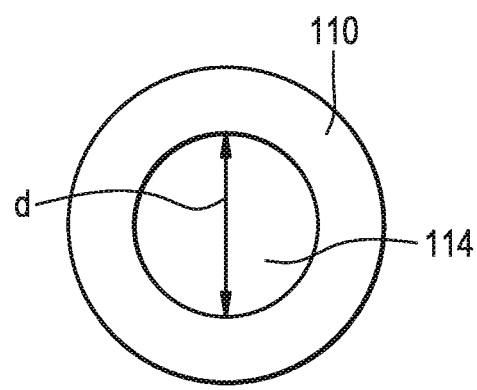
FIG. 2D is a front view of the tissue augmentation construct of FIG. 2A.
Figure 2C:
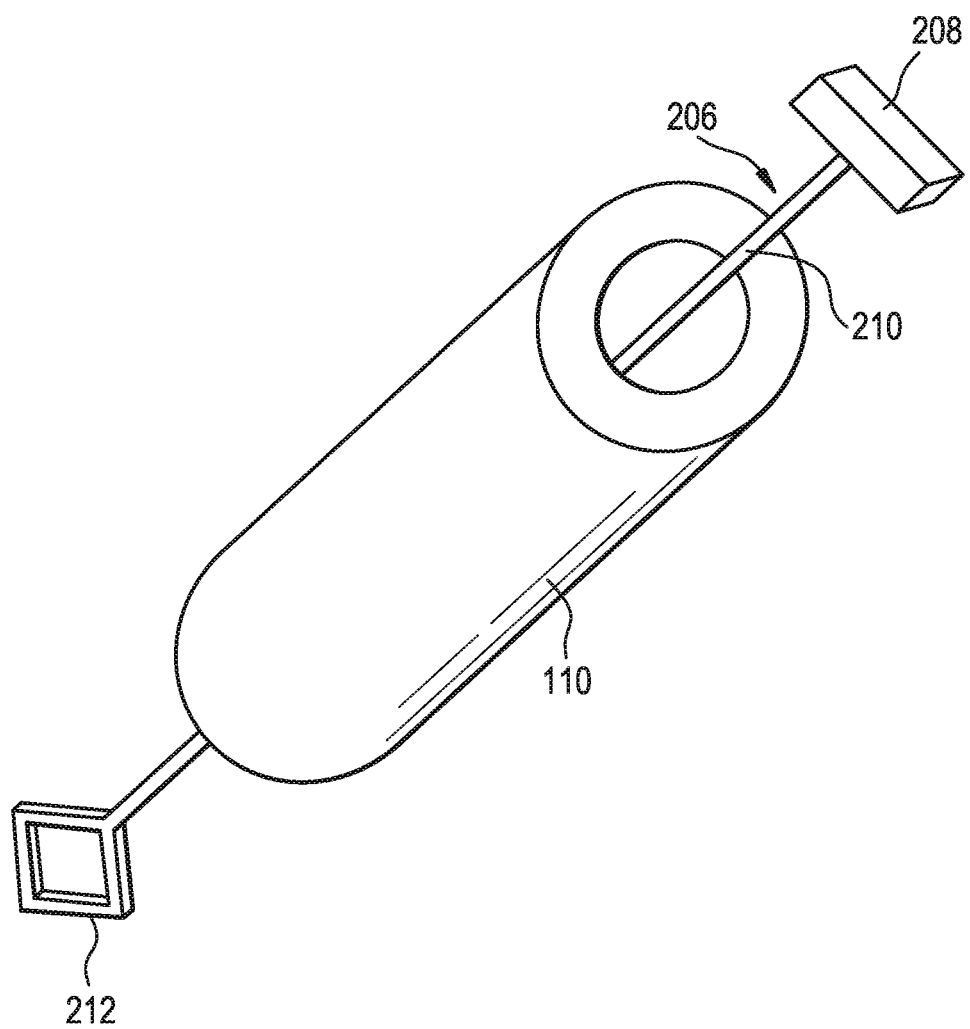
FIG. 2C is a perspective view of the tissue augmentation construct of FIG. 2B.
Figure 2E:
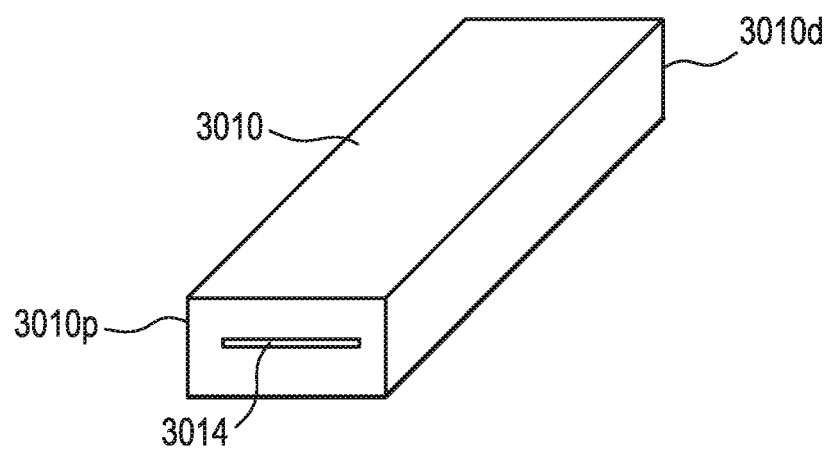
FIG. 2E is a perspective view of yet another exemplary embodiment of a tissue augmentation construct.
Figure 2F:
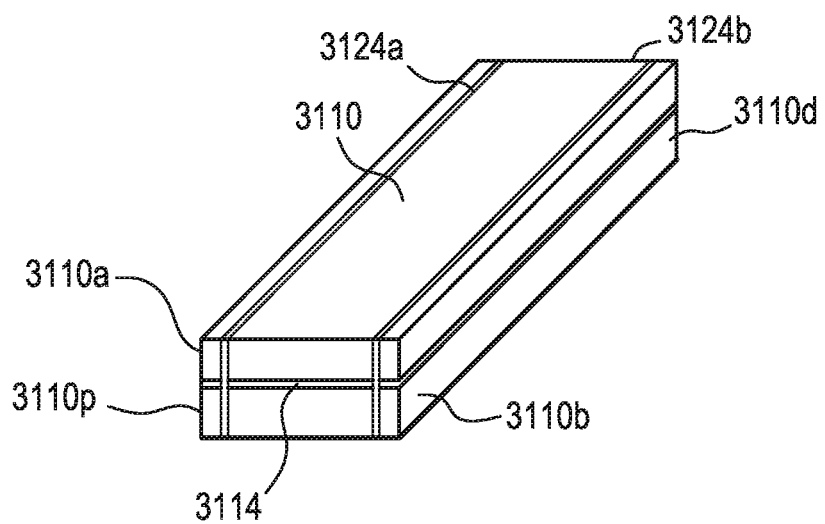
FIG. 2F is a perspective view of still another exemplary embodiment of a tissue augmentation construct.

An alternative construction of tissue augmentation bar 3010, tissue augmentation bar 3110, is shown in FIG. 2F. As shown in FIG. 2F, the cannulated bar 3110 is configured to be disposed on or otherwise associated with a suture limb, as described above with respect to the cannulated blocks 110, 3110. More particularly, the bar 3110 can have a substantially rectangular body with a rectangular bore or lumen 3114 extending therethrough from a proximal-most end 3110p to a distal-most end 3110d. The bore 3114 can be used, for example, to receive the suture limb so that the bar 3110 and suture limb can be associated with each other, as described in greater detail below. As shown, bar 3110 can be constructed of two portions of material, 3110a, 3110b. The two pieces of material 3110a, 3110b can be associated with each other by means of sutures 3124a, 3124b. The pieces of material 3110a, 3110b can be attached to each other such that lumen 3114 is formed using any manufacturing techniques discussed throughout the present disclosure. A variety of other sizes and shapes of the bars 3010, 3110 including ratios of the dimensions of the bar and associated components (e.g., the suture limb) can be utilized without departing from the spirit of the present disclosure.

Figure 2G:
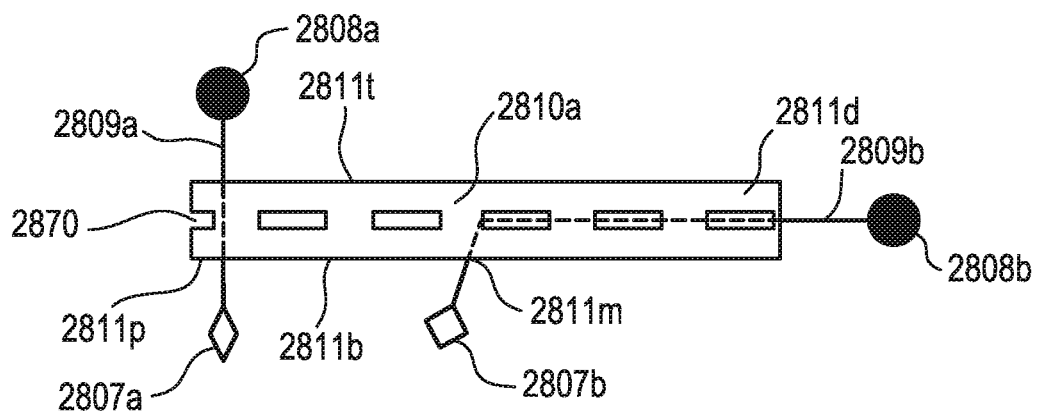
FIG. 2G is a side view of another exemplary embodiment of a tissue augmentation construct.
Figure 2H:
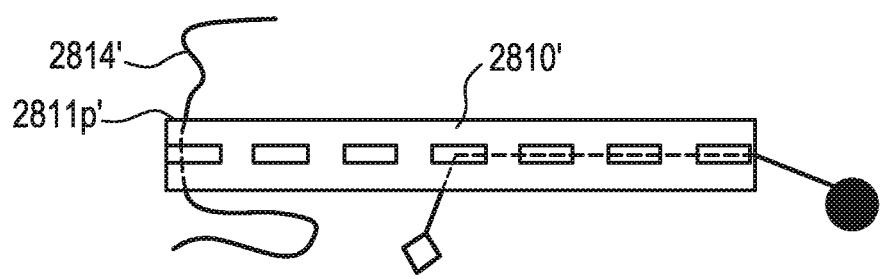
FIG. 2H is a side view of still another exemplary embodiment of a tissue augmentation construct.
Figure 2I:
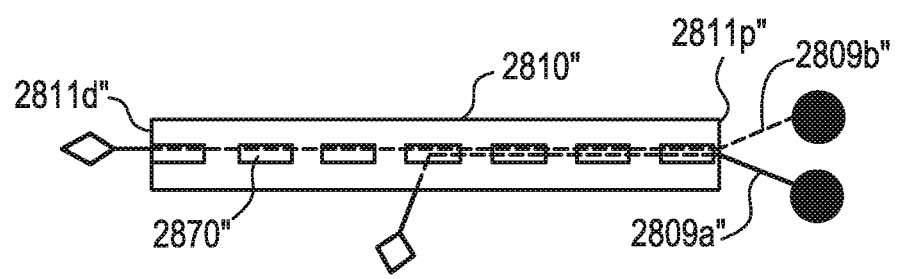
FIG. 2I is a side view of yet another exemplary embodiment of a tissue augmentation construct.

Further alternative configurations of tissue augmentation blocks 2810a, 2810', and 2810" are illustrated in FIGS. 2G, 2H, and 2I, respectively. As shown, the cannulated blocks 2810a, 2810', 2810" can all be substantially the same as tissue augmentation block 110, as shown in FIGS. 2A-2D. Alternatively, the cannulated blocks 2810a, 2810', 2810" can have configurations substantially similar to the tissue augmentation bars 3010, 3110. The cannulated blocks 2810a, 2810', 2810" can have a length that is substantially longer than the tissue augmentation blocks 110. In one exemplary embodiment, the block 2810a can have a length approximately in the range of about 15.0 millimeters to about 25.0 millimeters. Advantageously, blocks 2810a, 2810', 2810" can have a length that can extend from lateral anchors medially up and over a soft tissue repair to provide for additional protection for the repair and additional scaffolding to aid in healing.

A number of techniques can be used to associate the tissue augmentation blocks 110, 3010, 3110, 2810a, 2810', 2810" with a suture limb 112a. For example, as shown in FIG. 2A, the suture limb 112a is threaded or passed from the proximal-most end 110p to the distal-most end 110d of the tissue augmentation tube 110 without passing through, that is across, the body of the tube 110. In other words, the suture limb 112a does not pass into a sidewall of the body that defines the lumen 114. As such, the tube 110 is not coupled or attached to the suture limb 112a, and instead can freely pass along a length of the limb 112a unhindered or unrestricted. In other embodiments, the limb 112a can pass through, that is across, the body once or more to further secure a location of the tube 110 with respect to the limb 112a, thereby coupling or attaching the tube 110 to the suture limb 112a. A person skilled in the art will recognize a variety of other ways by which the tube 110 can be associated or coupled with the limb 112a without departing from the spirit of the present disclosure.

The tissue augmentation tube 110 can be threaded by hand on to the suture limb 112a, either at the surgical site, or outside of the body. Alternatively, as shown in FIGS. 2B and 2C, the tissue augmentation tube 110 can have a threader 206 inserted through the bore 114 prior to the tissue augmentation tube 110 being threaded onto the suture limb 112a. The threader 206 can include a proximal handle portion 208, an intermediate elongate portion 210, and a distal suture-receiving end 212. The proximal handle portion 208 can be configured to be easily gripped by a user, for instance by having a substantially rectangular shape as shown. Other shapes and features for gripping can be provided. The intermediate portion can be a filament portion 210 capable of having a tissue augmentation construct, e.g., the tissue augmentation tube 110, associated therewith, thereby allowing the threader 206 to be flexible. The distal suture-receiving end 212 can have a distal opening 212 through which a suture to be associated with an augmentation strip, e.g., suture limb 112a, can be disposed. In the illustrated embodiment, the distal opening 212 is flexible and, in some embodiments, can be made of a wire, a fiber, a thread, a cord, and/or other flexible structure or other material having similar characteristics. Because the distal opening 212 is flexible, it can change shape before, during, and after use, and thus while in the illustrated embodiment it has a diamond or kite-shape, other configurations are possible. Further, the flexible nature of the opening 212 can allow the opening 212 to collapse around a suture disposed therein to strangulate or otherwise hold the suture during use. In some embodiments, the intermediate portion 210 can also be made of a wire, a fiber, a thread, a cord, and/or other flexible structure. The term wire is not intended to imply that the structure is made of metal, or has metal characteristics, but the intermediate portion 210 and the distal suture-receiving end 212 can be made of metal.

FIGS. 2G-2I provide for additional configurations of suture limbs being associated with tissue augmentation constructs. As shown in FIG. 2G, the construct 2810a can include two threaders disposed therethrough for associating the construct 2810a with at least one suture limb. As illustrated in FIG. 2G, a first threader 2809a can be disposed through the block 2810a from a top surface 2811t to a bottom surface 2811a such that the handle 2808a is proximate the top surface 2811t and the receiving end 2807b is proximate the bottom surface 2811b. The first threader 2809a can be disposed through the block 2810a such that it intersects the central lumen 2870 of the block 2810a substantially perpendicularly relative thereto. Alternatively, the threader 2809a can be disposed at any angle relative to the central lumen 2870. The first threader 2809a can be disposed at the proximal end 2811p, or proximal half, of the block 2810a. A second threader 2809b can be disposed through a distal portion 2811d of the block 2810a. For example the second threader 2809b can extend from a distal end 2811d of the block 2810a through the lumen 2870 to a medial location 2870m of the lumen and out of the bottom 2811b of the block 2810a. In one exemplary embodiment the second threader 2809b can extend through the block 2810a such that a handle portion 2808b of the threader 2809b is proximate the distal end 2811d of the block 2810a and the receiving end 2807b of the threader extends out the bottom 2811b of the block 2810a. Alternatively, other suture threader configurations are contemplated as shown in FIGS. 2H and 2I and discussed below.

In one alternative suture threader configuration, as shown in FIG. 2I, block 2810' can include a pre-threaded suture 2814' in the proximal end 2811p' of the block, obviating the need for a second threader. The pre-threaded suture 2814' can be threaded into block 2810' at a location that is substantially similar to the second threader 2809b of FIG. 2G. The pre-threaded suture 2014' can be threaded into the block 2810' either before or after the block is associated with a repair suture, not shown. In a further alternative configuration, as shown in FIG. 2H, block 2810" can include two threaders 2809a" and 2809b". The threaders 2809a", 2809b" can be substantially similar to threaders 2809a, 2809b discussed above. As shown, the second threader 2809b" can be disposed through a central lumen 2870", for example from the proximal terminal end 2811p" to the distal terminal end 2811d". Alternatively, the second threader 2809b" can extend through any length of the central lumen 2870". The second threader 2809b" can associate suture limbs, not shown, with the block 2810" using techniques provided for throughout the present disclosure. The suture limbs can each exit the block 2810" at the distal end 2811d" along with a repair suture limb to be subsequently anchored into the bone at a location laterally offset from the soft tissue repair.

In use, a force $P_1$ can be applied to the handle portion 208 to move the filament portion 210 and the distal opening 212 in the direction of the force $P_1$ with respect to the augmentation tube 110. The distal opening 212, and thus the suture limb 112a coupled thereto, can be drawn into and through the augmentation tube 110 by way of this movement, thus disposing the augmentation tube 110 onto the suture limb 112a. As the distal opening 212 enters the augmentation tube 110, the opening 212 can be collapsed, e.g., compressed to a smaller width, around the suture limb 112a to strangulate the limb 112a, thus making it easier for the suture limb 112a to be drawn into a body of the augmentation tube 110. Once the augmentation tube 110 is disposed on or is otherwise associated with the suture limb 112a, the suture limb 112a can be disassociated with the distal opening 212 and the threader 206 can be discarded or reused since it is no longer associated with either the augmentation tube 110 or the suture limb 112a. The combination of the suture limb 112a and the augmentation tube 110 can then be used in a variety of procedures, as detailed further below. The process of disposing the augmentation tube 110 onto the suture limb 112a can occur outside of the body or inside the body, including proximate to the surgical site.

Similar to the tissue augmentation strip 10, by including the tissue augmentation tube 110 on the suture limb 112a, the suture limb 112a has a broader footprint, thus covering more surface area of the tissue. Further, the tube 110 may allow force applied to the tissue by the suture limb 112a to be distributed over a larger amount of surface area. The larger amount can be dependent on the surface area of the tissue augmentation tube 110. Thus, in embodiments where the diameter of the tissue augmentation tube 110 is at least three times greater than the diameter of the suture limb 112a, the force of the suture limb 112a on the tissue may be distributed over an area that is at least three times greater than would otherwise be if no tissue augmentation tube 110 was associated with the suture limb 112a. The increased tissue surface area coverage and distributed force of the tissue augmentation tube 110 may result in a reduced pressure peak on the soft tissue. Where the soft tissue has become degenerated due to injury or age, an increased tissue surface area coverage and a reduction in pressure can result in less chance of abrasion of the tissue. Further, the broader tissue coverage may enhance healing of otherwise compromised tissue and/or provide bulk to otherwise compromised or degenerate tissue and/or tendon.

Figure 3:
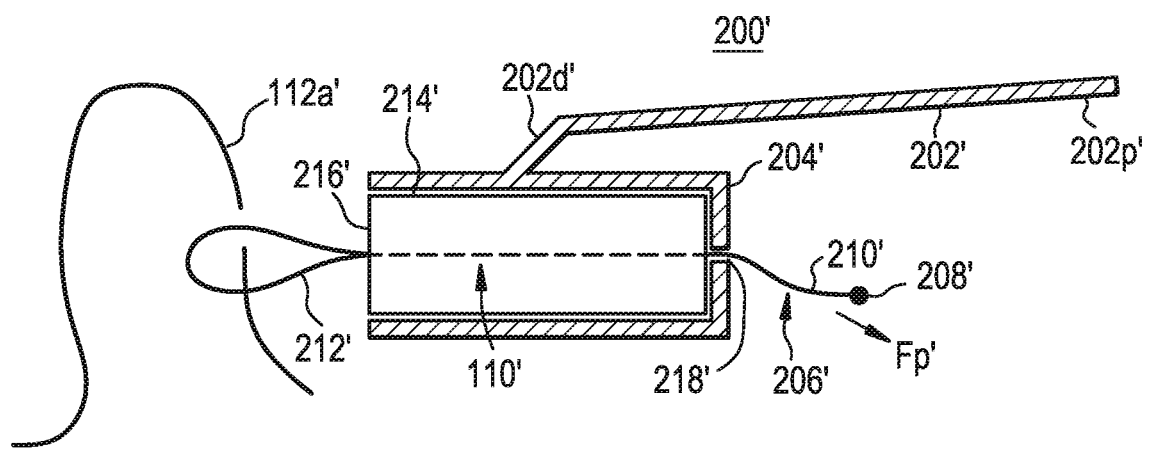
FIG. 3 is a side view of one exemplary tissue augmentation construct installation tool, the tool having a tissue augmentation similar to the tissue augmentation construct of FIG. 2A associated therewith.

Threaders like the threader 206 can also be used in conjunction with an installation tool to assist in associating an augmentation construct with a suture. FIG. 3 provides for a threader 206' that is similar to the threader 206 except that the proximal handle portion 208' and distal receiving end 212' have a slightly different shape. As shown, the proximal handle portion 208' is in the form of a gripping protrusion 208' that has a diameter that is greater than a diameter of the intermediate filament portion 210', thus allowing a user to easily grip the proximal handle portion 208'. A person skilled in the art will recognize that the proximal handle portion 208' can have most any shape. Likewise, a shape of the distal receiving end 212' can also have most any shape. In the illustrated embodiment, the distal receiving end 212' is a distal opening 212', but the opening is illustrated as being more rounded than the distal opening 212. However, as explained above, because the distal opening 212' can be flexible, even the illustrated embodiments can be manipulated into other shapes.

The installation tool 200' can include a handle portion 202' and a cartridge portion 204'. The handle portion 202' can be long such that the installation tool 200' can be inserted through a cannula into a surgical site inside of the body. Alternatively, the handle portion 202' can be any suitable length. As shown in FIG. 3, the handle 202' includes a proximate portion 202p' and a distal portion 202d'. The distal portion 202d' of the handle 202' can be angularly offset from the proximal portion 202p' to allow for the cartridge 204' to be oriented in a favorable orientation to thread the augmentation tube 110' onto the limb 112a'. Alternatively, the proximal portion 202p' and the distal portion 202d' can be in line with each other.

The distal portion 202d' can be attached to a cartridge 204' that is sized to receive an augmentation tube 110' to be threaded onto suture limb 112a'. The cartridge 204' can be cylindrical in shape, having an approximately circular cross section. Alternatively, the cartridge 204' can have a triangular, rectangular, or any other shape and/or cross section. The cartridge 204' can have a lumen 214' extending therethrough from a first opening 216' to a second opening 218'. The first opening 216' can be larger than the second opening 218'. Alternatively, the first opening 216' and the second opening 218' can be any desired size. As shown in FIG. 3, the first opening 216' can have a diameter that is substantially the same as the lumen 214' such that the augmentation tube 110' can be placed therethrough. The second opening 218' can have a diameter that is sized to receive a relevant portion of the threader 206' therethrough.

As shown in FIG. 3, a suture limb 112a' is inserted through the opening 212' and the threader 206' can be operated in a manner similar to the threader 206 to dispose the augmentation tube 110' onto the suture limb 112a'. For example, an operator can grasp the handle portion 208' of the threader 206' to pull the opening 212' through the cannula 114' of the augmentation tube 110' by the application of a force $F_P'$. The handle 208' can be pulled until the entirety of the threader 206' and a distal portion of the suture limb 112a' have passed through the second opening 218'. Once the suture limb 112a' has been threaded through the augmentation tube 110', the threaders 206' can be discarded or reused and the installation tool can release the augmentation tube 110' by actuation of a release mechanism (not shown). Alternatively, the augmentation tube 110' can be held in the cartridge 204' with an interference fit, such that no release mechanism is required. While reference is made to augmentation tube 110' and suture limb 112a', as noted above, the installation tool 200' can be used in the same manner with augmentation strip 10 of FIGS. 1A-1B, as well as other constructs provided for herein. Further, while threaders are discussed as being used in conjunction with an installation tool, the threader itself can be considered an installation tool since embodiments provided for herein allow the threader to be used to associate a suture with an augmentation construct without using the installation tool 200'.

Figure 4:
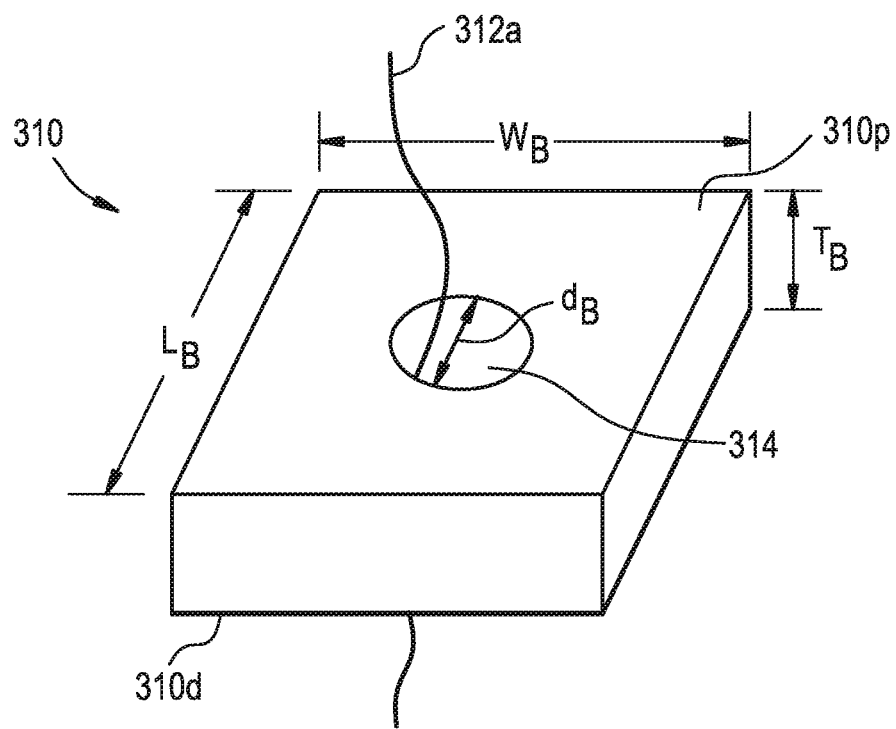
FIG. 4 is a perspective view of another exemplary embodiment of a tissue augmentation construct.

Tissue Augmentation Constructs—Tissue Augmentation Blocks Having a Washer, Disc, or Ring Configuration An exemplary embodiment of a tissue augmentation construct, as shown a tissue augmentation block 310, is provided for in FIG. 4. The augmentation block 310 has a configuration that can be described as a washer, disc, or ring, and the illustrated embodiment it is a square-shaped washer configured to be disposed on or otherwise associated with a suture limb 312a. For example, the washer 310 can have a substantially rectangular prism-shaped body with a bore or lumen 314 extending therethrough from a proximal-most end 310p to a distal-most end 310d. The bore 314 can be used, for example, to receive the suture limb 312a so that the washer 310 and limb 312a can be associated with each other, as described in greater detail below. As shown, the washer 310 has a length $L_B$ and a width $W_B$ which are substantially equal, and height TB which is less than the length $L_B$ and the width $W_B$. Alternatively, the washer 310 can have a more elongated rectangular shape having a length $L_B$ that is larger than the width $W_B$. In a further alternative, the length $L_B$, width $W_B$, and the height TB can be substantially equal, thereby forming a cube-shaped body. Further, the diameter dB of the lumen can be greater than a diameter of a filament or suture with which the washer 310 is associated, e.g., the suture limb 312a. In other embodiments the suture limb 312a can be threaded through the washer 310 without a preformed lumen. Once the block is associated with the suture limb 312a, the block can increase the surface area of compression of the system or device used in the surgical repair due to the increased surface area of the block.

A person skilled in the art will recognize that the dimensions of the length $L_B$, width $W_B$, thickness or height TB, and diameter dB of the washer 310 can depend on a variety of factors, including but not limited to the size of the filament with which it is to be associated, the anatomy of the patient, and the type of procedure being performed. In some embodiments, the washer 310 can have a length $L_B$ approximately in the range of about 3 millimeters to about 6 millimeters, a width $W_B$ in the range of about 3 millimeters to about 6 millimeters, and thickness or height TB approximately in the range of about 1 millimeter to about 3 millimeters. Alternatively, the length $L_B$, width $W_B$, and thickness or height TB can all be substantially equal and have a dimension approximately in the range of about 2 millimeters to about 5 millimeters. One benefit to the smaller dimensions of the washer 310 is that a surgeon can load a plurality of the washers 310 onto a single suture limb, as described further below, to allow for precision application of the washers on areas of the damaged tissue where they are required. For example, precision application of the washers can include moving the washers along a length of a suture limb to more precisely direct where force from the suture limb will be distributed across a greater surface area. In view of the present disclosures, it is clear that the thickness or height of the washers 310 can be substantially less than a length of suture limb on which the washers 310 are disposed. Any number of washers 310 can be disposed on the suture limb, including but not limited to up to 30. In some exemplary embodiments, the number of washers 310 provided on a single suture limb is approximately in the range of about 2 blocks to about 8 blocks.

Figure 5:
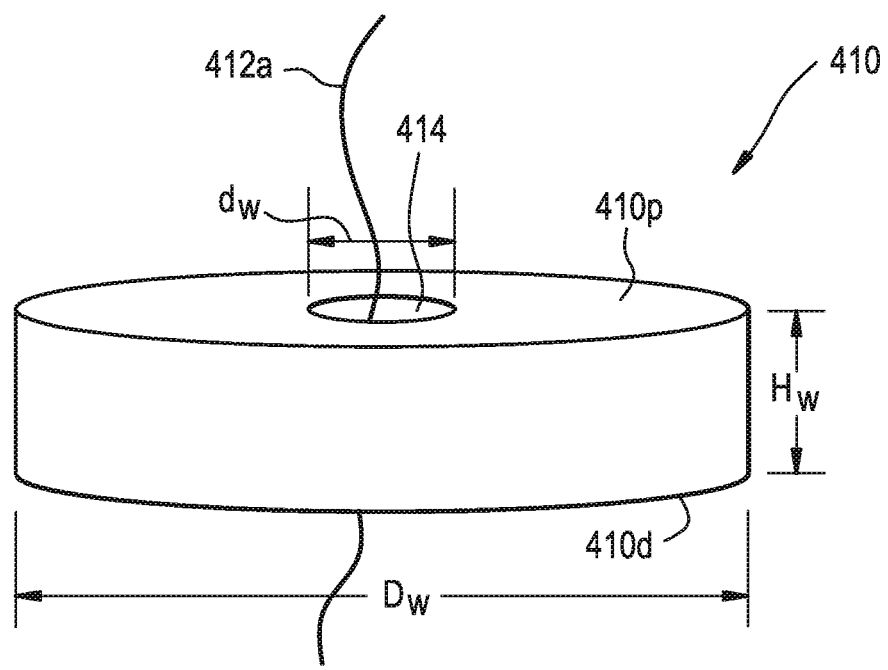
FIG. 5 is a perspective view of still another exemplary embodiment of a tissue augmentation construct.

An alternative embodiment of an augmentation construct configured to be effectively used in conjunction with other similarly sized constructs on the same suture limb is illustrated in FIG. 5. As shown, the tissue augmentation construct is a tissue augmentation block 410 that has a configuration that can be described as a washer, disc, or ring. In the illustrated embodiment, it is a ring or circular-shaped washer. For example, the tissue augmentation washer 410 can have a bore or lumen 414 extending therethrough from a proximal-most face 410p to a distal-most face 410d. The bore 414 can be used, for example, to receive the suture limb 412a so that the washer 410 and limb 412a can be associated with each other, or alternatively, the limb 412a can be associated with the washer 410 by threading it through the body of the ring without any preformed hole or bore.

A person skilled in the art will recognize that the dimensions of the diameter $D_W$, height $H_W$, and bore diameter $d_W$ of the washer 410 can depend on a variety of factors, including but not limited to the size of the filament with which it is to be associated, the anatomy of the patient, and the type of procedure being performed. In some embodiments, the diameter $D_W$ can be approximately in the range of about 3 millimeters to about 6 millimeters, height $H_W$ can be approximately in the range of about 1 millimeter to about 3 millimeters, and bore diameter $d_W$ can be approximately in the range of about 0.5 millimeters to about 2 millimeters. Similar to the washer 310, in view of the present disclosures, it is clear that the thickness or height of the washer 310 can be substantially less than a length of suture limb on which the washers 410 are disposed. Any number of washers 410 can be disposed on the suture limb, including but not limited to up to 30. In some exemplary embodiments, the number of washers 410 provided on a single suture limb is approximately in the range of about 2 washers to about 8 washers.

One benefit of the washers 310, 410 is that a surgeon can pass both anterior and posterior sutures through the washers 310, 410, as described further below, at the suture insertion point to prevent cheese wiring at the suture insertion point by the sutures. Further, the washers 310, 410, can be used in conjunction with any of the tissue augmentation constructs disclosed, including by disposing one or more washers 310, 410 onto the same suture limb on which another tissue augmentation construct is already, or will be, disposed.

A number of techniques known to those skilled in the art can be used to associate the washers 310, 410 with the respective suture limbs 312a, 412a. The suture limb 312a, 412a can be threaded or passed from the proximal-most end 310p, 410p to the distal-most end 310d, 410d of the washers 310 or 410 without passing into and/or through the body of the washers 310, or 410, i.e., the suture limb 312a, 412a extends directly through the lumen 314, 414. Thus, like the tube 110, the washers 310, 410 can freely pass along a length of the suture limb 312a, 412a unhindered or unrestricted since they are not coupled or attached to the suture limb 312a, 412a. In other embodiments, the limb 312a, 412a can pass through the body once or more to further secure a location of the washers 310 410 with respect to the limb 312a, 412a. A person skilled in the art will recognize a variety of other ways by which the washers 310, 410 can be associated with the limbs 312a, 412a without departing from the spirit of the present disclosure. For example, the washers 310 or 410 can be threaded by hand on to the suture limb 312a, 412a either at the surgical site, or outside of the body. Alternatively, one or more washers 310 or 410 can have a threader (not shown) inserted through the respective bores 314, 414 prior to the washers 310 or 410 being threaded onto the suture limb 312a, 412a. The threader can be the same or similar to the threaders 206, 206' described above and can be used to thread a suture limb 312a, 412a through the washer 310 or 410 at a surgical site.

Similar to augmentation blocks 10, 110, by including either, or both of, the washers 310 or 410 on a suture limb, force applied to the tissue by the suture limb is distributed over a larger amount of surface area. The larger amount is dependent on the surface area of the augmentation washer 310 or 410, as well as the number of washers used.

Materials for Forming Augmentation Constructs

The constructs discussed above, e.g., the blocks 10, 110, 3010, 3110, 310, and 410, as well as those provided for further below (including various patches or scaffolds) can be made of one or more biocompatible, bioresorbable materials so that after implantation into a patient to replace or repair connective tissue, the strip gradually degrades or remodels over time. The resorption profile of the constructs can be sufficiently long to reinforce and provide structure to tissue during the regeneration or healing process. A person skilled in the art can determine a suitable resorption profile, depending, at least in part, on the desired use of the construct, and can tailor the resorption profile by varying the materials used to form the construct.

While many different materials can be used to form the tissue augmentation constructs, either alone or in combination with other materials, in some instances the material is a biocompatible polymer. Exemplary embodiments of suitable biocompatible materials synthetic polymers, natural polymers, and combinations of the two. As used herein, the term "synthetic polymer" refers to polymers that are not found in nature, even if the polymers are made from naturally occurring biomaterials. As used herein, the term "natural polymer" refers to polymers that are naturally occurring. In embodiments where the tissue augmentation constructs includes at least one synthetic polymer, suitable biocompatible synthetic polymers can include polymers selected from the group that includes aliphatic polyesters, poly(amino acids), copoly(ether-esters), polyalkylene oxalates, polyamides, tyrosine derived polycarbonates, poly (iminocarbonates), polyorthoesters, polyoxaesters, polyamidoesters, polyoxaesters containing amine groups, poly(anhydrides), polyphosphazenes, polyurethanes, poly(ether urethanes), poly(ester urethanes), poly(propylene fumarate), poly(hydroxyalkanoate), polydioxanone, poly-hydroxybutyrate-co-hydroxyvalerate, polyamniocarbonate, polytrimethylene, polyoxaamides, elastomeric copolymers, and combinations or blends thereof. Suitable synthetic polymers for use in the tissue augmentation constructs can also include biosynthetic polymers based on sequences found in collagen, a collagen scaffold, pulverized collagen pieces, elastin, thrombin, silk, keratin, fibronectin, starches, poly(amino acid), gelatin, alginate, pectin, fibrin, oxidized cellulose, chitin, chitosan, tropoelastin, hyaluronic acid, ribonucleic acids, deoxyribonucleic acids, polypeptides, proteins, polysaccharides, polynucleotides, and combinations or blends thereof. The types of materials that can be used to construct tissue augmentation constructs, either wholly or in part, include non-absorbable polymers selected from the group that includes, but is not limited to, polyethylene, polypropylene, polyetheretherketone (PEEK), polytetrafluoroethylene, silicone, rubber, or other biocompatible non-absorbable polymers, and combinations thereof. Natural polymers for the use in augmentation strip 10 can be selected from the group that includes but is not limited to a fibrin-based material, collagen-based material, a hyaluronic acid-based material, a cellulose-based material, a silk-based material, a gelatin-based material, a glycoprotein-based material, a cellulose-based material, a polysaccharide-based material, a protein-based material, a fibronectin-based material, a chitin-based material, a pectin-based material, an elastin-based material, an alginate based material, a dextran-based material, an albumin-based material, a natural poly(amino acids) based material, a decellularized tissue, purified extracellular matrix (ECM), a demineralized bone matrix, and combinations thereof.

Still further, virtually any type of tissue can be used to form the tissue augmentation constructs, including but not limited to autograft tissue and allograft tissue, as well as human allogeneic tissue and xenogeneic tissue, which includes porcine, bovine, and equine among others. The tissue used can be selected from biological connective tissues that include ligament tissue, tendon tissue, a modeled tendon, skin tissue, muscle tissue, periosteal tissue, pericardial tissue, synovial tissue, dermal tissue, an acellular porcine dermal matrix, an acellular bovine dermal matrix, fascia, small intestine tissue, embryonic tissue, amniotic tissue, placental tissue, periodontal tissue, peritoneum tissue, vascular tissue, blood, and combinations thereof. The materials used to form the tissue augmentation constructs can be cross-linked and non-crosslinked, and any material provided for herein can be used in conjunction with other materials, whether synthetic, natural, or a combination thereof. Still further, the tissue augmentation constructs, and/or materials used to form the tissue augmentation constructs, can be treated with platelet-rich plasma (PRP), bone marrow, cells, and other bone and/or tissue growth-promoting materials.

The material used to form the tissue augmentation constructs can be made and/or formed, using a variety of techniques. These techniques include, but are not limited to, knitting them and weaving them. The overall construction of the materials can be described as being woven, knitted, non-woven, and/or a foam, among other constructions resulting from techniques known to a person skilled in the art. Further, a combination of techniques can be used for a single construct, and/or a portion thereof. The formation techniques can be used with materials, e.g., synthetic polymers and other materials provided for above, as well as tissue.

Tissue Augmentation Kits

The filaments and tissue augmentation constructs provided for herein can be included together as part of a soft tissue repair kit. Such a kit can also include components such as a threader, installation tool, bone anchors, and/or a bone drill. For example, one exemplary embodiment of a kit can include one or more tissue augmentation constructs and one or more threaders. In some instances, the tissue augmentation constructs can be pre-disposed on the threaders. The tissue augmentation constructs can include any of the constructs provided for herein or otherwise derivable from the present disclosures, including but not limited to the tissue augmentation blocks 10, 110, 3010, 3110, 310, 410 and the tissue augmentation patches 2210, 2310, 2410, and 2510, which are described below. The threaders can include the threaders 206, 206', as well as other threaders known to those skilled in the art or otherwise derivable from the present disclosures. In instances where tissue augmentation constructs are pre-disposed on the threader, the constructs can be disposed on the intermediate portion 208, 208' of the threaders 206, 206'.

The kit can also include other components used in conjunction with tissue augmentation constructs and threaders, including but not limited to one or more sutures, such as the sutures 12a, 112a, one or more installation tools, such as the installation tool 200', one or more implants, e.g., bone anchors, and one or more bone drills. In some exemplary embodiments the kit can include a tissue augmentation block 10, 110, 3010, 3110, 310, 410 for every suture limb 12a, 112a, 312a, 412a that will be anchored over the soft tissue. The types and configurations of the filaments, constructs, installation tools (which can include threaders as stand-alone installation tools), and bone anchors can be varied, thus providing the user options for use in any surgical procedure. Accordingly, any combination of blocks having a strip or tape configuration (e.g., strip 10), a cannulated tube configuration (e.g., tube 110), a cannulated bar configuration (e.g., bar 3010, bar 3110), and a washer configuration (e.g., washer 310, washer 410), can be mixed and matched by a surgeon, as desired, including by disposing them on the same suture limb. The selection of constructs to be used can depend, at least in part on a variety of factors, including but not limited to the size of the filament with which it is to be associated, the anatomy of the patient, and the type of procedure being performed.

The threader and/or installation tool can be a single device used to associate tissue augmentation constructs to limbs multiple times, or multiple threaders and tools can be provided to allow multiple strip-limb combinations to be formed or to allow for different configurations preferred by different users. The threader and/or installation tool can be specifically adapted to be used with particular tissue augmentation constructs, procedures, and/or surgeon's preferences without departing from the spirit of the present disclosure.

To the extent implants such as anchors are provided as part of a kit, or used in conjunction with any of the disclosures provided for herein, the implants can be any type of implant known to those skilled in the art that are used for various types of tissue repair procedures. For bone anchors, the anchors can be of a hard construction or a soft construction, and in some instances they can be knotless anchors, meaning filaments associated therewith do not need to have knots tied by the surgeon during the surgical procedure to couple the tissue to the filament and/or the anchor. Some exemplary embodiments of hard suture anchors for use in the kits or more generally with the present disclosures include Healix Ti™ anchors that are commercially available from DePuy Synthes, as well as Healix Advance™ anchors, Helix Advance Knotless™ anchors, Healix BR™ anchors, Healix PEEK™ anchors, Healix Transtend™ anchors, Bioknotless® anchors, Gryphon® anchors, Fastin® anchors, Versalok® anchors, Microfix® anchors, Minilok™ anchors, MicroQuickanchors® anchors, and Tacit® anchors, each of which is also commercially available from DePuy Mitek, Inc. Some exemplary embodiments of soft suture anchors for use in the kits or more generally with the present disclosures include those described in U.S. Pat. No. 9,345,567 of Sengun, the content of which is incorporated by reference herein in its entirety.

To the extent the kit includes a bone drill, any type of bone drill known by those having skill in the art for forming bone holes in which anchors can be disposed can be provided.

Methods of Use—Rotator Cuff Repairs

Exemplary methods for using systems, devices, and kits of the type described herein are now described in greater detail. While the methods described herein generally relate to attaching soft tissue to bone, and in this section of the disclosure are primarily discussed with respect to rotator cuff repairs, a person skilled in the art will recognize other types of procedures and repairs with which the constructs and the methods related to the same can be used. Further, to the extent a particular type of tissue augmentation construct is illustrated in the following embodiments, a person skilled in the art would understand how to employ other tissue augmentation constructs provided for herein without departing from the spirit of the present disclosures. Likewise, any sutures or anchors provided for herein or otherwise known to those having skill in the art can be used, including knotless anchors. Still further, while in the illustrated embodiments the lengths of sutures and limbs may be approximately equal, any suture or limb can be any desired length, and thus lengths of sutures and limbs do not need to be equal. Likewise, to the extent the techniques described below discuss having a certain number of suture limbs (e.g., one, two, three, etc.) extending from or otherwise associated with a suture anchor to perform the tissue repair, a person skilled in the art, in view of the present disclosures, will understand how a different number of limbs can be used to perform the same, or a similar type, of repair. A benefit that results from each of the methods described herein is that the tissue augmentation constructs can be associated with the suture being used in the repair in an on-demand manner, thus allowing a surgeon to quickly and easily associate one or more tissue augmentation constructs with the repair suture(s) to form desired footprints for the repair.

Rotator Cuff Repairs—Double Row Applications

Figure 6A:
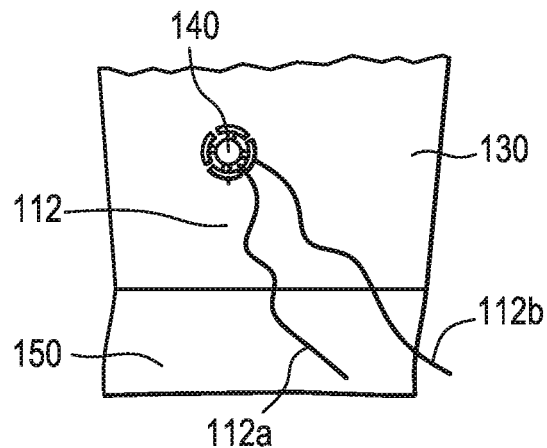
FIGS. 6A-6C are schematic sequential views of one exemplary embodiment for installing tissue augmentation constructs in a double row fixation.
Figure 6B:
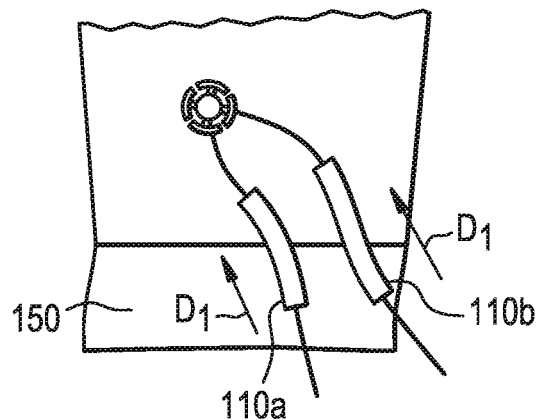
Figure 6C:
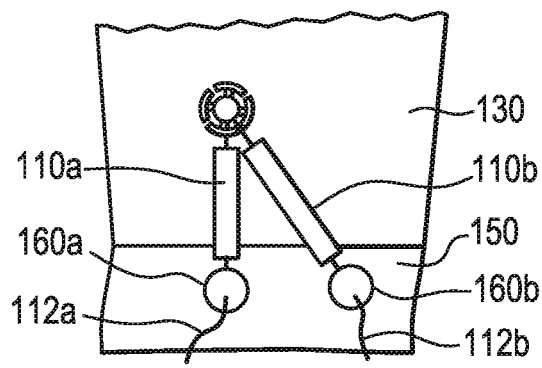

A first exemplary method of soft tissue repair using tissue augmentation blocks 110, illustrated as blocks 110a, 110b, in conjunction with a double row application or repair is shown in FIGS. 6A-6C. The method involves fixing a piece of soft tissue 130, e.g., rotator cuff, with respect to bone 150. If the tissue augmentation blocks 110a, 110b are dried, the tissue augmentation blocks 110a, 110b can require rehydrating ahead of the procedure. An incision can be made to perform the procedure using any one of a traditional open repair, an arthroscopic repair, or a mini-open repair. Once the surgeon has access to the surgical site and the tissue and bone have been prepared according to accepted surgical techniques, the surgeon can use a medial row stitch 140 to install the suture 112 in the soft tissue 130. Alternatively, any known stitch can be used. As shown in FIGS. 6A-6C, the medial row stitch 140 results in two suture limbs 112a, 112b extending outwardly from the soft tissue.

As shown in FIG. 6B, the tissue augmentation blocks 110a, 110b are disposed on suture limbs 112a, 112b, respectively. The tissue augmentation blocks 110a, 110b can be threaded onto the suture limbs 112a, 112b by hand, with an installation tool 200' (not shown), and/or with a threader 206, 206'. As discussed above with reference to FIG. 3, if the installation tool 200' is used, a suture limb 112a can be passed through the opening, or cinch loop, 212, then the handle portion 208 can be pulled to pull the threader 206 and suture limb through the tissue augmentation block 110a. Likewise, if just a threader 206, 206' is used, a force can be applied to the threader to draw the suture limb 112a into and through the tissue augmentation block. Once the suture limb 112a has been threaded in the tissue augmentation block 110a, the threader 206 can be removed, and, if the installation tool 200' was used, the tissue augmentation block 110a released from the installation tool 200'. The tissue augmentation blocks 110a, 110b can be threaded onto the suture limbs 112a, 112b at the surgical site inside of the body. Alternatively, the tissue augmentation blocks 110a, 110b can be threaded outside of the body.

Once the blocks 110a, 110b have been threaded onto the suture limbs 112a, 112b, they can be advanced in the direction $D_1$ along the respective suture limbs 112a, 112b. In the illustrated embodiment, the blocks 110a. 110b are disposed proximate to the medial stitch 140 because the length of the blocks 110a, 110b is similar to the length of the distance extending between the medial stitch 140 and the end of the tissue 130. However, in embodiments in which the length of the blocks 110a, 110b is less than that distance, the blocks 110a, 110b may not necessarily be proximate to the medial stitch 140, but can extend along some portion of the length of the limbs 112a, 112b extending between the medial stitch 140 and the end of the tissue 130. After the blocks 110a, 110b have been installed on the respective suture limbs 112a, 112b, the free ends of the suture limb 112a, 112b can be secured within the body. For example, the free ends of each suture limb 112a, 112b can be coupled to respective anchors 160a, 160b, as shown in FIG. 6C, which in some exemplary embodiments can be knotless anchors. The suture limbs 112a, 112b can then be tightened to secure the soft tissue 130 to the bone 150 before the anchors 160a, 160b are fully fixed in the bone 150, thus completing the double row lateral fixation associated with the medial stitch 140.

This procedure can be repeated as many times as required to satisfactorily fixate the soft tissue 130 to the bone 150. The blocks 110a, 110b provide a greater footprint for the limbs 112a, 1112b, and they may provide a greater surface area to distribute the loading forces of the suture limbs 112a, 112b onto the soft tissue 130. While the patient is healing from the procedure, new bands of tendon like tissue can form around the suture limbs 112a, 112b and into and around the blocks 110a, 110b to result in a more robust tissue formation in the soft tissue and between the soft tissue and bone. For example, blocks made from collagen scaffold or acellular dermal matrix material can be capable of remodeling while the patient is healing from the procedure into tendon like tissue and integrate with the native tissue. The additional coverage of tendon like tissue across the soft tissue can increase the strength of the tissue-to-bone connection and may prevent further injury.

Another exemplary soft tissue repair method is provided for in FIGS. 7A-7D. As shown, soft tissue 1030 is fixated to bone 1050 using an alternative double row application. Once the surgeon has access to the surgical site and the tissue, bone, and blocks 1010a-1010c have been prepared according to accepted surgical techniques, including those provided for herein, the surgeon can use medial row stitches 1040, 1042 to install sutures 1012, 1016 respectively, in the tissue 1030. The blocks 1010a-1010c can be similar to the blocks 110, 3010, 3110, or similar to other blocks and constructs as provided for in the present disclosure. Further, any known stitch can be used. The medial row stitch 1040 results in two suture limbs 1012a, 1012b extending outwardly from the soft tissue, and the second medial row stitch 1042 results in two suture limbs 1016a, 1016b extending outwardly from the soft tissue.

Figure 7A:
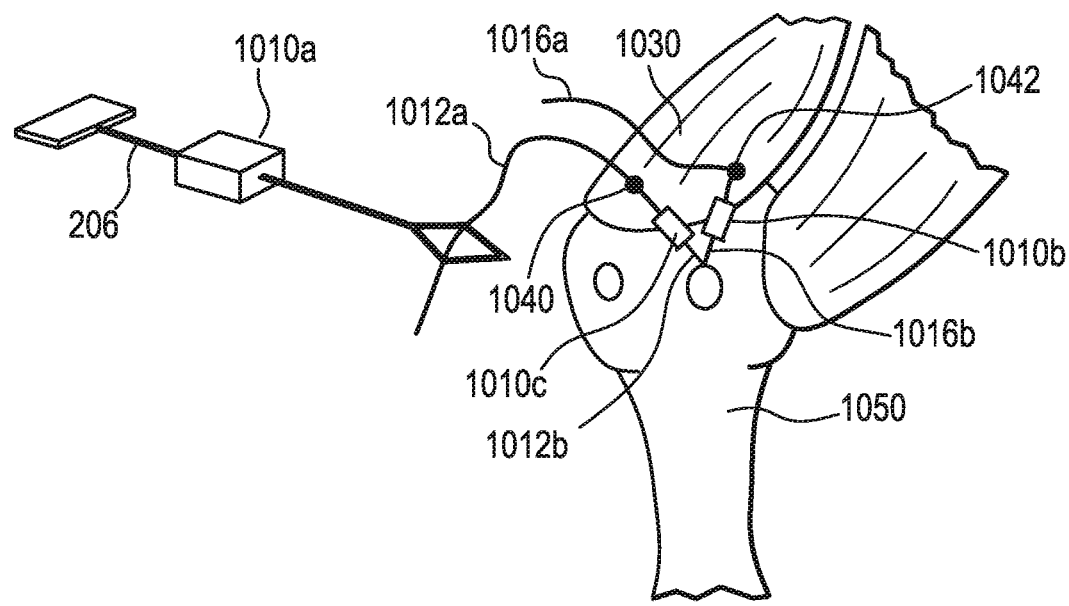
FIGS. 7A-7D are schematic sequential views of another exemplary embodiment for installing tissue augmentation constructs in a double row fixation.
Figure 7B:
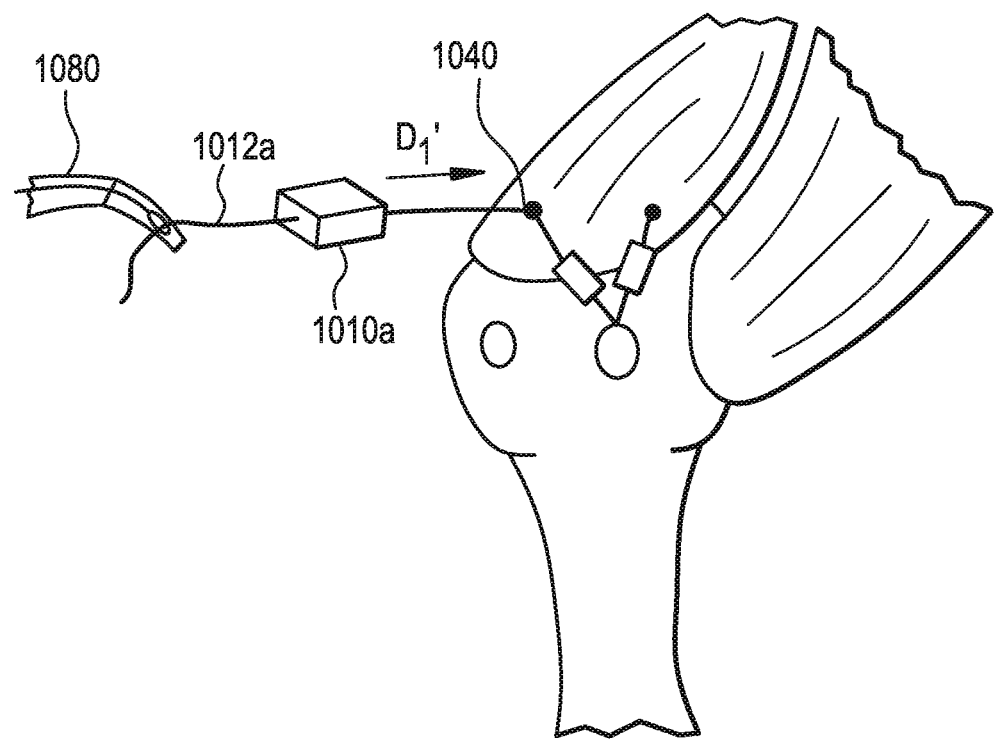

As shown in FIG. 7A, the blocks 1010a-1010c are threaded onto suture limbs 1012a, 1012b, 1016b, respectively, using techniques provided for throughout the present disclosure. For example, as illustrated in FIG. 7A, the block 1010a is threaded onto suture limb 1012a with the threader 206. Once the block 1010a has been threaded onto the suture limb 1012a, as shown in FIG. 7B, it can be advanced in the direction $D_1'$ along the suture limb 1012a until it is proximate the medial stitch 1040 since the length of the block 1010a is similar to the distance extending between the medial stitch 1040 and the end of the tissue 1030. Similarly, blocks 1010b, 1010c can be advanced along the suture limbs 1012b, 1016b until they are proximate the medial stitches 1040, 1042, respectively. The block 1010a can be advanced along the suture limbs with an instrument like a knot pusher 1080 or other instrument suitable for advancing the strip along the limb.

Figure 7C:
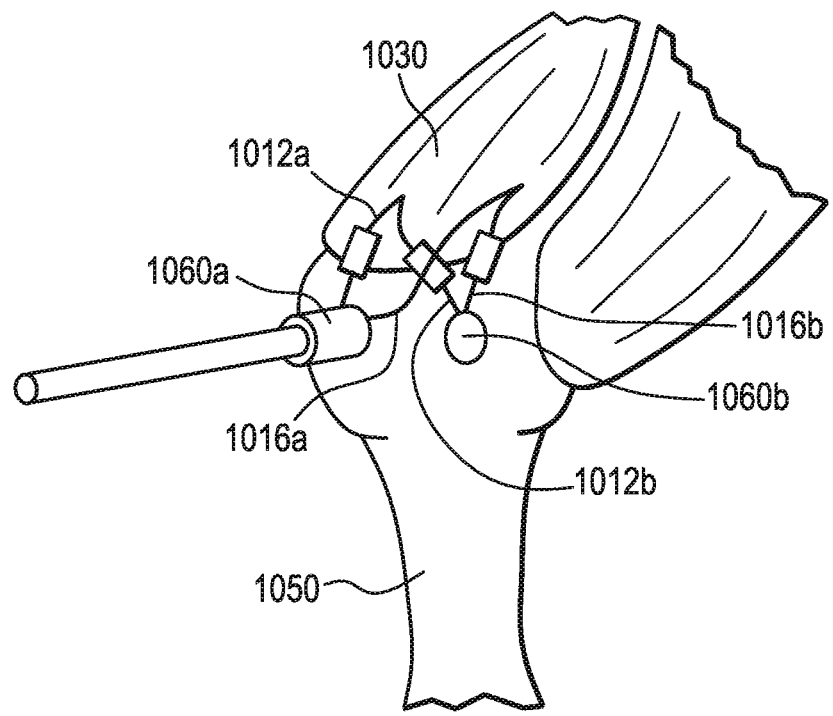
Figure 7D:
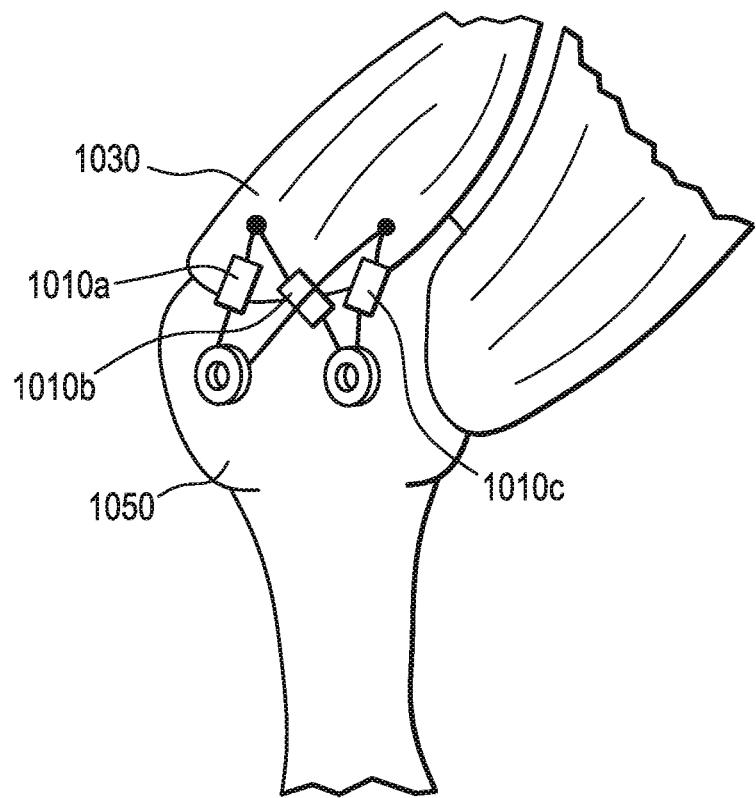

Once the blocks 1010b, 1010c have been installed on the respective suture limbs 1012b, 1016b, as shown in FIG. 7C, the free ends of suture limbs 1012b, 1016b can be secured within the body, for instance by attaching them to the anchor 1060b in a lateral row fixation. Similarly, once the block 1010a has been installed on the suture limbs 1012a, the free ends of the suture limbs 1012a, 1016a can be secured within the body, for instance, by attaching them to anchor 1060a in a lateral row fixation. As shown in FIG. 7C, the suture limbs 1012b, 1016b are installed into the anchor 1060b before the suture limbs 1012a, 1016a are installed into the anchor 1060a, such that suture limb 1016a rests atop the block 1010b. Alternatively, suture limb 1016a can be placed under suture limb 1012b by changing the order of fixation. The suture limbs 1012a, 1012b, 1016a, 1016b, can be tightened to secure the soft tissue 1030 to the bone 1050 before the anchors 1060a, 1060b are fully fixed in the bone 1050, as shown in FIG. 7D.

Figure 8A:
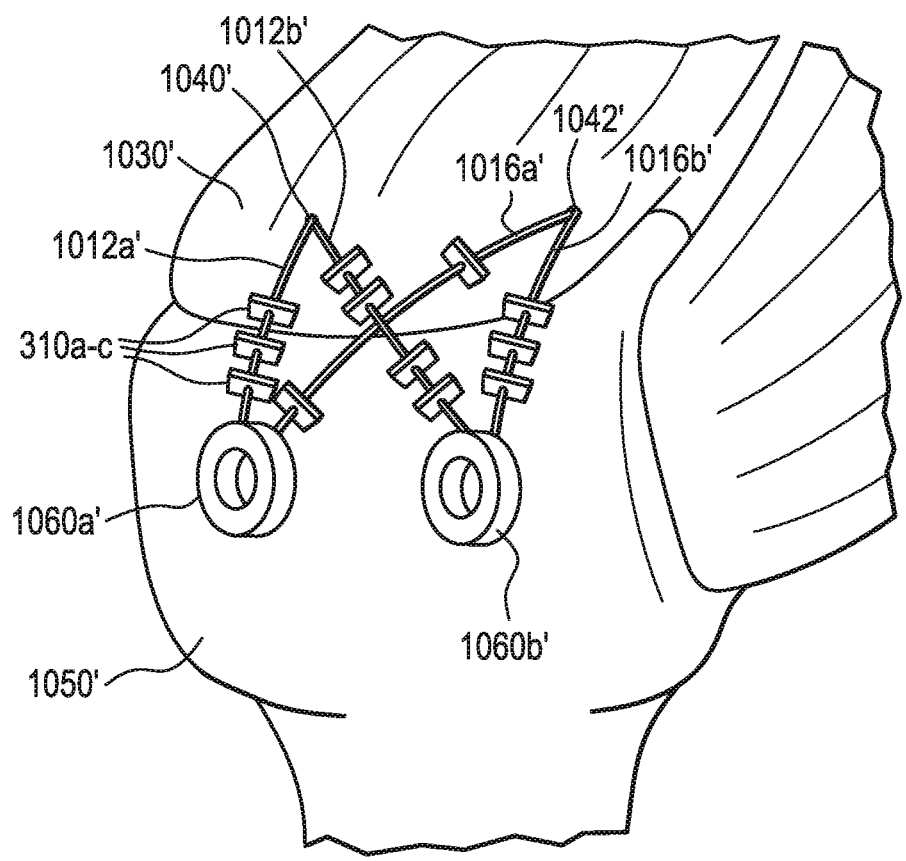
FIG. 8A is a schematic view of still another exemplary embodiment for installing tissue augmentation constructs in a double row fixation.
Figure 8B:
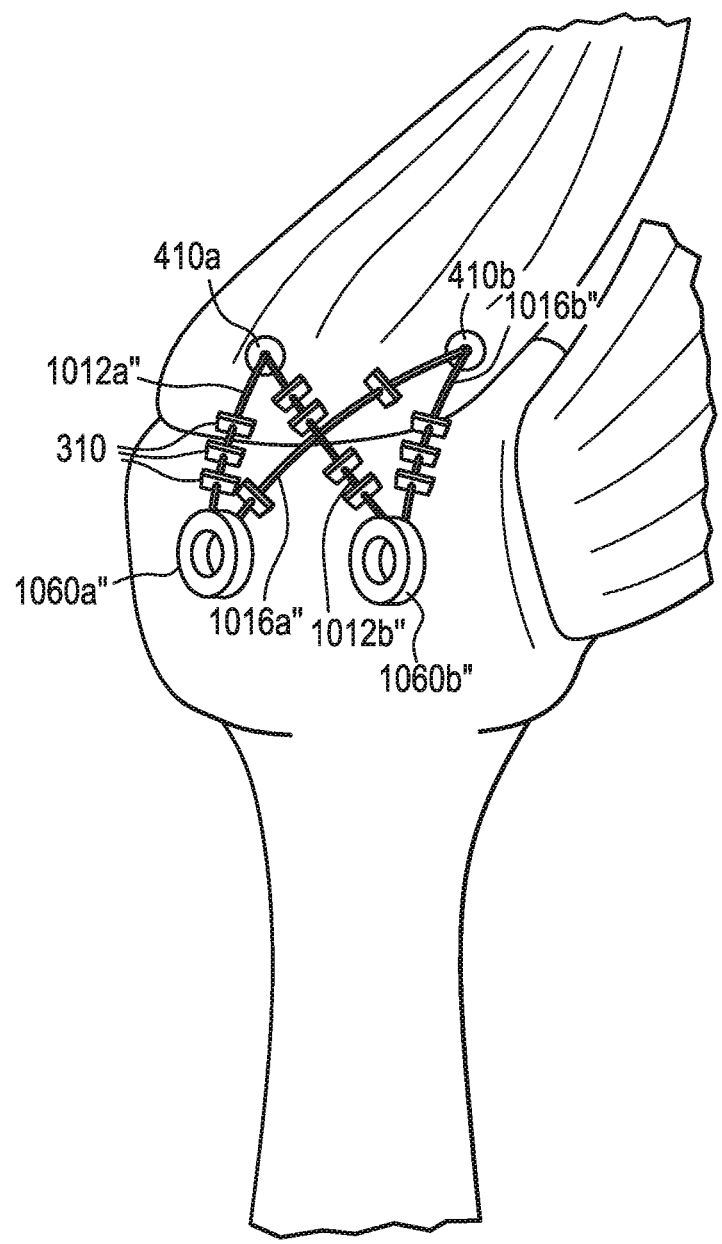
FIG. 8B is a schematic view of another exemplary embodiment for installing tissue augmentation constructs in a double row fixation.

An alternative exemplary method of soft tissue repair is illustrated in FIGS. 8A and 8B. The method fixates soft tissue 1030' to bone 1050' with an alternative double row application using the washers 310, as shown washers 310a, 310b, and 310c, in place of blocks 10, 110. The alternative double row application disclosed with respect to FIGS. 8A and 8B helps reduce added bulk that can occur when two constructs are stacked on top of each other when suture limbs cross each other as part of the repair design. Further, the use of washers in such formations helps reduce the possibility of any bunching that may occur when using constructs that are of a block configuration. Once the surgeon has access to the surgical site and the tissue, bone, and washers 310a-310c have been prepared according to accepted surgical techniques, including those provided for herein, the surgeon can use an initial mattress stitch to install sutures 1012', 1016' in the tissue 1030'. Alternatively, any known stitch can be used. A medial row stitch 1040' in the tissue 1030' results in two suture limbs 1012a', 1012b' extending outwardly from the tissue, and second medial row stitch 1042' results in two suture limbs 1016a', 1016b' extending outwardly from the tissue.

While the following discussion is made only to suture limb 1012a', for the sake of clarity, suture limbs 1012b', 1016a', 1016b', can have washers 310 threaded thereon in substantially the same manner. Washers 310a-310c are threaded onto suture limb 1012a', as illustrated in FIG. 8A. Alternatively, any number of washers 310 can be used on any of the suture limbs 1012a', 1012b', 1016a', 1016b'. The washers 310a-310c can be threaded onto the suture limb 1012a' by hand, with an installation tool, and/or with a threader using techniques provided for throughout the present application. Once washers 310a-310c have been threaded onto the suture limb 1012a' they can be advanced along the suture limb 1012a'. In the illustrated embodiment washers 310a-310c are disposed such that they are equally spread out over the tissue 1030' along the length of limb 1012a'. After the washers 310 have been installed on the respective suture limbs 1012a', 1012b', 1016a', 1016b', as shown in FIG. 8A, the free ends of the suture limbs 1012a', 1016a' and 1012b', 1016b' can be secured within the body, for instance, by attaching them to anchors 1060a' and 1060b', respectively. In the illustrated embodiment the suture limbs 1012b', 1016b' are coupled to the anchor 1060b' before the suture limbs 1012a', 1016a' are coupled into anchor 1060a', thus causing the suture limb 1016a' to rest atop the suture limb 1012b', although other configurations are possible without departing from the spirit of the present disclosure. The suture limbs 1012a', 1012b', 1016a', 1016b' can be tightened to secure the soft tissue 1030' to the bone 1050' before the anchors 1060a', 1060b' are fully fixed in the bone 1050'.

A further exemplary double row fixation method is illustrated in FIG. 8B. The method for fixing soft tissue 1030" to bone 1050" is substantially the same as the method illustrated in FIG. 8A but it further includes the use of the circular washers 410, as shown washers 410a and 410b, at a location of the medial stitch (not visible). The placement of the washers 410a, 410b as shown provides protection of the stitches disposed beneath the washers 410a, 410b, while also increasing the footprint of the suture limbs 1012a", 1012b", 1016a", 1016b" and allowing for the distribution of forces across a surface of the washers 410a, 410b that would otherwise be applied directly to the tissue 1030". In use, the washers 410a, 410b can be threaded onto the respective suture limbs 1012a", 1012b", 1016a", 1016b" before the washers 310' are threaded onto the suture limbs 1012a", 1012b", 1016a", 1016b". The double row fixation method can then be completed, for example, according to the process described above with regards to FIG. 8A. With respect to both the configurations illustrated in FIGS. 8A and 8B, the greater an angle formed by the sutures extending from the anchors 1060a', 1060b' and the washers 410a, 410b, the greater the stability of the repair.

Figure 9:
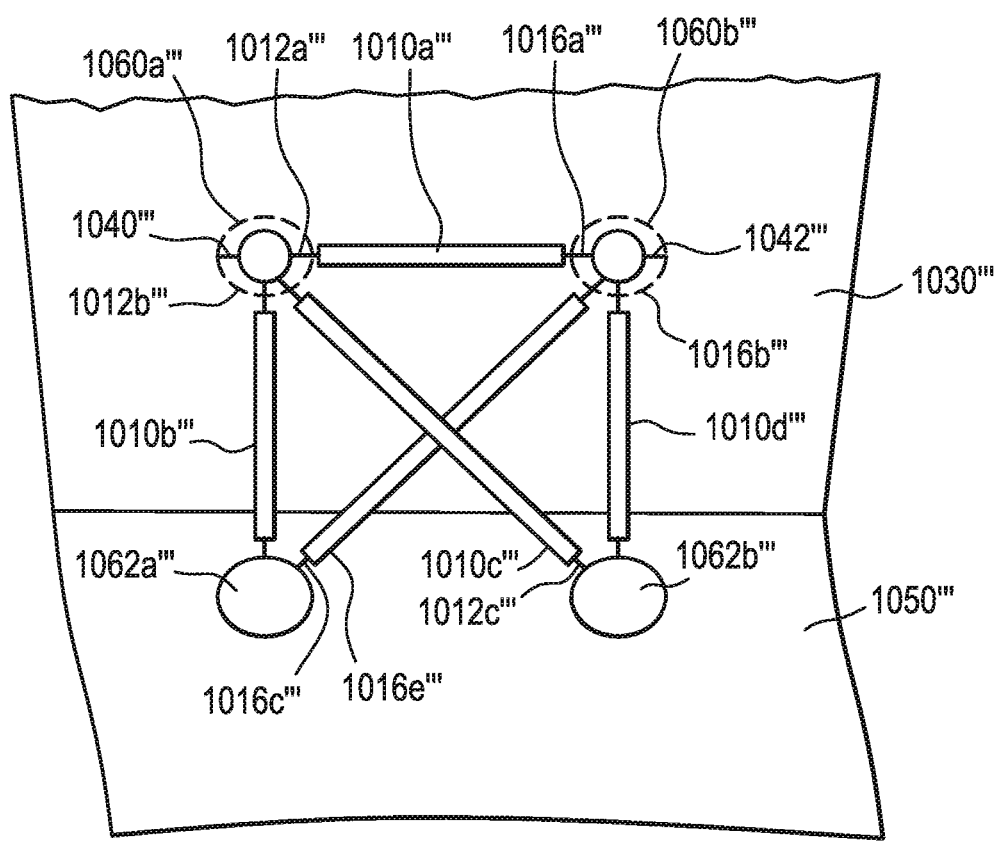
FIG. 9 is a schematic view of yet another exemplary embodiment for installing tissue augmentation constructs in a double row fixation.

A still further alternative method for securing soft tissue 1030''' to bone 1050''' using a double row fixation technique is illustrated in FIG. 9. Once the surgeon has accessed the surgical site and the tissue, bone, and blocks 1010a'''-d''' have been prepared according to the accepted surgical techniques, including those provided for herein, the surgeon can use initial mattress stitches 1040''', 1042''' to install sutures 1012a'''-c''' and 1016a'''-c''', respectively, in the tissue 1030'''. A first medial row anchor 1060a''' can be inserted into the bone 1050''' having three suture limbs 1012a'''-c''' extending therefrom, the three suture limbs 1012a'''-c''' being threaded through the tissue 1030''' with a first medial row stitch 1040'''. A second medial row anchor 1060b''' can be inserted into the bone 1050''' having three suture limbs 1016a'''-c''' extending therefrom, the three suture limbs 1016a'''-c''' being threaded through the tissue 1030''' with a second medial row stitch 1042'''.

As illustrated, block 1010a''', which can be in the form of a strip, tube, or cannulated block, among other disclosed configurations, is threaded onto one of the suture limbs 1012a''', 1016a''' using techniques provided for throughout this disclosure, and suture limbs 1012a''' and 1016a''' are tied together with a knot to secure the tissue 1030''' to the bone 1050'. Furthermore, once the knot has been formed, the block 1010a''' can be moved to cover the knot to reduce the possibility of tissue being damaged by the knot. Blocks 1010b''', 1010c''' can then threaded onto suture limbs 1012b''', 1012c''', respectively, using techniques provided for throughout this disclosure, and advanced to a location proximate the medial stitch 1040'''. Similarly, once blocks 1010d''', 1010e''' have been threaded onto the suture limbs 1016b''', 1016c''', they can be advanced to a location proximate the medial stitch 1042'''. After the blocks 1010b''', 1010d''' and 1010c''', 1010e''' have been installed on the respective suture limbs 1012b''', 1016b''' and 1012c''', 1016c''', the free ends of the suture limbs 1012b''', 1016b''' and 1012c''', 1016c''' can be secured within the body. For example, the free ends of each suture limb 1012b''', 1016c''' and 1012c''', 1016b''' can be coupled to the respective anchor 1062a''' and 1062b'''. The suture limbs 1012b''', 1012c''', 1016b''', 1016c''', can be tightened to secure the soft tissue 1030''' to the bone 1050''' before the anchors 1062a''', 1062b''' are fully fixed in the bone 1050'''.

Figure 10A:
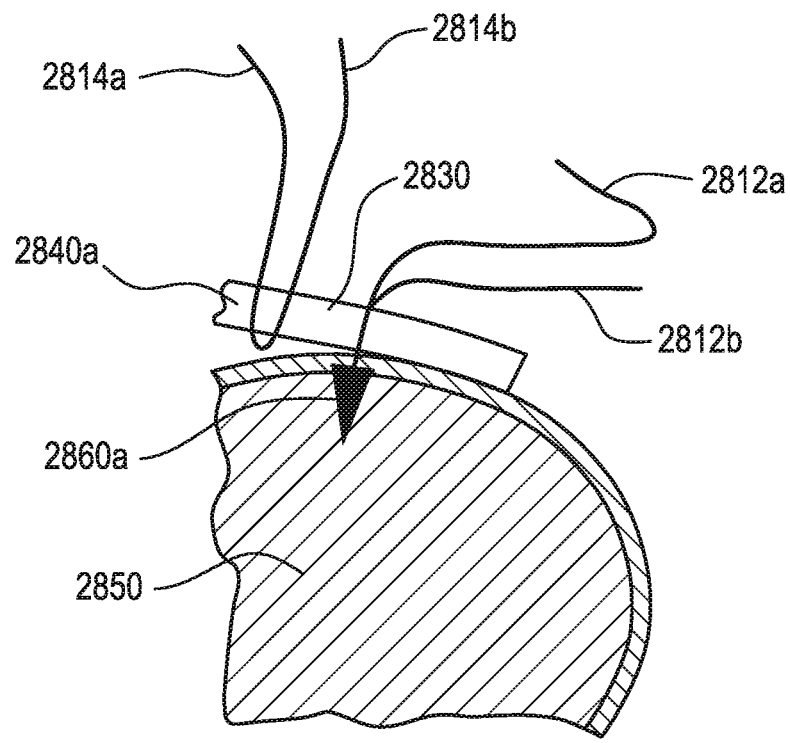
FIGS. 10A-10E are schematic sequential views of one exemplary embodiment for installing the tissue augmentation construct of FIG. 2G in a double row fixation.
Figure 10B:
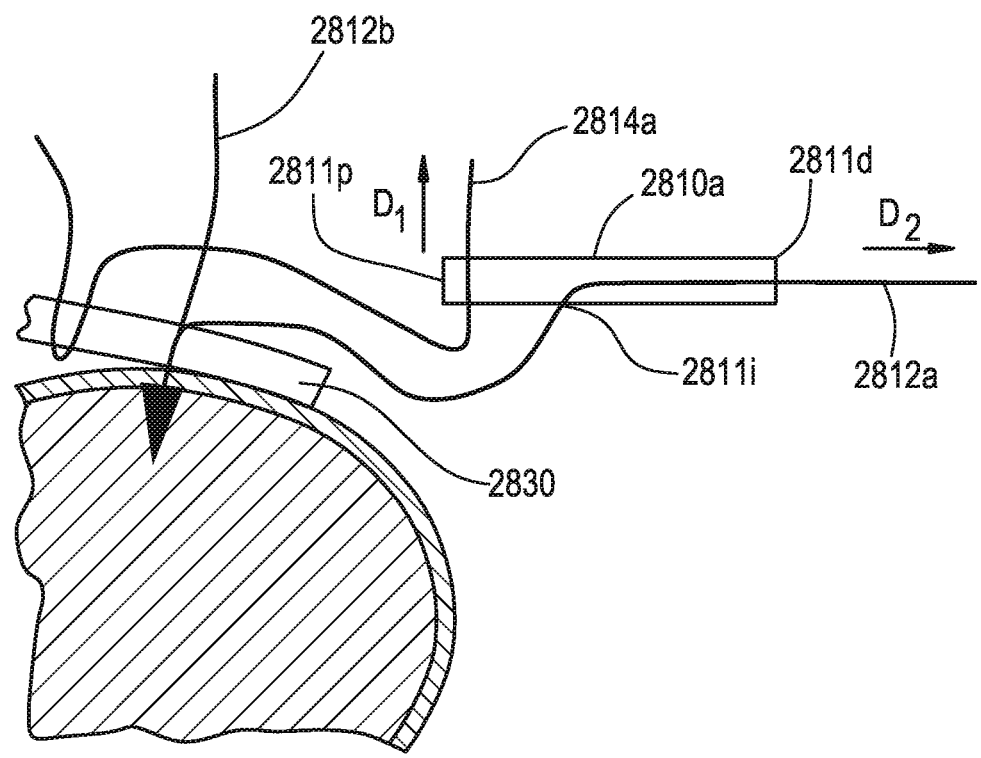
Figure 10C:
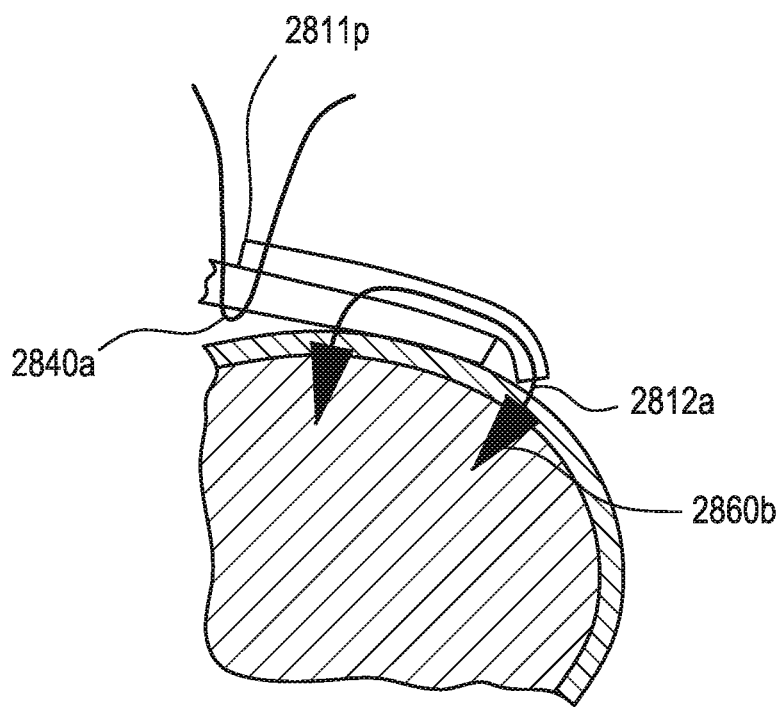
Figure 10D:
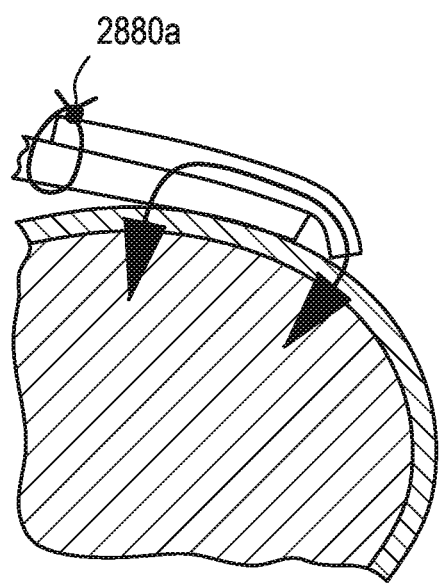
Figure 10E:
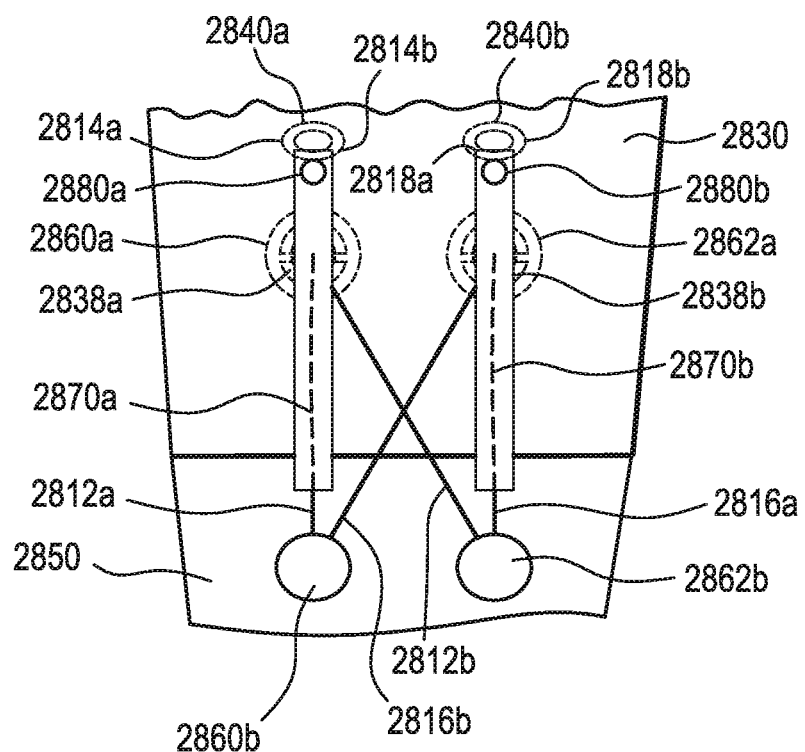

A further alternative double row fixation method of soft tissue repair is illustrated in FIGS. 10A-10E using the tissue augmentation construct 2810a of FIG. 2G, along with an identically configured tissue augmentation construct 2810b (as shown in FIG. 10E). The two constructs do not need to be identically configured, as they could be similarly configured and/or can have other configurations provided for herein or otherwise known to those skilled in the art. The method can fixate soft tissue 2830 to bone 2850 with an alternative extra-long block application to provide for additional coverage of the repair.

Once the surgeon has access to the surgical site and the tissue, bone, and tissue augmentation blocks have been prepared according to accepted surgical techniques including those provided for herein, the surgeon can insert a first anchor 2860a below the soft tissue 2830. The first anchor 2860a can have two suture limbs 2812a, 2812b extending therefrom. The two suture limbs 2812a, 2812b can be passed through the soft tissue 2830 to begin to assist in fixating the soft tissue 2830 to the bone 2850. A first mattress stitch 2840a can be made in the soft tissue 2030 medial to the first anchor 2860a. The first mattress stitch 2840a can result in two suture limbs 2814a, 2814b extending out of the soft tissue 2830.

The block 2810a can be threaded onto suture limbs 2812a, 2814a using techniques provided for throughout the present disclosure. For example, the suture limb 2814a can be associated with the proximal end 2811p of the first block 2810a by advancing the first threader 2809a in a first direction D1, as shown in FIG. 10B (the threader 2809a is not illustrated, but in view of the present disclosures, a person skilled in the art will understand how the threader 2809a can be operated to pass the suture limb 2814a through the proximal end 2811p of the first block 2810a). Further, the suture limb 2812a can be associated with an intermediate 2811i and distal portion 2811d of the block 2810a as shown by advancing the second threader 2809b in a second direction D2, as also shown in FIG. 10B. Although the respective threaders 2809a, 2809b for the respective suture limbs 2814a, 2812a are not illustrated, a person skilled in the art, in view of the present disclosures, will understand how the threaders can be operated to pass the respective suture limbs through portions of the first block 2810a. The block 2810a can then be advanced medially such that the proximal end 2811p of the block 2810a is proximate the first mattress stitch 2840a, as shown in FIG. 10C. This process can be repeated for the second block 2810b and its respective limbs 2816a, 2818b. For example, a second anchor 2862a can be installed below the soft tissue 2830, as shown in FIG. 10E, with the anchor 2862b having two repair suture limbs 2816a, 2816b extending from it. The two repair limbs 2816a, 2816b can be similarly passed through the soft tissue 2830 and a second mattress stitch 2840b (illustrated in FIG. 10E) can be made in the soft tissue 2030, medial to the second anchor 2862a. The second mattress stitch 2840b can result in two suture limbs 2818a, 2818b extending out of the soft tissue 2830. The resulting suture limbs 2816a, 2816b, 2818a, 2818b can be associated with block 2810b to continue the tissue fixation repair.

After the blocks 2810a, 2810b have been installed on the respective suture limbs 2812a, 2814a and 2816a, 2818a, the free ends of the suture limbs 2812a, 2812b, 2816a, 2816b can be secured within the body. For example, the free ends of each suture limb 2812a, 2816b and 2812b, 2816a can be coupled to the respective anchor 2860b and 2862b, as shown in FIGS. 10C and 10E. In the illustrated embodiment, suture limb 2812b and suture limb 2816b can be passed over the soft tissue 2830 to form an "X" configuration or shape such that suture limb 2812b is secured in the same anchor 2862b as suture limb 2816a and suture limb 2816b is secured in the same anchor 2860b as suture limb 2812a. Suture limbs 2812a, 2816a can be disposed through the respective central lumens 2870a, 2870b of the blocks 2810a, 2810b to increase the footprint of the suture limbs 2812a, 2816a, subsequently decreasing the likelihood of damaging the soft tissue 2830 as discussed above. Because the blocks 2810a, 2810b have a sufficient length, they can be installed so that they extend medially over first and second repairs 2838a, 2838b, as shown in FIG. 10E. The suture limbs 2812a, 2812b, 2816a, 2816b can then be tightened to secure the soft tissue 2830 to the bone 2850 before the anchors 2860b, 2862b are fully fixed in the bone 2850. The two limbs 2814a, 2814b can be tied together with a knot 2880a, and limbs 2818a, 2818b can be tied together with a knot 2880b to secure the proximal ends 2811p of the respective blocks 2810a, 2810b at a location medial of the repairs 2838a, 2838b, as shown in FIGS. 10D and 10E. A person skilled in the art will recognize a number of repairs that can be represented by the repairs 2838a, 2838b in view of the present disclosure and the skilled person's knowledge.

Rotator Cuff Repairs—Single Row Applications

Figure 11A:
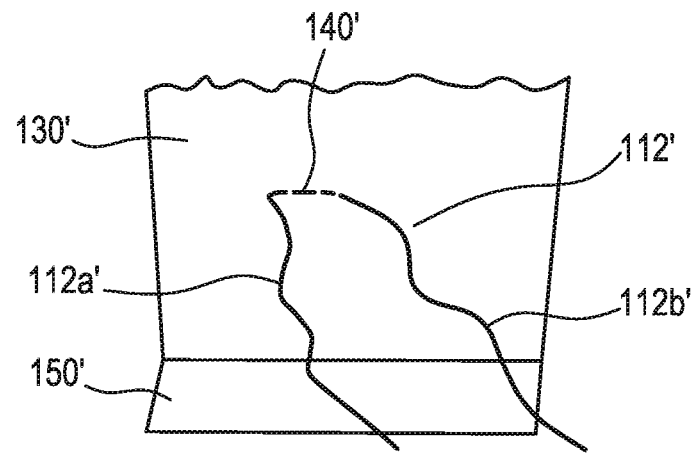
FIGS. 11A-11C are schematic sequential views of one exemplary embodiment for installing tissue augmentation constructs in a single row fixation.
Figure 11B:
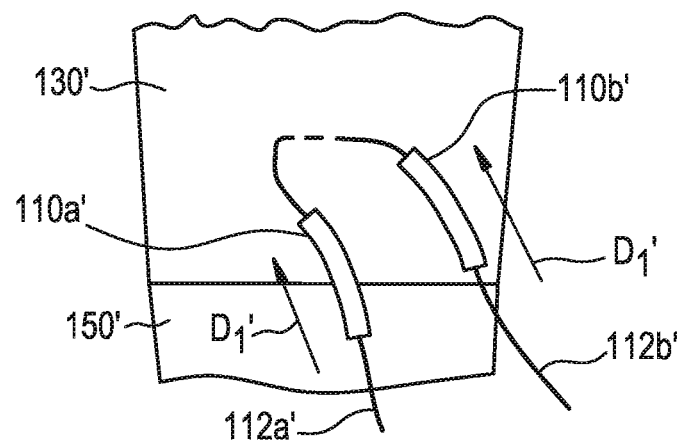
Figure 11C:
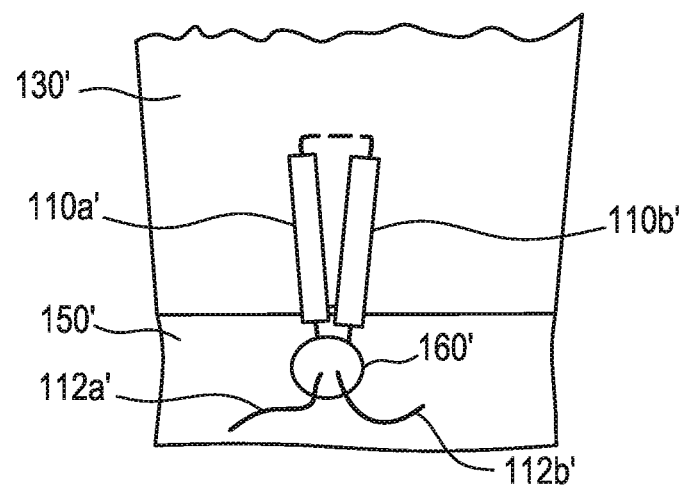

Another method of soft tissue repair is illustrated in FIGS. 11A-11C. The method fixates soft tissue 130' to bone 150' using a single row application. Once the surgeon has access to the surgical site and the tissue, bone, and blocks 110a', 110b' have been prepared according to accepted surgical techniques, including those provided for herein, the surgeon can use an initial mattress stitch to install suture 112' in the soft tissue 130'. Alternatively, any known stitch can be used. The mattress stitch 140' results in two suture limbs 112a', 112b' extending outwardly from the soft tissue.

As shown in FIG. 11B, the blocks 110a', 110b' are threaded on to suture limbs 112a', 112b', respectively, using techniques provided for throughout the present application. Once the blocks 110a', 110b' have been threaded onto the suture limbs 112a', 112b', they are advanced in the direction $D_1$' along the respective sutures until they are proximate the mattress stitch 140'. As described above, the location of the strips with respect to the stitch 140' can depend, at least in part, on the size of the blocks 110a', 110b' and the distance between the stitch 140' and the end of the tissue 130'. After the blocks 110a', 110b' have been installed on the respective suture limbs 112a', 112b', the free ends of the suture limbs 112a', 112b' can be secured within the body, for instance, by attaching them to a single anchor 160', as shown in FIG. 11C. The suture limbs 112a', 112b' can be tightened to secure the soft tissue 130' to the bone 150' before the anchor 160' is fully fixed in the bone 150', thus completing the single row fixation associated with the medial stitch 140'. In some exemplary embodiments a second anchor having two suture limbs extending therefrom, each limb having at least one tissue augmentation construct disposed thereon, can be implanted in a similar manner as the anchor 160', limbs 112a', 112b', and blocks 110a', 110b' with respect to the same tissue 130' and bone 150' to provide a second securement system for the tissue. As with all of the various configurations provided for herein, any number and combination of implants, e.g., bone anchors, sutures, and tissue augmentation constructs can be used to secure soft tissue to bone.

Figure 11D:
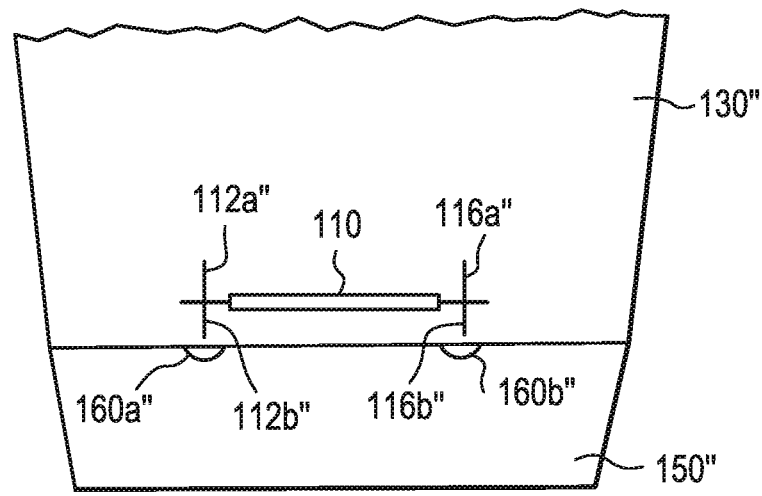
FIG. 11D is a schematic view of another exemplary embodiment for installing tissue augmentation constructs in a single row fixation.
Figure 11E:
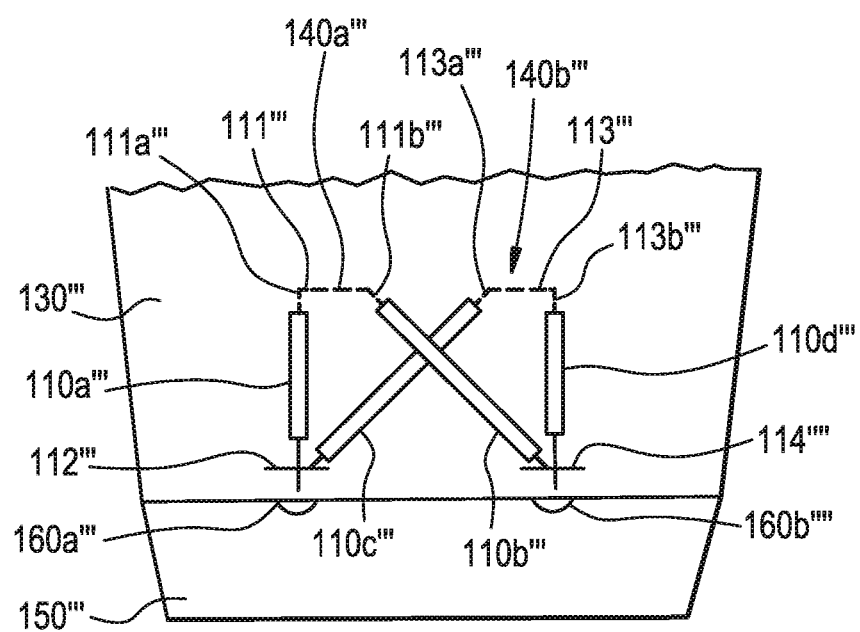
FIG. 11E is a schematic view of still another exemplary embodiment for installing tissue augmentation constructs in a single row fixation.
Figure 11F:
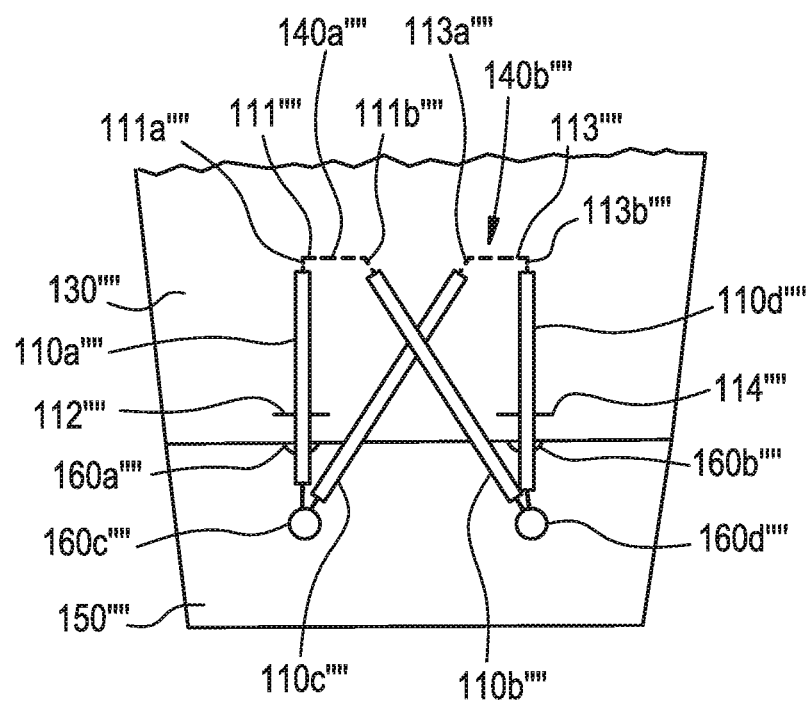
FIG. 11F is a schematic view of another exemplary embodiment for installing tissue augmentation constructs in a single row fixation.

Alternative single row applications are shown in FIGS. 11D-11F. In a first alternative single row application illustrated in FIG. 11D, a standard single row repair can be completed using two anchors 160a", 160b" installed in the bone 150" below the tissue 130". Anchors 160a", 160b" can each have two suture limbs 112a", 112b" and 116a", 116b" extending therefrom, respectively. Suture limbs 112a" and 116a" can be threaded through the soft tissue 130" and used to bring the soft tissue 130" into contact with the bone 150". Sutures limbs 112b" and 116b" can similarly be threaded through the soft tissue 130".

As shown in FIG. 11D, a tissue augmentation block 110" can be threaded on to one of the suture limbs 112b", 116b" using techniques provided for throughout this disclosure and advanced to a desired location with respect to the tissue 130". After the augmentation block 110" has been installed on one of the suture limbs, the free end of each suture limb 112b", 116b" can then be tied together using a knot, not shown. Furthermore, the block 110" can be moved into position such that it covers the knot, thereby minimizing any potential tissue abrasion by the knot, and is in contact with the tissue 130".

A second alternative single row application is illustrated in FIG. 11E. Similar to the procedure of FIG. 11D, a standard single row repair can be completed using two anchors 160a'", 160b'" installed in bone 150'" below tissue 130'". As shown, a first suture 111'" can be installed medially of the repair with a mattress stitch 140a'", such that two suture limbs 111a'", 111b'" extend from the tissue 130'", and a second suture 113'" can be installed medially of the repair with a second mattress stitch 140b'", such that two suture limbs 113a'", 113b'" extend from the tissue 130'". In some instances, after the two mattress stitches 140a'", 140b'" have been installed in the tissue 130'", anchors 160a'", 160b'" can be installed into the bone 150'" below the tissue 130'". Operative sutures 112'", 114'" can be used to couple the tissue 130'" to the anchors 160a'", 160b'" respectively attached thereto according to accepted surgical practice.

Tissue augmentation blocks 110a'"-d'" can be threaded on to the suture limbs 111a'", 111b'", 113a'", 113b'" using techniques provided for throughout this disclosure and can be advanced along the respective sutures to desired locations. The free ends of the suture limbs 111a'", 113a'" and 111b'", 113b'" can be tied to, and tightened about, operative sutures 112'", 114'" respectively.

FIG. 11F illustrates a further alternative single row application. A first suture 111"" can be installed medially with a mattress stitch 140a"" such that two suture limbs 111a"", 111b" " extend from the tissue 130"", and a second suture 113"" can be installed with a second mattress stitch 140b"" such that two suture limbs 113a"", 113b"" extend from the tissue 130"". After the first and second sutures 111"", 113"" have been installed, first and second medial anchors 160a"", 160b"" are installed in the bone 150"", below the tissue 130"". Operative sutures 112"", 114" " coupled to anchors 160a"", 160b"", respectively, can be used to perform the repair such that the tissue 130"" is brought into contact with the bone 150"", according to accepted surgical practices. Once the tissue 130"" has been repaired, blocks 110a""-d"" can be installed onto suture limbs 111a"", 111b"", 113a"", 113b"" using techniques provided for throughout this disclosure. Free ends of the suture limbs 111a"", 113a"" and 111b"", 113b"" can be secured within the body, for instance, by attaching them to anchors 160c"" and 160d"", respectively. The suture limbs 111a"", 111b"", 113a"", 113b"" can be tightened to further secure the blocks 110a""-d"" to the soft tissue 130"" such that the repairs made with the sutures 112"", 114"" are covered by tissue augmentation blocks.

Figure 12:
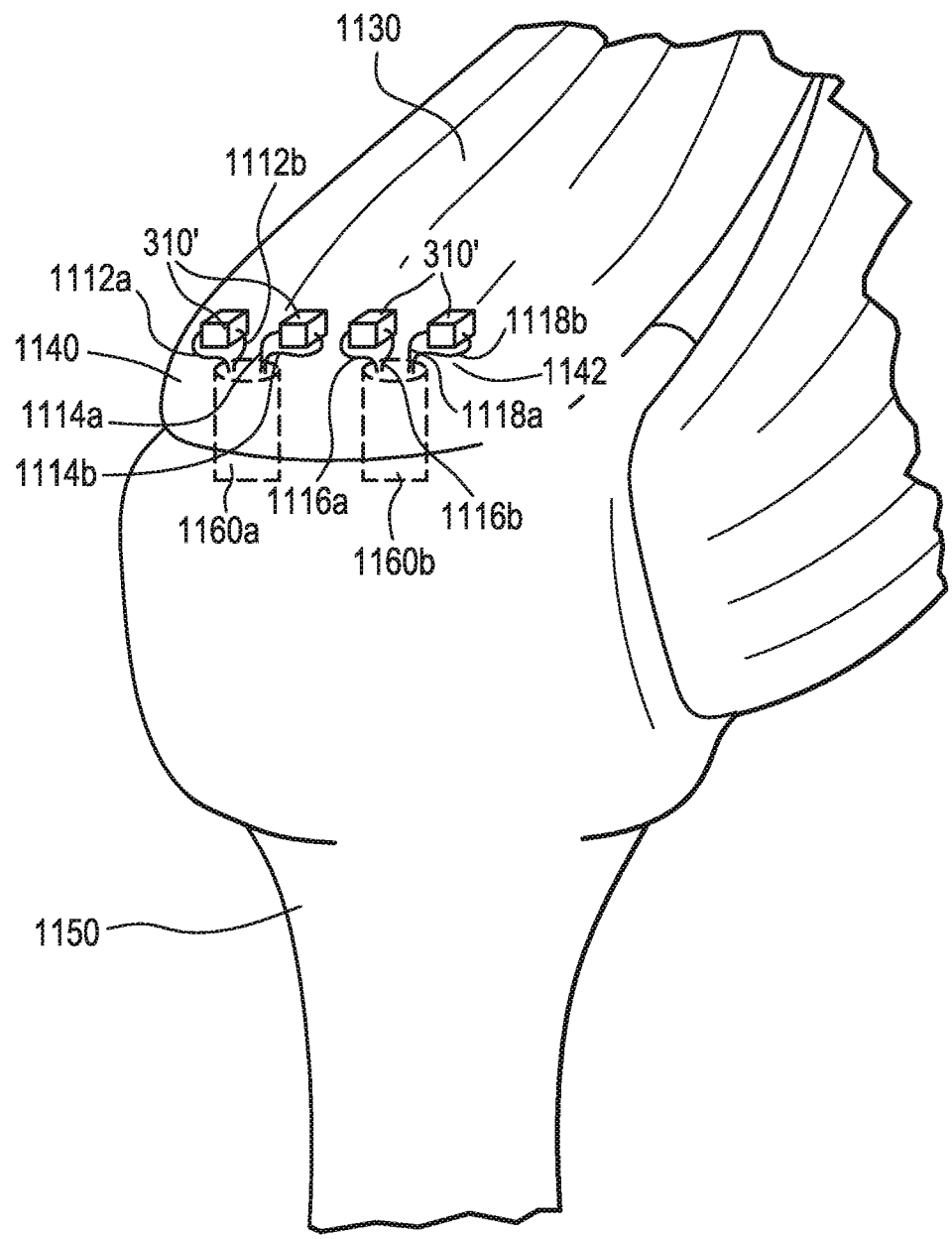
FIG. 12 is a schematic view of yet another exemplary embodiment for installing tissue augmentation constructs in a single row fixation.

A further exemplary method of soft tissue repair is illustrated in FIG. 12. The method fixates a piece of soft tissue 1130, e.g., rotator cuff, to bone 1150 using a single row fixation. Once the surgeon has access to the surgical site and the tissue, bone, and tissue augmentation block have been prepared according to accepted surgical techniques including those provided for herein, the surgeon can use a mattress row stitch 1140 to install sutures 1112, 1114 and mattress row stitch 1142 to install sutures 1116, 1118 in the soft tissue 1130. Sutures 1112, 1114 and 1116, 1118 are installed into anchors 1160a, 1160b, respectively, below the tissue 1130 in the bone 1150. As shown in FIG. 12, each of the mattress stitches 1140 and 1142 results in four suture limbs 1112a, 1112b, 1114a, 1114b and suture limbs 1116a, 1116b, 1118a, 1118b extending outwardly from the soft tissue.

At least one block 310' can be threaded on at least one of the suture limbs of each suture 1112, 1114, 1116, 1118. Block 310' can be similar to block 310, although one difference between the two is that a thickness of the block 310' is greater than the thickness of block 310. Alternatively, block 310' can have any suitable dimension as desired for a given procedure. In some embodiments, each of the suture limbs 1112a, 1114a, 1116a, 1118a can have a block 310' threaded thereon using techniques provided for throughout the present disclosure, and then the two suture limbs of each pair can be tied together. For example, suture limbs 1112a, 1112b can be tied together after block 310' has been threaded thereon. After the suture limbs 1112a, 1112b have been tied together, the block 310' can be moved over the knot to buffer, or cover, the knot. This process can be repeated for each of the suture limb pairs 1114a and 1114b, 1116a and 1116b, and 1118a and 1118b.

Figure 13:
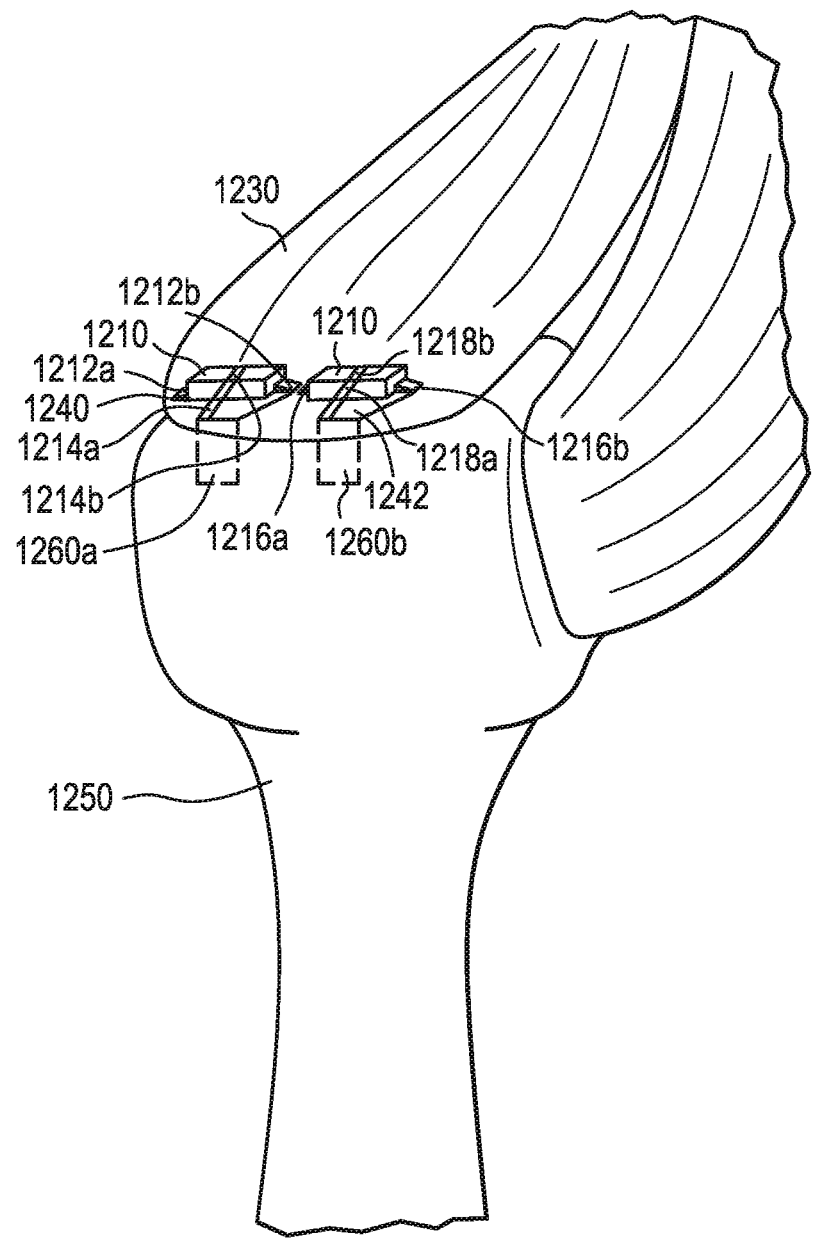
FIG. 13 is a schematic view of another exemplary embodiment for installing tissue augmentation constructs in a single row fixation.

A still further exemplary method of soft tissue repair is illustrated in FIG. 13. The method fixates a piece of soft tissue 1230, e.g., rotator cuff, to bone 1250 using a single row rip-stop stitch. Once the surgeon has access to the surgical site and the tissue, bone, and tissue augmentation constructs have been prepared according to accepted surgical techniques including those provided for herein, the surgeon can use a stitch 1240 to couple the sutures 1212, 1214 to anchor 1260a and a stitch 1242 to couple the sutures 1216, 1218 to anchor 1260b. Any known stitch can be used. As shown in FIG. 13, the stitch 1240 results in four suture limbs 1212a, 1212b, 1214a, 1214b extending outwardly from the soft tissue, and the stitch 1242 also results in four suture limbs 1216a, 1216b, 1218a, 1218b extending outwardly from the soft tissue.

A tissue augmentation block 1210 can be threaded on to one of the suture limbs associated with each mattress knot 1240, 1242 using techniques provided for throughout the present disclosure. The block 1210 in the illustrated embodiment is a construct similar to the bars 3010, 3110. In the illustrated embodiment, the suture limbs 1212a and 1216a each have the block 1210 associated with it. Once each of the suture limbs 1212a, 1216a has a block 1210 threaded thereon, the suture limbs 1212a, 1216a can be tied together with a complementary suture limb 1212b, 1216b, respectively. Furthermore, the block 1210 can be slid over the knot to buffer, or cover, the knot, as illustrated. Then the suture limbs 1214a, 1214b can be tied together over the top of block 1210 to create a rip-stop stitch. Advantageously, suture limbs 1214a, 1214b, once tied together will be prevented from tearing through the soft tissue 1230 because the block 1210 will act as a buffer thereby distributing the applied load. This process can be repeated for the second mattress stitch 1242.

Figure 14:
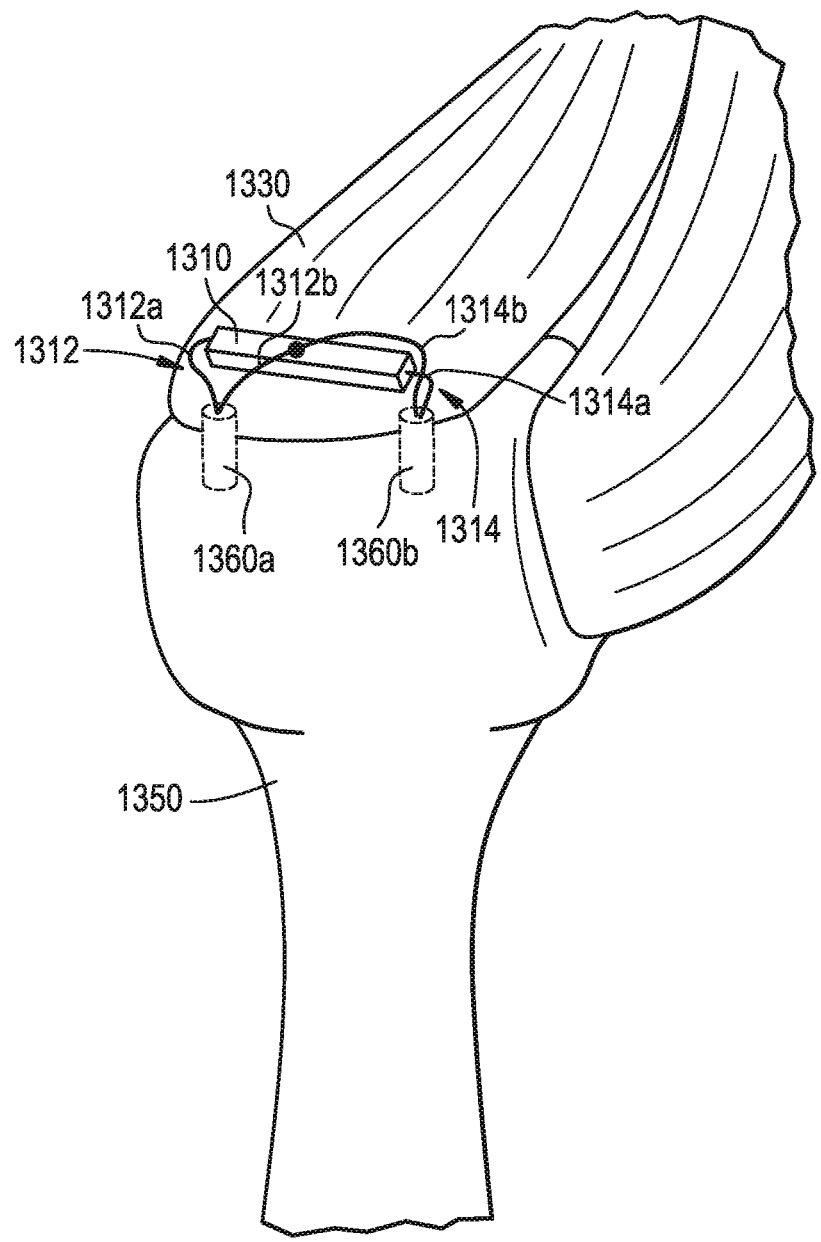
FIG. 14 is a schematic view of still another exemplary embodiment for installing tissue augmentation constructs in a single row fixation.
Figure 15:
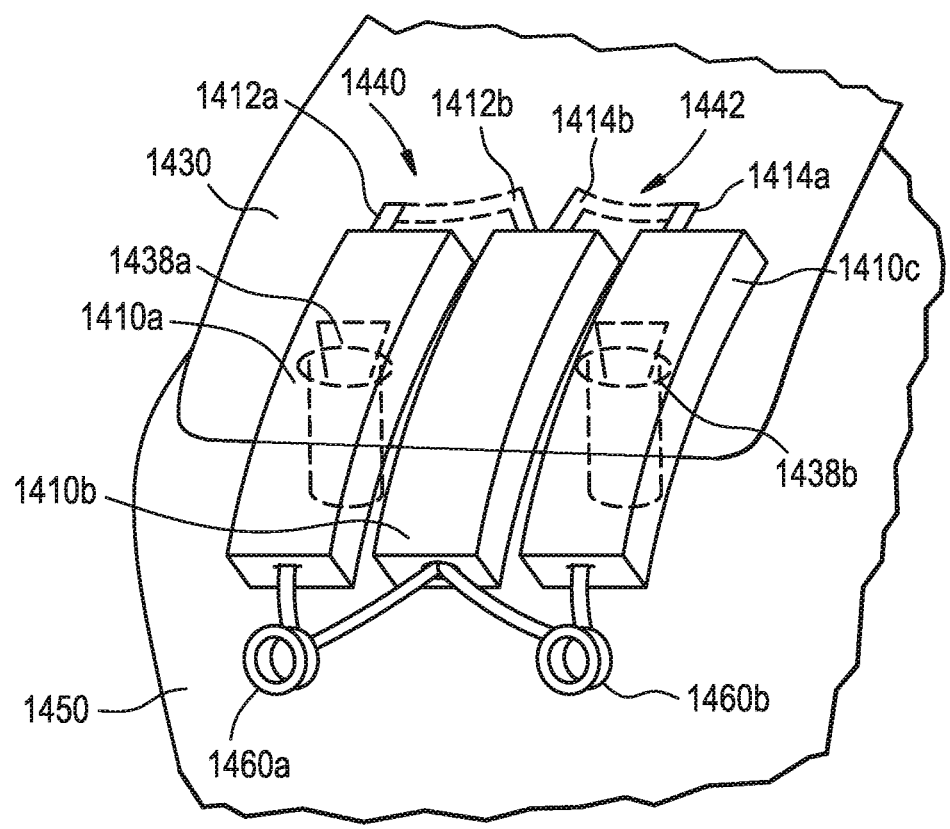
FIG. 15 is a schematic view of another exemplary embodiment for installing tissue augmentation constructs in a single row fixation.

FIG. 14 illustrates a further method of soft tissue repair. The method provides for fixating a piece of soft tissue 1330, e.g. rotator cuff, to bone 1350, using an anterior-posterior mattress stitch extending between anchors. Once the surgeon has access to the surgical site and the tissue, bone, and tissue augmentation block have been prepared according to accepted surgical techniques including those provided for herein, the surgeon can thread two limbs 1312a, 1312b of a suture 1312 coupled to an anchor 1360a through tissue 1330. Similarly, a second anchor 1360b can be implanted in the bone 1350 having suture limbs 1314a, 1314b of a suture 1314 extending from the anchor 1360b through tissue 1330. Any known stitch can be used.

One block 1310 can be threaded on to either of the suture limbs 1312a, 1314a of either anchor 1360a, 1360b using techniques provided for throughout the present disclosure. The illustrated block 1310 has a length approximately in the range of about 10 millimeters to about 20 millimeters, a width approximately in the range of about 2 millimeters to about 5 millimeters, and a height approximately in the range of about 1 millimeter to about 3 millimeters. Once the suture limb 1312a has a block 1310 threaded thereon, the suture limb 1312a can be tied together with the suture limb 1314a. Furthermore, after the suture limbs 1312a, 1314a have been tied together, the block 1310 can be slid over the knot, not shown, to buffer, or cover, the knot. Then the suture limbs 1312b, 1314b can be tied together over the block 1310. Advantageously, the suture limbs 1312b, 1314b, once tied together, will be prevented from tearing through the soft tissue 1330 because the block 1310 will act as a buffer between them distributing the applied load.

An alternative single row fixation method of soft tissue repair is illustrated in FIG. 14. The method fixates soft tissue 1430 to bone 1450 with an alternative, extra-long and extra-wide block application. Once the surgeon has access to the surgical site and the tissue, bone, and tissue augmentation blocks have been prepared according to accepted surgical techniques including those provided for herein, the surgeon can fixate the soft tissue 1430 to the bone 1450 according to accepted surgical techniques to create the repairs 1438a, 1438b, shown in phantom. Once the repairs 1438a, 1438b are completed, a first mattress stitch 1440 is made through the soft tissue 1430, medial to the soft tissue repair 1438a, and a second mattress stitch 1442 is made, medial to the repair 1438b, to install the sutures 1412 and 1414 in the soft tissue 1430. The first mattress stitch 1440 results in two suture limbs 1412a, 1412b extending outwardly from the soft tissue 1430, and the second mattress stitch 1442 results in two suture limbs 1414a, 1414b extending outwardly from the soft tissue. Alternatively, the stitches 1440, 1442 can be made before the repairs 1438a, 1438b are performed.

The blocks 1410a-1410c have a configuration that can be considered to be a larger version of some other block configurations provided for herein. As shown, the blocks 1410a-1410c have a substantially rectangular shape, like the cannulated block configurations 3010, 3110 of FIGS. 2E and 2F, but with a more substantial thickness. Other configurations of the blocks 1410a-1410c, particularly in view of the present disclosures, are also possible, including but not limited to configurations that are more akin to one or more of the tape strips 10, the tubes 110, and the washers 310, 410, or combinations thereof. In one exemplary embodiment, the blocks 1410a-1410c can have a length approximately in the range of about 15 millimeters to about 25 millimeters, a width approximately in the range of about 4 millimeters to about 5 millimeters, and a thickness approximately in the range of about 1 millimeter to about 3 millimeters.

The blocks 1410a, 1410c can be threaded onto suture limbs 1412a, 1414a using techniques provided for throughout the present disclosure. In the illustrated embodiment, the block 1410b has two suture limbs, the suture limbs 1412b and 1414b, associated with it. While this latter configuration can also be achieved using the techniques provided for throughout the present disclosure, in one exemplary method, a single installation tool can be used to associate both suture limbs 1412b, 1414b with the block 1410b at the same time. For example, the threader 206 (not shown) can be disposed in the block 1410b and can have both limbs passed through its distal opening 212 (not shown) before operating the threader as described above to associate the limbs 1412b, 1414b with the block 1410b. Alternatively, the block 1410b can have two threaders disposed therethrough to thread the suture limbs 1412b, 1414b individually therethrough. In a further alternative, a single threader can be threaded through the block 1410b to pull the suture limb 1412b through the block 1410b, and then the threader, or a different threader, can be inserted into the block 1410b to thread the suture limb 1414b through the block 1410b.

Once the blocks 1410a-1410c have been threaded onto the suture limbs 1412a, 1412b, 1414a, 1414b they can be advanced along the suture limbs 1412a, 1412b, 1414a, 1414b, respectively, until they are proximate the medial stitches 1040, 1042. One advantage of the blocks 1410a-1410c is that they can be sized to cover a substantial portion of a surgical site that includes a perimeter defined by the anchors 1460a, 1460b and the mattress stitches 1440, 1442. Other advantages of tissue augmentation constructs provided for herein are also applicable. After the blocks 1410a-1410c have been installed on the respective suture limbs, the free ends of the suture limbs 1412a, 1412b and 1414a, 1414b can secured within the body, for instance, by attaching them to anchors 1460a and 1460b, respectively. The suture limbs 1412a, 1412b, 1414a, 1414b, can be tightened to secure the soft tissue 1430 to the bone 1450 before the anchors 1460a, 1460b are fully fixed in the bone 1450.

The various embodiments described above can be used in conjunction with any of the other embodiments described above such that some of the soft tissue is secured with a double-row application and some portions are secured with the single row application. Still further, any number of suture limbs and tissue augmentation blocks can be used during any particular procedure, including disposing multiple strips on a single limb and/or using only a single limb or more than two limbs.

Rotator Cuff Repairs—Partial Tear Repairs

Figure 16A:
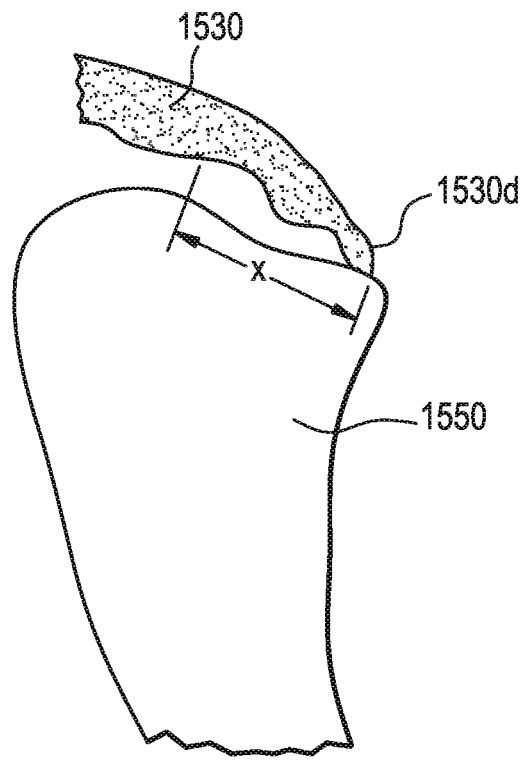
FIGS. 16A-16C are schematic views of yet another exemplary embodiment for installing tissue augmentation constructs in a single row fixation.
Figure 16B:
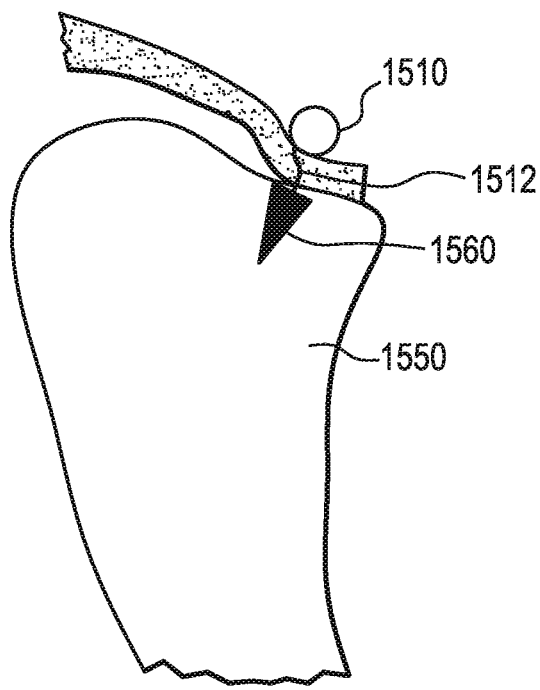
Figure 16C:
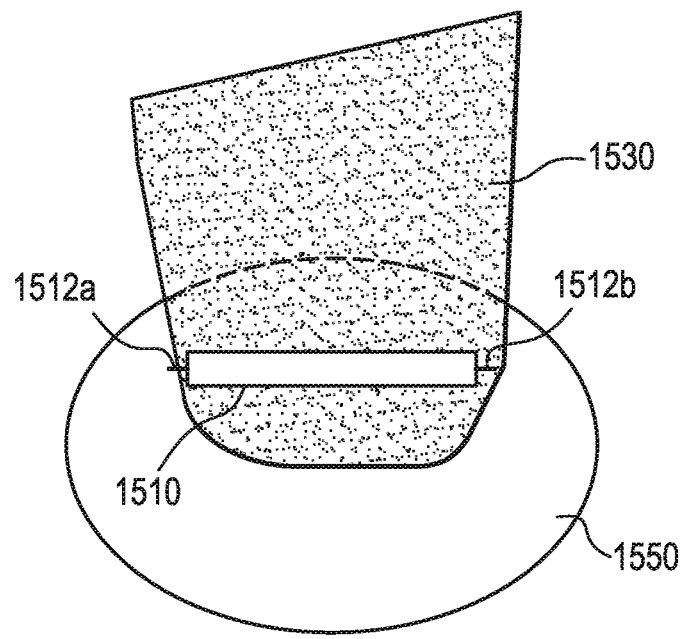

An exemplary method of partial tear soft tissue repair is illustrated in FIGS. 16A-16C. The method fixates a piece of soft tissue 1530, e.g. rotator cuff, to bone 1550 in a situation where a partial tear occurs. As shown in FIG. 16A, soft tissue 1530 is maintained in contact with the bone 1550 at 1530d. The length X shows what a "healthy" footprint of contact should be between the tissue 1530 and bone 1550. This procedure can aid in the reattachment of the soft tissue to the bone to create a "healthy" footprint. Prior art procedures can result in a depression at the attachment point due to the necessary compression of the suture against the tissue, thus causing a weakening of the tissue, and more generally, the rotator cuff.

Once the surgeon has access to the surgical site and the tissue, bone, and the tissue augmentation construct have been prepared according to accepted surgical techniques, including those provided for herein, the surgeon can install an anchor 1560 into the bone 1550. The anchor 1560 can have a suture 1512 coupled thereto having two suture tails 1512a, 1512b extending therefrom that can be passed through the soft tissue 1530. A block 1510 can be threaded onto at least one of the suture tails 1512a, 1512b. The block 1510 can be any of the configurations provided for herein, including but not limited to the blocks 10, 110, 3010, 3110, 310, and 410 and the patches 2210, 2310, 2410, and 2510, which are described below. The constructs 1510 can be threaded onto the suture limb 1512a, for example, using techniques provided for throughout the present disclosure, and advanced along the suture 1512a until it is proximate the tissue 1530. After the construct 1510 has been installed on one of the suture limbs, the free end of each suture limb 1512a, 1512b can then be tied together using a knot, not shown, to bring the damaged tissue 1530 into contact with the bone 1550. The construct 1510 can then be moved into position such that it covers the knot and is in contact with the tissue 1530. As shown in FIG. 16B, the construct 1510, once installed, can add height to the depression to build back height to the repaired tissue 1530.

Methods of Use—Non-Rotator Cuff Repairs

The present disclosure contemplates that the tissue augmentation constructs provided for herein have applications outside of rotator cuff repairs as augmentation constructs. Some, non-limiting examples of those alternative procedures are provided for below. These examples are by no means exhaustive. Further, a person having skill in the art will understand how some of the disclosures provided for in this non-rotator cuff repair section can be adapted for use in rotator cuff repair procedures. Each of the embodiments described below, including those discussed after the non-rotator cuff repairs (i.e., labrum repair or augmentation, ACL repair, Achilles repair, AC joint-repair, meniscal repair, and superior capsule reconstruction), are discussed with respect to using a tissue augmentation construct, which includes any of the blocks and patches disclosed herein or otherwise derivable from the present disclosure. A person skilled in the art, in view of the present disclosures, will understand how to adapt various tissue augmentation constructs for use in the various procedures. Further, in exemplary embodiments of each of the methods described in the present disclosure, collagen, for example, can be used as part of, or to form entirely or almost entirely, the construct. This allows the construct to grow in the area of the repair once healed. Other materials can also be used to form the constructs, including others that achieve a similar result as collagen.

Non-Rotator Cuff Repairs—Labrum Defect Corrections

Figure 17A:
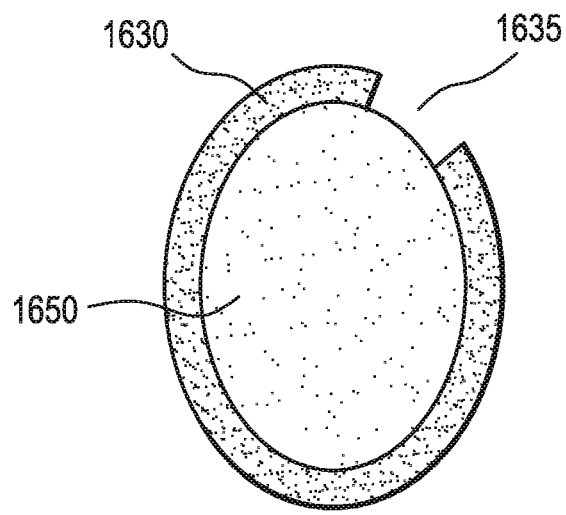
FIGS. 17A-17D are schematic sequential views of one exemplary embodiment for repairing soft tissue.
Figure 17B:
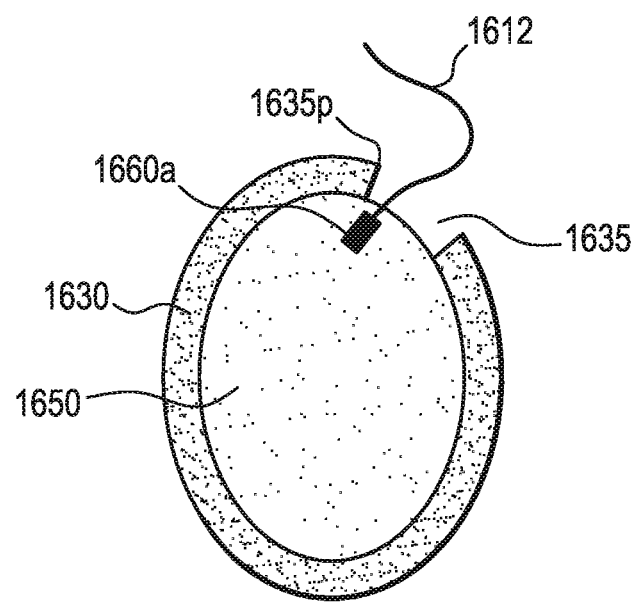
Figure 17C:
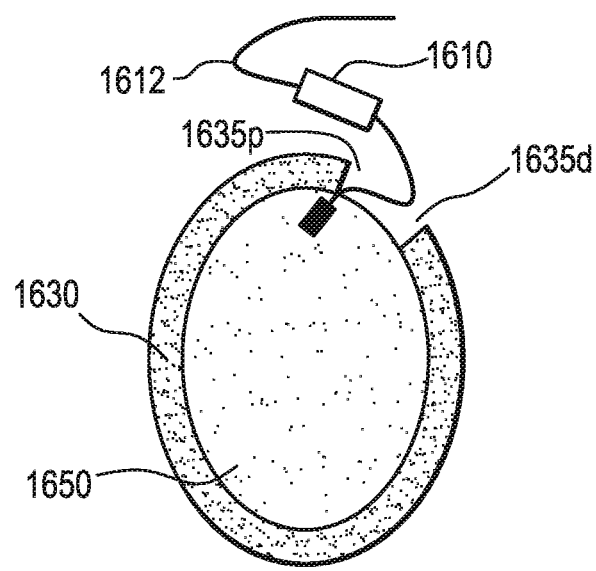
Figure 17D:
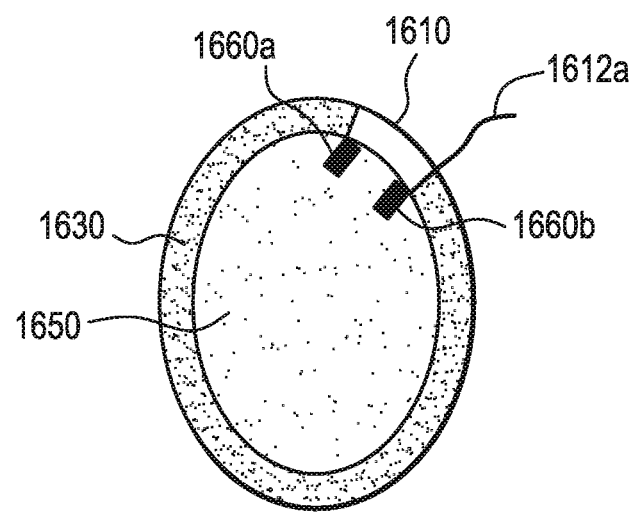

One alternative procedure is illustrated in FIGS. 17A-17D. The method uses a tissue augmentation construct 1610, or constructs, to fill in a gap where soft tissue 1630 has been damaged and torn from the bone 1650. For example, as shown in FIG. 17A, a labrum 1630 can have a tear or defect 1635 where a portion of the bone 1650 is exposed. Once the surgeon has access to the surgical site and the tissue, bone, and tissue augmentation construct have been prepared according to accepted surgical techniques including those provided for herein, the surgeon can install a first anchor 1660a into the bone at a proximal location 1635p of the tear 1635. The first anchor 1660a has a suture 1612 installed therein. The tissue augmentation construct 1610 can be threaded onto the suture limb 1612 using techniques provided for throughout the present disclosure, and advanced along the suture until the tissue augmentation construct 1610 is proximate the proximal end of the tear 1635*p*. Any type of tool provided for herein or otherwise known to those skilled in the art can be used to advance the construct 1610 towards the anchor 1660*a*, including a knot pushing tool. The tissue augmentation construct 1610 can be approximately the same length as defect 1635 once implanted, and can be pre-cut and/or cut at the surgical site in real time to assure proper fit.

After the tissue augmentation construct 1610 has been installed on the suture limb 1612, the free end of the suture limb 1612 can then be anchored down to the bone with a second anchor 1660*b*, such as a knotless-type fixation anchor. The tail of suture 1612 can be tightened before the anchor 1660*b* has been fully inserted into the bone. By locating the anchors 1660*a*, 1660*b* and construct 1610 in these locations, the construct 1610 ends up on a back edge of the glenoid rather than on its face and the repair can be used to rebuild the labrum rather than just fix the defect, as was more typical in previous labrum repair procedures. In an alternative embodiment, separate sutures extending from each of the two anchors 1660*a*, 1660*b* can be thread through the labrum on either side, the tissue augmentation construct 1610 can be disposed on one of the two sutures, the two sutures can be coupled together, e.g., using a knot. Furthermore, the tissue augmentation construct 1610 can be disposed over a location at which the two sutures are tied together to protect the location at which the sutures are coupled together.

Non-Rotator Cuff Repairs—ACL Repairs

Figure 18A:
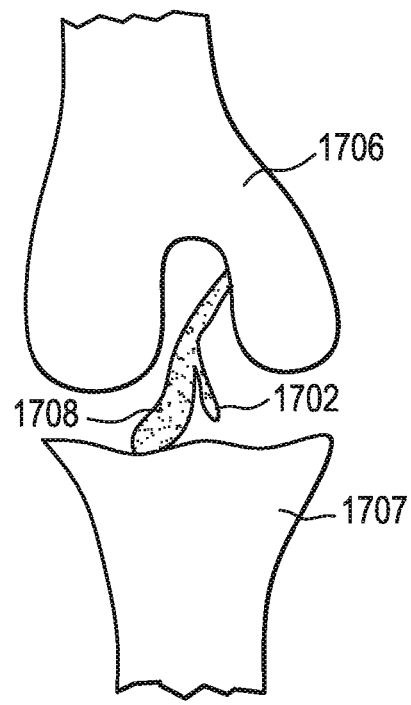
FIGS. 18A-18C are schematic sequential views of another exemplary embodiment for repairing soft tissue.
Figure 18B:
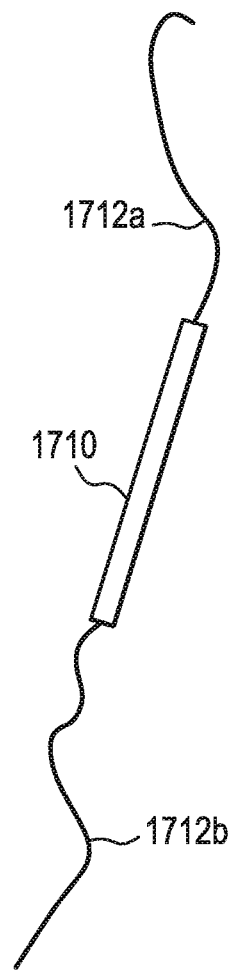
Figure 18C:
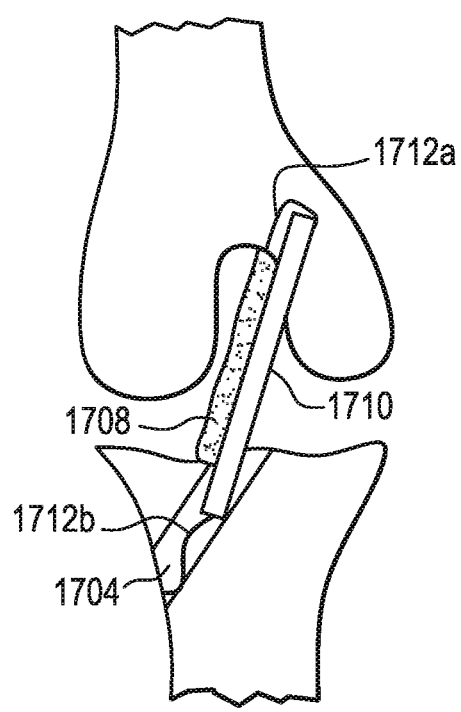

Another alternative procedure is illustrated in FIGS. 18A-18C. The method uses a tissue augmentation construct 1710, or constructs, to repair a torn ACL. For example, as shown in FIG. 18A, one bundle of the ACL 1702 is torn, or otherwise damaged. Once the surgeon has access to the surgical site and the tissue, bone, and tissue augmentation construct have been prepared according to accepted surgical techniques, the surgeon can begin the partial ACL repair. First, a bone tunnel 1704 is drilled through the femur 1706 and tibia 1707 next to the native, undamaged ACL 1708. Next, a tissue augmentation construct 1710, which as shown in FIG. 18B has suture limbs 1712*a*, 1712*b* extending from opposed ends, is prepared in the same manner as described above with regards to other embodiments. The construct 1710 can have a length approximately in the range of about 5 millimeters to about 100 millimeters. As shown in FIG. 18C, the construct 1710 can be threaded into the bone tunnel 1704 such that construct 1710 is in contact with the undamaged ACL 1708. The suture limbs 1712*a*, 1712*b* can be used to fix the construct 1710 within the bone tunnel according to known surgical techniques.

Alternatively, the construct 1710 can be used to augment an autograft implant. In situations where an autograft, or allograft, implant is too short, and/or too thin and not strong enough, to complete the repair, the construct 1710 can be sutured or otherwise coupled to the autograft implant to create an implant of the required size. In a further alternative, a construct having a lumen extending therethrough can be threaded over an autograft, or allograft, implant to further strengthen an autograft or allograft implant for an ACL repair.

Non-Rotator Cuff Repairs—Superior Capsule Reconstructions

Figure 19:
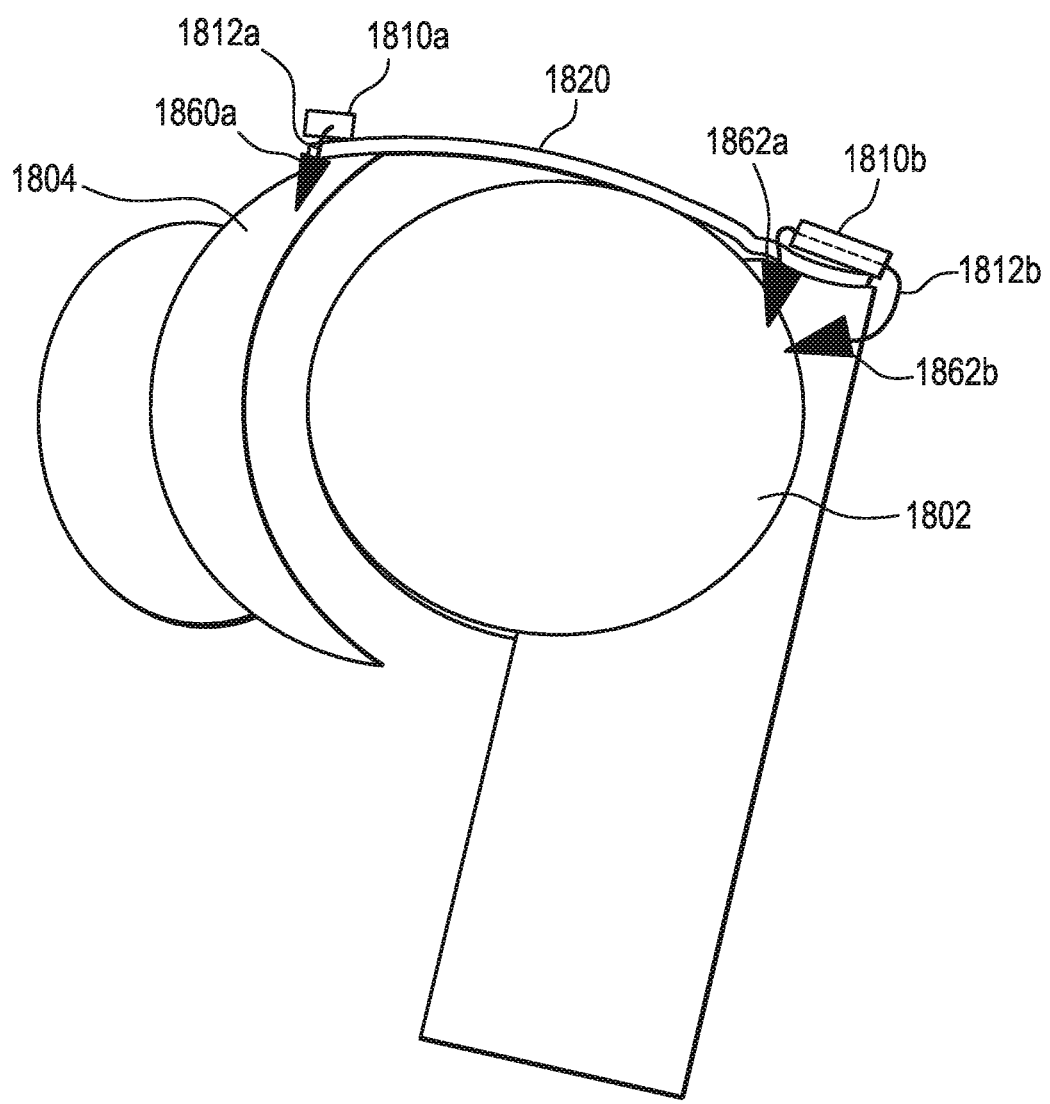
FIG. 19 is a schematic view of still another exemplary embodiment for repairing soft tissue.

Still another alternative procedure is illustrated in FIG. 19. The method can use at least one of tissue augmentation constructs 1810*a*, 1810*b* to assist in anchoring down a superior capsule reconstruction graft 1820 over a humeral head 1802. Once the surgeon has access to the surgical site and the tissue, bone, tissue augmentation constructs, and superior capsule reconstruction graft have been prepared according to accepted surgical techniques, including those provided for herein, the surgeon can affix one end of the graft 1820 to the glenoid rim 1804. The surgeon can affix one end of the graft 1820 to the glenoid rim 1804 by installing a first medial anchor 1860*a* having a suture 1812*a* extending therefrom. A first tissue augmentation construct 1810*a* can be thread onto the suture 1812*a* using techniques provided for throughout the present disclosure, and the construct 1810*a* can be tightened against the graft 1820 using techniques provided for herein or otherwise known to those skilled in the art, such as for example, by tying suture 1812*a* to suture 1812*b*, not shown, both of which extend from the anchor 1860*a*. The pressure of the construct 1810*a* on the graft 1820 can hold the graft 1820 at a desired location with respect to the glenoid rim 1804. An opposite end of the graft 1820 can be anchored proximate to the humeral head 1802 and a location and/or size of the graft 1820 adjusted so that the glenoid rim 1804 is brought into contact with the humeral head 1802 in accordance with techniques used in superior capsule reconstruction procedures.

While a number of different techniques can be used to couple the other end of the graft 1820 proximate to the humeral head 1802, in the illustrated embodiment first and second lateral anchors 1862*a*, 1862*b* are used in conjunction with a second tissue augmentation construct 1810*b* to make the repair. More particularly, in one exemplary embodiment, at least one of the anchors 1862*a*, 1862*b* can have a suture 1812*b* associated therewith and the second tissue augmentation construct 1810*b* can be disposed on at least a portion of the suture 1812*b* using techniques provided for in the present disclosure. The suture 1812*b* can extend between the two anchors 1862*a*, 1862*b*, against using any of the techniques provided for herein or otherwise known to those skilled in the art, and the construct 1810*b* can be tightened down against the graft 1820 to help maintain a location of the graft 1820 with respect to the humeral head 1802 while allowing the construct 1810*b* to better distribute any force applied by the suture 1812*b* across the surface area of the construct 1810*b*. Any number of tissue augmentation constructs can be used in the repair, and in alternative embodiments tissue augmentation constructs may only be used in conjunction with coupling the graft 1820 with only one of the glenoid rim 1804 and the humeral head 1802.

Figure 20A:
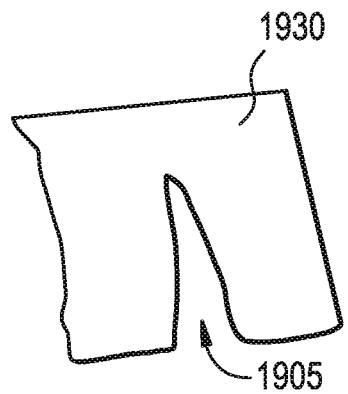
FIGS. 20A-20C are schematic sequential views of another exemplary embodiment for repairing soft tissue.
Figure 20B:
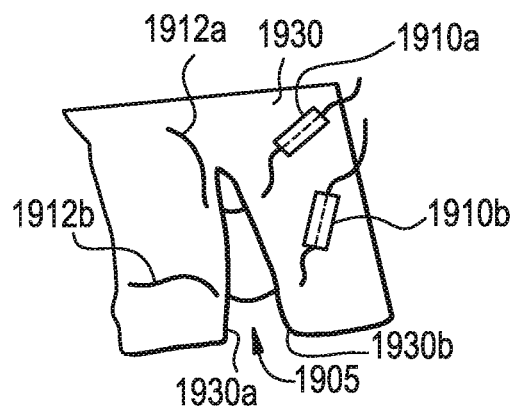
Figure 20C:
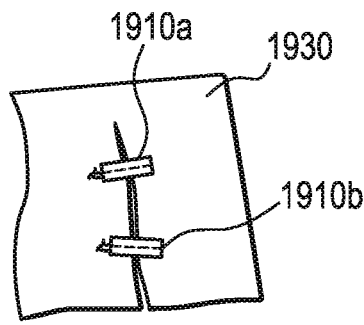
Figure 20D:
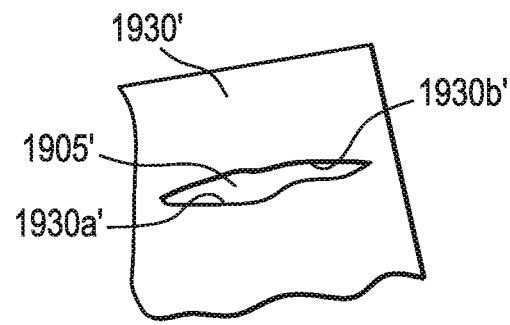
FIGS. 20D-20F are schematic sequential views of yet another exemplary embodiment for repairing soft tissue.
Figure 20E:
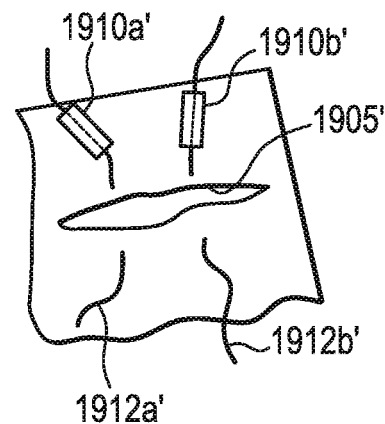
Figure 20F:
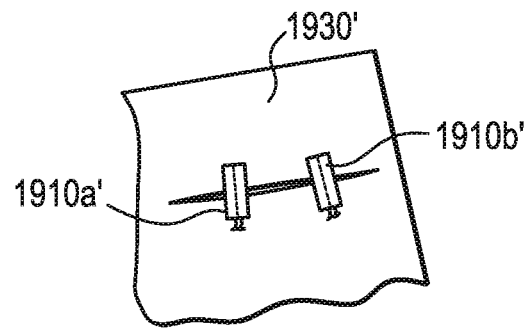

Repairing Soft Tissue by Closing Gaps—Rotator Cuff and Non-Rotator Cuff Examples Two exemplary embodiments for closing gaps or voids in tissue are illustrated in FIGS. 20A-F. The first illustrated embodiment, as shown in FIGS. 20A-20C, relates to a rotator cuff margin convergence, and the second, as shown in FIGS. 20D-20F, a hip capsular closure. However, a person skilled in the art will recognize other types of procedures these embodiments can be applied to in practice without departing from the spirit of the present disclosure.

FIG. 20A shows rotator cuff tissue 1930 having a void or gap 1905. First and second sutures 1912*a*, 1912*b* can be associated with first and second constructs 1910*a*, 1910*b* using techniques provided for throughout the present disclosure. As shown in FIG. 20B, a first free end of the first suture 1912*b* can be threaded into the rotator cuff tissue 1930 on a first side of the void 1905 and threaded back through the rotator cuff tissue 1930 on the opposite side of the void 1905. The first free end can be tied to the second free end to bring edges 1930*a*, 1930*b* of the void 1905 together. This process can be repeated for the second suture 1912*b* to complete the repair, as shown in FIG. 20C. The tissue augmentation constructs 1912a, 1912b can provide the many benefits provided for herein, including but not limited to increased surface area through which forces from the sutures 1912a, 1912a can be distributed, protection of a knot used to couple free ends of the sutures 1912a, 1912b, and providing a scaffold for new tissue to grow to create a stronger repair between the edges 1930a and 1930b, with the scaffold essentially becoming a new layer of tissue on top of the existing rotator cuff tissue 1930.

FIG. 20D shows hip capsular tissue 1930' having a void or gap 1905'. First and second sutures 1912a', 1912b' can be associated with first and second constructs 1910a', 1910b' using techniques provided for throughout the present disclosure. As shown in FIG. 20E, a first free end of the first suture 1912a' can be threaded into the hip capsular tissue 1930' on a first side of the void 1905' and threaded back through the hip capsular tissue 1930' on the opposite side of the void 1905'. The first free end can be tied to the second free end to bring edges 1930a', 1930b' of the void 1905' together. This process can be repeated for the second suture 1912b' to complete the repair, as shown in FIG. 20F. As with the tissue augmentation constructs 1912a, 1912b, the tissue augmentation constructs 1912a', 1912b' can provide the many benefits provided for herein, including the highlighted benefits provided for with respect to the constructs 1912a, 1912b.

Tissue Augmentation Constructs—Collagen Tacks/Buttons

Figure 21A:
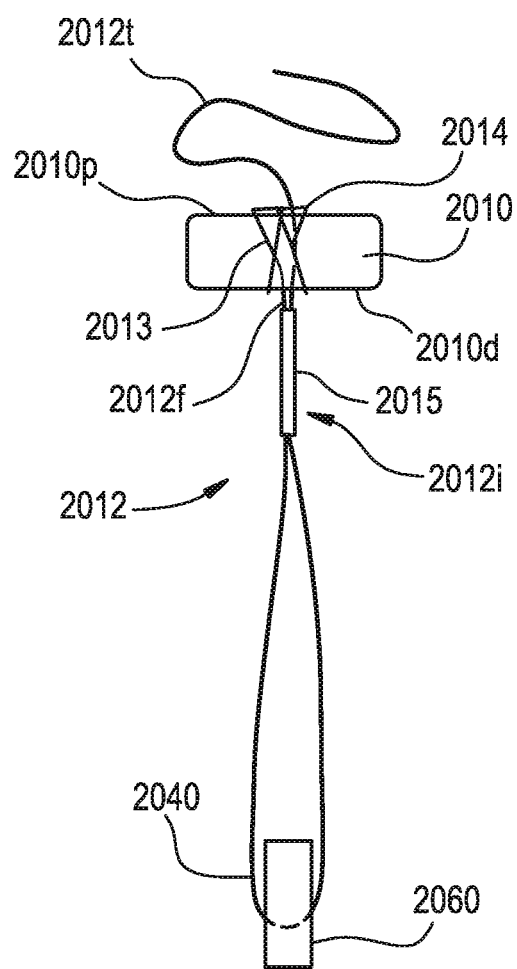
FIG. 21A is a schematic view of an exemplary embodiment of a tissue augmentation construct.
Figure 21B:
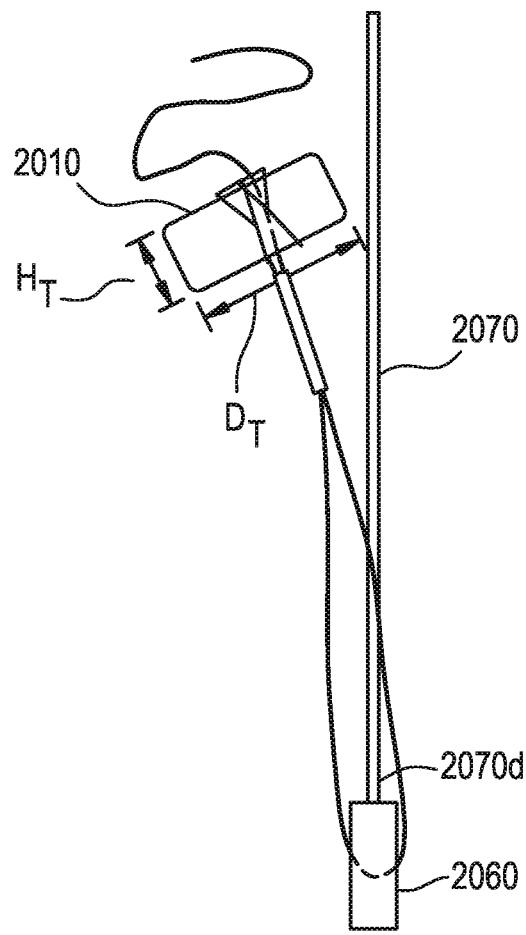
FIGS. 21B-21F are schematic sequential views of one exemplary embodiment for installing the tissue augmentation construct of FIG. 21A.

Another exemplary embodiment of a tissue augmentation construct is illustrated in FIGS. 21A and 21B. The tissue augmentation construct, as shown a tack or button 2010, has a generally cylindrical shape that is configured to be disposed on or otherwise associated with a suture 2012. More particularly, the tissue augmentation tack 2010 can have a substantially cylindrical body with a bore or lumen 2014 extending therethrough from a proximal-most end 2010p to a distal-most end 2010d. The bore 2014 can be used, for example, to receive the suture 2012 by means of a stitch 2013 so that the tack 2010 and suture 2012 can be associated with each other, as described in greater detail below. In alternative embodiments, the suture 2012 can be passed through the tack 2010 without a pre-defined lumen being formed in a body of the tack 2010, and/or the suture 2012 can be wrapped around or otherwise coupled to the tack 2010 without passing through it. As shown, the tack 2010 has a height $H_T$ that is less than a diameter $D_T$. Further, the diameter $D_T$ can be greater than a diameter of a filament or suture with which the tack 2010 is associated, e.g., the suture 2012, thereby increasing the footprint of the suture 2012 and the surface area of tissue augmentation of the system or device used in the surgical repair.

The suture 2012 can be any type of suture provided for herein or otherwise known to those skilled in the art. In the illustrated embodiment, the suture 2012 includes a self-locking mechanism 2015 associated with an intermediate portion 2012i of the suture 2012, a collapsible loop 2040 extending from one side of the self-locking mechanism 2015, and fixed and tensioning tails 2012f and 2012t extending from an opposite side of the self-locking mechanism 2015. The self-locking mechanism 2015 can take a variety of forms, and in the illustrated embodiment it has a finger-trap-like configuration formed by passing a first limb of the suture 2012 through a portion of a second limb of the suture 2012 before having the first limb exit the second limb to result in the fixed and tensioning tails 2012f, 2012t. The fixed tail 2012f can be wrapped around and/or coupled to the tack 2010, and as shown a stitch 2013 is used to help manage the fixed tail 2012 and attach it to the tack 2010. The tensioning tail 2012t can be used to help adjust a diameter of the collapsible loop 2040.

The collapsible loop 2040 can be coupled to an implant, e.g., a bone anchor 2060, and a diameter of the loop 2040 can be adjusted by moving the self-locking mechanism 2015 proximally away from the anchor 2060 and distally towards the anchor 2060 as shown in the illustrated embodiment, for instance by applying a force proximally away from the anchor 2060 to the tensioning tail 2012t. The anchor 2060 can be a low profile anchor so that the anchor 2060 can more easily pass through tendon. A person skilled in the art will recognize various suitable low profile anchors that can be used in conjunction with the present disclosure, including some such anchors that are provided for above, e.g., Gryphon® and Healix Transtend™ anchors.

A number of other suture configurations are possible, including some disclosed further below and others known to those skilled in the art. Some suture configurations that can be incorporated into this design include but are not limited to those disclosures provided for in U.S. Pat. No. 8,821,544, entitled "Surgical Filament Snare Assemblies," and U.S. Pat. No. 9,060,763, entitled "Systems, Devices, and Methods for Securing Tissue, the content of each which is incorporated by reference herein in their entireties.

A person skilled in the art will recognize that the dimensions of the height $H_T$ and diameter $D_T$ of the tissue augmentation tack 2010, as well as a diameter of the bore 2014, can depend on a variety of factors, including but not limited to the size of the filament with which it is to be associated, the anatomy of the patient, and the type of procedure being performed. In some embodiments a ratio of the diameter $D_T$ of the tack 2010 to a diameter of the suture limb 2012 can be approximately in the range of about 2:1 to about 100:1, and more particularly the diameter $D_T$ can be at least three times greater than the diameter of the filament or suture with which the tissue augmentation tack 2010 is associated in some instances. A variety of other sizes and shapes of the tissue augmentation tack 2010, including ratios of the dimensions of the tack and associated components (e.g., the suture 2012) can be utilized without departing from the spirit of the present disclosure.

While ratios can be useful to help describe the relationship between the tack 2010 and the filament 2012, and the relationship between the dimensions of the tack 2010, some exemplary, non-limiting dimensions for a tissue augmentation tack can also be useful in understanding the present disclosure. As mentioned above, these dimensions can be dependent on a variety of factors. In some embodiments, the height $H_T$ can be approximately in the range of about 1 millimeter to about 1 centimeter, and the diameter $D_T$ can be approximately in the range of about 1 millimeter to about 10 millimeters. The size of the diameter d of the bore 2014 can also depend on a variety of factors, including but not limited to the size of the limb to be passed therethrough. In some embodiments, the diameter d can be approximately in the range of about 0.5 millimeters to about 3 millimeters. Alternatively, bore 2014 may not be present and the filament 2012 can be passed through the tack 2010 without a bore. The tack 2010 can be made from any of the materials provided for above with respect to the other tissue augmentation constructs, including but not limited to collagen.

In some embodiments, as shown in FIG. 21B, an inserter tool 2070 can be used to install the anchor 2060 in a trans-tendon approach into a preformed bone bore in a bone 2050. The inserter tool 2070 can have a releasable mechanism (not shown) at a distal end 2070*d* that can releasably engage the anchor 2060 such that after installation of the anchor into bone 2050, the inserter tool can be removed. For example, the releasable mechanism can be a compression fit, a thread to engage the anchor 2060, a ball detent, or other releasable mechanisms that can be associated with the inserter tool 2070 in view of the present disclosures or otherwise known by those skilled in the art.

Figure 21E:
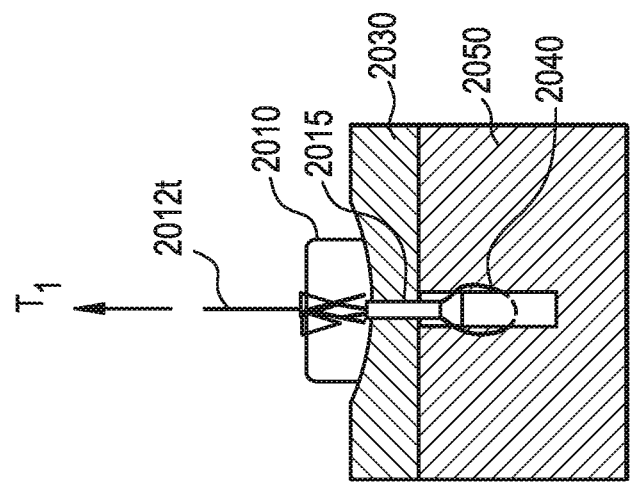
Figure 21D:
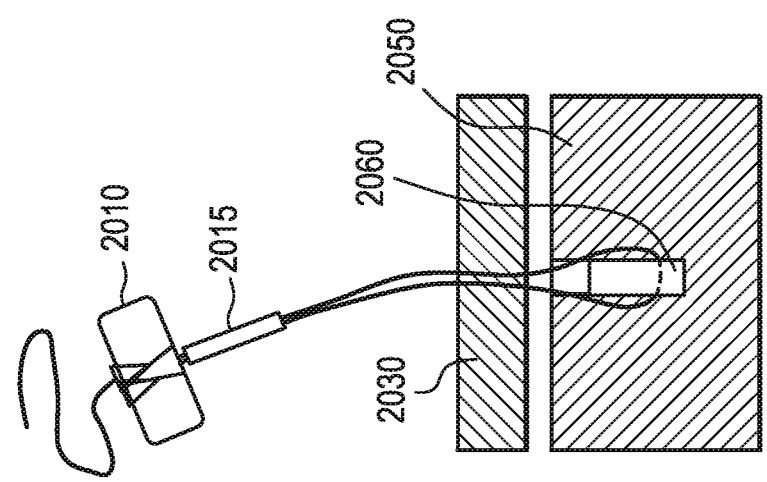
Figure 21C:
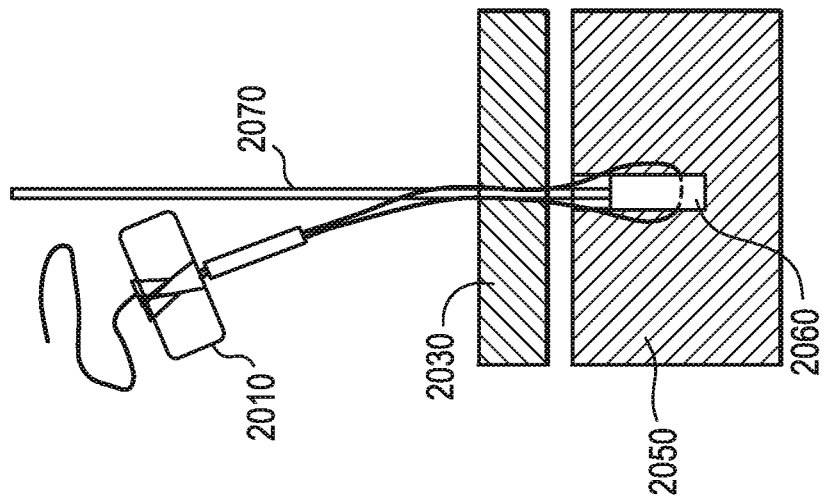

In use, the inserter tool 2070 can be used to insert the anchor 2060 through the tendon, or other soft tissue, 2030, as shown in FIG. 21C. The surgeon can then remove the inserter tool 2070 from the anchor 2060, after it has been secured into the bone 2050 below the tendon 2030, as shown in FIG. 21D. Once the anchor 2060 is secure in the bone 2050, tension can be applied to the tensioning tail in the direction $T_1$, as shown in FIG. 21E. As the tensioning tail 2012*t* is pulled, the diameter of the suture loop 2040 is reduced and the tack 2010 is brought into contact to the tendon 2030 to compress the tendon 2030 against the bone 2050. The self-locking mechanism 2015 maintains a location of the tensioning tail 2012*t* to keep the construct in a locked configuration. The tensioning tail can then be trimmed.

Numerous advantages result from the use of the tissue augmentation tack 2010. As illustrated in FIG. 21E, the resulting configuration is one in which the tack 2010 is disposed on top of the tissue 2030, and there are no hard components and/or knots exposed. This decreases the possibility of tissue abrasion, among other benefits. The same types of benefits provided for with other constructs provided for herein are also equally applicable. For example, when the tissue augmentation tack 2010 is made of collagen or other types of tissue-growth-promoting materials, the repair can result in a tissue remodel such that no component but the suture remains. Further, after the tack 2010 is advanced towards the anchor 2060 and secured at the tissue 2030, no suture management is really required post-procedure.

Figure 21F:
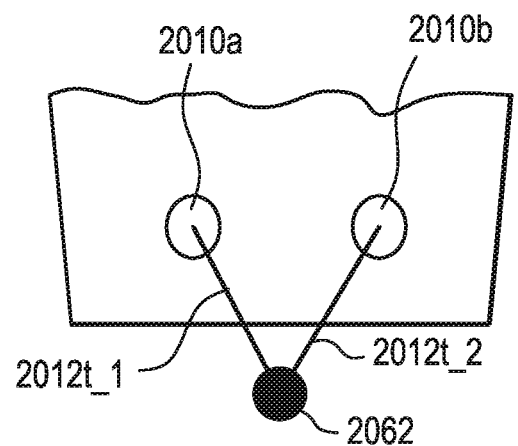
Figure 21G:
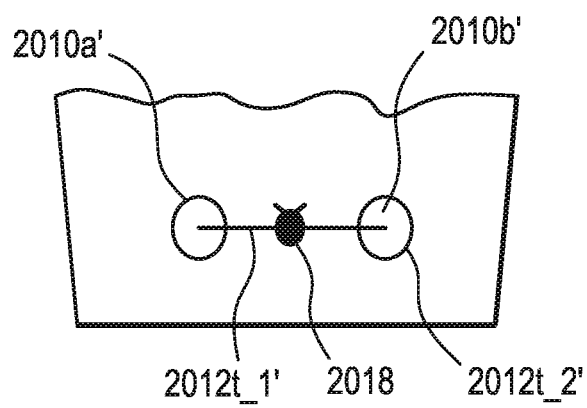
FIG. 21G is a schematic view of another exemplary embodiment for installing the tissue augmentation constructs of FIG. 21A.

Alternatively, if two tensioning tacks 2010*a*, 2010*b* are used, as shown in FIG. 21F, the tensioning tacks 2010*a*, 2010*b* can be installed in the same manner as described above with regards to FIGS. 21A-21E. Instead of trimming the tails 2012*t*_1, 2012*t*_2, the tensioning tails 2012*t*_1, 2012*t*_2 can be secured into a lateral row anchor 2062 to provide further compression of the tissue 2030 against the bone 2050. In a further alternative method, as shown in FIG. 21G, the two tensioning tails 2012*t*_1' and 2012*t*_2' can be tied together with a knot 2018. The knot 2018 can be covered by one or more additional tissue augmentation constructs as provided for herein.

Other non-limiting alternative embodiments of the tack 2010 are illustrated in FIGS. 21H and 21I as tacks 2010' and 2010", respectively, the alternatives focusing on other types of self-locking mechanisms associated with the respective sutures, 2012', 2012". The configuration of the suture 2012' includes a self-locking sliding knot 2015' configured to selectively restrict the movement of the tensioning tail 2012*t*' relative to the tack 2010'. A person skilled in the art will recognize many different types of self-locking knots 2015' that can be used in conjunction with the tack 2010'.

A further alternative tack 2010" is shown in FIG. 21I. The tack 2010" has substantially the same dimensions as the tack 2010, and can be made of substantially the same materials. The tissue augmentation tack 2010", however, has two bores 2014*a*", 2014*b*" extending from a proximal most surface 2010*p*" to a distal-most surface 2010*d*". The two bores 2014*a*", 2014*b*" can be parallel to one another, as shown in FIG. 21I, however other alternative configurations are contemplated. In some embodiments, no bores may exist and instead suture can be passed through or otherwise associated with the tack 2010" as provided for herein or otherwise known to those skilled in the art.

The suture 2012" used in conjunction with the tack 2010" can be similar to the suture 2012, but as shown it is manipulated into a configuration having two self-locking mechanisms 2015*a*" and 2015*b*" and two loops 2040*a*" and 2040*b*". The self-locking mechanisms 2015*a*" and 2015*b*" can be formed as described above or as otherwise known to those skilled in the art. In the illustrated embodiment, the self-locking mechanisms 2015*a*" and 2015*b*" have a finger-trap-like configuration formed by passing a first limb of the suture 2012" through a portion of a second limb of the suture 2012" before having the first limb exit the second limb to result in fixed and tensioning tails 2012*f*_1", 2012*f*_2" and 2012*t*_1" and 2012*t*_2". As shown, the fixed tails 2012*f*_1" and 2012*f*_2" can be coupled to the tack 2010" using one or more stitches 2013", and tensioning tails 2012*t*_1" and 2012*t*_2" can extend from the proximal-most end 20120*p*" of the tack 2010". The loops 2040*a*" and 2040*b*" can both be coupled to a suture implant, as shown an anchor 2060*a*", and as described above, the tensioning tails 2012*t*_1" and 2012*t*_2" can be operable to adjust a diameter of the respective loops 2040*a*" and 2040*b*". Although in the illustrated embodiment the self-locking mechanisms 2015*a*" and 2015*b*" are shown as having a finger-trap-like configuration, other types of self-locking mechanisms, including sliding knots, can be used in place of the illustrated self-locking mechanisms 2015*a*" and 2015*b*".

Figure 21J:
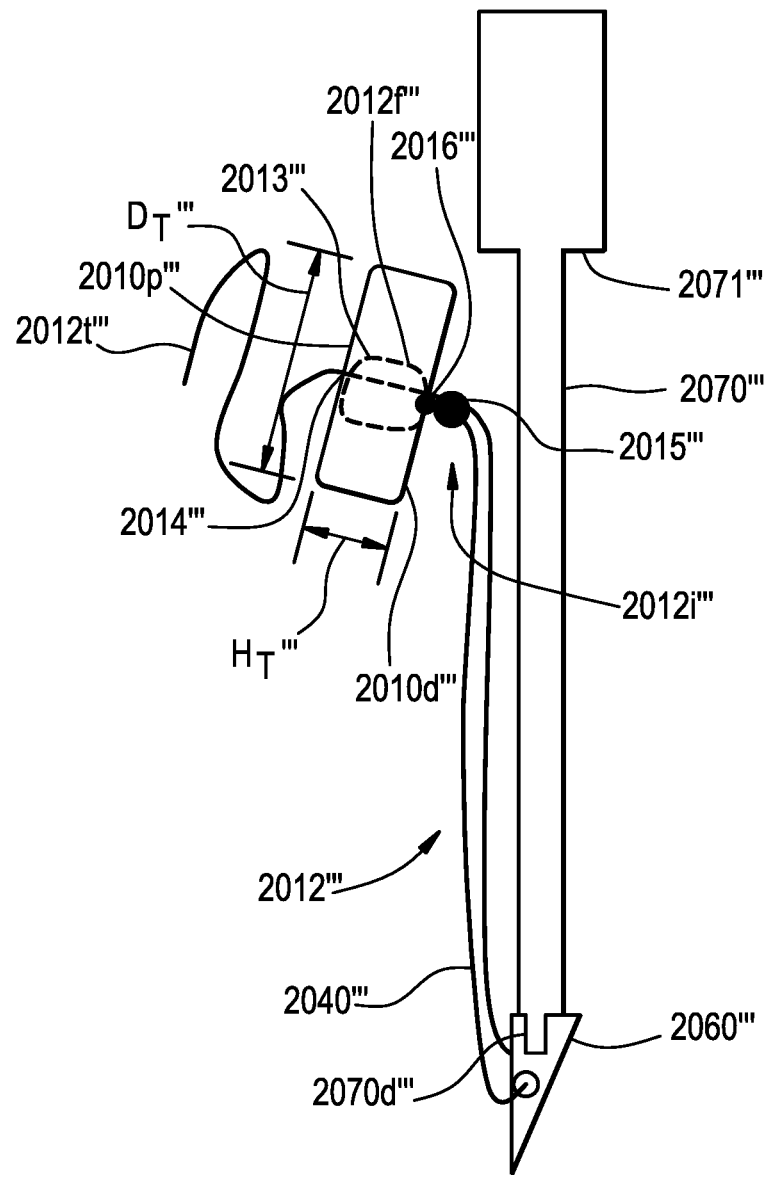
FIG. 21J is a schematic view of an alternative exemplary embodiment of the tissue augmentation construct of FIG. 21A and an inserter.

Another exemplary embodiment of a tissue augmentation tack 2010''' is illustrated in FIG. 21J. The tissue augmentation construct, as shown a tack or button 2010''', can be similarly configured as the tack 2010 shown in FIG. 21A. Accordingly, as shown, it includes a substantially cylindrical body with a bore or lumen 2014''' extending therethrough from a proximal-most end 2010*p*''' to a distal-most end 2010*d*''', and a suture 2012''' received by the lumen 2014'''. Similar to the tack 2010, a person skilled in the art will recognize that the dimensions of the height $H_T'$ and diameter $D_T'''$ of the tissue augmentation tack 2010''', as well as a diameter of the bore 2014''', can depend on a variety of factors, including but not limited to the size of the filament with which it is to be associated, the anatomy of the patient, and the type of procedure being performed. In some embodiments a ratio of the diameter $D_T'''$ of the tack 2010''' to a diameter of the suture limb 2012''' can be approximately in the range of about 2:1 to about 100:1. More particularly, the diameter $D_T'''$ can be at least three times greater than the diameter of the filament or suture with which the tissue augmentation tack 2010''' is associated in some instances. In other instances, the diameter $D_T'''$ can be at least five times greater than the diameter of the filament or suture with which the tissue augmentation tack, at least ten times greater, at least twenty times greater, or even greater, without departing from the spirit of the present disclosure.

The suture 2012''' includes a self-locking mechanism 2015''', shown as a sliding knot, associated with an intermediate portion 2012*i*''' of the suture 2012''', a collapsible loop 2040''' extending from one side of the sliding knot 2015''', and fixed and tensioning tails 2012*f*''' and 2012*t*''' extending from an opposite side of the sliding knot 2015''', e.g., extending from the distal side 2010*d*''' of the tack 2010'''. Alternatively, the self-locking mechanism 2015''' can be any adjustable and/or sliding mechanism or member (e.g., sliding knot) configured to define the collapsible loop

2040''' and change a size of the loop by moving the adjustable mechanism with respect to a portion of the suture 2012'''.

The tails 2012f''' and 2012t''' can operate in a similar manner as the tails 2012f and 2012t, and thus the tensioning tail 2012t''' can freely slide through the tack 2010''', and can be used to help adjust a diameter of the collapsible loop 2040'''. The sliding knot 2015''' can take a variety of forms, and in the illustrated embodiment it can be formed by creating a knot with the fixed tail 2012f''' and passing the tensioning limb 2012t' of the suture 2012''' through the sliding knot 2015'''. The fixed tail 2012f''' can then be secured to the tack 2010''' using any number of techniques known to those skilled in the art for creating a fixed relationship between a suture and an object. For example, the fixed tail 2012f''' can form a stitch 2013''' through the tack 2010''' to help couple the suture 2012''' to the tack 2010'''. As shown, the fixed tail 2012f''' is disposed in a circular pattern within the tack 2010''', thus burying a portion of the fixed tail 2012f''' within the tack 2010''' to keep it out of the way. Additionally, or alternatively, a locking knot 2016''' can be formed by the fixed tail 2012f''' being tied onto itself to secure the suture 2012''' to the tack 2010'''. In the illustrated embodiment, the locking knot 2016''' is disposed on the distal face 2010d''' of the tack 2010'''. Alternatively, it is contemplated that the locking knot 2016''' can be disposed on, or at least proximate to, any surface of the tack 2010''' provided the stitch 2013''' is generally fixed relative to the tack 2010'''. Other ways by which the fixed tail 2012f''' can be secured with respect to the tack 2010''' include using adhesive, such as glue, to secure a location of the fixed tail 2012f''' with respect to the tack 2010''', as well as other techniques known to those skilled in the art.

In embodiments where the locking knot 2016''' is disposed on the distal face 2010d''' of the tack 2010''', the distance between the locking knot 2016''' and the sliding knot 2015''' can be fixed. For example, a distance extending between the two knots can be approximately in the range of about 2 millimeters to about 10 millimeters. In some embodiments, it may be desirable to maintain the relative distance between the locking knot 2016''' and the sliding knot 2015''' to be as small as possible to create a low profile repair with the necessary compression of the soft tissue 2030''' against the bone 2050'''.

The collapsible loop 2040''' can be coupled to an implant, e.g., a bone anchor 2060''', and a diameter of the loop 2040''' can be adjusted by moving the sliding knot 2015''' proximally away from the anchor 2060''' and distally towards the anchor 2060''' as shown in the illustrated embodiment, for instance by applying a force proximally away from the anchor 2060''' to the tensioning tail 2012t'''. The anchor 2060''' can be a low profile anchor so that the anchor 2060''' can more easily pass through tendon. By way of non-limiting example, the anchor 2060''' can be a toggle anchor, such as a Minilok™ Quickanchor® suture anchor, which is commercially available from DePuy Synthes, Inc. A person skilled in the art will recognize various suitable low profile anchors that can be used in conjunction with the present disclosure, including hard anchors, soft anchors, and other toggle anchors.

FIG. 21J also illustrates an inserter tool 2070''' that can be used to help insert the anchor 2060''' into a bore formed in bone. Sizes, shapes, and configurations of the tool 2070''' can depend on a variety of factors, including but not limited to the sizes, shapes, and configurations with components with which it is used (e.g., a guide 2080''' and the anchor 2060'''), and in the illustrated embodiment a body of the tool 2070''' has a cylindrical or tubular shape. An outer diameter of the tool 2070' can change along the length of the tool 2070''', and thus, as shown, a first outer diameter at a proximal end 2070p''' has a greater diameter than a second outer diameter at an intermediate portion 2070i'''. A ledge 2071''' can be formed by the transition of the body from the first outer diameter to the second outer diameter. As shown, a distal end 2070d''' of the tool 2070''' can be configured to allow the anchor 2060''' to be removably coupled to the tool. Any number of configurations or mechanisms known for creating a releasable connection between an insertion tool and an anchor can be used. For example, the releasable mechanism can be a compression fit, a thread to engage the anchor 2060''', a ball detent, or other releasable mechanisms that can be associated with the inserter tool 2070''' in view of the present disclosures or otherwise known by those skilled in the art. A size and shape of the inserter tool 2070''' can depend on a variety of factors, including a size and shape of the anchor(s) with which it is designed to be used, a size and shape of other components with which it is to be used (e.g., a guide, as described below), and the type of surgical procedure being performed.

The tool 2070''' can optionally be used in conjunction with other instruments, such as those provided for in FIGS. 21K and 21L. More particularly, FIG. 21K illustrates a guide 2080''', and FIG. 21L illustrates a punch 2090''', each of which can be used in a variety of procedures, including but not limited to a trans-tendon approach into a bone bore.

In the illustrated embodiment, a body of the guide 2080''' has a cylindrical or tubular shape with a lumen 2085''' extending through an interior volume of the guide 2080''' from a proximal-most end of a proximal end 2080p''' to a distal-most end of a distal end 2080d''' of the guide 2080''', the lumen also having a cylindrical or tubular shape. As shown, an outer diameter of the body of the guide 2080''' changes along the length of the guide 2080'''. More particularly, the body is shaped such that the proximal end 2080p''' has a first outer diameter, an intermediate portion 2080i''' has a second outer diameter, and the distal end 2080d''' has a third outer diameter, with the first outer diameter being greater than the second outer diameter and the second outer diameter being greater than the third outer diameter. In some embodiments, a distal tip of the distal end 2080d''' can be configured to cut through soft tissue, such as a tendon. Alternatively, the distal end 2080d''' can have a serrated edge, a blunt edge, a rounded edge, or bone engaging features to grip or otherwise anchor the guide 2080''' to the bone 2050'''. The guide 2080''' can be used to guide instruments, such as the punch 2090''' and inserter 2070''', and implants, such as the anchor 2060''', through tendon 2030''' and into bone 2050'''.

As shown, an interior ledge 2081''' can be formed by the transition of the body from the first outer diameter to the second outer diameter, and a tapered portion 2083''' can provide for the transition of the body from the second outer diameter to the third outer diameter. The sizes of the outer diameters, and other portions of the guide 2080''' for that matter, can depend on a variety of factors, including but not limited to the sizes, shapes, and configurations of the instruments with which the guide 2080''' is used (e.g., the inserter tool 2070''', punch 2090''', and anchor 2060''') and the type of procedure being performed. A person skilled in the art will recognize other shapes and configurations of the guide 2080''' and lumen 2085''' are possible, including shapes in which the body of the guide 2080''' and the lumen 2085''' have differently shaped cross sections and/or shapes in which an outer diameter of the guide 2080''' does not change along its length. The diameter of the lumen 2085''' can be sized to receive both the punch 2090''' and the inserter tool 2070''', or any other surgical tools to be received by the guide 2080''' for use during a surgical procedure.

A longitudinal slot 2088''' can be formed along a length of the guide 2080''' on an exterior surface of the guide 2080'''. In the illustrated embodiment, the slot 2088''' extends an entire length of the guide 2080''' from the proximal-most end of the proximal end 2080p''' to the distal-most end of the distal end 2080d''', although in other embodiments it can only extend along a portion of the length. The slot 2088''' can have a width $W_G$ and depth (not shown) that is large enough to accommodate at least one suture limb 2012'''. In some embodiments, more than one slot may be formed in the exterior surface of the guide 2080'''. The slot can be formed in the exterior surface using any number of techniques known to those skilled in the art for forming a slot or channel in a surface, including but not limited to etching and milling. The slot 2088''' can help a surgeon control the tack 2010''' with respect to the surgical site since the tack 2010''' may have a diameter that is too big to be disposed through the lumen 2085''' of the guide 2080'''.

As illustrated in FIG. 21L, the punch 2090''' has a cylindrical or tubular shape, and is configured to be removably disposed through the lumen of the guide 2080''' such that a distal end 2090d''' of the punch 2090''' can extend distally beyond the distal end 2080d''' of the guide 2080''' when a proximal end 2090p''' of the punch 2090''' is engaged with the proximal end 2080''' of the guide 2080''' (see FIG. 21N). Similar to the guide 2080''', an outer diameter of the body of the punch 2090''' changes along the length of the punch 2090'''. As shown, the body is shaped such that a proximal end 2090p''' has a first outer diameter, an intermediate portion 2090i''' has a second outer diameter, and the distal end 2090d''' has a third outer diameter, with the first outer diameter being greater than the second outer diameter and the second outer diameter being greater than the third outer diameter. While the sizes of the first, second, and third outer diameters of the punch 2090''', as well as other portions of the punch 2090''', can depend on a variety of factors (e.g., the sizes, shapes, and configurations of the guide 2080''', other components used during a procedure, and the type of procedure being performed), in the illustrated embodiment the first outer diameter is sized such that it is greater than a diameter of the lumen 2085''' of the guide 2080''', and the second outer diameter is less than a diameter of the lumen 2085''' so that the punch 2090''' can be slidingly and removably received within the lumen 2085'''.

A ledge 2091''' that is formed by the transition from the first outer diameter to the second outer diameter of the punch 2090''' can be configured to engage the proximal-most end of the proximal end 2080p''' of the guide 2080'''. In other embodiments, the first and second outer diameters, and thus the ledge 2091''' can be configured to engage a ledge or other surface disposed within the guide 2080'''. When the ledge 2091''' is engaged with the guide 2080''', it prevents the punch 2090''' from traveling any further in a distal direction with respect to the guide 2080'''. Alternatively, or additionally, the punch 2090''' can include a stop surface 2093''', formed by a tapered portion, that can abut a corresponding surface in the guide 2080''' to prevent any further movement in a distal direction with respect to the guide 2080'''. Optionally, the punch 2090''' can have a lumen extending along at least a portion of the length, including along the whole length, to allow bone and other objects (e.g., tissue) to be removed during bone hole formation, or during other processes that can be performed while the punch 2090''' is disposed at the surgical site. In some embodiments, the distal end 2090d''' can be configured to form a bone hole. A person skilled in the art will recognize that components such as the inserter tool 2070''', guide 2080''', and punch 2090''' can be formed of a variety of materials, including but not limited to hardened stainless steel.

In use, the guide 2080''' can be used to guide both the punch 2090''' and the inserter tool 2070''' to the implantation site and function to manage the sutures 2012''' during the implantation process, as shown in FIGS. 21M-21R. While the description below describes both the creation of a bone hole 2052''' and soft tissue repair, one skilled in the art will understand that these discrete procedures can be performed separately or in conjunction with other procedures. In one aspect, the procedure can include the creation of a bone hole 2052''' with a trans-tendon approach. The distal tip 2080d''' of the guide 2080''' can be advanced to the surgical site such that it is proximate the soft tissue 2030''', e.g., a tendon. When the guide 2080''' is at the desired location, the operator can advance the punch 2090''' into the lumen of the guide 2080'''. Alternatively, the guide 2080''' can be advanced to the surgical site with the punch 2090''' already disposed, or partially disposed, therein. The surgeon can push the punch 2090''' through the tissue 2030''' and into the bone 2050''' to begin to form the bone hole 2052''' by applying a force F1 on the punch 2090'''. The surgeon can apply the force F1 until the punch tip 2090d''' has been advanced to the desired depth into the bone 2050''' and/or until the distal end 2080d''' of the guide 2080''' has passed through the tissue 2030''' and is in contact with a surface 2050a''' of the bone 2050''', as shown in FIG. 21N. The amount that the punch 2090''' is advanced into the bone 2050''' can be limited by the interaction between the ledge 2091''' of the punch 2090''' and the proximal-most end of the proximal end 2080p''' of the guide 2080''' and/or the interaction between stop surface 2091''' of the punch 2090''' and a corresponding surface adjacent to the lumen 2085''' of the guide 2080'''. Alternatively, or additionally, the stop surface 2093''' of the punch 2090''' can abut the interior ledge 2081''' of the guide 2080'''. In a further alternative, the punch 2090''' can be advanced into the bone 2050''' without the use of a guide 2080'''.

Figure 21P:
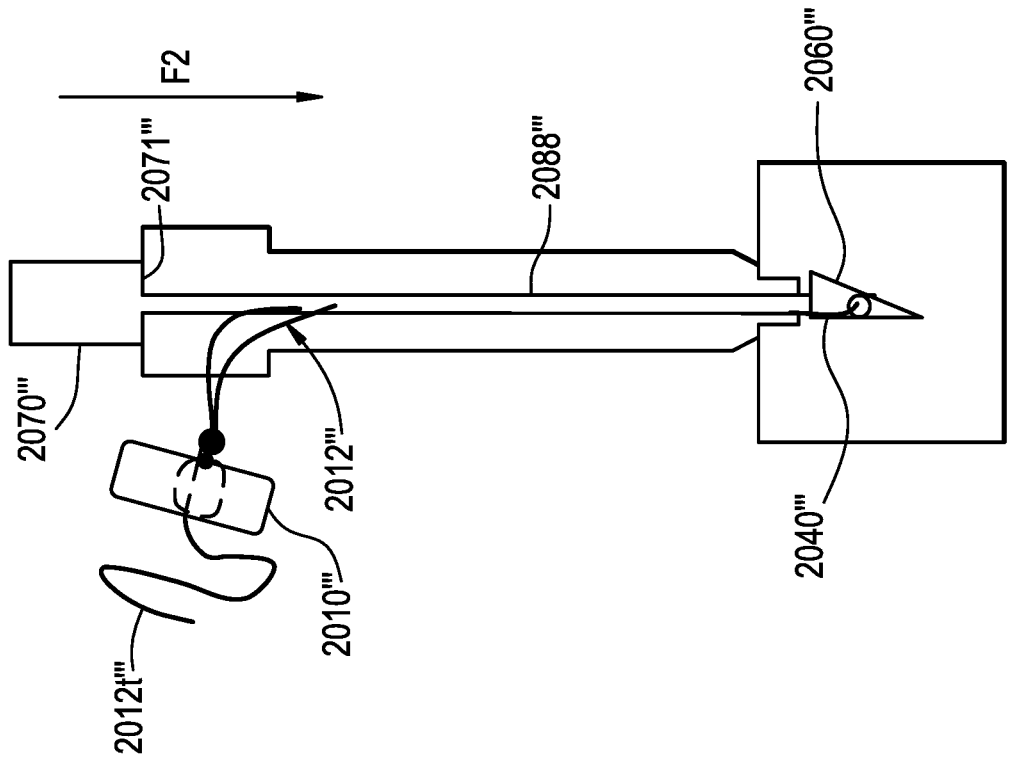
Figure 21O:
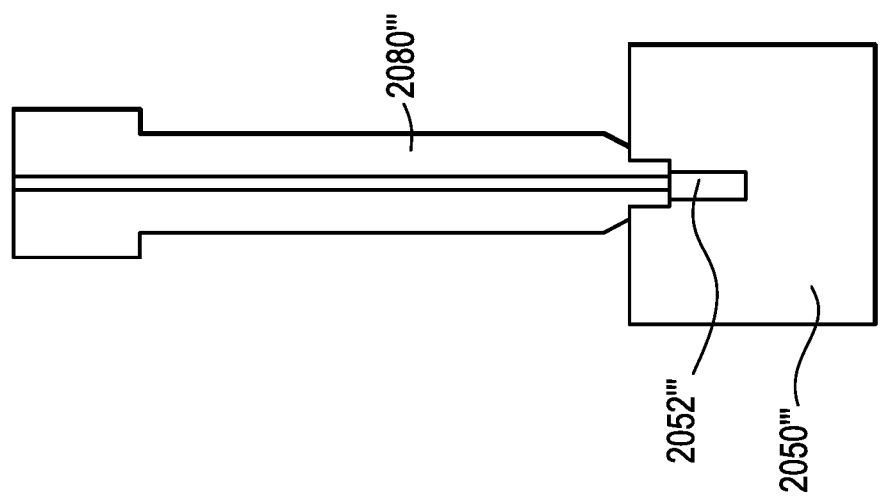

After the desired bone hole 2052''' has been formed, the punch 2090''' can be removed from the guide 2080''', thus providing access to the bone hole 2052''' via the lumen 2085''' of the guide 2080''', as shown in FIG. 21O. The guide 2080''' can be left at the surgical site, or alternatively removed. One advantage to leaving the guide 2080''' in place after the formation of the bone hole 2052''' is that the bone hole 2052''' is easily identifiable for installing an anchor 2060'''.

Similar to the installation of the suture construct shown in FIGS. 21B-21F, the inserter tool 2070''' can be used to insert the anchor 2060''' through the tendon, or other soft tissue, 2030''', as shown in FIG. 21P. The surgeon can insert the inserter tool 2070''' through the guide 2080''' such that the anchor 2060''' is advanced through the lumen of the guide 2080''' by applying a force F2 in a direction as shown. The depth of the insertion can be controlled, at least in part, by the location of the ledge 2071''' of the inserter tool 2070''' with respect to a length of the guide 2080'''. At least one of the suture limbs 2012''' can be received within the slot 2088''' of the guide 2080''' so that the suture limbs can be easily managed during the implantation of the anchor 2060''' into the bone hole 2052''' in the bone 2050'''. The easy management of the suture limbs 2012''' likewise allows for easier control of the tack 2010''' as it is advanced towards the surgical site because often the tack 2010''' is too large to be disposed through the lumen 2085''' of the guide 2080'''. In some embodiments, the collapsible loop 2040''' can be collapsed to advance the tack 2010''' at least partially towards the surgical site while the guide 2080''' is still positioned at the surgical site. Alternatively, any adjustment of the size of the loop 2040''' can occur after the guide 2080''' has been removed.

Figure 21R:
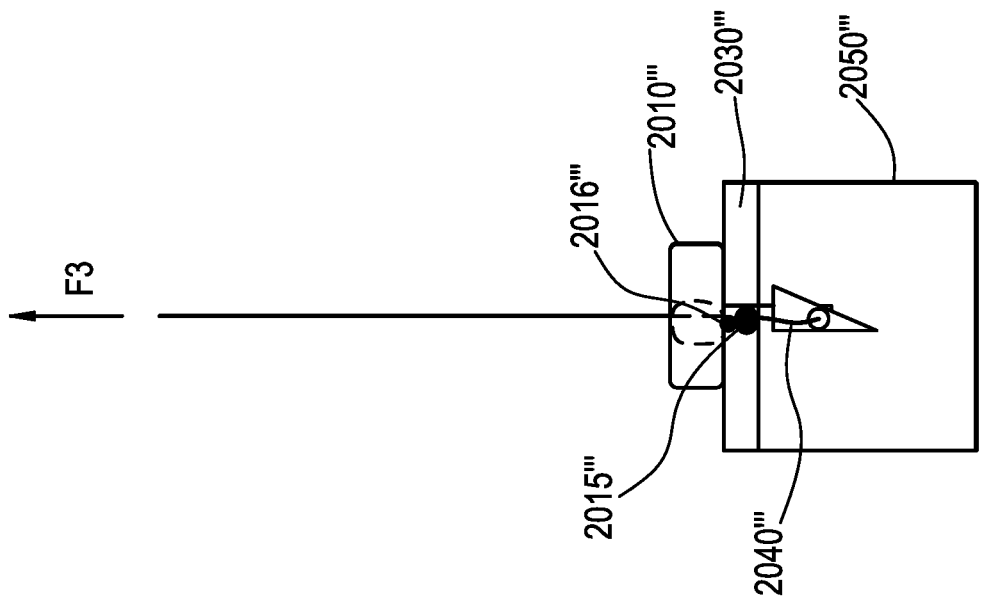
Figure 21Q:
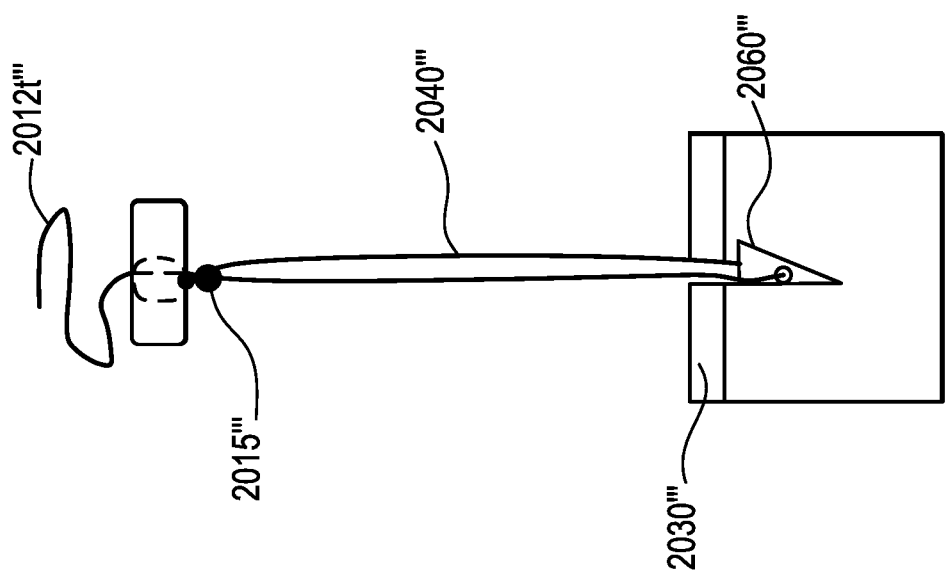

FIG. 21Q illustrates the surgical site after the guide 2080''' has been removed. Likewise, the anchor 2060''' has been detached from the inserter tool 2070''' and the tool also removed from the surgical site. As shown, the anchor 2060''' has been secured with respect to the bone 2050''' below the tendon 2030'''. The anchor 2060''' can be secured with respect to the bone 2050''' using a number of different techniques, depending, at least in part, on the type of anchor being used. For example, since in the illustrated embodiment the anchor 2060''' is a toggle anchor, a force can be applied to the anchor to toggle it (e.g., a force in an upwards direction away from the surgical site can be applied to the suture 2012''' to cause the anchor 2060''' to toggle into the bone). If the anchor is a soft anchor, action to actuate the anchor to cause it to secure itself within the bone can be performed. For example, the soft anchor can be formed from a flexible construct (e.g., a suture or filament, among other flexible constructs known to those skilled in the art and/or incorporated by reference herein) such that tensioning of a tensioning tail can actuate the soft anchor from an unstressed configuration (sometimes referred to as an unanchored configuration), in which the soft anchor has a first length and a first diameter, to a stressed configuration (sometimes referred to as an anchored configuration), in which the soft anchor has a second length that is less than the first length and a second diameter that is greater than the first diameter. An anchor formed from a flexible construct does not have to be entirely formed of a flexible construct, but often it is substantially formed of one or more flexible constructs. The soft anchor can be configured to be inserted into a bone hole when in the unstressed configuration and secured at a location, such as at the end of a bone hole, proximate to or otherwise at bone, when in the stressed configuration. The soft anchor can be actuated, for example, by applying tension to the flexible construct to move it from the unstressed configuration to the stressed configuration. Tension can be applied by applying force to a tail or a portion of flexible construct of or otherwise associated with the soft anchor. As noted above, some exemplary embodiments of soft suture anchors and methods for actuating such a soft anchor with the present disclosures include those described in U.S. Pat. No. 9,345,567 of Sengun. In further alternatives, the anchor can be a self-punching anchor, and/or the anchor can be a combination of a self-punching anchor used in combination with an insertion device known to those skilled in the art. Such an anchor and/or anchor-insertion device combination can be inserted directly into bone without forming a bone hole prior to insertion. In cases where a self-punching anchor and/or a self-punching anchor-insertion device combination is used, the procedure can be performed without the use of the punch 2090''' and/or the guide 2080''', ore equivalents thereof.

Once the anchor 2060''' is secured in the bone 2050''', tension can be applied to the tensioning tail 2012t''' in the direction F3, as shown in FIG. 21R. As the tensioning tail 2012t''' is pulled, the diameter of the suture loop 2040''' is reduced and the tack 2010''' is brought into contact to the tendon 2030''' to compress the tendon 2030''' against the bone 2050'''. As noted above, in one preferred embodiment the distance between the locking knot 2016''' and the sliding knot 2015''' is minimized to permit the tendon 2030''' to be compressed as much as is needed against the bone 2050'''. If the distance between the locking knot 2016''' and the sliding knot 2015''' is too great, the surgeon may not be able to achieve the desired amount of compression between the tendon 2030''' and the bone 2050'''. The sliding knot 2015''' can be a self-locking knot to maintain a location of the tensioning tail 2012t''' to keep the construct in a locked configuration. Alternatively, if the sliding knot 2015''' is not a self-locking knot, then the surgeon can tie any necessary knots to fix the diameter of the suture loop 2040'''. The tensioning tail can then be trimmed. The fixed tail can likewise be trimmed if it is exposed and it would be desirable to trim it.

Methods of Manufacturing Tissue Augmentation Constructs

The tissue augmentation constructs provided for herein can be manufactured using a number of different techniques, some of which are provided for below. Other techniques known to those skilled in the art or developed subsequent to the present disclosure, particularly in view of the present disclosure, can also be used to manufacture the various configurations of tissue augmentation constructs disclosed.

Methods of Manufacturing Tissue Augmentation Constructs—Blocks Having a Tape Configuration In one exemplary embodiment of making a tissue augmentation tape or strip 10, the material being used to make the strip 10 can be cut into a desired shape. For example, in embodiments in which the strip is being manufactured from either autograft tissue, allograft tissue, or xenograft tissue, if the tissue is harvested prior to the procedure, the fresh tissue can be cut into the desired shape, e.g., for the strip 10, a generally rectangular shape having a length L, a width W, and a thickness T as shown in FIG. 1A. Whether the strip is made from harvested material or not, acquisition of the material to make the strip can be achieved using any techniques known to those skilled in the art. In accordance with the present disclosure, the tape or strip 10 can have any shape, for example the tissue can be cut into an oval shape, a circular shape, a triangular shape, etc. Further, the tissue need not be cut with a traditional scalpel or scissors. In some instances it can be sized with the use of a punch, a computer numerical control machine, a laser cutter, or other known manufacturing techniques.

Once the tissue is formed into the desired shape, a threader can be associated with the strip 10. For example, similar to the suture limb 12a as shown in FIG. 1B, an intermediate filament portion 210 of the threader 206 can be threaded through the strip 10 with the use of a running stitch. The stitch can pass back-and-forth across the body of the tape strip 10 as many times as desired. In alternative embodiments, the intermediate filament portion 210 of the threader 206 can just pass from one of the tape strip 10 to the other without ever passing out of the body. After the threader 206 has been installed, the strip 10 can be dried for packaging. Alternatively, the threader 206 can be inserted after the tissue has been dried. Further, the strip 10 need not be dried.

Figure 22A:
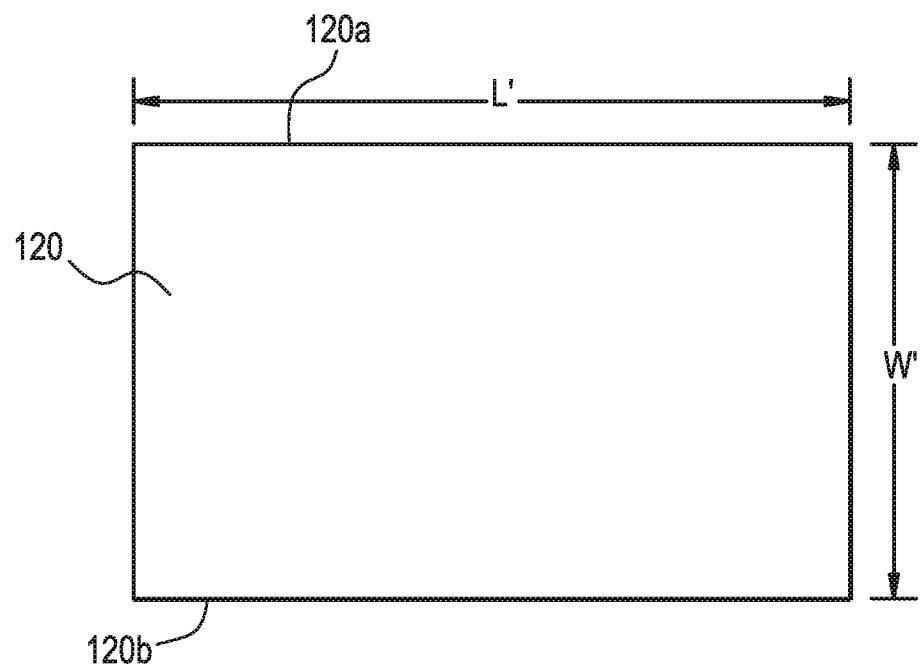
FIGS. 22A-22C are schematic sequential views of one exemplary embodiment for manufacturing the tissue augmentation construct of FIG. 2A.
Figure 22B:
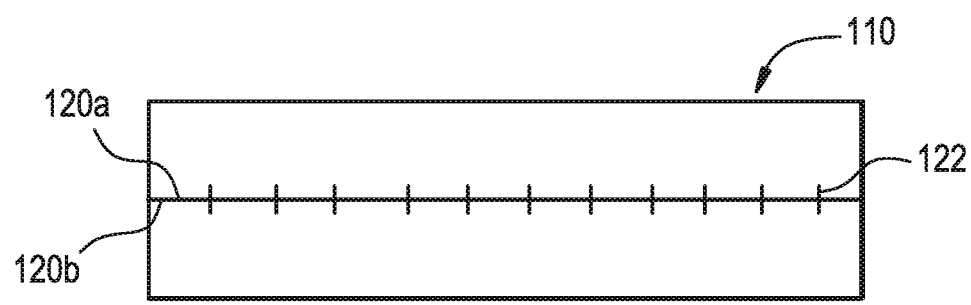
Figure 22C:
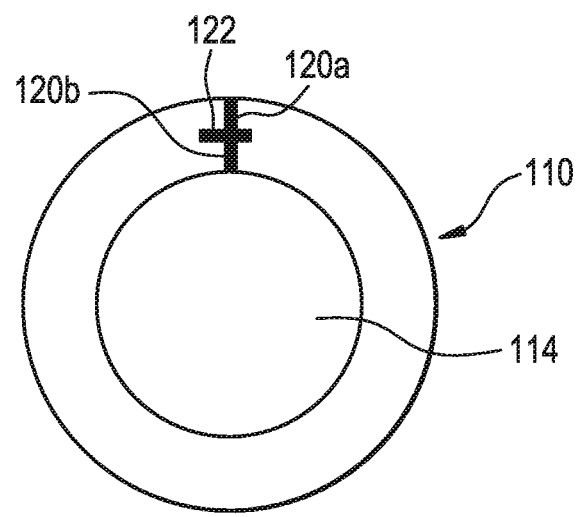

Methods of Manufacturing Tissue Augmentation Constructs—Blocks Having Tube Configurations An exemplary embodiment for making a tissue augmentation tube 110 is illustrated in FIGS. 22A-22C. The material being used to make the tube 110 can be harvested or otherwise acquired using techniques known to those skilled in the art. The material can then be shaped using any of the techniques described above with respect to the strip 10, elsewhere herein, or otherwise known to those skilled in the art. As shown in FIG. 22A, a piece of material 120 can be harvested having a length L' and a width W'. The width W' can be equal to approximately D*π, were D is the diameter of the tube 110, as shown in FIG. 2B. As shown in FIG. 22A, the piece of material 120 can be generally rectangular, having a first end 120*a* and a second end 120*b* with the width W' extending therebetween. Alternatively, the piece of material 120 can have any shape.

Once the piece of material 120 has been cut out, the first and second ends 120*a*, 120*b* can be brought proximate to one another and subsequently attached to one another, thereby forming a tube. As shown in FIGS. 22B and 22C, the first and second ends 120*a*, 120*b* are attached using a suture, or filament, 122 to stitch the ends together. Alternatively, the first and second ends 120*a*, 120*b* can be attached to one another with the use of glue, collagen bond, staples, light curing, crosslinking, mechanical interlock, dehydration, or other techniques for attaching soft tissue to soft tissue known to those skilled in the art. A threader 206 can be inserted into the tube 110 before the two ends 120*a*, 120*b* are attached, or after. The tube 110 can be dried for packaging. Alternatively, the tube 110 can be maintained in a hydrated form, without dehydrating the block 110 (this is the case with any construct discussed herein or otherwise derivable therefrom). An alternative method for manufacturing a tissue augmentation tube is provided for in FIGS. 23A-23C. In this method, multiple tubes 110*a*-110*c* can be made at a time from a single material, or as shown two pieces of material, one piece disposed above the other.

As shown, a first piece of material 130*a* and a second piece of material 130*b* are placed one on top of the other. Similar to earlier embodiments, the material 130*a*, 130*b* can be acquired, sized, and shaped using any techniques provided for herein or otherwise known to those skilled in the art. As shown in FIG. 23B, first and second pieces of material 130*a*, 130*b* can have a length L' and a width that is determined as a function of the number of tubes 110*a*-110*c* desired. Specifically, each tube 110 has a diameter, or width, D, as noted above. Therefore, the piece of material can have a width that is equal to the number of tubes 110 desired multiplied by D. Alternatively, the manufacturing can be planned to allow for a select amount of space to be formed between each strip that is formed. In some embodiments, a single piece of material (not shown) having a generally rectangular shape can be used, with the piece being folded in half to create a first piece of material and a second piece of material as shown, one layered upon the other.

Once the two pieces of material 130*a*, 130*b* have been cut to the desired size, pins 132*a*-132*c* can be placed therebetween. The pins 132*a*-132*c* can be placed approximately parallel to one another and perpendicular to a long edge 131 of the material. The pins 132*a*-132*c* can be spaced such that there is sufficient space between each pin 132*a*-132*c* to allow for attachment and separation of the individual tubes 110*a*-110*c*.

Figure 23A:
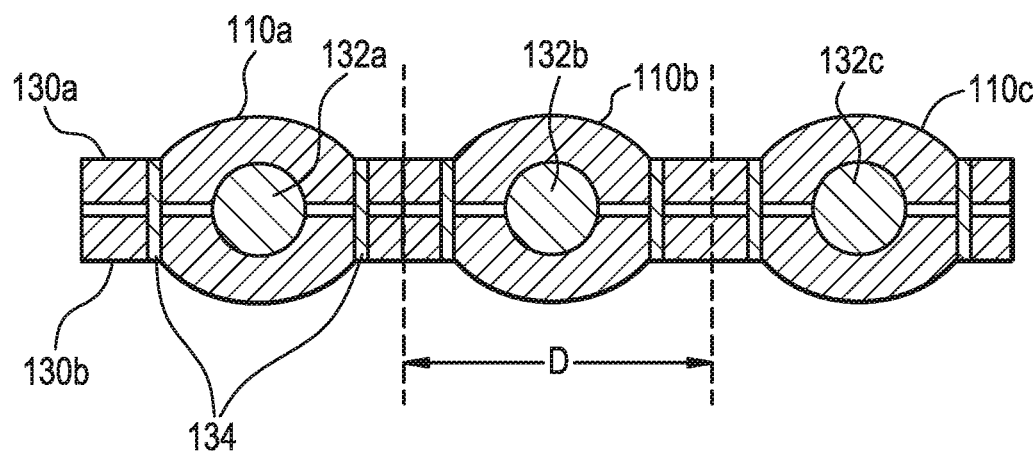
FIG. 23A is a front view of a plurality of tissue augmentation constructs during an exemplary embodiment for manufacturing tissue augmentation constructs.
Figure 23B:
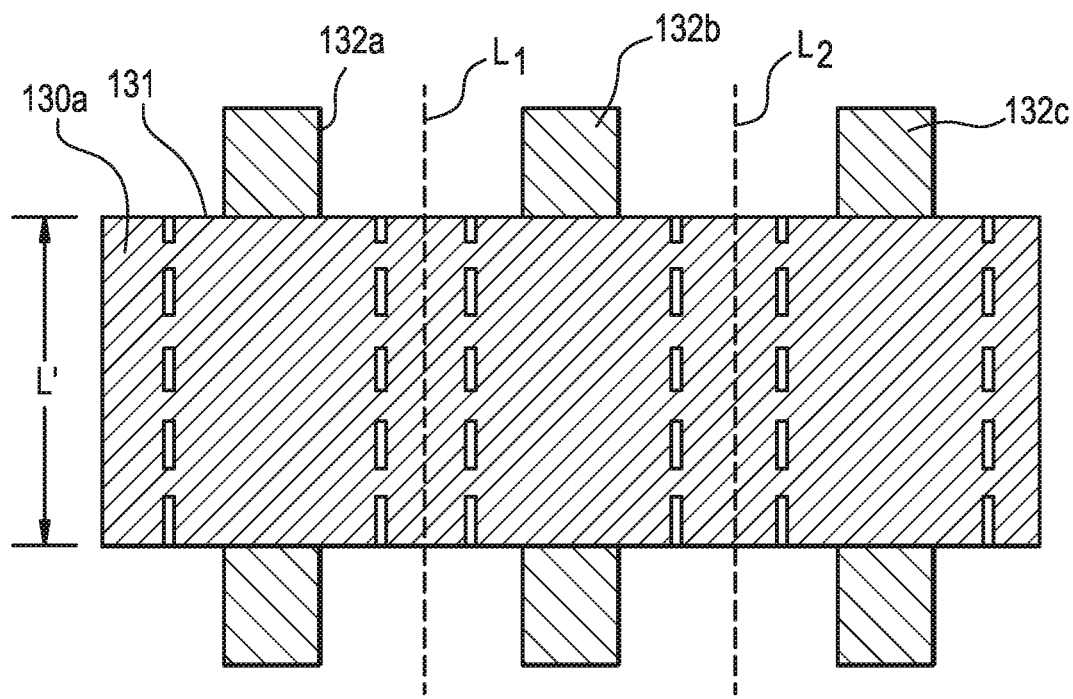
FIG. 23B is a top view of the plurality of tissue augmentation constructs of FIG. 23A.
Figure 23C:
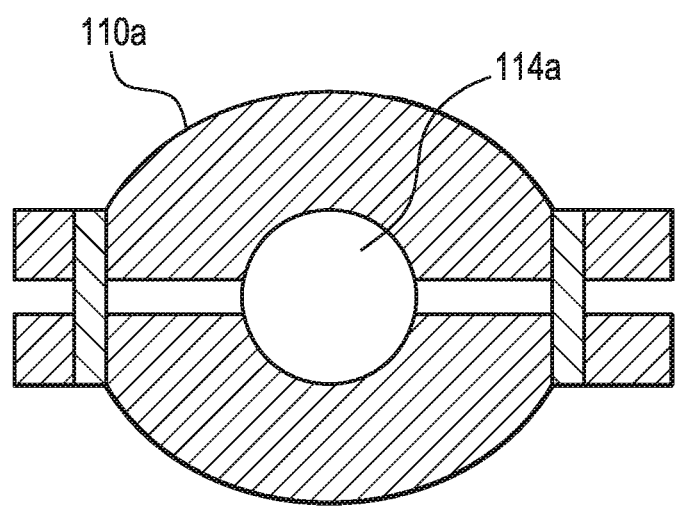
FIG. 23C is a front view of one tissue augmentation construct of the plurality of tissue augmentation constructs of FIG. 23A.

As shown in FIGS. 23A-23C, the first and second pieces of material 130*a*, 130*b* are attached using sutures 134 to stitch the two pieces together to form a tube around the pin 132*a*. Alternatively, the first and second pieces of material 130*a*, 130*b* can be attached to one another with the use of glue, collagen bond, staples, light curing, or other known techniques. Once all of the tubes 110*a*-110*c* have been stitched, the individual tubes 110*a*-110*c* can be cut along lines $L_1$ and $L_2$. The lines $L_1$ and $L_2$, as shown in FIG. 23B, are approximately parallel to the pins 132*a*-132*c*. Once the individual tubes 110*a*-110*c* have been cut, the pins 132*a*-132*c* can be removed, as shown in FIG. 23C, leaving a bore or lumen 114*a*. A threader 206 can be associated with the lumen 114*a* in manners provided for herein with respect to the lumen 114 of the tube 110 to pass a suture limb through the lumen.

This methods of manufacturing tubular constructs can also be used in similar manners to manufacture cannulated constructs like the bars 3010, 3110 illustrated in FIGS. 2E and 2F. In such instances, the pins 132*a*-132*c* can be removed once the cannulations are formed using them, and the two layers of material 130*a'*, 130*b'* can be lightly compressed, or can relax by themselves, towards each other. As a result, the lumen 114*a'* can transform from a tubular shape, as shown in FIG. 23C, to a slit shaped lumen 114*a'*, as shown in FIGS. 2E and 2F. As described above, the overall shape of the construct 3010, 3110 can be generally rectangular prisms. In the construction of the construct 3010, 3110, for example, the use of pins 132*a'*-132*c'* may be omitted altogether. Alternatively, the pins 132*a'*-132*c'* may be replaced with skewer blades, not shown, so that the shape of the lumen 114*c'* starts as a slit rather than starting with a tubular shape.

Figure 24A:
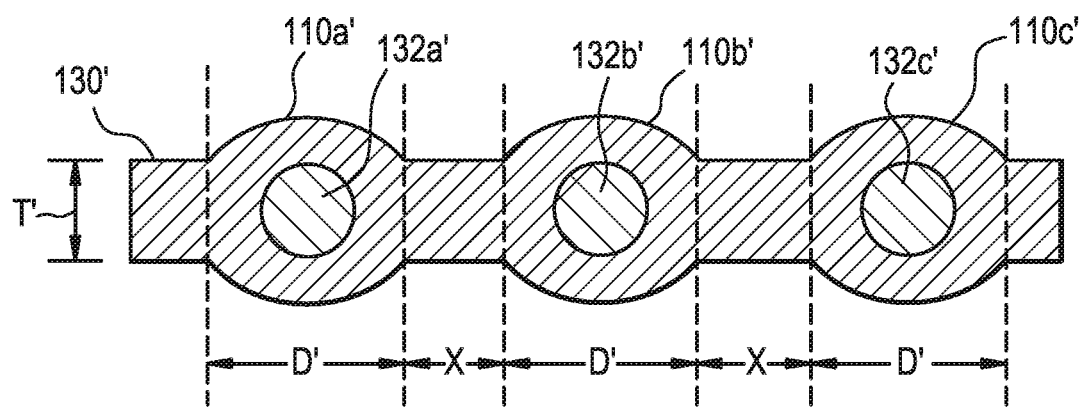
FIG. 24A is a front view of a plurality of tissue augmentation constructs during another exemplary embodiment for manufacturing tissue augmentation constructs.
Figure 24B:
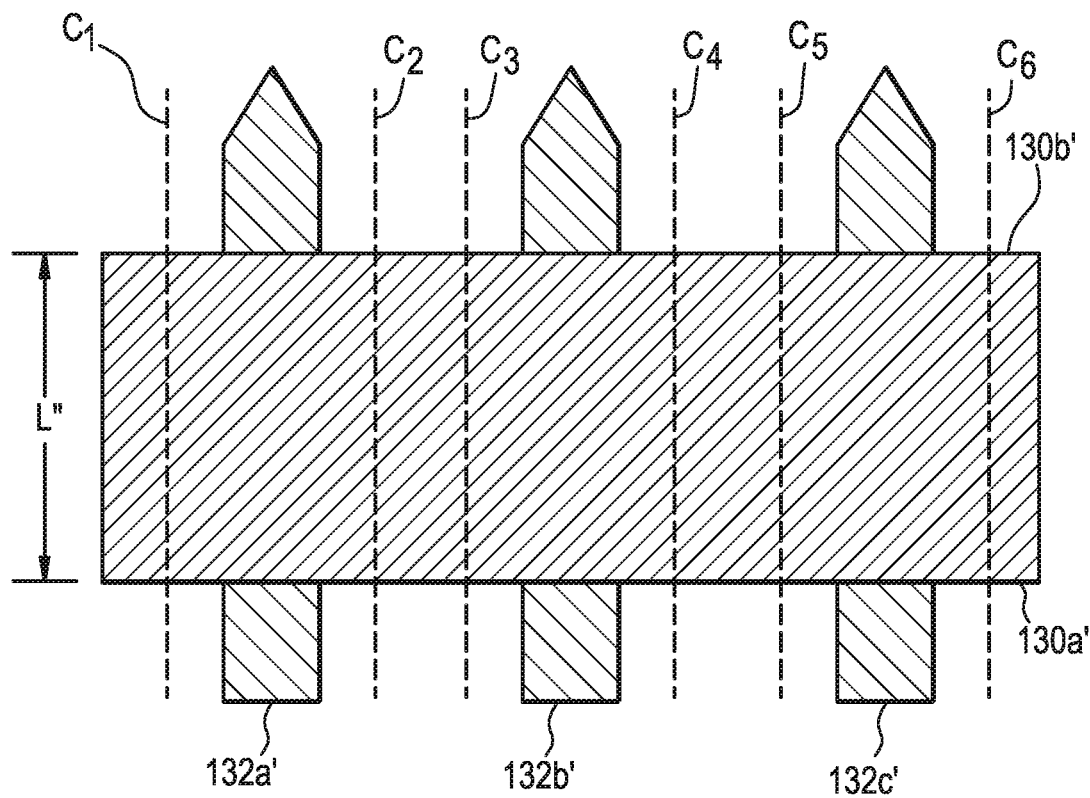
FIG. 24B is a top view of the plurality of tissue augmentation constructs of FIG. 23A.
Figure 24C:
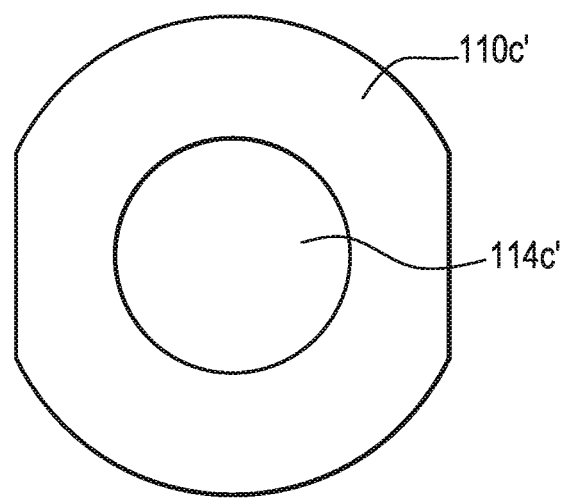
FIG. 24C is a front view of one tissue augmentation construct of the plurality of tissue augmentation constructs of FIG. 23A.

A further alternative method for manufacturing a tissue augmentation tube is provided for in FIGS. 24A-24C. This method also allows for multiple tube 110*a'*-110*c'* to be made at a time from a single material, or from multiple pieces of material if desired. As shown, a piece of material 130' can have a length L" and a width that is determined based upon the number of tubes desired. Specifically, each tube 110*a'*-110*c'* has a diameter, or width, D'. Therefore, the piece of material can have a width that is equal to the number of augmentation blocks 110' desired multiplied by D'. Alternatively, the width can include an additional space X between each tube 110', which can be accounted for when forming the size of the piece of material 130'. As with any of the embodiments provided for herein, a thickness of the material can vary, depending on a variety of factors, including but not limited to the size and shape of the other components and tissue with which the tube is being used, the anatomy of the patient, and the type of procedure being performed. In some exemplary embodiments, a thickness T' as illustrated in FIG. 24A, can be approximately in the range of about 0.5 millimeter to about 10 millimeters.

Once the piece of material 130' has been cut to the desired size, pins 132*a'*-132*c'* can be inserted through the piece of material 130' from a first edge 130*a'* to a second edge 130*b'*. The pins 132*a'*-132*c'* can be inserted such that they are approximately parallel to one another and approximately perpendicular to the first and second edges 130*a'*, 130*b'* of the material 130'. The pins 132*a'*-132*c'* can be spaced such that there is sufficient space between each pin 132*a'*-132*c'* to allow for separation. The pins 132*a'*-132*c'* can be sized to have a diameter that is approximately equal to the diameter of the resulting lumen 114".

Figure 25:
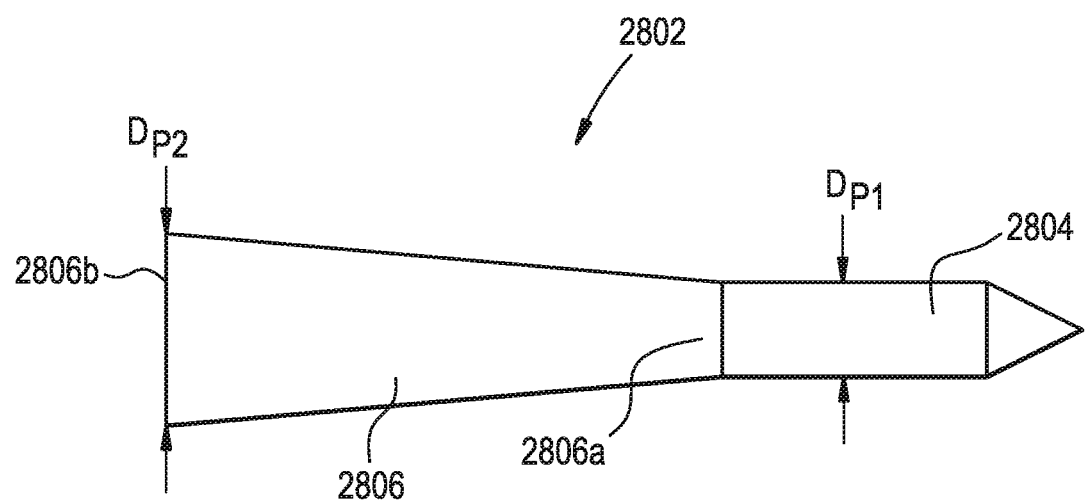
FIG. 25 is a side view of one exemplary embodiment of a distal end of a tool for manufacturing the tissue augmentation construct of FIG. 2A.

Alternatively, as shown in FIG. 25, a trocar 2802 can be used to form a lumen 114" in a piece of material. Trocars are generally known to those skilled in the art, and thus a detailed description related to trocars is unnecessary. In fact, in the illustrated embodiment, only a distal end of the trocar 2802 is shown, the distal end including a tip 2804 and a shaft 2806 with which the tip 2804 is associated, e.g., coupled. A distal-most end of the tip 2804 is pointed and sharp, and is thus configured to puncture tissue. The shaft 2806 of the trocar distally extends from a housing (not shown) to help guide the trocar in the material.

The trocar 2802 is unique in comparison to other trocars because the shaft 2806 has a gradually increasing diameter in a proximal direction P, i.e., towards the housing. More particularly, the tip 2804 has a, substantially constant, diameter $D_{P1}$ approximately in the range of about 0.10 millimeters to about 1 millimeter, with, as shown, the distal-most tip having a diameter that is even smaller than $D_{P1}$. The shaft 2806 has a gradually increasing diameter, starting from the first diameter $D_{P1}$ and terminating at a second diameter $D_{P2}$ approximately in the range of about 0.5 millimeters to about 5 millimeters. Other dimensions are certainly possible, depending, at least in part, on the desired lumen size, the instruments with which the trocar will be used, and surgeon preference.

The gradually increasing diameter of the shaft 2806 allows for more precise lumen formation in tissue. By starting with a trocar having a shaft that has a smaller diameter proximate to the distal tip 2804, it is easier to position and advance the trocar 2802 in soft biological tissue. In use, the tip 2804 can be positioned, for example, on the first edge of a piece of material and advanced by applying pressure and/or twisting the trocar 2802 as it is advanced towards a second side of the tissue to form an initial lumen. As the trocar 2802 is advanced distally towards the second side, a size of the opening that it forms increases gradually, from $D_{P1}$ to $D_{P2}$. This is different than typical trocars, which generally have a single size shaft associated with a distal tip.

Turning back to FIGS. 24A-24C, once all of the pins 132a'-132c' have been inserted, the individual tubes 110a'-110c' can be cut along lines $C_1$-$C_6$. The lines $C_1$-$C_6$, as shown in FIG. 24B, are approximately parallel to the pins 132a'-132c'. Once the individual tubes 110a'-110c' have been cut, the pins 132a'-132c' can be removed, as shown in FIG. 24C, leaving a lumen 114a'. A threader 206 can be associated with the lumen 114a' in manners provided for herein.

The methods of manufacture illustrated herein need not be performed in the order prescribed. For example, with respect to the methods of FIGS. 23A-23C and FIGS. 24A-24C, the pins 132a-132c and 132a'-132c' can be removed before the tubes 110a-110c and 110a'-110c' are cut apart. Further, the tubes 110a-110c and 110a'-110c' can be dried at any suitable point during the manufacturing process. Moreover, this process can be used to create any number of blocks having any number of shapes or configurations, including but not limited to tubular or rectangular, for example a single tissue augmentation block 110a and 110a', two augmentation blocks, or more than three augmentation blocks. Still further, the manufacturing technique provided for with respect to various manufacturing embodiments can be modified in view of the present disclosures to manufacture other tissue augmentation constructs. By way of non-limiting example, blocks having a tape or strip configuration can be formed in view of the present disclosures, thereby allowing multiple strips to be formed from a single piece of material and/or multiple pieces of material stacked on top of each other if such additional thickness and/or additional material is desired. The techniques can likewise be adapted for forming augmentation washers, such as by forming the disclosed blocks 110, 3010, or 3110, and then cutting them along their length to form washers.

Methods of Manufacturing Tissue Augmentation Constructs—Coring

In some embodiments of the various tissue augmentation constructs disclosed, including blocks, strips, tubes, bars, washers, patches, and tacks, one or more lumens or cannulations may be formed in a body of the construct. Some techniques for forming such lumens that involve using pins are provided above. Another exemplary technique for creating such lumens involves coring, as shown and described with respect to FIGS. 26A-26I.

Figure 26A:
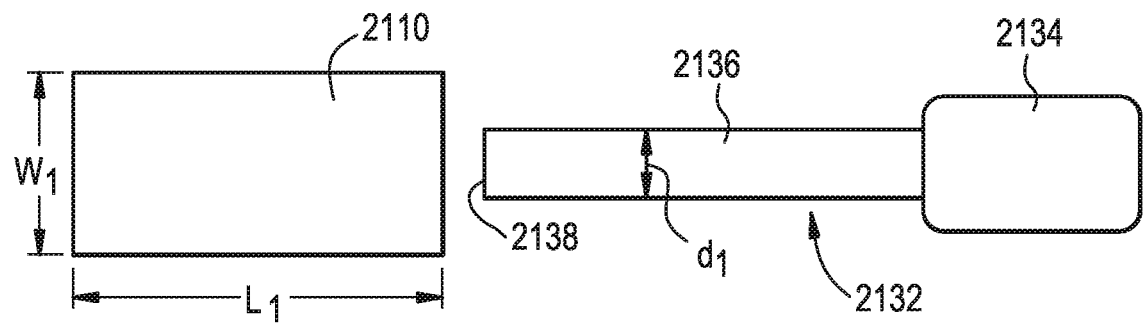
FIGS. 26A-26C are schematic sequential views of another exemplary embodiment for manufacturing a tissue augmentation construct.

As shown in FIG. 26A, a precut portion of a construct 2110 having a length $L_1$ and a width $W_1$ can be prepared to be cored. A tool can be used to core the construct 2110, such as a coring tube 2132. The coring tube 2132 can have a handle 2134 at a proximal end and a hollow tube 2136 at a distal end. The hollow tube 2134 of the coring tube 2132 can have a distal edge 2138 that can be sharpened or serrated to create a clean cut. The hollow tube 2134 can have a diameter $d_1$ that is less than the $W_1$ of the construct. The diameter $d_1$ can be chosen based on the suture size desired for a given procedure.

Figure 26B:
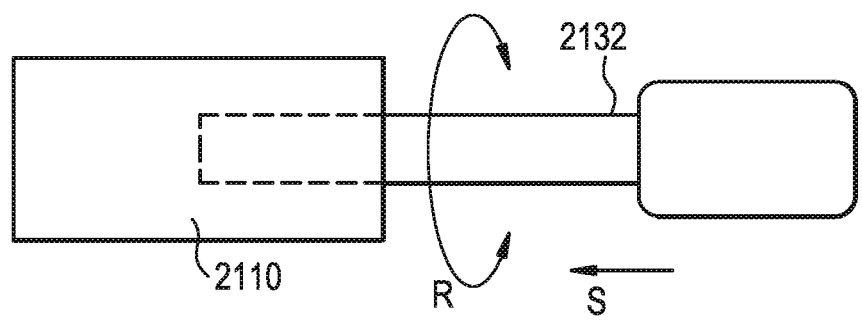
Figure 26C:
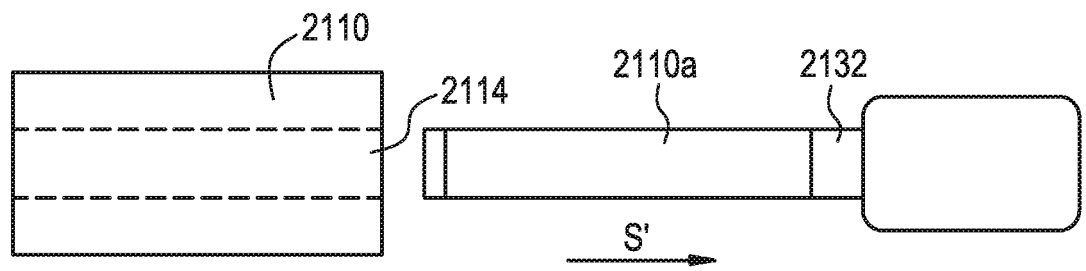
Figure 26D:
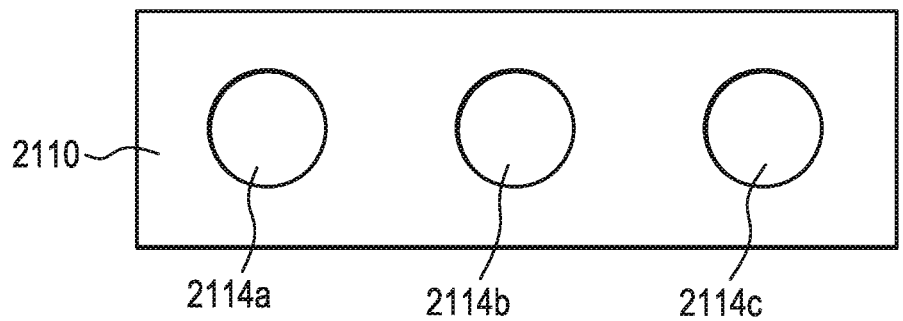
FIG. 26D is a side view of one tissue augmentation construct that can result from the manufacturing process illustrated in FIGS. 26A-26C.
Figure 26E:
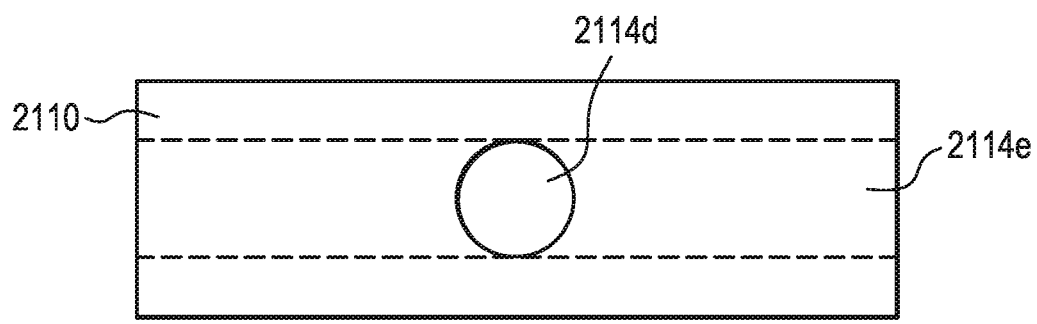
FIG. 26E is a side view of an alternative tissue augmentation construct that can result from the manufacturing process illustrated in FIGS. 26A-26C.
Figure 26F:
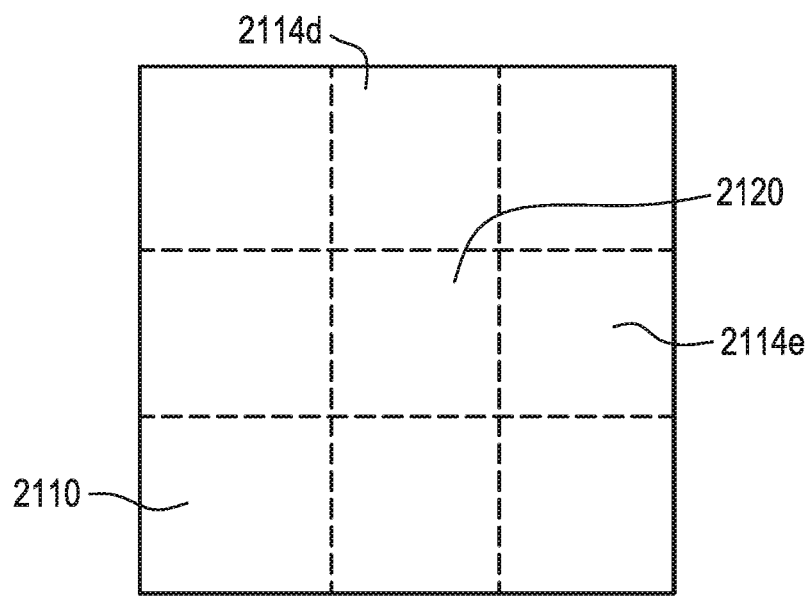
FIG. 26F is a top view of the tissue augmentation construct of FIG. 26E.

As shown in FIG. 26B, the coring tube 2132 can be advanced in the direction S while being rotated in the direction R. The rotation and linear translation of the tool 2132 can provide for a cleaner cut; however, the tool can be pushed through only in the direction S, without any rotation. As shown in FIG. 26C, once the distal end of the coring tube 2132 has been advanced along the entire length of the construct 2110, it can be removed in an opposite direction S', thereby removing the portion of material 2110a and leaving a circular lumen 2114. As shown in FIG. 26D, a plurality of lumens 2114a-2114c can be created in a single construct 2110. Alternatively, the construct of FIG. 26D can be cut into strips that run parallel to the lumens 2114a-2114c, thereby forming multiple constructs with each including only one lumen. In a further alternative embodiment, as shown in FIGS. 26E and 26F, at least two bores 2114d, 2114e can be created in a construct 2110 such that they intersect at some location 2120 in the construct.

Figure 26G:
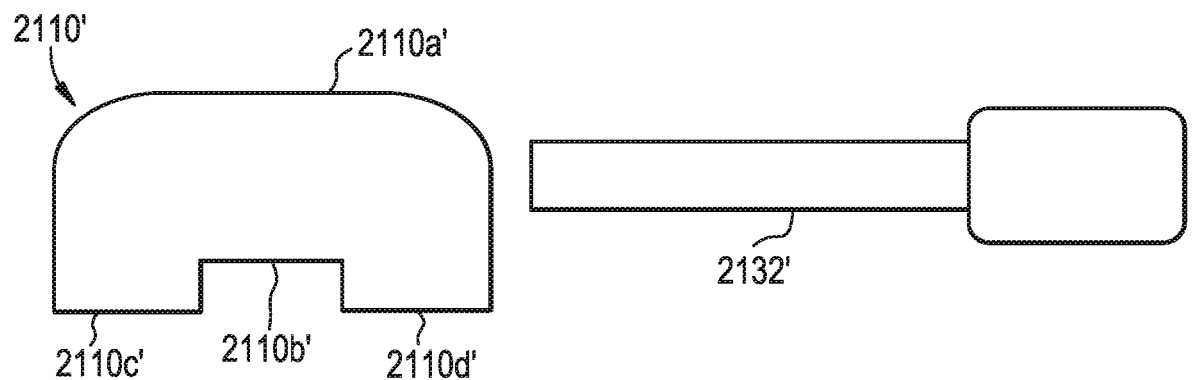
FIGS. 26G-26I are schematic sequential views of yet another exemplary embodiment for manufacturing a tissue augmentation construct.
Figure 26H:
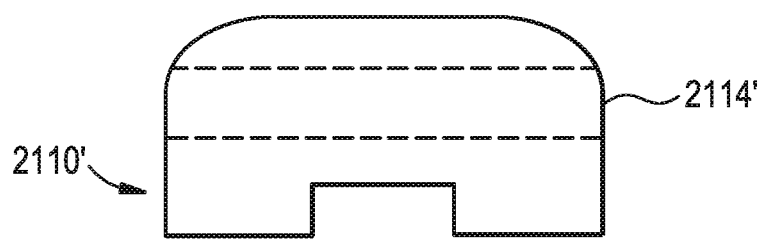
Figure 26I:
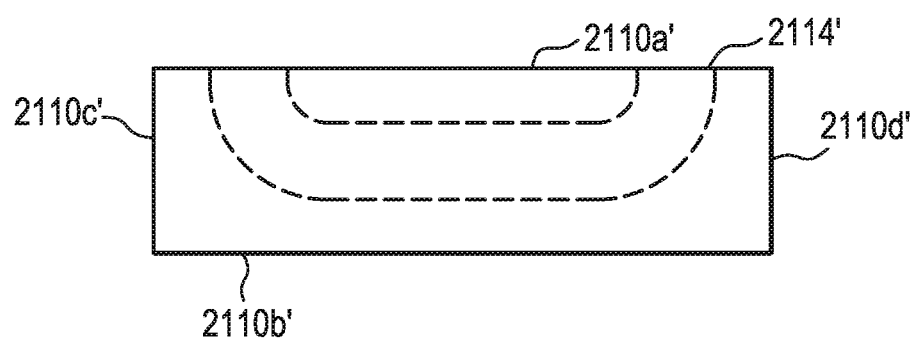

In alternative coring embodiments, illustrated in FIGS. 26G-26I, a curved lumen 2114' can be created using the coring tube 2132'. As shown in FIG. 26G, a generally U-shaped construct 2110' having first and second generally curved shaped edges 2110a', 2110b' and two straight edges 2110c', 2110d', is prepared to be cored. Similar to the embodiment of FIG. 26A-26C, a coring tube 2132' is used to core out a lumen 2114' through the construct that enters and exits along edge 2110a'. In FIG. 26H, the lumen 2114' is shown as being substantially linear. Once the lumen 2114' has been created, the construct can be stretched, or otherwise rearranged, such that the edges 2110a'-d' are all substantially straight to create a generally rectangular construct 2110', as shown in FIG. 26I.

Method of Manufacturing Tissue Augmentation Constructs—Tunneling Station

In a further alternative method of manufacturing, a construct formation tunneling station is provided. As shown in FIG. 27A, a construct formation tunneling station 3200 can include a stage 3220 for holding a tissue augmentation construct, a lumen formation tool 3224 for forming a lumen in the construct, and a guide 3228 for helping to locate the lumen formation tool 3224 with respect to the construct being held by the stage 3220.

In an exemplary embodiment, the construct stage 3220 can support and guide a piece of material 3230 from which constructs can be formed. The construct stage 3220 can be a self-centering compression stage to maintain a piece of material 3230 at a fixed height through the stage 3220. The self-centering of the construct stage 3220 can be accomplished according to accepted manufacturing techniques. The construct stage 3220 can include two stages 3220a, 3220b which are able to move towards and away from one another, Y1, Y2 to self-center and compress the material 3230. Alternatively, only one stage 3220a, 3220b can translate, or the stages 3220a, 3220b can be fixed relative to one another. The first stage 3220a can have a distal face 3219a that is opposed to the proximal face 3219b of the second stage 3220b. Each of the distal face 3219a and the proximal face 3219b can include semi-circular reliefs 3221a, 3221b that are able to accommodate the material 3230 upon insertion of the lumen formation tool 3222, as shown in FIGS. 27B and 27C. The construct stage 3220 can include mechanisms, not shown, to advance the material 3230 in a direction Z to automate the manufacturing process, for instance, as described below with respect to FIG. 27J.

The construct formation tunneling station 3200 can include a lumen formation tool 3224 that can include a guide 3228 and a cutting tool 3222. In the illustrated embodiment, the guide 3228 can generally include a lumen 3227 and can be fixed relative to the construct stage 3220 by connectors 3226a, 3226b to ensure that the relative orientation of the tool 3224 and the stage 3220 remains fixed such that the orientation of the lumen within a construct formed by the jig station 3200 is within accepted manufacturing tolerances from construct to construct. Alternatively, the guide 3228 can be secured to the stage 3220 with only one connector, or more than two connectors. Further, while the lumen forming tool 3224 is shown physically connected to the construct stage 3220, alternatively, the tool 3224 and the stage 3220 can be separate pieces that are fixed relative to one another, e.g., attached to the same work table, to ensure proper lumen forming alignment.

A cutting tool 3222 can be disposed within the guide 3228, including by being removably and replaceably associated with the guide 3228, such that the tool 3222 can freely rotate R and translate X within the guide 3228. In some embodiments, the tool 3222 can be a needle as shown in FIG. 27D. Alternatively, the cutting tool can be a spear, as shown in FIG. 27E, for example a Premier Edge MVR knife available from Oasis Medical of Glendora, California The spear can include a proximal stem portion 3222p having a substantially circular cross sectional shape and a distal spear portion 3222d. The distal spear portion can have a plurality of straight sharp edges 3223. The plurality of straight sharp edges 3223 can have a smooth transition from the proximal stem portion 3222p of the tool.

In further alternative embodiments the cutting tool 3222 can have a number of alternative designs. For example, a trocar as shown in FIG. 27F, a drill bit as shown in FIG. 27G, a coring tube as shown in FIG. 27H, or a straight blade as shown in FIG. 27I. Each of the alternative tools can be used to create a lumen within a construct 3210 according to accepted manufacturing techniques provided for throughout the present disclosure.

In an exemplary method of use, multiple tubes 3210a-3210d can be made at a time from a single length of material, or from multiple pieces of material if desired. As shown, a piece of material 3230 can have a length L and a width W. The width W of the material can be the length of the resulting construct while the length L can be determined based upon the number of constructs desired. Specifically, each construct 3210a-3210d has a diameter, or width, D. Therefore, the piece of material can have a length L that is equal to the number of constructs 3210 desired multiplied by D. Alternatively, the length L can include an additional space between each construct 3210, which can be accounted for when forming the size of the piece of material 3230. As with any of the embodiments provided for herein, a thickness of the material can vary, depending on a variety of factors, including but not limited to the size and shape of the other components and tissue with which the construct is being used, the anatomy of the patient, and the type of procedure being performed.

Once the piece of material 3230 is advanced into the stage 3220, the lumen forming tool 3224 can be actuated such that the cutting tool 3222 can be inserted through the piece of material 3230 from a first edge 3230a to a second edge 3230b, as shown in FIGS. 27I-K. Depending on the type of cutting tool 3222 used, the lumen forming tool 3224 can either translate the tool 3222 in a direction X, or rotate and translate the tool 3222 in the directions X and R into the material 3230. Actuation of the cutting tool 3222 can be performed automatically with an actuator. Alternatively, the cutting tool 3222 can be manually actuated by a user. The cutting tool 3222 can then be retracted leaving a lumen 3214a-3214c. The material 3230 can then be advanced, in the direction Z, a predetermined distance and the process can be repeated to create additional constructs. Individual constructs 3210a-3210d can then be separated from the piece of material 3230 as shown in FIGS. 27K and 27L. For example, the individual constructs 3210a-3210d can be separated by means of a punch 3290a-3290d or other cutting mechanisms as provided for throughout the present disclosure.

An alternative construct forming jig station 3200', as illustrated in FIG. 27M, can provide for parallel lumen formation. As shown in FIG. 27M, the stage 3220' can accommodate a larger length L' of the material 3230'. For example, as illustrated in FIG. 27M, the stage 3220' can accommodate a length required to create three constructs. Alternatively, the stage 3220' can extend to accommodate any number of constructs. The stage 3220' can, similar to the stage of the jig station 3200, have semi-circular reliefs and can be self-centering. Similar to the embodiment of FIGS. 27A-27L, the station 3220' can include a plurality of lumen forming tools 3224a', 3224b', 3224c' that are each aligned in parallel with each other. Alternatively, the plurality of tools 3224a', 3224b', 3224c' can be oriented at any angle relative to one another. The lumen forming tools 3224a', 3224b', 3224c' are aligned such that each of the respective cutting tools 3222a', 3222b', 3222c' each translate towards the stage in parallel directions. In the illustrated embodiment three lumen forming tools 3224a', 3224b_3224c' are shown, however any number of lumen forming tools can be provided for. After each of the lumen forming tools 3224a', 3224b', 3224c' have been actuated and retracted to create lumens 3214a', 3214b', 3214c' in the material 3230', the material 3230' can be advanced in the direction D'. The individual constructs 3210a', 3210b', 3210c' can be separated according to techniques provided for herein. Alternatively, constructs that include a plurality of lumens can be cut from the material to form patches or scaffolds, as discussed further below.

Methods of Manufacturing Tissue Augmentation Constructs—General Methods

The embodiments described above represent some specific techniques associated with manufacturing blocks having particular configurations, e.g., strips, tubes, bars, and washers. More general techniques such as coring are also provided. Such techniques can be adapted by a person skilled in the art for use in other configurations of tissue augmentation constructs in view of the present disclosures. Still further, the present disclosure provides for even more general techniques and methods that can be used to form the various tissue augmentation constructs disclosed herein derivable from the present disclosures. The methods provided for in this section can be used as standalone methods, in conjunction with each other, and/or in conjunction with the other manufacturing techniques provided for in the present disclosure.

In some embodiments, the constructs can be fully, or partially, manufactured by phase separation techniques, lyophilization, knitting, weaving, electrospinning, rapid prototyping (e.g., 3-D printing) or combinations of thereof. In order to facilitate tissue in growth, perforations can be created in the construct using thermal, electrical, or/and mechanical means, among others. For example, the perforations can be created by a laser or a sharp object such as a needle, punch, or die. The size of a perforation can be any suitable size, but preferably, the perforations are sized to allow tissue in-growth. More preferably, the perforations size can be approximately in the range of about 50 microns to about 2000 microns, and even more preferably, approximately in the range of about 50 microns to about 1000 microns.

In some embodiments, a biological tissue including, but not limited to, an allograft or xenograft tissue, may, optionally, be incorporated within the various tissue augmentation constructs, thus forming a two-layer construct. The combination of a biological tissue within the various tissue augmentation constructs can provide for enhanced biological performance and mechanical performance of a resulting construct.

For example, as shown in FIG. 28, a construct 2710 (as shown a patch or scaffold, which is described in greater detail below) can include a reconstituted collagen matrix or a biodegradable polymer, 2702 or any of the other materials described herein for use in a tissue augmentation construct (e.g., autograft, xenograft, pulverized collagen pieces, porcine dermis, etc.), and a biological component, such as an extracellular matrix (ECM) 2704, attached to one side of the matrix 2702 using techniques known to those skilled in the art. The reconstituted collagen matrix or biodegradable polymer can be, or can be part of, a first layer, and the biological component can be, or can be part of, a second layer, with a thickness and a surface area of the first layer being larger, and as shown substantially larger, than a thickness and a surface area of the second layer. In other embodiments, the biological component, e.g., the ECM 2704, can be disposed on opposed sides of the matrix 2702 and/or coated or soaked onto the matrix 2702. A person skilled in the art will recognize a number of different attachment options that can be used to couple the ECM(s) 2704 to the matrix 2702, including but not limited to gluing and stitching. The inclusion of the ECM 2704 or other biological component can help integrate the augmentation construct with the tissue with which the construct is being used. In one exemplary embodiment, the matrix 2702 can have a thickness $T_1$ approximately in the range of about 1 millimeter to about 4 millimeters, and the ECM layer can have a thickness approximately in the range of about 80 microns to about 3 millimeters.

In some embodiments, a biological component can be coated onto the tissue augmentation construct, or incorporated in the tissue augmentation construct. If a biological component is coated onto the tissue augmentation construct, the biological component is preferably associated with at least a portion of the construct. For example, the biocompatible construct can include an adhesion agent for anchoring the suspension of the biological component to a scaffold. The adhesion agent can be an anchoring agent, a cross-linking agent (i.e., chemical or physical), and combinations thereof. Suitable anchoring agents can include, for example, hyaluronic acid, fibrin glue, fibrin clot, collagen gel, alginate gel, gelatin-resorcin-formalin adhesive, mussel-based adhesive, dihydroxyphenylalanine (DOPA) based adhesive, chitosan, transglutaminase, poly(amino acid)-based adhesive, cellulose-based adhesive, polysaccharide-based adhesive, synthetic acrylate-based adhesives, platelet rich plasma (PRP), platelet poor plasma (PPP), clot of PRP, clot of PPP, Matrigel, Monostearoyl Glycerol co-Succinate (MGSA), Monostearoyl Glycerol co-Succinate/polyethylene glycol (MGSA/PEG) copolymers, laminin, elastin, proteoglycans, and combinations thereof.

Cross-linking can be achieved using physical means and chemical agents. Examples of chemical agents used to cross-link can include dehydrothermal (DHT) treatment, divinyl sulfone (DVS), polyethylene glycol divinyl sulfone (VS-PEG-VS), hydroxyethyl methacrylate divinyl sulfone (HEMA-DIS-HEMA), formaldehyde, glutaraldehyde, aldehydes, isocyanates, alkyl and aryl halides, imidoesters, N-substituted maleimides, acylating compounds, carbodiimide, hexamethylene diisocyanate, 1-Ethyl-3-[3-dimethylaminopropyl]carbodiimide hydrochloride (EDC or EDAC), hydroxychloride, N-hydroxysuccinimide, light (e.g., blue light and UV light), pH, temperature, and combinations thereof.

The biological components can be one or more effectors that promote healing and/or regeneration of the affected tissue at the site of injury. The biological component of a construct can include heterologous or autologous growth factors, proteins, matrix proteins, peptides, antibodies, antibiotics, anti-inflammatories, therapeutic agents, chemotactic agents, antimicrobial agents, antibiotics, anti-inflammatory agents, compounds that minimize or prevent adhesion formation, compounds or agents that suppress the immune system, cell attachment mediators, biologically active ligands, integrin binding sequence, enzymes, cytokines, glycosaminoglycans, polysaccharides, viruses, virus particles, nucleic acids, analgesics, cells, platelets, platelet rich plasma (PRP), minced extracellular particles, minced tissue fragments, hydroxyapatite, tricalcium phosphate, bioactive glass, biphasic calcium phosphate, calcium sulfate, other bone and/or tissue growth-promoting materials, and combinations thereof.

As described herein, in some embodiments the tissue augmentation construct can have one or more through holes or bores extending therethrough. The through hole(s) can be a slit or a passage with different cross-sectional shapes, for example, circular, elliptical, square, rectangular, etc. The through hole(s) can be created by any tool that can remove materials including mechanical, thermal, or electrical tools. Alternatively, the through hole(s) can be a slit(s) that can be created by any tool that results in the separation of two surfaces.

In some embodiments, the construct can be made of more than one layer. The layers of the construct can be made of the same material or different materials. The layers can be bonded or fused together using sutures, mechanical, electrical, and chemical fastening techniques. Examples of bonding or fusing can include, for example, tissue welding, staples, rivets, tissue tacks, darts, screws, pins, arrows, cross-linking, vacuum pressing, compression, compression combined with dehydration, vacuum pressing combined with dehydration, or a biological adhesive or a combination of thereof. Dehydration in this context can include, for example, freeze-drying (i.e., lyophilization). Biological adhesives can include, for example, fibrin glue, fibrin clot, collagen gel, alginate gel, gelatin-resorcin-formalin adhesive, mussel-based adhesive, dihydroxyphenylalanine (DOPA) based adhesive, chitosan, transglutaminase, poly (amino acid)-based adhesive, cellulose-based adhesive, polysaccharide-based adhesive, synthetic acrylate-based adhesives, platelet rich plasma (PRP), platelet poor plasma (PPP), clot of PPP, Matrigel, Monostearoyl Glycerol co-Succinate (MGSA), Monostearoyl Glycerol co-Succinate/ polyethylene glycol (MGSA/PEG) copolymers, laminin, elastin, hyaluronic acid, proteoglycans, and combinations thereof.

In some embodiments the construct can include a reinforcing material. The reinforcing material can be comprised of any absorbable or non-absorbable textile having, for example, woven, knitted, warped knitted (i.e., lace-like), non-woven, and braided structures. In one embodiment, the reinforcing material can have a mesh-like structure. Mechanical properties of the material can be altered by changing the density or texture of the material, the type of knit or weave of the material, the thickness of the material, or by embedding particles in the material.

Mechanical properties of the reinforcing material can additionally be altered by creating sites within the construct where fibers are physically bonded with each other or physically bonded with another agent, such as, for example, an adhesive or a polymer. The fibers used to make the reinforcing component can be, for example, monofilaments, yarns, threads, braids, or bundles of fibers. These fibers can be made of any biocompatible material including, but not limited to, bioabsorbable materials such as polylactic acid (PLA), polyglycolic acid (PGA), polycaprolactone (PCL), polydioxanone (PDO), trimethylene carbonate (TMC), copolymers or blends thereof. The fibers can also be made from any biocompatible materials based on natural polymers including silk and collagen-based materials. Alternatively, the fibers can also be made of any biocompatible fiber that is nonresorbable, such as, for example, polyethylene, nylon, polyester, polyethylene terephthalate, poly(tetrafluoroethylene), polycarbonate, polypropylene, polyurethane, and poly(vinyl alcohol).

In another embodiment, the construct may incorporate hydroxyapatite, tricalcium phosphate, Bioglass, biphasic calcium phosphate, calcium sulfate, and other bone-promoting materials within the whole construct or localized in a portion of the construct where bone regeneration is desired. Bioglass is a silicate containing calcium phosphate glass, or calcium phosphate glass with varying amounts of solid particles added to control resorption time. Bioglass is one example of materials that can be spun into glass fibers and used as a reinforcing material. Bioglass can also be incorporated into the construct in a powder form. Suitable solid particles may be added include iron, magnesium, sodium, potassium, and combinations thereof.

In some embodiments, both the biocompatible construct and the reinforcing material may be formed from a thin, perforation-containing elastomeric sheets with pores or perforations to allow tissue in-growth. A sheet can be made of blends or copolymers of polylactic acid (PLA), polyglycolic acid (PGA), polycaprolactone (PCL), and polydioxanone (PDO).

The construct can be formed partially or completely from a polymeric foam component, having pores with an open cell pore structure. The pore size can vary, but preferably, the pores are sized to allow tissue in-growth. In some embodiments, the pore size is approximately in the range of about 40 microns to about 1000 microns, and in other embodiments, the pore size is approximately in the range of about 50 microns to about 500 microns. The polymeric foam component can be made from natural or/and synthetic materials, such as reconstituted collagen. The polymeric foam can be non-crosslinked or crosslinked. The polymeric foam component can, optionally, contain a reinforcing component, such as for example, textiles as discussed above. In some embodiments, the polymeric foam component can contain a reinforcing component which can be integrated with the reinforcing component such that the pores of the foam component penetrate the mesh of the reinforcing component and interlock with the reinforcing component.

In some embodiments the polymeric foam component of the tissue implant may be formed as a foam by a variety of techniques well known to those having skill in the art. For example, the polymeric starting materials may be foamed by lyophilization, supercritical solvent foaming, which is described at least in European Patent Application No. 464,163, the contents of which is incorporated by reference herein in its entirety, gas injection extrusion, gas injection molding or casting with an extractable material (e.g., salts, sugar, or similar suitable materials).

A polymeric foam component of engineered tissue repair implant devices of the present disclosure may be made by a polymer-solvent phase separation technique, such as lyophilization. A polymer solution can be separated into two phases by any one of the four techniques: (a) thermally induced gelation/crystallization; (b) non-solvent induced separation of solvent and polymer phases; (c) chemically induced phase separation, and (d) thermally induced spinodal decomposition. The polymer solution can be separated in a controlled manner into either two distinct phases or two bi-continuous phases. Subsequent removal of the solvent phase usually leaves a porous structure with a density less than the bulk polymer and pores in the micrometer ranges. Additional information about the solvent phase is provided in Microcellular Foams via Phase Separation, J. Vac. Sci. Technol., A. T. Young, Vol. 4(3), May/June 1986, the contents of which is incorporated by reference herein in its entirety.

The steps involved in the preparation of these foams include, for example, choosing the right solvents for the polymers to be lyophilized and preparing a homogeneous solution. Next, the polymer solution can be subjected to a freezing and vacuum drying cycle. The freezing step phase can separate the polymer solution and vacuum drying step can remove the solvent by sublimation and/or drying, leaving a porous polymer structure or an interconnected open cell porous foam. Suitable solvents that may be used in the preparation of the foam component can include, for example, formic acid, ethyl formate, acetic acid, hexafluoroisopropanol (HFIP), cyclic ethers (e.g., tetrahydrofuran (THF), dimethylene fluoride (DMF), and polydioxanone (PDO)), acetone, acetates of C2 to C5 alcohols (e.g., ethyl acetate and t-butylacetate), glyme (e.g., monoglyme, ethyl glyme, diglyme, ethyl diglyme, triglyme, butyl diglyme and tetraglyme), methylethyl ketone, dipropyleneglycol methyl ether, lactones (e.g., γ-valerolactone, δ-valerolactone, β-butyrolactone, γ-butyrolactone), 1,4-dioxane, 1,3-dioxolane, 1,3-dioxolane-2-one (ethylene carbonate), dimethylcarbonate, benzene, toluene, benzyl alcohol, p-xylene, naphthalene, tetrahydrofuran, N-methylpyrrolidone, dimethylformamide, chloroform, 1,2-dichloromethane, morpholine, dimethylsulfoxide, hexafluoroacetone sesquihydrate (HFAS), anisole, and mixtures thereof. Among these solvents, one exemplary solvent is 1,4-dioxane. A homogeneous solution of the polymer in the solvent is prepared using standard techniques.

The applicable polymer concentration or amount of solvent that may be utilized can vary with each system. In one embodiment, the amount of polymer in the solution can vary from about 0.5% to about 90% by weight. In another embodiment, preferably, the amount of polymer in the solution can vary from about 0.5% to about 30% by weight. The amount of polymer in the solution can vary depending on factors such as the solubility of the polymer in a given solvent and the final properties desired in the foam.

In embodiments of the construct that include a polymeric foam, solids may be added to the polymer-solvent system to modify the composition of the resulting polymeric foam surfaces. As the added particles settle out of solution to the bottom surface, regions will be created that will have the composition of the added solids, not the foamed polymeric material. Alternatively, the added solids may be more concentrated in desired regions (i.e., near the top, sides, or bottom) of the resulting tissue augmentation construct, thus causing compositional changes in all such regions. For example, concentration of solids in selected locations can be accomplished by adding metallic solids to a solution placed in a mold made of a magnetic material (or vice versa).

A variety of types of solids can be added to the polymer-solvent system. In one embodiment, the solids are of a type that will not react with the polymer or the solvent. The added solids can have an average diameter of less than about 2 millimeters. In other embodiments, added solids can have an average diameter of about 50 microns to about 1000 microns. The solids can be present in an amount such that they will constitute from about 1 volume to about 50 volume percent of the total volume of the particle and polymer-solvent mixture (wherein the total volume percent equals 100 volume percent).

Exemplary solids include, for example, particles of demineralized bone, calcium phosphate particles, Bioglass particles, calcium sulfate, or calcium carbonate particles for bone repair, leachable solids for pore creation and particles of bioabsorbable natural polymers, bioabsorbable synthetic polymers, non-bioabsorbable materials, minced extracellular particles, minced tissue fragments, or any biocompatible materials that is not soluble in the solvent system.

Exemplary leachable solids include, for example, non-toxic leachable materials such as salts (e.g., sodium chloride, potassium chloride, calcium chloride, sodium tartrate, sodium citrate, and the like), biocompatible mono and disaccharides (e.g., glucose, fructose, dextrose, maltose, lactose and sucrose), polysaccharides (e.g., starch, alginate, chitosan), water soluble proteins (e.g., gelatin and agarose). Leachable materials can be removed by immersing the foam with the leachable material in a solvent in which the particle is soluble for a sufficient amount of time to allow leaching of substantially all of the particles. The solvent can be chosen so that it does not dissolve or detrimentally alter the foam. One preferred embodiment can include water as the extraction solvent, for example distilled-deionized water. Such a process is described further in U.S. Pat. No. 5,514, 378, the contents of which is incorporated by reference herein in its entirety. Preferably the foam will be dried after the leaching process is complete at low temperature and/or vacuum to minimize hydrolysis of the foam unless accelerated absorption of the foam is desired.

Non-bioabsorbable materials can include, for example, bioinert ceramic particles (e.g., alumina, zirconia, and calcium sulfate particles), polymers such as polyethylene, polyvinylacetate, polymethylmethacrylate, polypropylene, poly(ethylene terephthalate), silicone, polyethylene oxide, polyethylene glycol, polyurethanes, polyvinyl alcohol, natural polymers (e.g., cellulose particles, chitin, and keratin), and fluorinated polymers and copolymers (e.g., fluoride, polytetrafluoroethylene, and hexafluoropropylene). In one embodiment, it is possible to add solids (e.g., barium sulfate) that will render the tissue implants radio opaque. Those solids that may be added also include those that will promote tissue regeneration or healing, as well as those that act as buffers, reinforcing materials or porosity modifiers.

As discussed above, polymeric foam components can contain a reinforcing component. The construct can be made by injecting, pouring, or otherwise placing, the appropriate polymer solution into a mold set-up comprised of a mold and the reinforcing elements of the present disclosure. The mold set-up can be cooled in an appropriate bath or on a refrigerated shelf and then lyophilized, thereby providing a reinforced construct.

In embodiments that utilize a polymeric foam, one or more of the biological components provided for throughout the present disclosure can be added either before or after the lyophilization step. In the course of forming the polymer foam component, it can be beneficial to control the rate of freezing of the polymer-solvent system. The type of pore morphology that is developed during the freezing step is a function of factors such as the solution thermodynamics, freezing rate, temperature to which it is cooled, concentration of the solution, and whether homogeneous or heterogeneous nucleation occurs. The orientation of the polymeric fibers can be regulated be controlling the pore orientation. The pores orientation in the polymeric form component can be customized, for example, by controlling the temperature gradient induced during the freezing cycle. Controlling the orientation of fibers can result in an improvement in the mechanical properties in the direction that the fibers are oriented.

The required general processing steps for a construct that uses polymeric foam can include the selection of the appropriate materials from which the polymeric foam will be made. The processing steps can additionally include selection of the materials of the reinforcing components if used. If a mesh reinforcing material is used, the proper mesh density should be selected. Further, the reinforcing material should be properly aligned in the mold, the polymer solution should be added at an appropriate rate and, preferably, into a mold that is tilted at an appropriate angle to avoid the formation of air bubbles, and the polymer solution must be lyophilized.

In embodiments that utilize a mesh reinforcing material in a polymeric foam, for example, the reinforcing mesh should be selected to be of a certain density. That is, the openings in the mesh material should not be so small so as to impede proper bonding between the foam and the reinforcing mesh as the foam material and the open cells and cell walls thereof penetrate the mesh openings. Without proper bonding the integrity of the layered structure can be compromised, leaving the construct fragile and difficult to handle. The density of the mesh can determine the mechanical strength of the construct. The density of the mesh can vary according to the desired use for tissue repair. In addition, the type of weave used in the mesh can determine the directionality of the mechanical strength of the construct, as well as the mechanical properties of the reinforcing material, such as for example, the elasticity, stiffness, burst strength, suture retention strength, and ultimate tensile strength of the construct. By way of non-limiting example, the mesh reinforcing material in a foam-based biocompatible construct of the present disclosure can be designed to be stiff in one direction, yet elastic in another, or alternatively, the mesh reinforcing material can be made isotropic.

During lyophilization of the reinforced foam in those embodiments that utilize a mesh reinforcing material in a polymeric foam, several parameters and procedures can be helpful to produce implants with the desired integrity and mechanical properties. For example, if reinforcement material is used, it can be beneficial to maintain the reinforcement material substantially flat when placed in the mold. To ensure the proper degree of flatness, the reinforcement (e.g., mesh) can be pressed flat using a heated press prior to its placement within the mold. Further, in the event that reinforcing structures are not isotropic, it can be desirable to indicate this anisotropy by marking the construct to indicate directionality. The marking can be accomplished by embedding one or more indicators, such as dyed markings or dyed threads, within the woven reinforcements. The direction or orientation of the indicator can, for example, indicate to a surgeon the dimension of the implant in which physical properties are superior.

In embodiments that utilize polymeric foam, as noted above, the manner in which the polymer solution is added to the mold prior to lyophilization can help contribute to the creation of a tissue implant with adequate mechanical integrity. Assuming that a mesh reinforcing material will be used, and that it will be positioned between two thin (e.g., approximately 0.75 millimeters) shims, the mesh can be positioned in a substantially flat orientation at a desired depth in the mold. The polymer solution can be poured in a way that allows air bubbles to escape from between the layers of the foam component. The mold can be tilted at a desired angle and pouring is effected at a controlled rate to best prevent bubble formation. A number of variables will control the tilt angle and pour rate. For example, the mold should be tilted at an angle of greater than about one degree to avoid bubble formation. In addition, the rate of pouring should be slow enough to enable any air bubbles to escape from the mold, rather than to be trapped in the mold.

In those embodiments that utilize a mesh reinforcing material in a polymeric foam, the density of the mesh openings can be an important factor in the formation of the construct with the desired mechanical properties. For example, a low density, or open knitted mesh material, can be used. One example of such a material is a 90:10 copolymer of glycolide and lactide, sold under the tradename VICRYL, which is available from Ethicon, Inc. of Somerville, New Jersey One exemplary low density, open knitted mesh is Knitted VICRYL VKM-M, which is also available from Ethicon, Inc. of Somerville, New Jersey Other materials can include but are not limited to polydioxanone and a 95:5 copolymer blend of lactide and glycolide.

In embodiments that utilize a polymeric foam, a through opening can be created by placing a rod in the polymeric foam solution/slurry before it has set. After the polymeric form is formed, the rod can be removed. For example, if the polymeric foam is made by lyophilization, the rod is removed after the freeze and vacuum drying cycle. The rod can have any desired shape.

The polymeric foam component can, optionally, contain one or more layers made of the materials discussed above. In one embodiment, the foam component can be integrated with the material(s) by creating pores in the materials and then the polymeric foam component penetrate the pores created in the materials(s) and interlock with the material(s). In another embodiment, pores are formed in materials of two layers, and the two layers are put together to best align the pores. The two layer combination can be placed in a polymeric solution or slurry, and the polymeric foam can be formed by one of the methods provided for herein or otherwise known to those skilled in the art.

In some embodiments, a construct can be formed from an expanding media that can advantageously provide added compression at the repair site. One non-limiting example of such a construct 2910 is shown in FIG. 29A, in which the construct is a patch or scaffold (as described in greater detail below). For example, the construct 2910 can be formed from a woven or braided mesh having a core 2904 surrounded or sandwiched between two layers 2902a, 2902b. The two layers 2902a, 2902b can be referred to as a jacket. The core 2904 can be made from a variety of materials that are capable of expanding, such as silicone loaded with salt, sodium polyacrylate, polyacrylamide copolymer, polyurethanes, and other absorbent polymers and hydro gels, while the jacket 2902a, 2902b can be more rigid so that the core can compress against the jacket as it expands in use. Non-limiting exemplary materials that can be used to form the jacket 2902a, 2909b include fabric and filament such as polyethylene, polypropylene, polyester, poly(ethylene terephthalate), nylon, polyurethanes and silk. Further non-limiting exemplary materials that can be used to form the jacket 2902a, 2902b include bioabsorbable materials such as polylactic acid (PLA), polyglycolic acid (PGA), polycaprolactone (PCL), polydioxanone (PDO), trimethylene carbonate (TMC), copolymers or blends thereof. Some materials that can be used in conjunction with the construct include, but are not limited to, those disclosed and provided for in U.S. Pat. No. 8,870,915, entitled "Joining Element," the contents of which is incorporated by reference herein in its entirety. The construct 2910 can have a length $L_P$ and a thickness $T_P$, as shown in FIG. 29A, and can include at least one suture limb 2911 for affixing the construct to one or more repair sites. In the illustrated example the construct 2910 includes four suture limbs 2911, 2912, 2913, 2914 associated with it. The limbs can be from the same or different sutures.

In use, as shown in FIG. 29B, the construct 2910 can be placed over the repair sites 2938a, 2938b, and the suture limbs 2911, 2912, 2913, 2914 can be fixed within respective anchors 2961, 2962, 2963, 2964. As with other disclosures, the repairs associated with the repair sites 2938a, 2938b can be any type of repair provided for herein or otherwise known to those skilled in the art. The construct 2910 can be further affixed to a location medial of the repairs 2938a, 2938b with sutures, staples, or other devices and components used to fixate tissue with respect to bone. As shown, sutures 2940a-2940c provide the fixation. The construct 2910 can be exposed to an aqueous solution, for example after installation, such that the silicone and salt filled core can absorb the fluid to cause the construct to expand in at least one dimension and contract in at least one other dimension based on the configuration of the construct 2910. In the illustrated example, the expansion causes the construct 2910 to increase in thickness $T_P$ while contracting and decreasing across its length $L_P$. The decrease in the length $L_P$ after the construct 2910 is installed can increase the compressive forces to the soft tissue 2930 to bring the tissue into more uniform contact with the bone 2950 due, at least in part, to the limited space for fixation of the construct 2910, the configuration of the construct 2910, and the surface geometry of the attachment site. One skilled in the art will appreciate that a configuration of a construct having a core, capable of expanding, sandwiched between layers or a jacket can be used with other construct configurations provided for herein, including those that are not necessarily a patch or scaffold, to provide for added compressive forces at repair sites. A further discussion of tissue augmentation patches and scaffolds is provided below.

Unless specified otherwise, any of the materials, and any of the techniques disclosed for forming materials, can be used in conjunction with any of constructs provided for herein. This includes any combination of materials. Likewise, the manufacturing techniques disclosed can generally be used, or adapted to form the various constructs provided for herein. The use of materials and manufacturing techniques for various tissue augmentation constructs is within the spirit of the present disclosure.

Tissue Augmentation Constructs—Tissue Augmentation Patches

Tissue augmentation constructs can also come in form of a patch or scaffold that can be associated with one or more limbs of suture to increase a footprint of the one or more limbs and to provide additional surface area across which forces to be distributed, among other benefits articulated throughout the present disclosure, e.g., enhancing healing of otherwise compromised tissue and/or providing bulk to otherwise compromised or degenerate tissue and/or tendon. The patches can be disposed on, or even attached or coupled, to the suture rather than just sitting on top of operative sutures. Further, the instant patches can be delivered to the surgical site and threaded onto sutures using a suture threader as described herein, thereby obviating the need for extensive suturing of each edge of a patch. A number of different techniques can be used to associate the illustrated patches with suture, including threading the suture through the patch and/or disposing the suture in between layers of a scaffold. The patch can then be disposed proximate to a surgical site as described. Methods of manufacturing a scaffold or patch, and methods of installing various scaffolds and patches, are also provided for below. The systems and methods disclosed herein allow for quick, easy, and affordable techniques for preventing damage to tissue by tensioned suture. Like the other constructs described above, a surgeon can apply the patch(es) in an on-demand manner to create desired suture footprints for the repair. A person skilled in the art will recognize that the disclosures provided for herein related to tissue augmentation blocks, e.g., by way of non-limiting example, the materials used to form the tissue augmentation blocks 10, 110, 3010, 3110, 310, 410, among other constructs, can be applied to the patches discussed below.

One exemplary embodiment of a tissue augmentation construct 2210 having a patch or scaffold configuration is provided for in FIGS. 30A and 30B. As shown, the tissue augmentation patch 2210 has a rectangular-shaped body and can be disposed on or otherwise associated with suture limbs 2212a, 2212b. In the illustrated embodiment the patch 2210 includes bores or lumens 2214a, 2214b are formed in the body and extend therethrough from a proximal-most end 2210p to a distal-most end 2210d. The bores 2214a, 2214b can be used, for example, to receive the suture limbs 2212a, 2212b so that the patch 2210 and limbs 2212a, 2212b can be associated with each other. As shown in FIG. 30B, the patch 2210 can be pre-threaded with suture threaders 2206a, 2206b. The threaders 2206a, 2206b are of a similar nature as the threader 206', and can also be configured in a manner akin to the threader 206 or in manners otherwise known to those skilled in the art and/or derivable from the present disclosures. As shown, the patch 2210 has a length $L_P$ that is substantially equal to a width $W_P$, and it also has a thickness $T_P$. Further, the thickness $T_P$ can be greater than a diameter of a filament or suture with which the tissue augmentation patch 2210 is associated, e.g., the suture limb 2212a.

A person skilled in the art will recognize that the dimensions of the length $L_P$, the width $W_P$, and the thickness $T_P$ of the tissue augmentation patch 2210, as well as a diameter of the bores 2214a, 2214b, can depend on a variety of factors, including but not limited to the size of the filament with which it is to be associated, the anatomy of the patient, and the type of procedure being performed. Some exemplary, non-limiting dimensions for a tissue augmentation patch 2210 can be useful in understanding the present disclosure.

In some embodiments, the length $L_P$ can cover a significant portion, to almost an entire portion, of a length of tissue extending between a stitch made in tissue and a bone anchor used to help secure the tissue. In some embodiments, the length $L_P$ and width $W_P$ can be approximately in the range of about 10 millimeters to about 50 millimeters, and the thickness $T_P$ can be approximately in the range of about 0.5 millimeters to about 5 millimeters. The size of the diameter of the bores 2214a, 2214b can also depend on a variety of factors, including but not limited to the size of the limb to be passed therethrough. In some embodiments, the diameter can be approximately in the range of about 0.5 millimeters to about 3 millimeters.

A number of techniques known to those skilled in the art can be used to associate the patch 2210 with the suture limbs 2212a, 2212b. Suture limbs 2212a, 2212b can be threaded or passed from the proximal-most end 2210p to the distal-most end 2210d of the patch 2210 without passing across the body of the patch 2210, i.e., without passing through sidewalls that define the bores 2214a, 2214b. As a result, the patch 2210 can freely pass along a length of the limbs 2212a, 2212b unhindered or unrestricted. In other embodiments, the limbs 2212a, 2212b can pass across the body once or more, e.g., like the embodiment of the strip or tape 10 illustrated in FIG. 1B, to further secure a location of the patch 2210 with respect to the limbs 2212a, 2212b. In still other embodiments, the limbs 2212a, 2212b can be passed through the patch 2210 from the proximal-most end 2210p to the distal-most end 2210d by passing through the body while only entering and exiting the body one time, for instance when no bores 2214a, 2214b are provided. Of course, the limbs 2212a, 2212b do not necessarily have to extend all the way to the proximal-most or distal-most ends 2210p, 2210d, but instead can enter and or exit the patch 2210 at some other location across its surface area. A person skilled in the art will recognize a variety of other ways by which the patch 2210 can be associated with the limbs 2212a, 2212b without departing from the spirit of the present disclosure.

The tissue augmentation patch 2210 can be threaded by hand on to the suture limbs 2212a, 2212b, either at the surgical site, or outside of the body. Alternatively, as shown in FIG. 30B, the threaders 2206a, 2206b can be operated to associated the suture limbs 2212a, 2212b with the patch 2210, with the operation being akin to either the threader 206 or the threader 206' described above, and thus including proximal handle portions 2208a, 2208b, intermediate elongate portions 2207a, 2207b, and distal suture-receiving ends 2209a, 2209b. Accordingly, the tissue augmentation patch 2210 can be associated with the intermediate elongate portions 2207a, 2207b, as shown by passing the intermediate elongate portions 2207a, 2207b through the lumens 2214a, 2214b, and the limbs 2212a, 2212b can be coupled to the distal suture-receiving ends 2209a, 2209b. The proximal handle portions 2208a, 2208b can be grasped and pulled away from the tissue augmentation patch 2210 to advance the limbs 2212a, 2212b towards and into the patch 2210.

After the patch 2210 has been successfully associated with the limbs 2212a, 2212b, the threaders 2206a, 2206b can be disassociated with the limbs 2212a, 2212b and the tissue augmentation patch 2210 and can be either discarded or re-used.

Similar to the earlier described tissue augmentation strips, associating the tissue augmentation patch 2210 with the suture limbs 2212a, 2212b increases the footprint of the suture limbs 2212a, 2212b and may allow force applied to the tissue by the suture limbs 2212a, 2212b to be distributed over a larger amount of surface area, i.e., the surface area of the patch 2210. The increased distributed force of the tissue augmentation patch 2210 may result in a reduced pressure peak on the soft tissue. Where the soft tissue has become degenerated due to injury or age, an increased tissue surface area coverage and a reduction in pressure can result in less chance of abrasion of the tissue. Further, the larger surface area of the tissue augmentation patch 2210 can provide for a larger scaffold for new tissue to generate over the repair to further strengthen the repair site. The broader tissue coverage provided by the patch 2210 may enhance the healing of otherwise compromised tissue and/or provide bulk to otherwise compromised or degenerate tissue and/or tendon.

Methods of Manufacturing Tissue Augmentation Constructs—Tissue Augmentation Patches The tissue augmentation patch 2210 can be manufactured using a number of different techniques, some of which have been previously discussed above with regards to the tissue augmentation blocks 10, 110. In one exemplary embodiment of making a tissue augmentation patch, illustrated by FIGS. 30C-30E, the material being used to make the patch 2210 can be harvested or otherwise acquired using techniques known to those skilled in the art. The material can then be shaped using any of the techniques described above, for instance those described with respect to the strip 10, or otherwise known to those skilled in the art in view of the present disclosures. A piece of material can be harvested having a length $L_P$, a width $2W_P$, and a thickness $\frac{1}{2} T_P$. The width $2W_P$ can be double the resulting width $W_P$ of the patch 2210 and the thickness $\frac{1}{2} T_P$ can be half of the thickness of the resulting patch 2210. As shown in FIG. 30D, the piece of material 2220 can have a first end 2220a and a second end 2220b with the width $2W_P$ extending therebetween. Alternatively, the piece of material 2220 can have any shape.

Once the piece of material 2220 has been cut out, two pins 2222a, 2222b can be placed onto the same side of the material, approximately ¼ of the width $2W_P$ away from the first and second ends 2220a, 2220b, respectively. The two ends 2220a, 2220b, can be folded over the respective pins 2222a, 2222b, and brought proximate to one another and subsequently attached to one another, thereby forming the patch 2210. As shown in FIGS. 30C and 30D, the four rows of stitches 2224a-2224d can be stitched into the folded patch such that they are substantially parallel to one another. Further, the first and the fourth stitches 2224a, 2224d can be located substantially parallel to and proximate the pins 2222a, 2222b, respectively. Still further, the stitches 2224a, 2224d can create the two lumens 2214a, 2214b that are held open by the pins 2222a, 2222b. After the stitching is complete, the pins 2222a, 2222b can be removed, leaving the patch 2210 as shown in FIG. 30E. Alternatively, no pins are required to manufacture the patch 2210. The second and the third stitches 2224b, 2224c can be located substantially parallel to and proximate the two ends 2220a, 2220b. Further alternatively, in place of stitches, the material 2220 can be secured to itself with the use of glue, collagen bond, staples, light curing, or other techniques known to those skilled in the art for attaching soft tissue to soft tissue and provided for throughout the present disclosure. In embodiments that include threaders predisposed in the patch 2210, threaders 2206a, 2206b can be inserted into the lumens 2214a, 2214b before the two ends 2220a, 2220b are attached, or after. Like the other constructs provided for herein, the patch 2220 can be dried for packaging at any suitable point during the manufacturing process.

An alternative method of manufacturing the patch 2210 can include harvesting a piece of material that can be harvested having a length $L_P$, a width $W_P$, and a thickness $T_P$. The piece of material 2220 can have a first end 2220a and a second end 2220b with the width $W_P$ extending therebetween. A first pin 2222a can be inserted, or pierced, into the material 2220 proximate and parallel to the first end 2220a to create a first lumen 2214a. A second pin 2222b can be inserted, or pierced, into the material 2220 proximate and parallel to the second end 2220b to create a second lumen 2214b. In a further alternative, a coring tube can be used in place of the pins 2222a, 2222b, as described above with respect to FIGS. 26A-26I. The patch 2210 can be made from any of the materials provided for above with respect to the blocks 10, 110, 3010, 3110, 310, and 410, and any other constructs, noted above. Furthermore, the patch 2210 can have any shape, including rectangular, trapezoidal, ovoid, circular, square, pentagonal, hexagonal, octagonal, etc.

A further alternative method of manufacturing a patch 3320 can include the use of a parallel production tunneling station 3300, similar to the tunneling stations 3200, 3200' of FIGS. 27A-27M. As shown in FIG. 31A, a stage 3320 can accommodate a larger length L of the material 3330. For example, as illustrated in FIG. 31A, the stage 3320 can accommodate two patch constructs 3310a, 3310b. Alternatively, the stage 3320 can extend to accommodate any number of constructs. The stage 3320 can, similar to the stage of the tunneling station 3200', have a plurality of semi-circular reliefs that can be aligned with lumen formation tools 3324a, 3324b, 3324c, 3324d, and the stage 3320 can be self-centering.

Similar to the tunneling stations 3200, 3200' of FIGS. 27A-27M, the tunneling station 3300 can include a plurality of lumen formation tools 3324a, 3324b, 3324c, 3324d. In the illustrated embodiment, the lumen formation tools 3324a, 3324b forms a first station 3323a, and the lumen formation tools 3324c, 3324d forms a second station 3323b. As shown, the lumen formation tools 3324a, 3324b can be angularly offset from one another, for example approximately up to about 30 degrees from one another. In one embodiment, the lumen formation tools 3324a, 3324b can be angularly offset from one another approximately 16 degrees from one another. The lumen formation tools 3324c, 3324d of the second station 3323b can be similarly offset relative to one another, or alternatively, can be angularly offset at a different angle. The second station 3323b can be disposed on an opposite side of the stage 3320 from the first station 3323a, thus providing for easier parallel lumen formation. In an alternative embodiment, each of the lumen forming tools 3324a, 3324b, 3324c, 3324d can be aligned in parallel with each other. The lumen formation tools 3324a, 3324b, 3324c, 3324d can be aligned such that each of the respective cutting tools 3322a, 3322b, 3322c, 3322d can translate towards the stage to create the lumens 3314a, 3314b, 3314c, 3314d in the material 3330. In the illustrated embodiment, two lumen formation stations 3323a, 3323b are shown, however any number of lumen forming stations can be provided.

After each of the lumen formation tools 3324*a*, 3324*b*, 3324*c*, 3324*d* has been actuated and retracted to create lumens 3314*a*, 3314*b*, 3314*c*, 3314*d* in the material 3330, the material 3330 can be advanced in the direction D as shown in FIG. 31A. The individual constructs 3310*a*, 3310*b*, 3310*c* can then be separated by means of a punch 3190*a*-3190*c*, or other cutting mechanisms as provided for throughout the present disclosure or otherwise known to those skilled in the art. The resulting constructs 3310*a*, 3310*b*, 3310*c*, 3310*d* are illustrated in FIGS. 31B and 31C, with the resulting patches 3310*a*, 3310*b*, 3310*c*, 3310*d* having a generally trapezoidal shape. A person skilled in the art will recognize that any number of patch shapes can be formed in view of the present disclosures. For example, the lumen formation tools 3324*a*, 3324*b*, 3324*c*, 3324*d* can be parallel to each other to create patches having parallel lumens and a rectangular shape.

Methods of Use—Tissue Augmentation Patches

One exemplary method of installing a tissue augmentation patch 2210 is illustrated in FIG. 30F. The illustrated method provides for a piece of soft tissue 2230, e.g., rotator cuff, fixated to bone 2250. Either a single row or a double row repair can be used. Once the surgeon has access to the surgical site and the tissue, bone, and tissue augmentation patch have been prepared according to accepted surgical techniques including those provided for herein, the surgeon can perform a tissue repair (not visible because it is underneath the patch 2210) according to accepted surgical techniques. As shown in FIG. 30F, a suture 2212 extending from an anchor (not shown) used in the repair is installed into the tissue 2230 medially from the repair such that two suture limbs 2212*a*, 2212*b* extend out from the tissue 2230.

The tissue augmentation patch 2210 can be threaded onto the suture limbs 2212*a*, 2212*b* using techniques provided for throughout the present disclosure, and subsequently advanced along the respective suture limbs 2212*a*, 2212*b* until it is proximate a medial stitch 2242. After the tissue augmentation patch 2210 has been installed on the suture limbs 2212*a*, 2212*b*, the free end of each suture limb 2212*a*, 2212*b* can be secured within the body. For example, the free ends of each suture limb 2212*a*, 2212*b* can be coupled to respective anchors 2260*a*, 2260*b* in a lateral row fixation. The suture limbs 2212*a*, 2212*b* can then be tightened to secure the patch 2210 against the repair before the anchors 2260*a*, 2260*b* are fully fixed in the bone 2250.

The tissue augmentation patch 2210 can provide a greater footprint for the suture limbs 2212*a*, 2212*b* and a greater surface area to distribute the loading forces of the suture limbs 2212*a*, 2212*b* onto the soft tissue 2230. While the patient is healing from the procedure, the patch can remodel into tendon-like tissue and integrate with the underlying native tissue. The additional coverage of tendon-like tissue across the soft tissue can increase the strength of the soft tissue to bone connection and may prevent further injury.

Another exemplary method of installing a tissue augmentation patch 2210' is provided for in FIGS. 30G-30I, this time illustrating a piece of soft tissue 2230', e.g., rotator cuff, being fixated to bone 2250' using a double row repair. Once the surgeon has access to the surgical site and the tissue, bone, and tissue augmentation patch have been prepared according to accepted surgical techniques including those provided for herein, the surgeon can install first and second medial anchors 2260*a*', 2260*b*' in the bone 2250'. The first and second medial anchors 2260*a*', 2260*b*' have sutures 2212', 2216' associated therewith. As shown in FIG. 30G, sutures 2212' and 2216' can have suture limbs 2212*a*', 2212*b*' and 2216*a*', 2216*b*' extending from the respective anchors 2260*a*' and 2260*b*', with the limbs being threaded through the tissue 2230', for example using one or more medial stitches 2242*a*', 2242*b*'.

The patch 2210' can have similar properties as the patch 2210 and can be threaded onto the suture limbs 2212*a*', 2216*a*' using techniques provided for throughout the present disclosure. The patch 2210' can subsequently be advanced in the direction $D_1$ along the respective suture limbs 2212*a*', 2216*a*', as shown in FIG. 30H, until it is proximate the medial stitches 2242*a*', 2242*b*'. After the patch 2210' has been installed on the suture limbs 2212*a*', 2216*a*', the free end of each of the suture limbs 2212*b*', 2216*b*' can be placed over the patch 2210' in an X- or crossed configuration as shown in FIG. 30I. Then the suture limbs 2212*a*', 2216*b*' can be installed into lateral anchor 2262*a*', and the suture limbs 2212*b*', 2216*a*' can be installed into lateral anchor 2262*b*' in a lateral row fixation. The suture limbs 2212*a*', 2212*b*', 2216*a*', 2216*b*' can then be tightened to secure the soft tissue 2230' to the bone 2250' before the lateral anchors 2262*a*', 2262*b*' are fully fixed in the bone 2250'. The same benefits described above with respect to the method of using the patch 2210 are equally applicable to this embodiment of using the patch 2210'. Further, the crossed nature of the suture configuration provides additional stability for holding the tissue 2230' at the desired location with respect to the bone 2250'.

A further exemplary embodiment of installing a tissue augmentation patch 2210" is illustrated in FIGS. 30J-L and can be used with either a single or double row repair described above with regards to FIGS. 30F-I. The illustrated patch 2210" has been threaded onto suture limbs 2212*a*", 2216*a*" according to techniques provided for throughout the present disclosure. The illustrated method provides for forming collapsible loops 2212*l*", 2216*l*" and associated knots 2270*a*", 2270*b*" disposed on a distal end 2210*d*" of the patch 2210". The collapsible loops 2212*l*", 2216*l*" and associated knots 2270*a*", 2270*b*" can be formed on respective suture limbs 2212*a*", 2216*a*" after the suture limbs have been threaded through the patch 2210". In one exemplary embodiment the knots can be, for example, sliding knots, figure eight knots, or finger traps, among other knot types. The knots 2270*a*", 2270*b*" can be larger than the associated lumens through which the suture limbs 2212*a*", 2212*b*" are threaded through such that the knots 2270*a*", 2270*b*" cannot be pulled through. The knots 2270*a*", 2270*b*" can be formed after the patch 2210" has been advanced in the direction D1 until it is proximate the soft tissue 2230".

After the loops 2212*l*", 2216*l*" have been formed, the suture limb 2216*b*" can be guided through the loop 2212*l*" and the suture limb 2212*b*" can be guided through the loop 2216*l*", as illustrated in FIG. 30K. Once the suture limbs 2212*b*", 2216*b*" have been threaded through the suture loops 2212*l*", 2216*l*", the suture limbs are beneficially maintained in a desired configuration. The suture limbs 2212*a*", 2216*b*" can then be installed into a lateral anchor 2262*a*", and the suture limbs 2212*b*", 2216*a*" can be installed into a lateral anchor 2262*b*" in a lateral row fixation. At this point, the collapsible loops 2212*l*", 2216*l*" can be collapsed by the application of a force on suture limbs 2212*a*", 2216*a*", thereby securing suture limbs 2212*b*", 2216*b*" in an X- or crossed configuration as shown in FIGS. 30K and 30L. The suture limbs 2212*a*", 2212*b*", 2216*a*", 2216*b*" can then be tightened to secure the soft tissue 2230" to the bone 2250" before the lateral anchors 2262*a*", 2262*b*" are fully fixed in the bone 2250". One benefit of the knots 2270*a*", 2270*b*" and loops 2212*l*", 2216*l*" is that the patch 2210" can be prevented from sliding laterally towards anchors 2262*a*", 2262b" and fixed relative to the bone 2250" and 2230". By collapsing the loops 2212l", 2216l" around the sutures limbs 2212a", 2212b", 2216a", 2216b", unintentional sliding of the patch 2210" with respect to the sutures limbs 2212a", 2212b", 2216a", 2216b" can be prevented. The loops and knots can be beneficially applied to any of the constructs provided for herein to prevent lateral sliding and to retain the construct after implantation, including but not limited to tissue augmentation blocks and tissue augmentation patches.

Tissue Augmentation Constructs—Additional Tissue Augmentation Patches, Methods of Using the Same, and Methods of Manufacturing the Same Another exemplary embodiment of a tissue augmentation construct 2310 having a patch or scaffold configuration is illustrated in FIG. 32A. As shown, the tissue augmentation patch 2310 has a rectangular-shaped body and is generally similar in nature and construction to the tissue augmentation patch 2210. The patch 2310 differs in that it includes additional lumens 2314a-2314d extending therethrough from a proximal-most end 2310p to a distal-most end 2310d for having threaders 2306a-2306d, and thus suture limbs 2312a, 2312b, 2316a, 2316b after operating the threaders 2306a-2306d, disposed therein. Optionally the threaders 2306a-2306d may not be used and the suture limbs 2312a, 2312b, 2316a, 2316b may be associated with the patch 2310 using any technique provided for herein or otherwise known to those skilled in the art. As shown in FIG. 32A, the lumens 2314a, 2314d can be substantially parallel to the sides of the patch 2310 that extend between the proximal-most end surface 2310p and the distal-most end surface 2310d, and the lumens 2314b, 2314c can form a substantially X-shaped or crossed configuration. When the threaders 2306a and 2306b are associated with the patch 2310 in the illustrated embodiment, or in other embodiments illustrated herein having a patch with two threaders associated therewith, an intermediate portion 2307a of the first threader 2306a can be disposed at a location that is more proximate to a first side 2310a of the patch 2310 than a second, opposite side 2310b of the patch and an intermediate portion 2307b of the second threader 2306b can be disposed at a location that is more proximate to the second side 2310b than the first side 2310a. When the threaders 2306c and 2306d are also associated with the patch 2310, an intermediate portion 2307c of the third threader can be disposed diagonally with respect to the patch 2310 such that a distal receiving end 2309c of the third threader 2306c is proximate to a distal receiving end 2309a of the first threader 2306a, while a proximal handle 2308c of the third threader 2306c is proximate to a proximal handle 2308b of the second threader 2306b, and an intermediate portion 2307d of the fourth threader can be disposed diagonally with respect to the patch 2310 such that a distal receiving end 2309d of the fourth threader 2306d is proximate to a distal receiving end 2309b of the second threader 2306b, while a proximal handle 2308d of the fourth threader 2306d is proximate to a proximal handle 2308a of the first threader 2306a.

A person skilled in the art will recognize that in any embodiments in which multiple threaders are used in conjunction with a construct, a location of the proximal and distal ends of the threaders can be different than the illustrated embodiments, depending, at least in part, on the type of procedure being performed, the components being used to perform the procedure, and the preferences of the user. Thus, in any illustrated embodiments, locations of the proximal and distal ends of the threaders can be switched in other embodiments. Further, in any of the illustrated embodiments, a location of any threader with respect to a tissue augmentation construct prior to using the threaders to associate a suture with the tissue augmentation construct is considered a pre-installation configuration, and after a threader has been used to associate a suture with a tissue augmentation construct and subsequently removed, such a configuration is considered a post-installation configuration.

As shown, the patch 2310 has a length $L_P$' that is substantially equal to a width $W_P$ and it also has a thickness $T_P$'. Further, the thickness $T_P$' can be greater than a diameter of a filament or suture with which the tissue augmentation patch 2310 is associated, e.g., the suture limb 2312a. In other embodiments, the suture limbs 2312a, 2312b, 2316a, 2316b can extend through the lumens 2314a-2314d without necessarily having been disposed in the lumens 2314a-2314d using threaders. The limbs 2312a, 2312b, 2316a, 2316b can extend in the same hybrid parallel and crossed configuration illustrated and described with respect to the locations of the threaders 2306a-2306d.

A person skilled in the art will recognize that the dimensions of the length $L_P$ the width $W_P$ and the thickness $T_P$' of the tissue augmentation patch 2310, as well as a diameter of the bores 2314a-2314d, can depend on a variety of factors, including but not limited to the size of the filament with which it is to be associated, the anatomy of the patient, and the type of procedure being performed. Alternatively, the patch 2310 can have any other shape (e.g., rectangular, trapezoidal, ovoid, circular, square, pentagonal, hexagonal, octagonal, etc.) and the lumens 2314a-2314d can follow any path (e.g., they can follow edges). The exemplary, non-limiting dimensions provided above for the patch 2210 can also be applicable to the size of the patch 2310, with the understanding that other dimensions are possible. Likewise, a number of techniques known to those skilled in the art can be used to associate the patch 2310 with the suture limbs 2312a, 2312b, 2316a, 2316b, and the techniques described above with respect to the patch 2210 can be adapted for use in conjunction with the patch 2310. Thus, in view of the present disclosures, a person having skill in the art will understand how to operate the threaders 2306a-2306d to associate the suture limbs 2312a, 2312b, 2316a, 2316b with the patch 2310.

One exemplary method of installing the patch 2310 is provided for in FIGS. 32B-32E. The illustrated method provides for a piece of soft tissue 2330, e.g., rotator cuff, fixated to bone 2350. Either a single row or a double repair can be used. Once the surgeon has access to the surgical site and the tissue, bone, and tissue augmentation patch have been prepared according to accepted surgical techniques including those provided for herein, the surgeon can perform single row repairs 2340a, 2340b of the tissue 2330 according to accepted surgical techniques. Alternatively, one repair can be made to the tissue 2330, or more than two repairs can be completed. As shown in FIG. 32C, a first suture 2312 can be inserted into the tissue 2330 medially from the repairs 2340a, 2340b such that two suture limbs 2312a, 2312b extend out from the tissue 2230, and likewise, a second suture 2316 can be inserted into the tissue 2330 medially from the repairs 2340a, 2340b such that two suture limbs 2316a, 2316b extend out from the tissue 2230. In the illustrated embodiment, the sutures 2312, 2316 are inserted into the tissue 2330 using mattress stitches 2342a, 2342b, respectively, though other stitches can be used.

As shown in FIG. 32D, the suture limbs 2312a, 2312b, 2316a, 2316b are threaded into lumens 2314a-2314d, respectively, using techniques provided for throughout the present disclosure, e.g., operating the threaders 2306a-2306d, and the patch 2310 can be advanced along the respective suture limbs 2312a, 2312b, 2316a, 2316b until the proximal end 2310p is proximate the medial stitches 2342a, 2342b. After the patch 2310 has been installed on the suture limbs 2312a, 2312b, 2316a, 2316b, the free end of each suture limb 2312a, 2316b can be secured within the body. For example, as shown in FIG. 32E, the free ends of each suture limb 2312a, 2316b and 2312b, 2316a can be coupled to lateral anchor 2362a and 2362b, respectively, in a lateral row fixation. The suture limbs 2312a, 2312b, 2316a, 2316b can then be tightened to secure the patch 2310 against the repair 2340 before the lateral anchors 2360a, 2360b are fully fixed in the bone 2350.

Another exemplary method of installing a tissue augmentation patch 2310' is provided for in FIGS. 32F-32H, this time illustrating a piece of soft tissue 2330', e.g., rotator cuff, being fixated to bone 2350' using a double row repair. Once the surgeon has access to the surgical site and the tissue, bone, and patch have been prepared according to accepted surgical techniques including those provided for herein, the surgeon can install first and second medial anchors 2360a', 2360b' in the bone 2350'. The first and second medial anchors 2360a', 2360b' have sutures 2312', 2316' associated therewith. As shown in FIG. 32F, sutures 2312' and 2316' can have suture limbs 2312a', 2312b' and 2316a', 2316b' extending from the respective anchors 2360a' and 2360b', with the limbs being threaded through the tissue 2330', for example using one or more medial stitches 2342a', 2342b'.

The patch 2310' can have similar properties as the patch 2310 and can be threaded onto suture limbs 2312a', 2312b', 2316a', 2316b' using techniques provided for throughout the present disclosure. The patch 2310' can subsequently be advanced along the suture limbs 2312a', 2312b', 2316a', 2316b' until the proximal end 2310p' is proximate the medial stitches 2342a', 2342b', as shown in FIGS. 32G and 32H. After the patch 2310' has been installed on the suture limbs 2312a', 2312b', 2316a', 2316b', the free ends of each of the suture limbs 2312a', 2316b' and 2312b', 2316a' can then be installed into respective lateral anchors 2362a' and 2362b' in a lateral row fixation. The suture limbs 2312a', 2312b', 2316a', 2316b' can then be tightened to secure the patch 2310' against the repair 2340' before the lateral anchors 2360a', 2360b' are fully fixed in the bone 2350'. The same benefits described above with respect to the method of using the patch 2210' are equally applicable to the embodiments of using the patches 2310 and 2310', including the benefits resulting from the crossed nature of the suture configuration. Additional benefits of these two embodiments will also be clear to those having skill in the art in view of the present disclosures.

The patch 2310 can be manufactured using a number of different techniques, some of which have been previously discussed above at least with regards to the tissue augmentation blocks 10, 110 and other constructs. The patch 2310, and thus also the patch 2310', can be made from any of the materials provided for above with respect to the tissue augmentation blocks 10, 110, 3010, 3110, 310, and 410, and/or other constructs described herein. In one exemplary embodiment of making a patch, illustrated by FIGS. 32I and 32J, the material being used to make the patch 2310 can be harvested or otherwise acquired using the same techniques as described above with respect to the patch 2210. As shown in FIG. 32I, the piece of material 2320 can have a first end 2320a and a second end 2320b with the width $2W_P'$ extending therebetween. Alternatively, the piece of material 2320 can have any shape.

Once the piece of material 2320 has been cut out, the two ends 2320a, 2320b, can be folded over approximately ¼ of the width $2W_P'$ away from the first and second ends 2320a, 2320b, respectively, and brought proximate to one another and subsequently attached to each other, thereby forming the patch 2310. As shown in FIG. 32J, the patch 2310 is stitched together to form the folded patch. The stitching 2324a-2324d is performed such that the two parallel lumens 2314a, 2314b are created in combination with the X shaped lumens 2314c, 2314d. The first stitch 2324a can be substantially V-shaped, having both ends located at the distal most end 2310d of the patch 2130 and the vertex of the V-shape pointing towards the proximal most end 2310p of the patch 2130. The second stitch 2324b can be substantially V-shaped, having both ends located at the proximal most end 2310p of the patch 2130 and the vertex of the V-shape pointing towards the distal most end 2310d of the patch 2130. The third and fourth stitches 2324c, 2324d can be substantially triangular in shape and can be substantially mirror images of the other to define the lumens 2314a, 2314d. Alternatively, pins can be placed along where the lumens 2314a-2314d are to be located, and then the patch 2310 can be stitched together to manufacture the patch 2310. The pins can be removed once the patch is manufactured. Further alternatively, in place of stitches the material 2320 can be secured to itself with the use of glue, collagen bond, staples, light curing, or other techniques for attaching soft tissue to soft tissue known to those skilled in the art and provided for throughout the present disclosure.

In embodiments that include threaders predisposed in the patch 2310, threaders 2306a-2306d can be inserted into the lumens 2314a-2314d before the two ends 2320a, 2320b are attached, or after. The patch 2320 can be dried for packaging at any suitable point during the manufacturing process. Further alternatives for forming the patch 2310 in accordance with the present disclosures include but are not limited to harvesting a piece of material and using pins to pierce or puncture it to create the lumens 2314a-2314d, as described at least with respect to FIGS. 30C-30E, and/or using a coring device or tube to create the lumens 2314a-2314d, as described at least with respect to FIGS. 26A-26I.

Many more configurations of patches and sutures are within the scope of the present disclosures. Configurations can be derived from making adjustments to various parameters or variables provided for and discussed throughout the present application. Some parameters or variables that can be changed to provide for various configurations include: (1) the number of layers used to form the patch (e.g., one layer, two layers); (2) the orientation of a first set of suture limbs with respect to each other and the patch (e.g., across the patch in a manner in which the limbs are not intersecting, across the patch in a manner in which the limbs intersect each other); (3) a location of a second set of suture limbs with respect to the patch (e.g., on top of the patch, through the patch); (4) the orientation of the second set of suture limbs with respect to each other and the patch (e.g., across the patch in a manner in which the limbs are not intersecting, across the patch in a manner in which the limbs intersect each other); (5) the inclusion of one or more "stitches" with the first set of suture limbs, referred to herein as "loops" and "jogs," to fixate the patch with respect to at least one suture limb; (6) whether the second set of suture limbs is disposed in lumens formed in the patch; (7) whether additional sutures are provided (e.g., medial center suture, lateral center suture); and (8) a location of the first set of suture limbs with respect to the second set of suture limbs (e.g., inside of the second set of suture limbs, outside of the second set of suture limbs).

A small sample of some patch configurations illustrating options for the above-listed parameters or variables is shown in FIGS. 33A-33E. Some configurations can be better than others in aiding patch delivery and/or aiding the attachment of the patch to soft tissue. One skilled in the art will understand that the various parameters can be mixed and matched to arrive at a large number of configurations, many of which are not explicitly illustrated herein, but are derivable based on the understanding provided about each of the variables and the constructs more generally as disclosed in the present application. To assist in understanding some of the options associated with the above-listed parameters, each parameter is discussed in more detail below with a limited number of example configurations illustrated. However, it is contemplated that the instant disclosure encompasses each discrete combination of parameters in conjunction with many of the different patch configurations provided for in the present disclosure. Further, like reference numbers are used across each of the examples illustrated in FIGS. 33A-33E as the parameters are interchangeable across various configurations using the same materials (e.g., patch, sutures, and anchors).

One parameter that can be changed to achieve various patch configurations is the number of layers that form each patch. For example, each patch can include a single layer of material with lumens being formed in the single layer for disposing suture limbs therethrough, as illustrated in FIGS. 26D-26F, 30A, 30B, and 31A-31C. The single layer can include a tissue-facing or tissue-engaging surface, also referred to herein as a bottom side 3410*d* of the patch 3410, and a second surface that is opposed to the tissue-facing surface (e.g., the surface that is visible in FIGS. 33A-33E), also referred to herein as a top side 3410*p* of the patch 3410. Alternatively, each patch can include two or more layers of material stitched together to form a single patch with lumens being formed between two or more layers for disposing suture limbs therethrough, as illustrated in FIGS. 32A-32J. When a second layer is used, each layer includes a tissue-facing surface and a second surface that is opposed to the tissue-facing surface. In such embodiments, the tissue-facing surface of the patch is formed by the tissue-facing surface of the bottom, or more distal, patch, and the second surface of the patch that is opposed to the tissue-facing surface is formed by the second surface of the top, or more proximal, patch. Even in patches that include multiple layers, a lumen can be formed in a single layer. In embodiments where the patch includes two layers, the stitching can form lumens as described with reference to FIGS. 32A-32J. For the sake of simplicity, a first set of suture limbs 3412, 3414 and a second set of suture limbs 3416, 3418 will be referenced in the following discussion, however a single set may be used. As discussed above, in embodiments where two layers of material are used, each layer can be formed from different materials to provide a variety of advantages, including but not limited to: the overall thickness of the patch configuration may not limited by a biological source, a level of cellular activity can be controlled (e.g., a high tissue integration layer on a tissue facing side and an adhesion barrier layer on the opposite side), and other material characteristics can be varied between each layer (e.g., toughness, biologic/synthetic, thick/thin, high-/low-porosity, etc.).

Figure 33A:
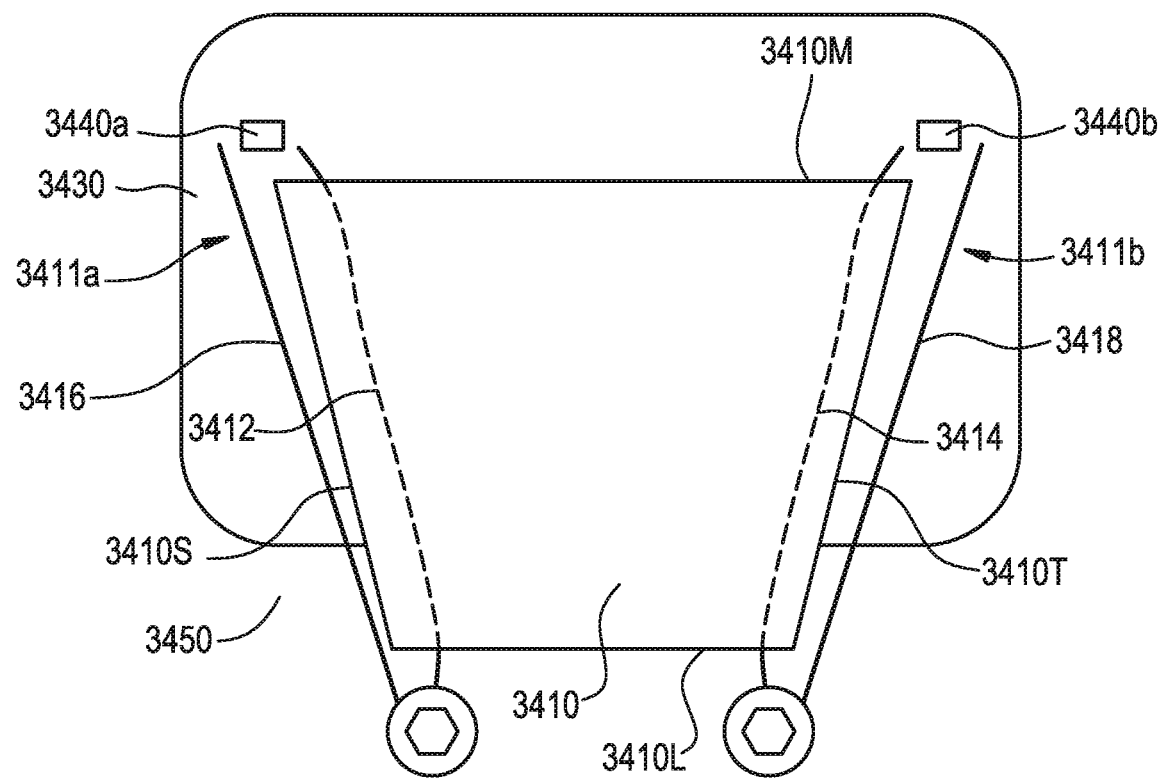

As shown in FIG. 33A, two inverted mattress stitches 3440*a*, 3440*b* can be formed in the soft tissue, medial to any repairs (the repairs not being shown). More particularly, a first suture 3411*a* can be used to form a first inverted mattress stitch 3440*a* and a second suture 3411*b* can be used to form a second inverted mattress stitch 3440*b*. The first mattress stitch 3440*a* can result in suture limb 3412 and suture limb 3416 extending therefrom, and the second mattress stitch 3440*b* can result in suture limb 3414 and suture limb 3418 extending therefrom. For the purposes of discussion only, suture limbs 3412 and 3414 are defined as a first set of suture limbs, and suture limbs 3416 and 3418 are defined as a second set of suture limbs. For the sake of simplicity, each of the embodiments shown in FIGS. 33A-33E illustrates two mattress stitches and therefore a discussion will not be repeated for each figure.

Further, as shown in each embodiment, the suture limbs 3412, 3414 of the first set of suture limbs are generally through the patch 3410. This can include configurations in which the suture limbs 3412, 3414 extend through the patch 3410 for an entire length of the patch, that is from the medial edge 3410M to the opposed lateral edge 3410L, or configurations in which the suture limbs 3412, 3414 extend through the patch 3410 for a portion of the length. Generally the suture limbs 3412, 3414 extend along a length that extends substantially between the medial and opposed lateral edges 3410M, 3410L. For example, as shown in FIG. 33D, the suture limbs 3412, 3414 do not extend the entire length of the patch 3410, but do extend a substantial portion of that length. The substantial portion of the length can be at least about 50 percent of the length, or alternatively at least about 75 percent of the length, or further alternatively at least about 90 percent of the length.

As the suture limbs 3412, 3414, and the suture limbs 3416, 3418 are passed through the patch, they are passed by leading a terminal end of the suture limb through, above, and/or below a portion of the patch 3410. The terminal end that is described as being passed through the patch in the illustrated embodiments can be considered a terminal lateral end since that is the end that is being passed towards the lateral edge 3410L and towards illustrated anchors 3460*a*, 3460*b*. When terminal lateral ends are described as being coupled to an anchor, a person skilled in the art will recognize that it is not the terminal lateral end of the suture limb itself that necessarily is attached to the anchor because when associating a suture with an anchor, the terminal end may extend some distance beyond the anchor, for instance as a result of tying the suture to the anchor. Thus, a description of a terminal lateral end of a suture limb being attached or otherwise coupled to an anchor does not require that the very end of the suture itself is touching or coupled directly to the anchor. Rather, it just indicates that some portion of that limb that a person skilled in the art would understand in view of the present disclosure qualifies as a terminal end of the system when forming the patch-suture configuration is the described terminal lateral end. Further, as shown, the anchors 3460*a*, 3460*b* are disposed on opposite sides of a central longitudinal axis 3410*c* extending between the medial and lateral sides 3410M, 3410L of the patch 3410. Generally, when the terminal lateral ends of the various suture limbs are being associated with the anchor, the terminal lateral ends can be described as being proximate to each other. A person skilled in the art will recognize that even if the terminal lateral ends are associated with different anchors on the same side of the scaffold, and/or associated with one or more other fixtures (including but not limited to bone, tissue, and medical implants) on the same side of the scaffold, the terminal lateral ends of the suture limbs on that side can still be described as being proximate to each other in view of the present disclosure.

A second parameter that can be changed to achieve various patch configurations relates to the orientation of the first set of suture limbs with respect to each other and the patch. For example, each of the first set of suture limbs 3412, 3414 can be disposed across the patch 3410 from a medial edge 3410M to a lateral edge 3410L in a manner such that the limbs do not intersect each other, as shown in FIG. 33A. In the illustrated embodiment, the limbs 3412, 3414 extend substantially parallel to respective outer side edges 3410S, 3410T of the patch 3410 and are disposed on separate halves of the central longitudinal axis 3410c. This configuration can provide for added securement of the edges 3410S, 3410T when the limbs 3412, 3414 are extended over the edges. A person skilled in the art will recognize that the limbs 3412, 3414 can be oriented in many other manners with respect to each other and the patch 3410 without causing them to intersect. For example, the first set of suture limbs 3412, 3414 can be disposed across the patch 3410 from the medial edge 3410M to the lateral edge 3410L in a manner such that the limbs extend substantially straight across the patch 3410 and are thus substantially parallel to one another. Examples of limbs configured in such a manner are illustrated at least in FIGS. 30A-30L (e.g., limbs 2212a and 2212b, limbs 2212a' and 2216a', and limbs 2212a" and 2216a").

In a further alternative, the first set of suture limbs 3412, 3414 can be disposed across the patch 3410 from the medial edge 3410M to the lateral edge 3410L in a manner such that the limbs do intersect each other. For example, the limbs 3412, 3414 can be disposed across the patch 3410 to form an "X" configuration or shape, like the limbs 2212b' and 2216b' of FIG. 30I, the limbs 2312b, 2316b of FIGS. 32A-32E, the limbs 2312b', 2316b' of FIGS. 32F-32H, and limbs 3416 and 3418 of FIG. 33B (which are described as the second set of limbs but are referenced for purposes of generally showing an intersecting configuration). This configuration can provide for a more distributed compression over a larger area of the construct. A person skilled in the art will recognize that the limbs 3412, 3414 can be oriented in many other manners with respect to each other and the patch 3410 while still intersecting each other. Further, to the extent the limbs 3412, 3414 are described as being disposed across the patch, they can extend across a top surface of the patch, through the patch (e.g., through a single layer, disposed between two layers), or a combination of both across the top surface of the patch and through the patch. Additionally, the limbs 3412, 3414 do not have to be oriented in a similar manner. For example, the limb 3412 can extend substantially parallel to the outer side edge 3410S, or extend substantially straight across the patch 3410 with the limb 3412 remaining on one side of the central longitudinal axis 3410c, while the limb 3414 extends more diagonally such that it crosses over the central longitudinal axis 3410c.

A third parameter that can be changed to achieve various patch configurations relates to a location of a second set of suture limbs with respect to the patch. For example, the second set of suture limbs 3416, 3418 can be disposed through the patch as they extend from the medial edge 3410M to the lateral edge 3410L, similar to the orientation of the limbs 2312b and 2316b and limbs 2312b' and 2316b' of FIGS. 32A-32J. Advantageously, when at least one suture limb is disposed through the patch, the patch can be more secure after installation. Alternatively, the second set of suture limbs 3416, 3418 can be disposed over a top surface of the patch 3410, similar to the orientation of the limbs 2212b and 2216b, limbs 2212b' and 2216b', and limbs 2212b" and 2216b" of FIGS. 30A-30L. In some instances, some portion of any second limbs can extend through the patch while some other portion extends on top of the patch, and the configuration of this parameter for any limb does not have to be the same as any other limb.

A fourth parameter that can be changed to achieve various patch configurations relates to the orientation of the second set of suture limbs with respect to each other and the patch. For example, each of the second set of suture limbs 3416, 3418 can be disposed across the patch 3410 from the medial edge 3410M to the lateral edge 3410L in a manner such that the limbs do not intersect each other, or in a manner such that they do intersect. Such configuration possibilities are similar to those discussed above with respect to the second parameter, which was for the orientation of the first set of suture limbs with respect to each other and the patch. Further, in some instances the second suture limbs 3416, 3418 may not extend over or through the patch 3410, but rather, may extend around and/or adjacent to the patch 3410. First suture limbs 3412, 3414 can also be configured in a manner in which at least a portion of them extend around and/or adjacent to the patch 3410 rather than on top of or through the patch.

By way of non-limiting example, FIG. 33A illustrates an embodiment in which the second set of limbs 3416, 3418 do not intersect and extend around and adjacent to the patch 3410; thus, the limbs 3416, 3418 do not extend over or through the patch 3410. By way of further non-limiting examples, FIGS. 33C and 33E each illustrate embodiments in which the second set of limbs 3416, 3418 do not intersect and extend on top of the patch 3410. As shown in FIG. 33D, it is possible to combine various orientations across the length extending between the medial and lateral edges 3410M and 3410L. For example, as shown the limbs 3416, 3418 do not intersect, but the orientation of the limbs with respect to the patch 3410 changes as the limbs extend between the medial and lateral edges 3410M and 3410L. More particularly, as shown, a first portion $3416p_1$, $3418p_1$ of each of the limbs 3416, 3418 extends around and/or adjacent to the patch 3410, a second portion $3416p_2$, $3418p_2$ of each of the limbs 3416, 3418 extends on top of the patch 3410, and a third portion $3416p_3$, $3418p_3$ of each of the limbs 3416, 3418 extends through the patch 3410. The orientation of the first set of suture limbs 3412, 3414 can likewise have different configurations across their length.

Figure 33B:
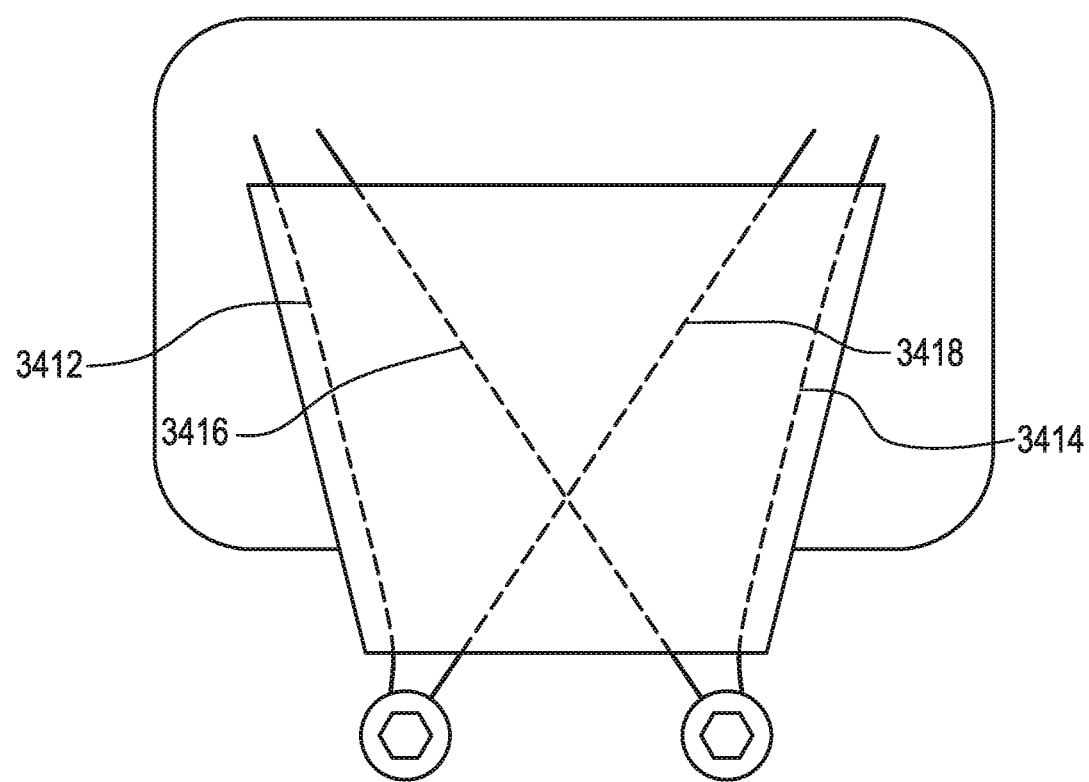

FIG. 33B, on the other hand, provides for an embodiment in which the second set of suture limbs 3416, 3418 do intersect. As shown, the limbs 3416, 3418 are disposed across the patch 3410 (as shown, through the patch), to form an "X" configuration or shape, like the limbs 2212b and 2216b' of FIG. 30I, the limbs 2312b, 2316b of FIGS. 32A-32E, and the limbs 2312b', 2316b' of FIGS. 32F-32H. An "X" configuration can provide for a more distributed compression over a larger area of the construct. A person skilled in the art will recognize that the limbs 3416, 3418 can be oriented in many other manners with respect to each other and the patch 3410 while still intersecting each other. Further, while in the illustrated embodiment of FIG. 33B the limbs 3416, 3418 extend through the patch 3410, they can also extend across a top surface of the patch and/or around or adjacent to the patch, or any combination thereof. Likewise, limbs extending through the patch can extend through a single layer and/or be disposed between two layers.

A fifth parameter that can be changed to achieve various patch configurations relates to the inclusion of one or more "stitches" in conjunction with the first set of suture limbs. As described in the present disclosure, these "stitches" can be referred to as "loops," as shown and described with respect to FIG. 33C, and "jogs," as shown and described with respect to FIG. 33D. As described in greater detail below, the stitches for loops and jogs both involve passing a terminal end of the suture limb through at least a portion of the patch (e.g., through a proximal-most surface of the patch) and then to and through the lateral edge of the patch. Loops can involve the suture limb passing an entire length of the patch extending between the medial and lateral edges, while jogs can involve the suture limb passing through a portion of the length that is not necessarily the entire length (although it can be a substantial portion of the length). The loops and jogs are used to help fixate the patch with respect to at least one suture limb.

Figure 33C:
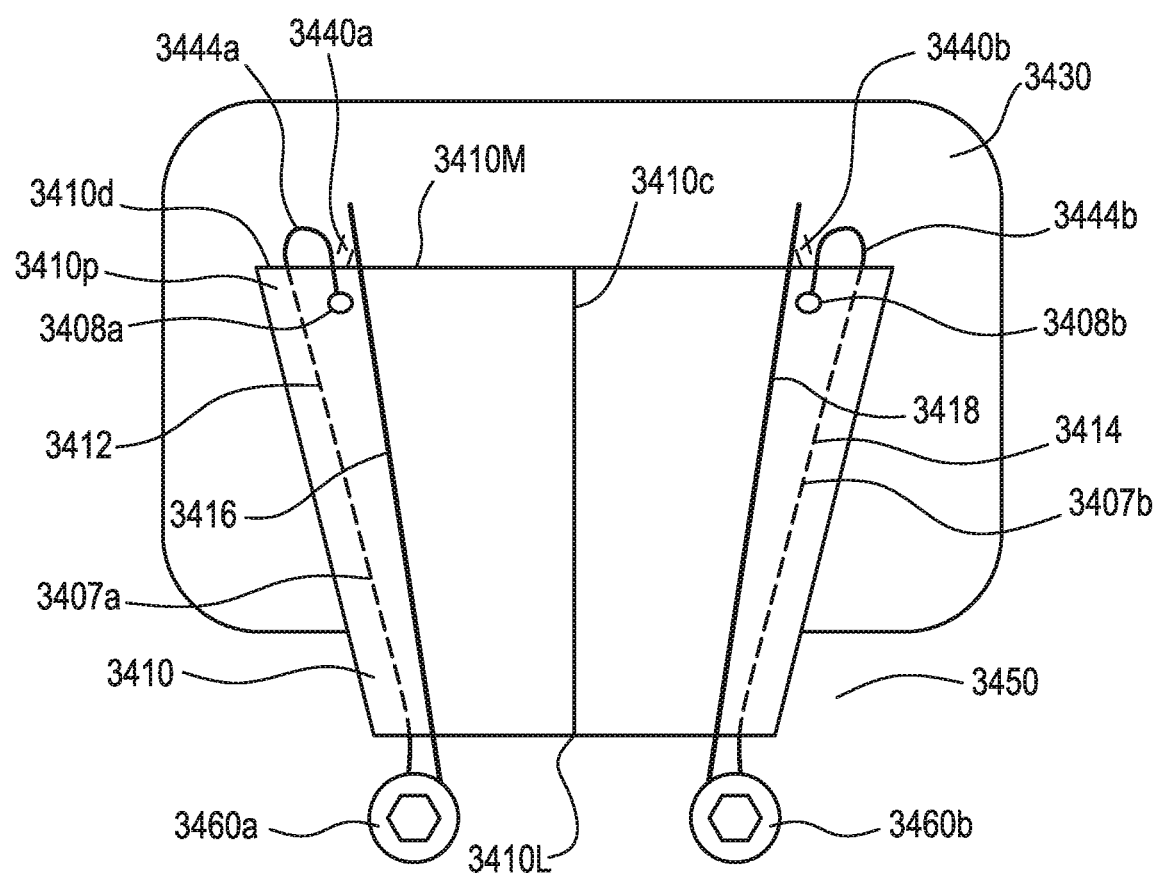
Figure 33D:
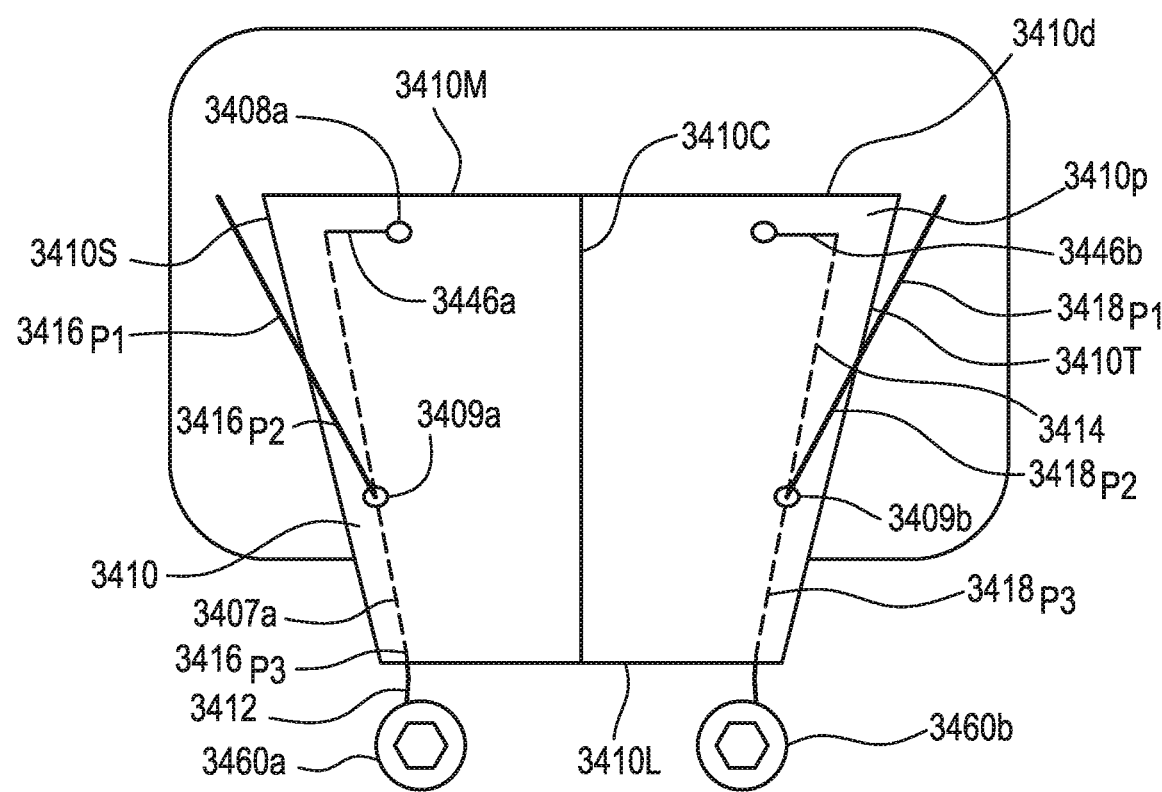

As illustrated in FIG. 33C, a loop stitch or loop 3444a can be formed by passing a suture limb 3412 from the bottom side 3410d of the patch 3410, which faces the soft tissue 3430, to the top side 3410p of the patch 3410 at a location 3408a proximate to the medial edge 3410M. The location 3408a can be a preformed lumen, or it can be a lumen formed while advancing the suture limb 3412 through the patch 3410, for instance because the material of the patch 3410 is braided such that the limb 3412 can be passed through it. The patch 3410 can include at least one lateral lumen 3407a, 3407b that extends from the medial edge 3410M to the lateral edge 3410L. Alternatively, the lumens 3407a, 3407b may not be preformed or exist and may instead just be locations within the patch 3410 through which filament can be passed, for instance between two layers or through a single layer that has a material conducive to having a material passed therethrough. The suture 3412 can then be threaded medially to enter the lumen 3407a at the medial edge 3410M and extend through the lumen to the lateral edge 3410L. Once tension is applied to the loop 3444a and the loop is brought into contact with the patch 3410, the suture limb 3412 can be fixed relative to the patch 3410 such that the patch 3410 will not drift along the suture 3412 after implantation. The loop 3444a can also provide for additional stability during patch installation. This process can be repeated for suture limb 3414 to form a second loop stitch or loop 3444b. The loops 3444a, 3444b can be formed in vivo, or alternatively can be formed before the patch is introduced into the surgical site using patch delivery systems described below. The free end of each suture limb 3412, 3416 and 3414, 3418, also referred to herein as terminal lateral ends, can then be secured within the body using techniques provided for throughout the present disclosure. For example, as shown in FIG. 33C, the free ends of each suture limb 3412, 3416 and 3414, 3418 can be coupled to lateral anchor 3460a and 3460b, respectively, in a lateral row fixation. The suture limbs 3412, 3414, 3416, 3418 can then be tightened to secure the patch 3410 against the repair before the lateral anchors 3460a, 3460b are fully fixed in the bone 3450.

Alternatively, in place of a loop, the suture limb 3412 of the first set of suture limbs 3412, 3414 can be used to form a jog. As illustrated in FIG. 33D, a jog stitch or jog 3446a can be formed by passing the suture limb 3412 from the bottom side 3410d of the patch 3410 to the top side 3410p of the patch 3410 at a location 3408a proximate to the medial edge 3410M, and then advancing the suture limb 3412 towards the outer edge 3410S before passing the suture limb 3412 back into the patch 3410 from the top side 3410p and towards the bottom side 3410d. The suture limb 3412 can then be advanced towards the lateral side 3410L. In the illustrated embodiment, the suture limb 3412 is passed through a lateral lumen 3407a that extends from the medial edge 3410M to the lateral edge 3410L. Alternatively, the lumen 3407a, and/or its illustrated counterpart lumen 3407b, may not be preformed or exist and may instead just be locations within the patch 3410 through which filament can be passed, for instance between two layers or through a single layer that has a material conducive to having a material passed therethrough. Like with the embodiment in FIG. 33C, the location 3408a can be a preformed lumen, or it can be a lumen formed while advancing the suture limb 3412 through the patch 3410, for instance because the material of the patch 3410 is braided such that the limb 3412 can be passed through it. As shown, the portion of the limb 3412 extending through the patch 3410 extends a substantial portion of the length of the limb that extends between the medial and lateral edges 3410M and 3410L, but not the entire length.

When forming the jog 3446a, the suture 3412 can be advanced towards the outer edge 3410S any desired distance based, at least in part, on the size of the patch 3410 and desired configuration of the patch and suture combination. By way of non-limiting example, in some embodiments the jog 3446a can extend substantially perpendicular to the central longitudinal axis 3410c and can have a length approximately in the range of about 1.0 millimeters to about 5.0 millimeters away from the location 3408a. Once tension is applied to the jog 3446a and the jog 3446a is brought into contact with the patch 3410, the suture limb 3412 can thus be fixed relative to the patch 3410 such that the patch 3410 will not drift along the suture limb 3412 after implantation. The jog 3446a can also provide for additional stability during patch installation. A second jog stitch 3446b can be formed with the second limb 3414. The jog stitches 3446a, 3446b can be formed in vivo, or alternatively can be formed before the patch 3410 is introduced into the surgical site using patch delivery systems described below. Alternately, the two sutures of the first set of sutures 3412, 3414 can be associated with the patch 3410 with different stitches, or no additional stitches. Further, in some instances, a combination of loops and jogs can be used.

A sixth parameter that can be changed to achieve various patch configurations relates to whether the second set of suture limbs is disposed in lumens formed in the patch, or alternatively, through portions of the patch through which the first set of suture limbs is passed. One illustration of such a configuration is illustrated in FIG. 33D. As shown, the second set of suture limbs 3416, 3418 can be introduced into the respective lumens 3407a, 3407b of the patch 3410, along with one of the suture limbs 3412, 3414 of the first set of suture limbs. This occurs at a location 3409a, 3409b that is lateral to the medial edge 3410M of the patch 3410. This configuration of the second set can provide for a further securing of the patch in an anterior-posterior direction. A person skilled in the art will recognize a location at which the second, or first, set of suture limbs is disposed within the patch 3410 can vary without departing from the spirit of the present disclosure.

Figure 33E:
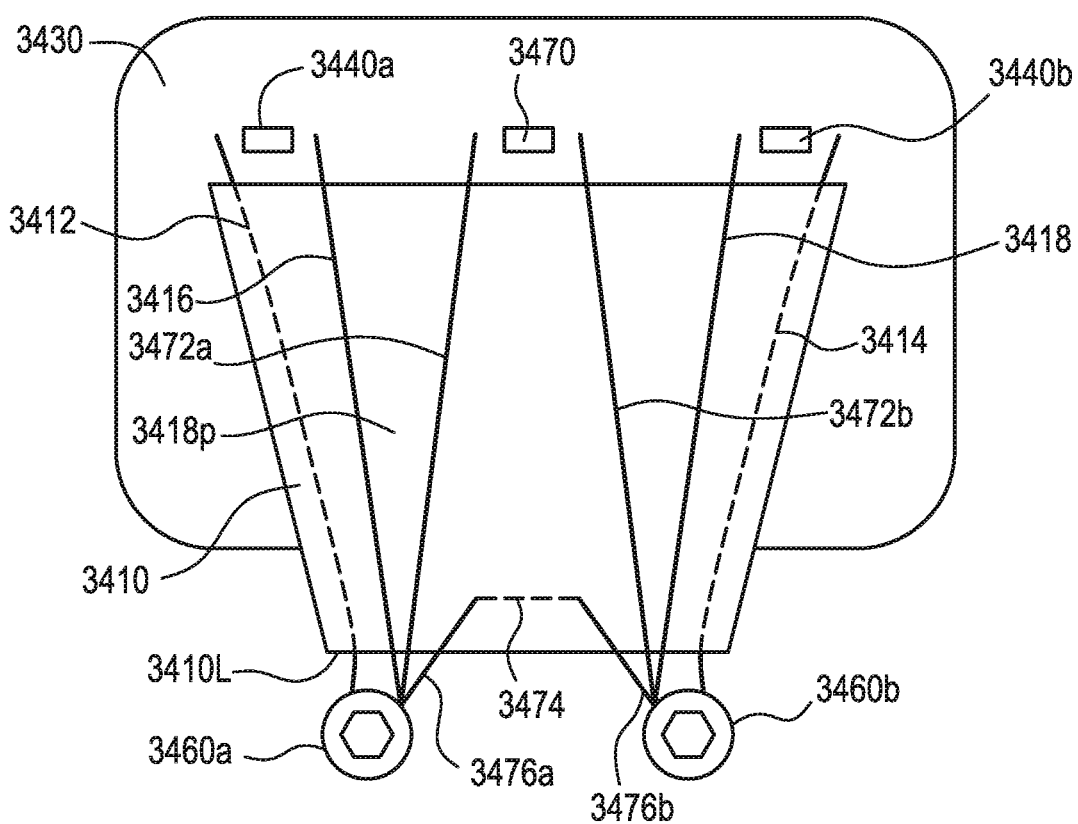

A seventh parameter that can be changed to achieve various patch configurations is the inclusion of additional sutures, such as central medial sutures or central lateral sutures, to provide additional securement of the patch at discrete locations from the lumens. For example, as shown in FIG. 33E, one or more central medial inverted mattress stitches 3470 can be made in the soft tissue 3430 medial to the patch 3410. In the illustrated embodiment, the stitch 3470 is approximately in-line with the first and second mattress stitches 3440a, 3440b, although other configurations, locations, and number of stitches are possible without departing from the spirit of the present disclosure. The central medial inverted mattress stitch 3470 can be generally aligned with a center of the patch 3410 in some instances, such as the illustrate embodiment. The central medial stitch 3470 can result in suture limbs 3472a, 3472b extending therefrom. The suture limbs 3472a, 3472b can be disposed over a proximal face 3410p of the suture patch 3410 and secured with suture anchors 3460a, 3460b, respectively, according to techniques provided for herein.

Alternatively, or in addition to the central medial inverted mattress stitch 3470, a central lateral mattress stitch 3474 can be pre-loaded onto the patch at a location in the lateral half of the patch. Alternatively, the central lateral mattress stitch 3474 can be formed in the patch 3410 in vivo. The central lateral mattress stitch 3474 can be generally aligned with a center of the patch 3410. Like the medial inverted mattress stitch, a number of different configurations, locations, and number of stitches are possible, and in the illustrated embodiment the inverted mattress stitch 3474 results in suture limbs 3476a, 3476b extending from the patch 3410. In the illustrated embodiment, the suture limbs 3476a, 3746b are disposed over the proximal face 3410p of the suture patch 3410 and are additionally secured in suture anchors 3460a, 3460b. Both the central medial stitch and lateral central stitch can provide for additional compression of the patch against the soft tissue to aid in healing. While the patch 3410 illustrated in FIG. 33E illustrates both a central medial mattress stitch and a central lateral mattress stitch in the same embodiment, in other embodiments only one or neither may be provided. Further, other locations for additional stitches are also possible without departing from the spirit of the present disclosure.

An eighth parameter that can be changed to achieve various patch configurations is a location of the first set of suture limbs with respect to the second set of suture limbs. More particularly, this parameter relates to whether the limbs of the first set of suture limbs are disposed inside or outside of the limbs of the second set of suture limbs, where outside represents being further from the central longitudinal axis 3410c. In the embodiments illustrated in FIGS. 33A and 33D, the first set of suture limbs is disposed inside of the second set of suture limbs, while in the embodiments illustrated in FIGS. 33B, 33C, and 33E, the first set of suture limbs is disposed outside of the second set of suture limbs. More particularly with respect to FIG. 33D, the first set of suture limbs is disposed inside the second set of suture limbs until they converge at the location 3409a, at which point they are substantially aligned. Thus, the orientation of the first set of suture limbs with respect to the second set of suture limbs can change between the medial and lateral edges 3410M, 3410L, including having some portion that is inside the other and some portion that is outside of the other. Further, a person skilled in the art will recognize that not each limb of the set of limbs needs to be disposed in the same respect, meaning that some limbs of the first set of limbs can be disposed inside of one or more limbs of the second set of limbs, and likewise some limbs of the first set of limbs can be disposed outside of one or more limbs of the second set of limbs in the same patch configuration.

Notably, most any of the aforementioned parameters or variables can be mixed and matched in one or more patch configurations without departing from the spirit of the present disclosure. Accordingly, there are many different configurations that can result from the present disclosure. The term "most any" is used because a person skilled in the art will recognize that, depending on the value of some of these parameters, some of the other parameters may not be adjustable, and a person skilled in the art will recognize as such in view of the present disclosures and the skilled person's knowledge. FIGS. 33A-33E represent a small sampling of possible configurations intended to illustrate various configurations based on the eight parameters identified in the present disclosure. Each of the illustrated configurations can be used in conjunction with various procedures. FIG. 33C represents one particularly useful configuration in that it provides for the stability provided for by the loops 3444a, 3444b, provides for a configuration in which the first set of limbs are disposed approximately straight through the patch 3410 to provide additional securement of the edges 3410S, 3410T. Further, the configuration is additionally particular useful because the second set of limbs are disposed approximately straight (as opposed to crossed in an "X" configuration or shape) over the patch 3410 to aid in the medialization of the patch and ease of tensioning of the limbs, the four limbs decrease the likelihood of undesirable "cheese-wiring," and the configuration does not include additional stitches or the like, making it easier and/or quicker to perform than some options that include additional stitches.

Still another exemplary embodiment of a tissue augmentation construct 2410 having a patch or scaffold configuration is illustrated in FIGS. 34A and 34B. As shown, the patch 2410 has a rectangular-shaped body having generally rounded corners. Alternatively, the patch 2410 can have any shape, for example circular. The patch 2410 can be disposed on or otherwise associated with sutures 2412, 2416. As shown, the patch 2410 has a length $L_P''$ that is substantially equal to a width $W_P''$ and it also has a thickness $T_P''$.

A person skilled in the art will recognize that the dimensions of the length $L_P''$ the width $W_P''$ thickness $T_P''$ of the augmentation patch 2410 can depend on a variety of factors, including but not limited to the size of the filament with which it is to be associated, the anatomy of the patient, and the type of procedure being performed. The exemplary, non-limiting dimensions provided above for the patch 2210 can also be applicable to the size of the patch 2410, with the understanding that other dimensions are possible. Likewise, a number of techniques known to those skilled in the art can be used to associate the augmentation patch 2410 with the sutures 2412, 2416. Nevertheless, FIGS. 34A and 34B illustrate one exemplary method for using suture threaders 2406a, 2406b to associate the patch 2410 with the sutures 2412, 2416.

As shown in FIGS. 34A and 34B, the sutures limbs 2412, 2416 are threaded to the patch 2410 at medial locations 2411a, 2411b of the patch, respectively, to secure the sutures 2412, 2416 relative to the patch 2410 in a pre-installation configuration. In the illustrated embodiment the medial locations 2411a, 2411b are located approximately midway between opposing sides 2410a, 2410b of the patch 2410, although other locations are possible. The sutures 2412 and 2416 can be stitched, or otherwise threaded, onto the patch 2410 such that two suture limbs 2412a, 2412b and 2416a, 2416b, respectively, extend from a proximal surface of the patch 2410. The suture limb 2412a and 2416a can each have a first portion that includes a hollow self-locking mechanism 2470a and 2470b having a lumen 2472a and 2472b extending therethrough. In the illustrated embodiment the self-locking mechanisms 2470a, 2740b are finger-trap-like configurations, although other self-locking mechanisms provided for herein or otherwise known to those skilled in the art in view of the present disclosures can also be used.

The self-locking mechanisms 2470a and 2470b can each have a length that is less than the distance extending between the side 2410a of the patch 2410 and the respective stitches 2411a and 2411b. The suture threaders 2406a, 2406b can be inserted through the respective self-locking mechanisms 2470a, 2470b such that a proximal handle portion 2408a, 2408b is located proximate to the respective medial locations 2411a, 2411b, and the distal suture-receiving ends 2409a, 2409b are located more proximate to the side 2410a than the side 2410b. The suture limbs 2412a, 2416a can have respective leading tails 2413a, 2413b extending from the self-locking mechanisms 2470a, 2740b. As shown, the leading tail 2413a, 2413b of each suture 2412, 2416 can be threaded from a proximal side 2410p to the distal side 2410d of the patch 2410, at a location that is more proximate to the side 2410a than the side 2410b. Further, as illustrated, the suture limbs 2412b, 2416b are threaded from the proximal side 2410p to the distal side 2410d of the patch 2410, at a location that is more proximate to the side 2410b than the side 2410a, thereby forming trailing tails. A person skilled in the art will recognize a variety of other ways by which the patch 2410 can be associated with the sutures 2412, 2416 without departing from the spirit of the present disclosure.

FIGS. 34C-34J provide for one exemplary method of installing the tissue augmentation patch 2410 to help secure a piece of soft tissue 2430, e.g., rotator cuff, to bone 2450 using a single row repair 2432. Like the many other methods provided for herein, the patch 2410 and related techniques can also be used in other types of repairs, such as double row repairs. Once the surgeon has access to the surgical site and the tissue, bone, and tissue augmentation patch have been prepared according to accepted surgical techniques including those provided for herein, as shown in FIG. 34C, the tissue 2430 can be fixed to the bone 2450 using a suture 2403 coupled to an anchor 2404 that inserted into the bone 2450. While one suture 2403 and one anchor 2404 are shown, a plurality can be used in order to effectively fix the tissue 2430 relative to the bone 2450. Further, in the illustrated embodiment only the components associated with one of the threaders and sutures is visible because of the point of view illustrated, but a person skilled in the art will understand that the other threader and suture can be operated in a similar manner. Reference may be made to both components, even though only one is visible, for ease of description.

Once the tissue 2430 has been fixated to the bone 2450, the leading tails 2413a, 2413b can be stitched into the tissue, medial of the repair, as shown in FIG. 34D. In the illustrated embodiment, the leading tails 2413a, 2413b are threaded into, and back out of, the tissue 2430 using, for example, a mattress stitch 2442a. As shown in FIG. 34E, the leading tail 2413a can be coupled to the suture-receiving end 2409a of the suture threader 2406a, and the suture threader 2406a can be subsequently operated as provided for in the present disclosure to advance the leading tail 2413a into the lumen 2472a of the self-locking mechanism 2470a. A similar action can be taken with respect to the leading tail 2413b so that it becomes disposed in the lumen 2472b of the self-locking mechanism 2470b, although, as indicated above, this is not visible in the point of view illustrated. After distal ends of the tails 2413a, 2413b have been passed through the respective self-locking mechanisms 2470a, 2740b such that the distal ends are visible and able to be grabbed by a user, as shown in FIG. 34F, the threaders 2406a, 2406b can be disconnected from the tails 2413a, 2413b and disposed of and/or prepared for future use. In the illustrated embodiment, the self-locking mechanisms 2470a, 2470b can operate such that the respective leading tails 2413a, 2413b can only advance in one direction, or can optionally be selectively lockable.

As shown in FIG. 34G, the operator can apply a force $F_P$ to the leading tails 2413a, 2413b to advance the patch 2410 towards the mattress stitch 2442a. More specifically, as the force $F_P$ is applied to the leading tail 2413a, a loop 2415a defined by the self-locking mechanism 2470a is collapsed, as illustrated by the resulting configuration in FIG. 34H. A similar result occurs when the force $F_P$ is applied to the leading tail 2413b.

The patch 2410 is an installed location, as shown in FIG. 34H, when the repair 2432 has been covered by the patch 2410. More particularly, the illustrated installed configuration shows that the side 2410a of the patch 2410 is proximate to the mattress stitch 2442a. As a result, when the side 2410b of the patch 2410 is coupled to a location in the body, the patch 2410 is able to bend over as shown and more securely protect and integrate with the tissue 2430. This is because the patch 2410 can stretch to provide for a tighter fit. The patch 2410, in combination with the sutures 2412, 2416, operate together as a single continuous suture or belt, which can better share the load than using multiple stitches. A person skilled in the art will recognize that other lengths of the patch 2410, other locations for the medial stitches 2411a, 2411b, and other locations for a distal terminal end of the self-locking mechanisms 2472a, 2742b, among other factors, can be adjusted to achieve other installed configurations in accordance with the present disclosures. Alternatively, the patch 2410 can be located medial to the repair 2432, or any other location that is desired for a given procedure.

Any number of techniques for securing a location of the side 2410b of the patch 2410 within the body can be used, including those provided for herein. In the illustrated embodiment, after the patch 2410 has been installed onto the tissue 2430, as shown in FIGS. 34I and 34J, the leading tail 2413a and the trailing tail 2412b are coupled to the anchor 2460a and the leading tail 2413b and trailing tail 2416b are coupled to the anchor 2460b. The leading tails 2413a, 2413b and the trailing tails 2412b, 2416b can then be tightened to secure the patch 2410 against the repair before the anchors 2460a, 2460b are fully fixed in the bone 2450. Once the patch 2410 is secured within the body, the patch 2410 does not generally flex much or move so that way the patch 2410 can protect and heal in manners described throughout the present application with respect to augmentation constructs generally. Alternatively, the trailing tails 2412b, 2416b can both be secured to the patch 2410 at a location proximate the anchors 2406a, 2406b to allow for the patch to stretch over the tissue.

In an alternative method, the leading tail 2413b and the trailing tail 2412a can be coupled to the anchor 2460a and the leading tail 2413a and the trailing tail 2416b can be coupled to the anchor 2460b, as shown in FIG. 34K. Such a configuration provides for a crossed pattern that can provide benefits as described above when discussing crossed patterns. In yet a further alternative embodiment, the leading tails 2413a, 2413b can be cut proximate to where they exit the self-locking mechanisms 2470a, 2470b, respectively, such that only the trailing tails 2412b, 2416b are secured into the anchors 2406a, 2406b, respectively. This is because in certain self-locking mechanism configurations, such as the finger-trap-like configuration illustrated, allows the trailing tails 2412b, 2416b to carry the load. A person skilled in the art, in view of the present disclosures, will further recognize that various suture sizes and configurations can be adjusted in view of the flexible patch 2410 to help share the load.

The tissue augmentation patch 2410 can be manufactured using a number of different techniques which have been previously discussed above with regards to tissue augmentation constructs, including but not limited to the tissue augmentation patches 2210, 2310. Further, the patch 2410 can be made from any of the materials provided for above with respect to the patches 2210, 2310, including materials that promote healing and tissue growth, for example collagen. As a result, while the patient is healing from the procedure, the patch can remodel into tendon-like tissue and integrate with the underlying native tissue. The additional coverage of tendon like tissue across the soft tissue can increase the strength of the soft tissue to bone connection and may prevent further injury.

Another exemplary embodiment of a tissue augmentation construct 2510 having a patch or scaffold configuration is illustrated in FIGS. 35A-35D. The patch 2510 has a shape and size similar to that of the patch 2410, and can be disposed on or otherwise associated with sutures 2512a, 2512b, 2516a, 2516b. A number of techniques provided for throughout the present disclosure can be used to couple or otherwise associate the patch 2510 with the sutures 2512a, 2512b, 2516a, 2516b. As shown in FIG. 35A, the sutures 2512a, 2516a are threaded to the patch 2510 at medial locations 2511a, 2511b of the patch, respectively, to secure the sutures 2512a, 2516a relative to the patch 2510. The medial locations 2511a, 2511b, can be similar to the comparable medial locations 2411a, 2411b of the patch 2410, and thus can lead to some of the same benefits described above. The sutures 2512a, 2516a can be stitched or otherwise fixed onto the patch 2510 such that the sutures 2512a, 2516a extend from a proximal surface of the patch 2510. First portions of the sutures 2512a, 2516a can each include a hollow self-locking mechanism 2570a, 2570b having a lumen 2572a, 2572b extending therethrough. In the illustrated embodiment the self-locking mechanisms 2570a, 2570b are finger-trap-like configurations, although other self-locking mechanisms provided for herein or otherwise known to those skilled in the art in view of the present disclosures can also be used.

The self-locking mechanisms 2570a, 2570b can have lengths that are less than the distance extending between the side 2510a of the patch 2510 and the respective medial locations 2511a, 2511b. Suture threader 2506a, 2506b can be inserted through respective lumens 2572a, 2572b of the self-locking mechanisms 2570a, 2572b and can be configured in a similar manner as the suture threaders 2406a, 2406b described above. The sutures 2512a, 2516a can include leading tails 2513a, 2513b which, as shown, can extend respectively from the self-locking mechanisms 2570a, 2570b. As shown in FIGS. 35A and 35B, the leading tails 2513a, 2513b are threaded from a proximal side 2510p to the distal side 2510d of the patch 2510, at a location that is proximate to the side 2510a of the patch 2510.

Unlike the previous embodiment of the tissue augmentation construct 2410 in which the trailing tails were part of the filament used to form the self-locking mechanisms and the leading tails, trailing tails of the tissue augmentation construct 2510 are separate filaments that are not part of the filaments used to form the self-locking mechanisms 2570a, 2570b or the leading tails 2513a, 2513b. As shown, the suture 2512b is a trailing tail that includes a mattress stitch at a location that is proximate to the side 2510b of the patch 2510, and the suture 2516b is a trailing tail that includes a simple stitch at a location that is also proximate to the side 2510b. More particularly, each of the trailing tails 2512b and 2516b pass from a proximal side 2510p of the patch 2510 to a distal side 2510d of the patch 2510. By providing separate leading and trailing tails, a user can have additional control over the construct 2510 since the tails can operate independently. It can, for example, enhance the stretching of the construct 2510 that occurs at either end 2510a, 2510b. Notably, this embodiment illustrates some non-limiting ways by which sutures can be associated with tissue augmentation constructs, and thus in other embodiments both trailing tails 2512b, 2516b can use similar stitches. A person skilled in the art will recognize a variety of other ways by which the patch 2510 can be associated with the sutures 2512a, 2512b, 2516a, 2516b without departing from the spirit of the present disclosure.

The method of installing the tissue augmentation patch 2510, which is illustrated in FIGS. 35C and 35D by way of an installed configuration, can be similar to the method described above with respect to the patch 2410, and the installed configuration is illustrated without including the steps leading thereto. As shown, the medial locations 2511a, 2511b of the patch 2510 are proximate to an edge of the tissue 2530, and the edge 2510b is disposed proximate to anchors 2560a, 2560b by way of the trailing tails 2512b, 2516b being coupled and tightened thereto. Alternatively, the patch 2510 can be located medial to the repair, or any other location that is required for the procedure.

Yet another exemplary embodiment of a tissue augmentation construct 2610 having a patch or scaffold configuration is illustrated in FIGS. 36A-36I. The patch 2610 has a shape and size similar to that of the patches 2410 and 2510, and can be disposed on or otherwise associated with sutures 2612, 2616. A number of techniques provided for throughout the present disclosure can be used to couple or otherwise associate the patch 2610 with the sutures 2612, 2616. As shown in FIG. 36A, the sutures limbs 2612, 2616 are threaded into the patch at medial locations 2611a, 2611b of the patch 2610, respectively, to secure the sutures 2612, 2616 relative to the patch 2610. The medial locations 2611a, 2611b, can be similar to the comparable medial locations 2411a, 2411b of the patch 2410, and thus can lead to some of the same benefits described above.

The suture 2612 can be stitched or otherwise fixed onto the patch 2610 such that two suture limbs 2612a, 2612b extend from a proximal surface 2610p of the patch 2610. Each of the suture limbs 2612a and 2612b can have a first portion that includes a hollow self-locking mechanism 2670a, 2670b having a lumen 2672a, 2672b extending therethrough, respectively. In the illustrated embodiment the self-locking mechanisms 2670a, 2670b are finger-trap-like configurations, although other self-locking mechanisms provided for herein or otherwise known to those skilled in the art in view of the present disclosures can also be used.

The self-locking mechanisms 2670a, 2670b can have lengths that are less than the distance extending between the respective sides 2610a, 2610b of the patch 2610, as shown, and the medial location 2611a. Suture threaders 2606a, 2606b can be inserted through respective lumens 2672a, 2672b of the self-locking mechanisms 2670a, 2672b and can be configured in a similar manner as the suture threaders 2406a, 2406b described above. The suture limbs 2612a, 2612b can include leading tails 2613a, 2613b which, as shown, can extend respectively from the self-locking mechanisms 2670a, 2670b. As shown in FIGS. 36A and 36B, the leading tails 2613a, 2613b are threaded from the proximal side 2610p to the distal side 2610d of the patch 2610, at location that are proximate to the respective sides 2610a, 2610b of the patch 2610.

The suture 2616 can be stitched or otherwise fixed onto the patch 2610 in substantially the same manner as the suture 2612, and thus includes self-locking mechanisms 2670c, 2670d associated with suture limbs 2616a, 2616b, with the self-locking mechanisms 2670c, 2670d having leading tails 2613c, 2613d extending therefrom, respectively. As shown in FIG. 36A, the resulting patch 2610 can be symmetrical with regards to a first axis $A_1$ and a second axis $A_2$. A person skilled in the art will recognize a variety of other ways by which the patch 2610 can be associated with the sutures 2612, 2616 without departing from the spirit of the present disclosure.

Figure 36C:
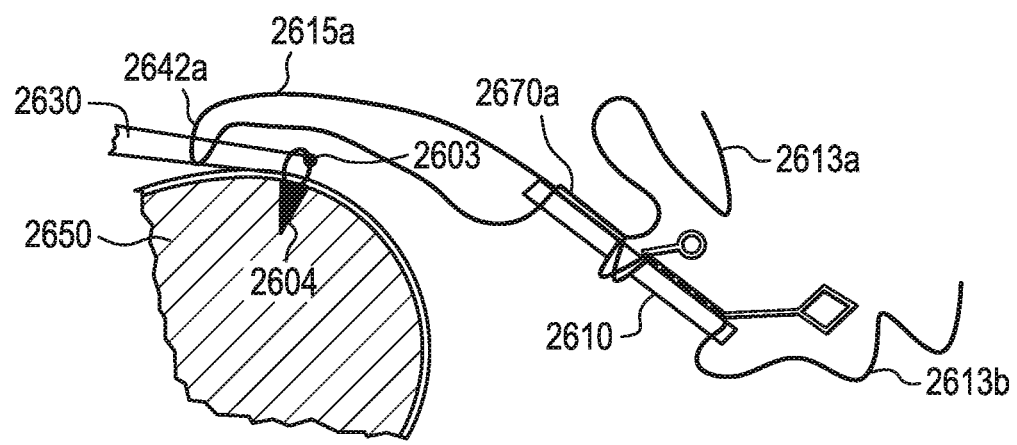

FIGS. 36C-36I provide for one exemplary method of installing the tissue augmentation patch 2610 to help secure a piece of soft tissue 2630, e.g., rotator cuff, to bone 2650 using a single row repair. Like the many other methods provided for herein, the patch 2610 and related techniques can also be used in other types of repairs, such as double row repairs. Once the surgeon has access to the surgical site and the tissue, bone, and tissue augmentation patch have been prepared according to accepted surgical techniques including those provided for herein, as shown in FIG. 36C, the tissue 2630 can be fixed to the bone 2650 using a suture 2603 coupled to an anchor 2604 that inserted into the bone 2650. While one suture 2603 and one anchor 2604 are shown, a plurality can be used in order to effectively fix the tissue 2630 relative to the bone 2650. Further, in the illustrated embodiment only the components associated with one of the sutures is visible because of the point of view illustrated, but a person skilled in the art will understand that the other suture and related components can be operated in a similar manner.

Figure 36D:
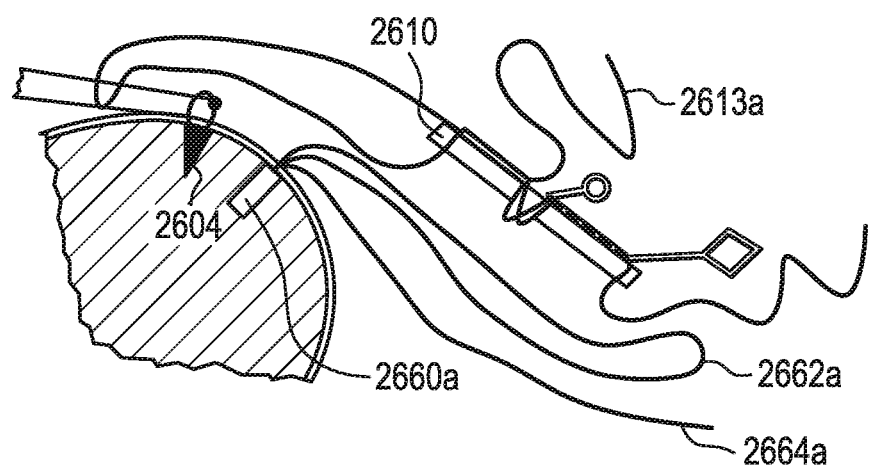

Once the tissue 2630 has been fixated to the bone 2630, the leading tails 2613a, 2613c can be stitched into the tissue, medial of the repair, as shown in FIG. 36C. As shown, the leading tail 2613a is threaded into, and back out of, the tissue 2630 using, for example, a mattress stitch 2642a. The leading tail 2613a can then be coupled to the distal suture-receiving end 2609a of the suture threader 2606a, and the suture threader 2606a can be subsequently operated as provided for in the present disclosure to advance the leading tail 2613a into the lumen 2672a of the self-locking mechanism 2670a, thereby forming a loop 2615a. After the distal end of the tail 2613a has been passed through the self-locking mechanisms 2670a such that the distal end is visible and able to be grabbed by a user, as shown in FIG. 36D, the threader 2606a can be disconnected from the tail 2613a and disposed of and/or prepared for future use. In the illustrated embodiment, the self-locking mechanism 2670a can operate such that the leading tail 2613a can only advance in one direction, or can optionally be selectively lockable. The leading tail 2613c can be similarly threaded through the self-locking mechanism 2670c, in conjunction with the threader 2606c.

An anchor 2660a can be inserted into the bone 2650, laterally offset from the repair anchor 2604, having a collapsible loop 2662a and a tensioning tail 2664a associated therewith. The tensioning tail 2664a can be used to collapse the collapsible loop 2662a towards the anchor 2660a. The leading tail 2613c can be similarly threaded through the self-locking mechanism 2670c, and a second lateral anchor 2660b (FIG. 36I) and collapsible loop (not visible) can be similarly installed into the bone 2650.

Figure 36E:
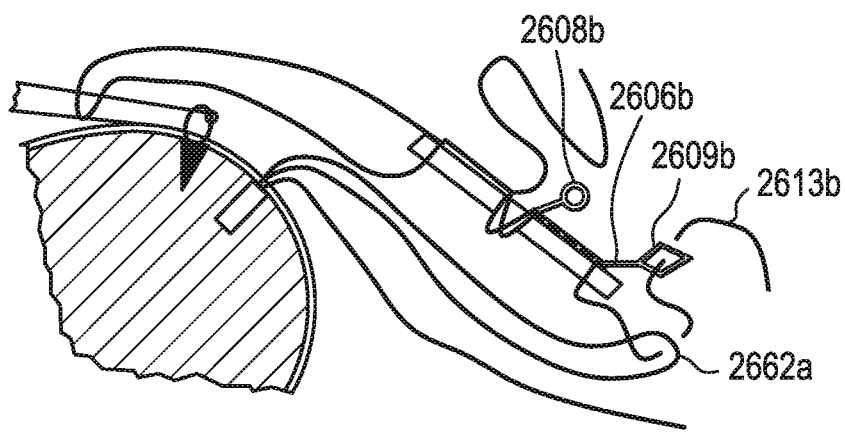
Figure 36F:
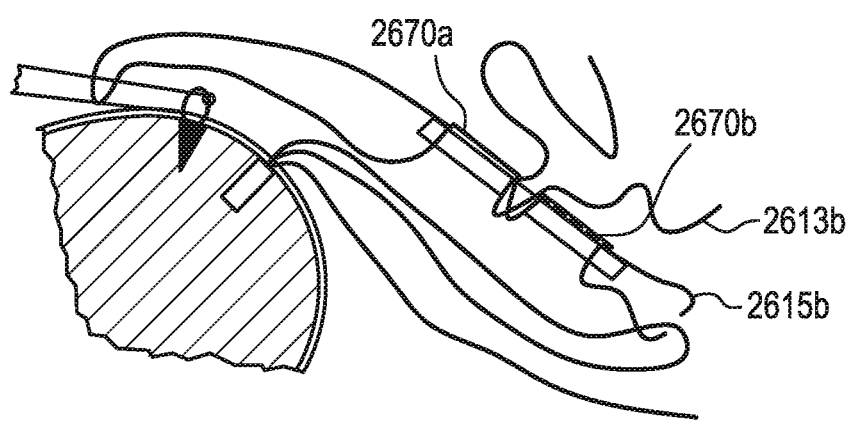

As shown in FIGS. 36E and 36F, the trailing tail 2613b can be looped through the collapsible loop 2662a and then coupled to the distal suture-receiving end 2609b of the suture threader 2606b. The suture threader 2606b can be subsequently operated as provided for in the present disclosure to advance the trailing tail 2613b into the lumen 2672b of the self-locking mechanism 2670b, thereby forming a loop 2615b. After the distal end of the tail 2613b has been passed through the self-locking mechanisms 2670b such that the distal end is visible and able to be grabbed by a user, as shown in FIG. 36F, the threader 2606b can be disconnected from the tail 2613b and disposed of and/or prepared for future use. In the illustrated embodiment, the self-locking mechanism 2670b can operate such that the leading tail 2613b can only advance in one direction, or can optionally be selectively lockable. The leading tail 2613d can be similarly threaded through the self-locking mechanism 2670d, in conjunction with the threader 2606d.

Figure 36G:
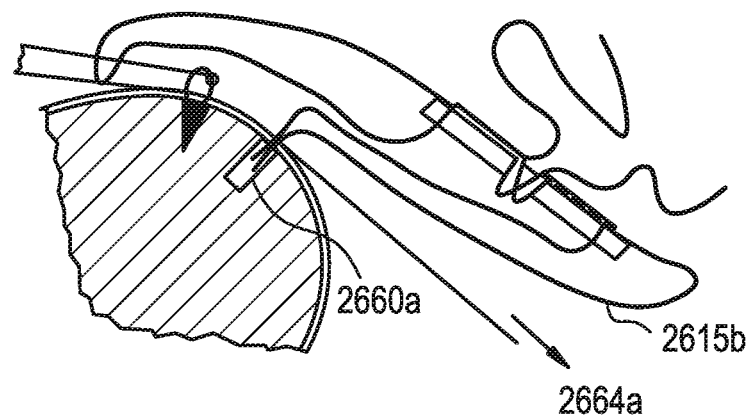

As shown in FIG. 36G, the collapsible loop 2662a can be collapsed towards the anchor 2660a, thereby bringing a portion of the loop 2615b towards anchor 2660a. The trailing tail 2613d can be similarly looped through a collapsible loop (not shown) associated with the anchor 2660b to bring a portion of that collapsible loop towards the anchor 2660b, as seen at least in FIG. 36I.

Figure 36H:
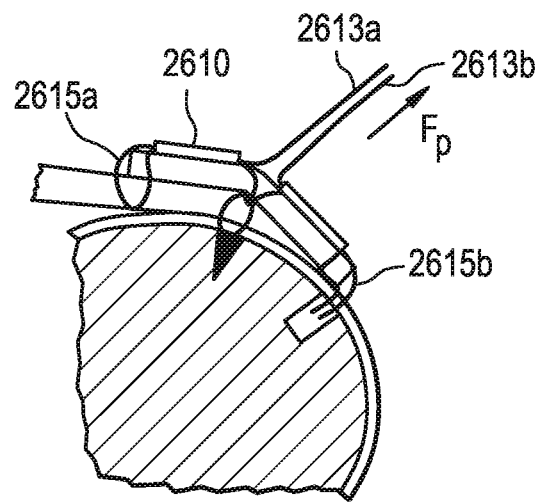
Figure 36I:
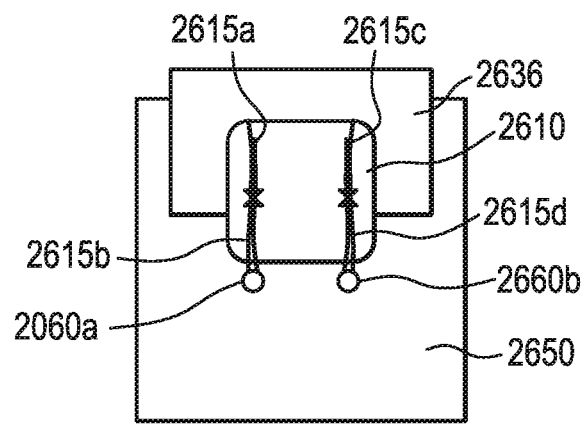

As shown in FIG. 36H, the operator can apply a force $F_P$ to the leading tail 2613a, trailing tail 2613b, leading tail 2613c, and trailing tail 2613d to advance the patch 2610 towards the repair. The patch 2610 is in an installed location, shown in FIG. 36H, when the repair has been covered by the patch 2610, similar to the installed configuration described above with respect to the patch 2410, and when slack in the loops 2615a-2615d has been removed. Thus, adjustments to positioning of the patch 2610 and related components can also be achieved in manners similar as described with respect to the patch 2410. After the patch 2610 has been installed onto the tissue 2630, as shown in FIGS. 36H and 36I, the excess portion of the tails 2613a-2613d that extend out of the self-locking mechanisms 2670a-2670d can be cut to remove excess material.

Tissue Augmentation Patch Delivery Tools

Tools that aid in the delivery and suture management of tissue augmentation constructs can reduce the complexity and time involved with the procedures are also provided for in the present disclosure. Some such tools, including threaders and the installation tool 200', are provided for above. The disclosure in this section focuses on some delivery tools that can be used in conjunction with patches or scaffolds, although a person skilled in the art will recognize how many different constructs provided for herein can be used in conjunction with various delivery tools and systems provided for herein without departing from the spirit of the present disclosure. In other words, just because the disclosures provided below primarily illustrate delivery tools used in conjunction with patches or scaffolds, other tissue augmentation constructs can also be used in conjunction with delivery tools of the nature provided for, even if some modifications by a skilled person would be desirable and/or necessary to accommodate the different configurations. Such modifications would be possible in view of the present disclosures and knowledge of the skilled person. The tools for delivering scaffolds as illustrated include construct management folding cards (FIGS. 37A-37E), construct management release cartridges (FIGS. 38A-38E), construct management deconstructable boxes (FIGS. 39A-39F), construct management boxes configured to mount to a cannula (FIG. 40), and construct delivery insertion tools (FIGS. 41A-41E and 42A-42C).

Figure 37A:
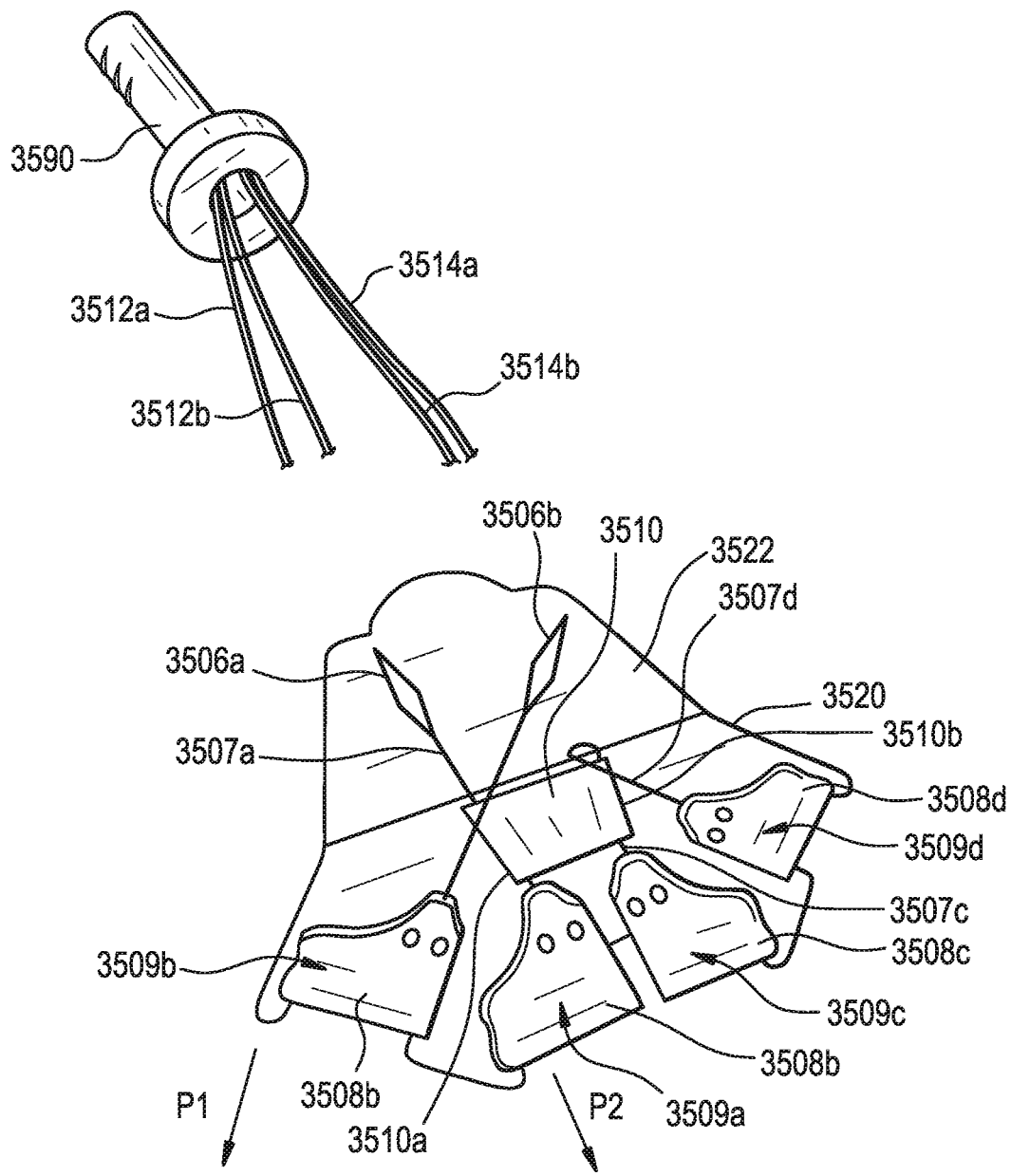

One exemplary embodiment of a construct management folding card is illustrated in FIGS. 37A-37E. As shown in FIG. 37A, a construct management folding card 3520 can secure or otherwise hold a patch or scaffold 3510 having threaders 3509a-3509d disposed in the patch for implantation at a surgical site. The card 3520 can include a bottom patch securing portion 3524 and a top flap 3522. The top flap 3522 can be folded over, as shown along a crease 3526, the bottom portion 3524 to protect the patch 3510 and threaders 3509a-3509d during transport. While in the illustrated embodiment the card 3520 utilizes a folding configuration with a crease to protect the patch, many other configurations of a card that protects the patch can be used without departing from the spirit of the present disclosure, including embodiments provided for herein or otherwise derivable therefrom. For example, the bottom portion 3524 and the top flap 3522 can be separate pieces that are coupled together using any number of techniques known to those skilled in the art. The card 3520 can be formed of any suitable material including plastics, cardboard, and metals.

A plurality of threaders for associating filament with the patch 3510 are also provided. The threaders can include a tab or handle 3508a-3508d, a filament 3507a-3507d attached therethrough, and a loop 3506a-3506d at the end of the filament. For example, a suture limb can be associated with the loop and a user can draw the filament, and therefore the loop and suture limb associated therewith, through the patch by grasping the tab. In some embodiments, the threaders 3509a-3509d can be disposed through the patch 3510 in a manner that enables the suture limbs 3512a, 3514a to form loops 3540a, 3540b at the medial edge 3510M of the patch 3510, like the loops 3440a, 3440b illustrated in FIG. 33C. Any number of patch-threader and patch-filament configurations are possible for the construct, and in the illustrated embodiment the filament 3507a of the first threader 3509a is disposed in the patch 3510 approximately parallel to a first outer side edge 3510a of the patch 3510, and the filament 3507b of the second threader 3510b is disposed in the patch 3510 at an approximately 45 degree angle relative to the filament 3510a. The third and fourth threaders 3510c, 3510d, and their associated filaments 3507c, 3507d, are disposed proximate the second outer side edge 3510b of the patch in a similar fashion as shown.

Figure 37B:
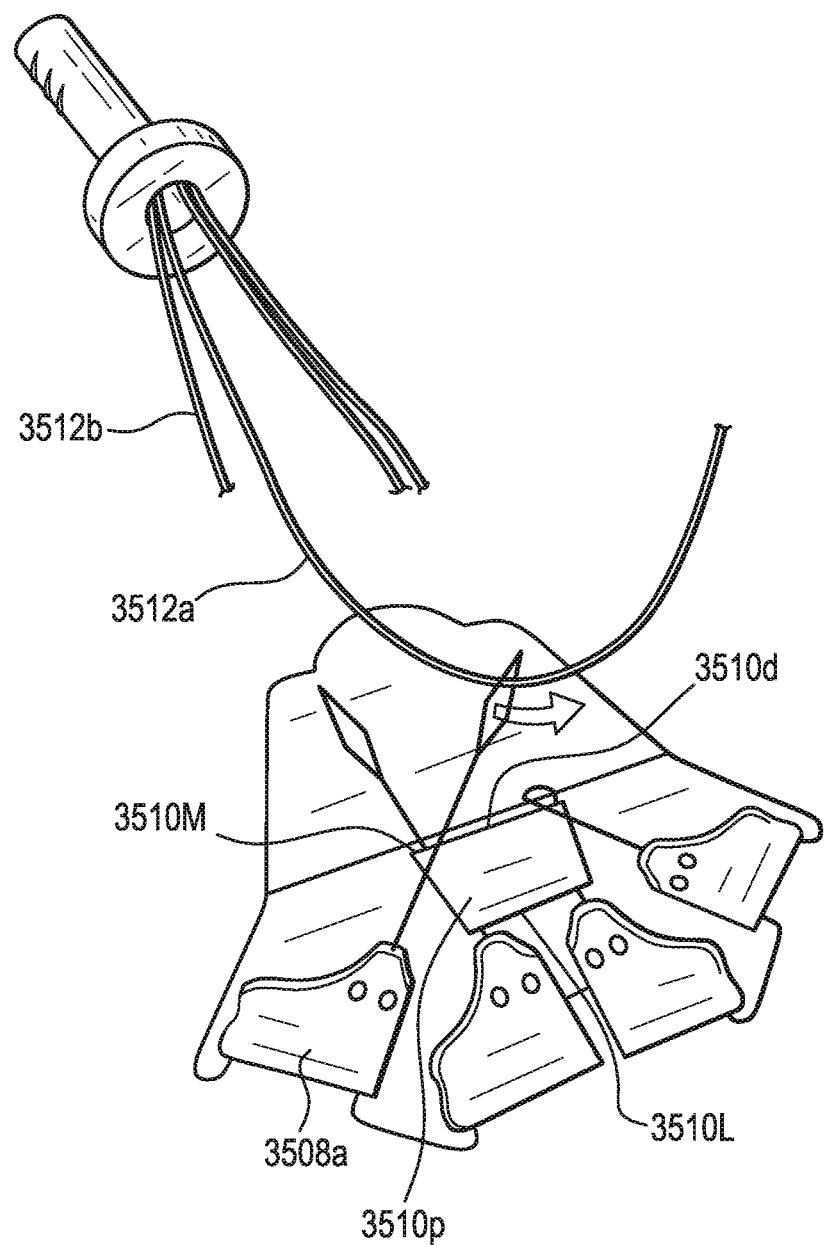
Figure 37C:
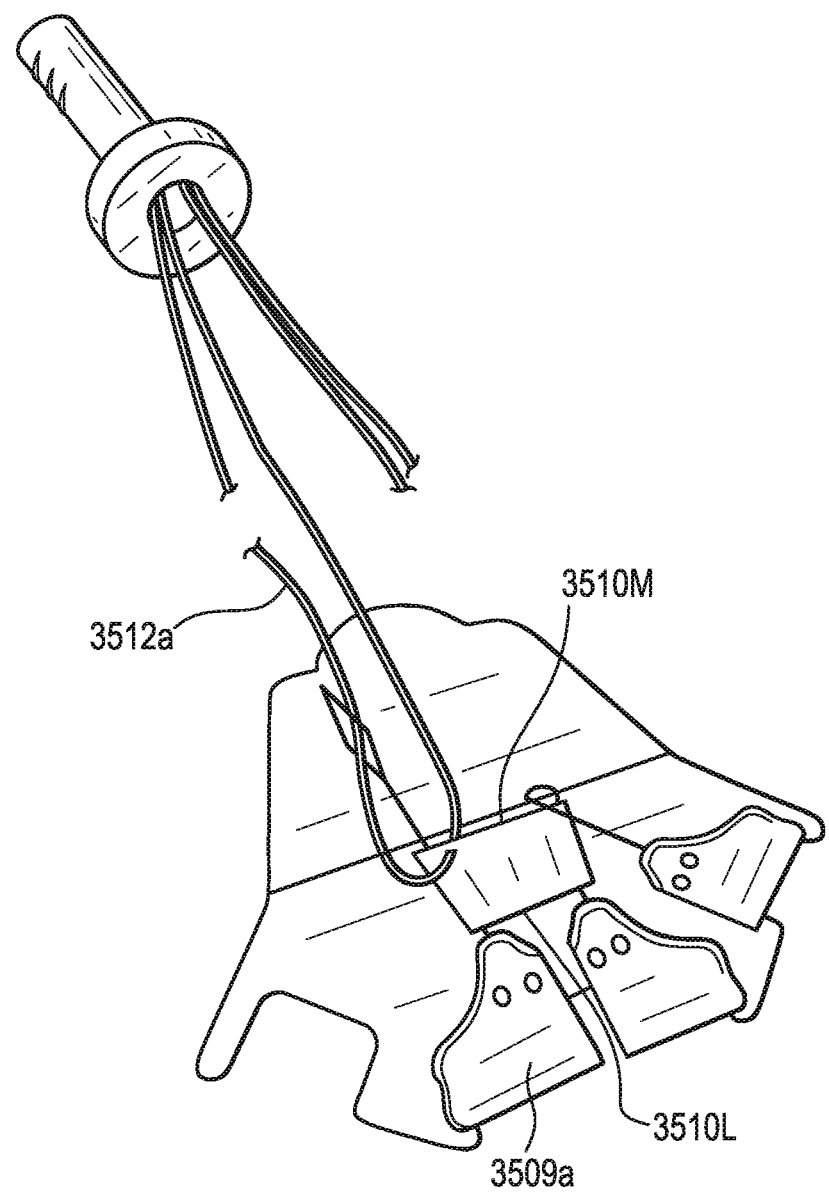

In use, as shown in FIGS. 37B-37E, once the surgeon has access to the surgical site, for example through the cannula 3590, and the surgical site has been prepared according to accepted surgical techniques, the suture limbs 3512a, 3512b, 3514a, 3514b can be brought outside the patient through the cannula 3590. The top flap 3522 of the card can be unfolded to expose the patch 3510 and the suture threaders 3509a-3509d. As discussed above, a loop 3540a can be formed by first inserting the suture limb 3512a through the second threader 3509b and pulling the threader in a direction P1 from a distal side 3510d to a proximal side 3510p of the patch 3510, as shown in FIG. 37B. The suture limb 3512a can then be disposed through the first threader 3509a and advanced through a lumen, not shown, from the medial edge 3510M of the patch to the lateral edge 3510L of the patch in a direction P2, as shown in FIG. 37C.

Figure 37D:
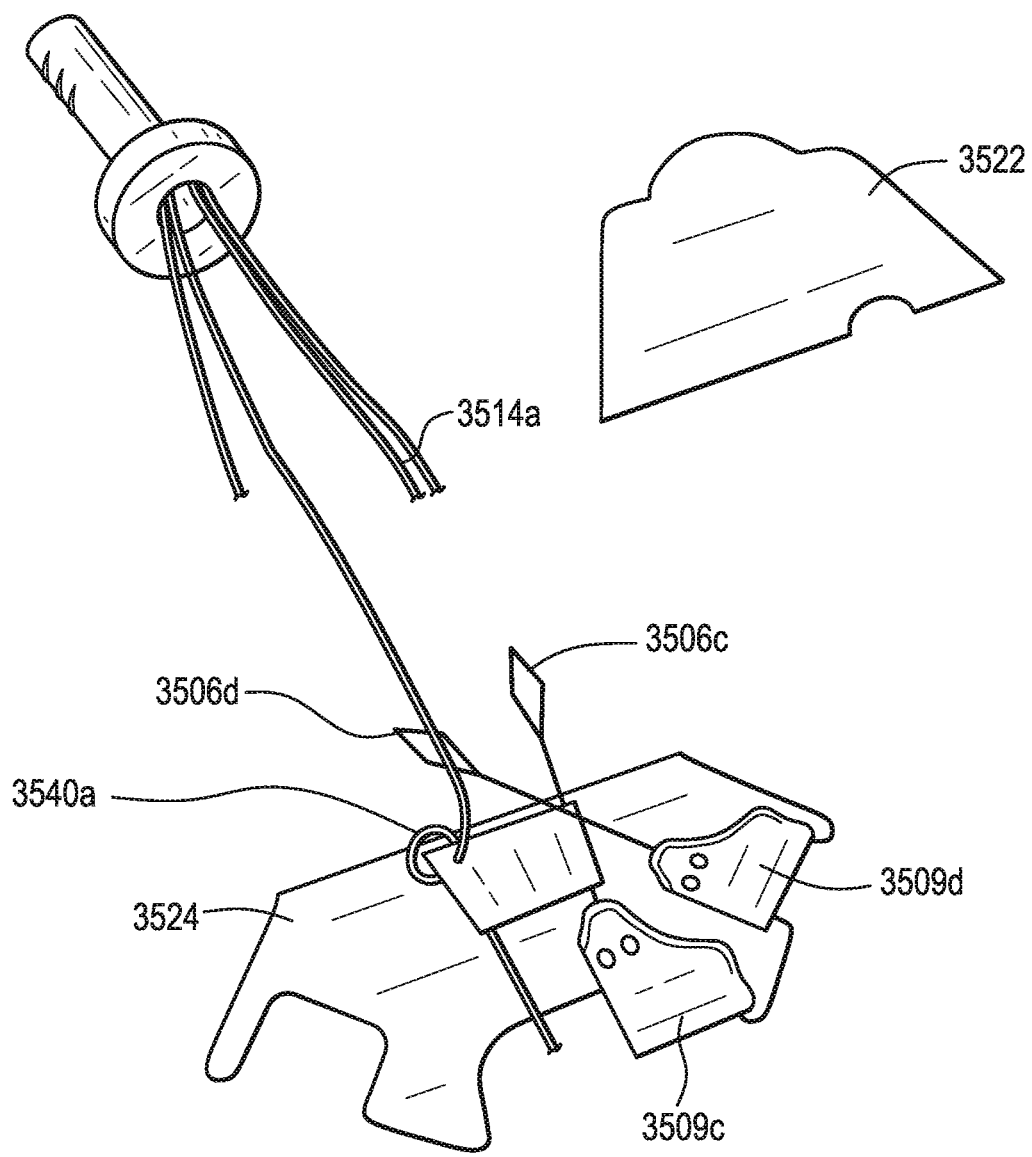
Figure 37E:
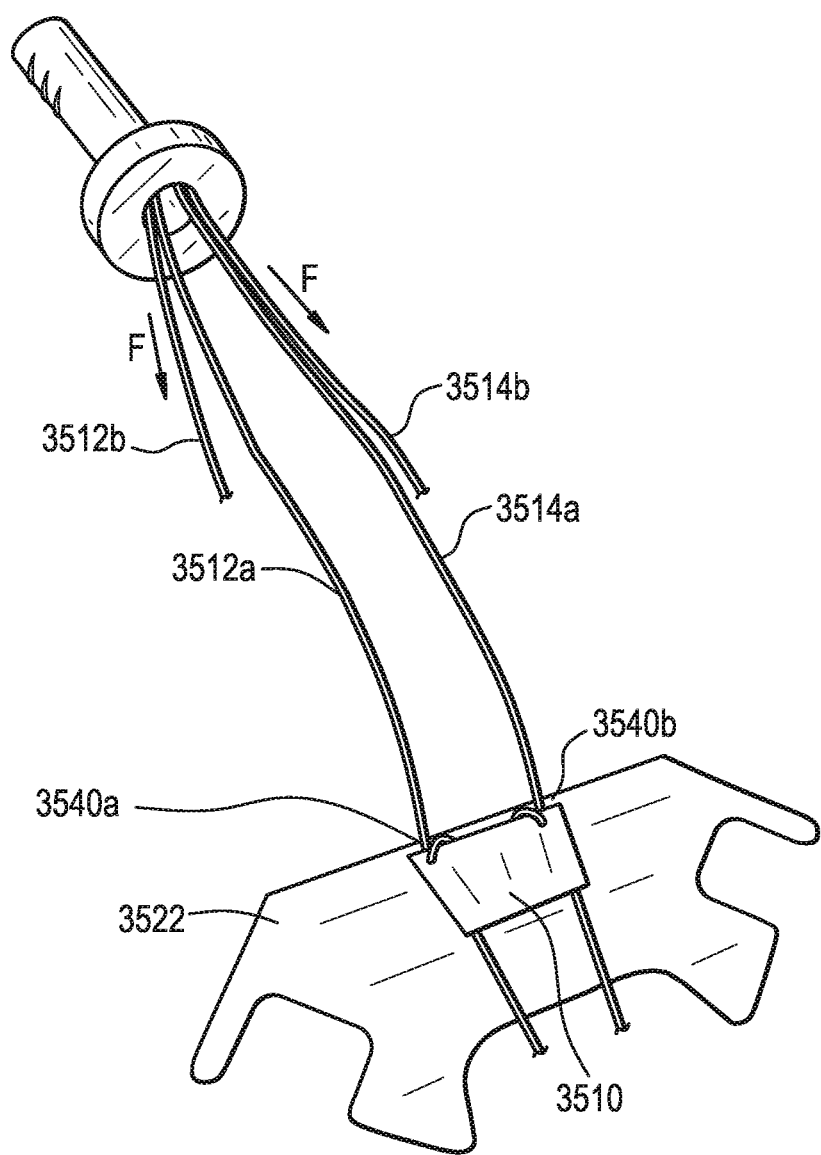

As illustrated in FIG. 37D, the top flap 3522 can be removed from the card 3520 and the card 3520 can be turned over to provide access to the threaders 3509c, 3509d. In the illustrated embodiment, access is initially limited to the first two threaders 3509a, 3509b to prevent a user from unintentionally associating the suture limb 3512a with threaders 3509c, 3509d. Alternatively, the card 3520 may not include the top flap 3522 thereby providing access to all of the threaders 3509a-3509d at the same time. In the illustrated embodiment, the flap 3522 is detached along the crease, for instance by providing a perforation along the crease, although many techniques known to those skilled in the art for separating one portion of a card or paper from another can be used. Suture 3514a can be threaded through the patch 3510 using threaders 3509c, 3509d to create a second loop 3540b using the technique provided for suture 3512a. Once the suture limbs 3512a, 3514a have been threaded into the patch 3510, as shown in FIG. 37E, the patch 3510 can be removed from the bottom portion 3524 and can be introduced into the surgical site to complete the repair, according to accepted surgical techniques including those provided for herein. Slack in suture limbs 3512a, 3514a can be created when introducing the patch construct into the surgical site. The suture limbs 3512a, 3512b, and 3514a, 3514b, respectively, are part of single sutures that can be disposed in the soft tissue with an inverted mattress stitch, not shown. The loop stitches 3540a, 3540b can fix the respective suture limbs 3512a, 3514b relative to the patch. As such, application of force F on one of the suture limbs 3512b, 3514a of each pair can remove slack from the other limbs 3512a, 3514a of the pair as the suture slides through the mattress stitch. Thus, the slack, not shown, can be reduced by applying the force F on the two free suture limbs 3512b, 3514b to pull slack out of the surgical site. In alternative embodiments, the threaders 3509a-3509d can be disposed through the patch 3510 in many other configurations, including but not limited to those provided above, to create any of the aforementioned configurations (e.g., forming a jog instead of a loop). Further, although a patch 3510 is shown, any construct can be advantageously used with the construct management cards of the nature described with respect to FIGS. 37A-37E. The construct management folding card 3520 can be disposed after use or reused as provided for herein.

One exemplary embodiment of a construct management release cartridge is illustrated in FIGS. 38A-38D. As shown, a construct management release cartridge 3620 can secure or otherwise hold a patch or scaffold 3610 having threaders 3609a, 3609b disposed in the patch for implantation at a surgical site. The cartridge 3620 can releasably secure the patch 3610 and its associated threaders 3609a, 3609b by using a release mechanism 3660 to expose the patch 3610. The release mechanism 3660 can advantageously prevent the construct 3610 from being released before the user is ready to insert the construct 3610. In the illustrated embodiment, the cartridge 3620 includes two threaders 3609a_3609b configured to thread suture limbs 3612a, 3612b through the construct. For example, a single threader 3609a can be used to thread a single suture limb 3612a into the patch. The threader 3609a can have a 3608a handle disposed on a first side 3620a of the cartridge 3620 and a suture receiving end 3607a exiting on a third side 3620c. The intermediate portion of the threader 3609a can be disposed in a track 3624a of the cartridge 3620. The track 3624a can define a path for forming a loop when a suture limb 3612a is disposed through the patch 3610, similar to the loop of FIG. 33C. Alternatively, a single threader, or more than two threaders, can be disposed through the patch 3610. As shown in the illustrated embodiment, the second threader 3610b can similarly have a handle 3608b disposed at the first side 3620a of the cartridge and a suture receiving end 3607b exiting on a fourth side 3620d. The second threader 3609b can be disposed in a second track 3624b.

The release mechanism 3660 can be disposed proximate a second side 3620b, which can be opposite a first side 3610a. The release mechanism 3660 can generally include a release button 3662 and retaining features 3664a, 3664b. As illustrated in FIG. 38C, the release button 3662 and retaining features 3664 can be a unitary piece that can be actuated to move in a proximal/distal direction D. In one embodiment, as shown in FIG. 38C, the retaining features 3664a, 3664b can be J or hook shaped to retain the threader or suture limb in the cartridge. For example, the distal end 3665a, 3665b of the retaining feature 3664a, 3664b can, in a locked configuration, be disposed against the distal side 3620d of the cartridge such that the suture limb 3612a is retained by the cartridge 3620. Upon actuation of the release button 3662, the distal ends 3665a, 3665b of the retaining features 3664a, 3664b can be offset from the distal side 3620d to permit the suture limbs to be released. The release button 3662 can be disposed on the proximal side 3620p of the cartridge and the retaining features 3664a, 3664b can be disposed on the distal side 3620d of the cartridge. The retaining features 3664a, 3644b can retain the patch 3610 in the cartridge by holding the threaders 3609a, 3609b, or suture limbs 3612a, 3612b, until the operator is ready to install the patch 3610. An alternative release mechanism 3660' is illustrated in FIG. 38D and can include a pivotable release button 3662' that can flex in a direction D' to release a suture limb 3612a, shown in phantom. The cartridge 3620' can include a proximal portion 3620p' that has an approximately 10 degree draft to aid guiding a suture 3612a' during release. The alternative cartridge 3620' can further include an overhang 3666' that can prevent accidental release.

In use, first and second suture limbs 3612a, 3612b can be threaded onto the patch 3610 by application of a force on the handles 3608a, 3608b of the respective threaders 3609a, 3609b using techniques provided for throughout the present disclosure. Once the first and second suture limbs 3612a, 3612b have been threaded into the patch 3610, for instance, by forming loops (not shown), the limbs 3612a, 3612b can be retained in the cartridge 3620 by the retaining features 3664a, 3664b. A user can then activate the release button 3662 to disengage the retaining features 3664a, 3664b to free the loops, and thus the patch 3610, from the cartridge 3620. The patch 3610 and suture limbs 3612a, 3612b can then be advanced into the surgical site and the soft tissue repair can be completed using techniques provided for throughout the present disclosure or otherwise known to those skilled in the art.

An alternative construct delivery cartridge 3720 similar to the cartridge 3620 of FIGS. 38A-38D is illustrated in FIGS. 38E and 38F. Similar to the cartridge 3620, cartridge 3720 can retain a patch 3710 and threaders, as shown two threaders 3709a, 3709b disposed in threading tracks 3724a, 3724b. In an alternative to the release mechanisms 3660, 3660', the cartridge consists of a bottom portion 3720a and a top patch retaining portion 3720b. Once the suture limbs (not shown) are threaded into the patch 3710 using techniques provided for throughout the present disclosure or otherwise known to those skilled in the art in view of the present disclosure, the top patch retaining portion 3720a of the cartridge can be removed from the bottom retaining portion 3720b to release the patch 3710 and suture limbs from the cartridge 3720, as shown in FIG. 38F. For example, in some embodiments, a finger hold 3780 can be disposed on the top portion 3720a to provide a user a means for releasing the top portion 3720a from the bottom portion 3720b. Any number of configurations for attaching one component to another can be used to releasable couple the top portion 3720a to the bottom portion 3720b, including but not limited to any number of male-female mating elements. For example, the top portion 3720a can include a retaining lip on a distal surface, not shown, that can retain the bottom portion 3720b. Alternatively, the top portion 3720a and the bottom portion 3720b can be releasable coupled via an interference fit. The patch 3710 and suture limbs can then be advanced into the surgical site and the soft tissue repair can be completed using techniques provided for throughout the present disclosure.

The threaders provided for with respect to the delivery tools of FIGS. 37A-38F, as well as provided for elsewhere in the present disclosure, can have a number of different configurations. FIGS. 38G and 38H provide for one, non-limiting exemplary embodiment. As shown, the threader 3809 has a handle 3807 associated with an intermediate portion 3810 that includes a suture receiving end 3808. The intermediate portion 3810 can be manufactured from a flexible strand of nylon, or other flexible and durable materials. In some instances, the intermediate portion 3810 can be formed from a doubled over thread having a first half 3810a and a second half 3810b. The handle portion can have any shape that is ergonomically designed to aid a user in removing the threader 3809 from an associated construct. The handle can include a plurality of ridges 3830a-3830c that can extend across the handle 3807 to provide a user added grip. Alternatively, the handle 3807 can include any number of ridges or other surface features to enhance the grip of a user on the handle. In the illustrated embodiment, the handle portion 3807 has three lumens 3804a-3804c extending from a first side 3807a to a second side 3807b. The openings 3806a-3806c of the lumens 3804a-3804c on the second side 3807b can be formed in a recess 3830, as shown in FIG. 38H. The lumens and openings help allow the intermediate portion 3810, and thus the suture receiving end 3808, to be associated with the handle portion 3807, as illustrated. Further, the handle can include a notch 3832 formed between the first and second lumens 3804a, 3804b for retaining the intermediate portion 3810.

To manufacture the threader 3809, the free end 3810f of the intermediate portion 3810 can be threaded from the first side 3807a of the handle 3807 through first lumen 3804a to the second side 3807b of the handle. The intermediate portion 3810 can then be threaded into the second lumen 3804b from the second side 3807b of the handle thereby creating a first loop 3812a. The free end 3810f can be then threaded through the second lumen 3804b to the first side 3807a of the handle, into the third lumen 3804c, over the first end 3807a, through to the second side 3807b of the handle. The free end 3810f of the intermediate portion can then be threaded through the first loop 3812a. Tension can be applied to suture receiving end 3808 of the intermediate portion 3810 to tighten the portion of the intermediate portion 3810 threaded through the handle 3807 until the slack has been removed. When the slack has been removed, the free end 3810f of the intermediate portion can be locked in place in the notch 3832. The portion of the intermediate portion 3810 that is disposed on the second side 3807b of the handle 3807, after the slack has been removed, can be disposed entirely in the recess. The first loop 3812a and the locked portion of the free end 3810f can be disposed in the notch 3830 without the need for any additional knots or retaining features. Advantageously, the intermediate portion 3810 of the threader 3809 can easily be replaced due to wear.

Figure 39A:
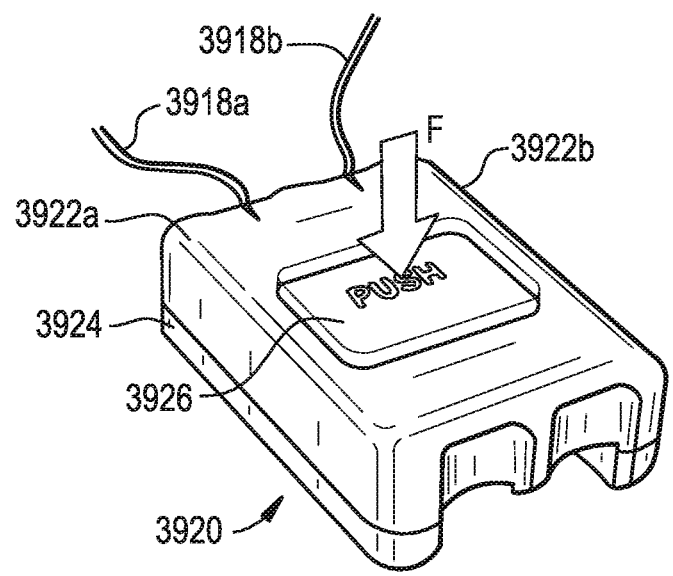
Figure 39B:
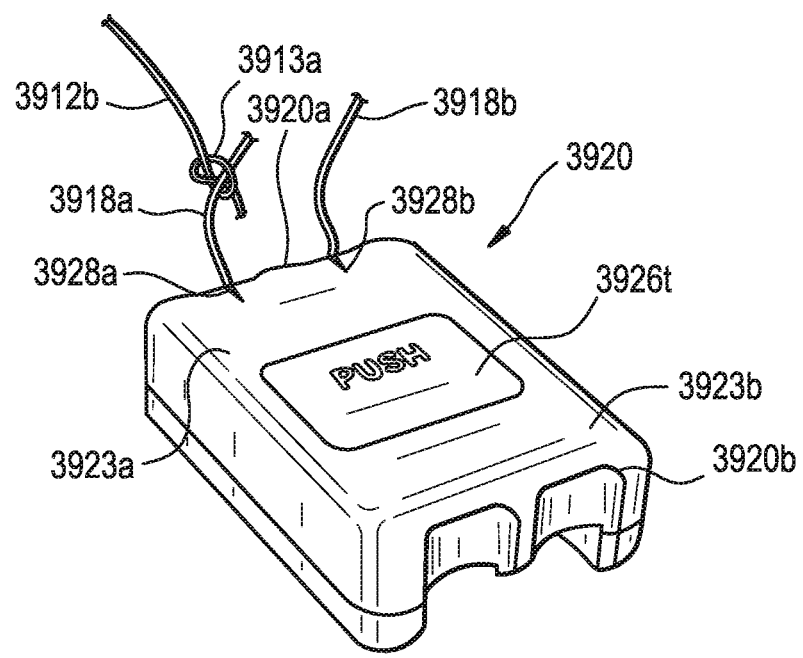

One exemplary embodiment of a construct management deconstructable box 3920 is illustrated in FIGS. 39A-39F. The box 3920 can be configured to secure a construct, such as a patch or scaffold 3910, to enable the construct to be easily associated with operative sutures, as shown sutures 3912a, 3912b, 3914a, 3914b. The box 3920 can generally include a base portion 3924, a first top compartment 3922a, a second top compartment 3922b, and a retaining button 3926. The box 3920 can be configured to hold the patch 3910 and one or more threaders within in it, and in the illustrated embodiment the box 3920 has two threaders 3909a, 3909b disposed within it. The patch 3910 can be pre-threaded with the first and second threaders 3909a, 3909b and two suture limbs 3918a, 3918b. The patch 3910 can be initially retained in the box 3920 by the first and second top compartments 3924a, 3924b and the push button 3926. The slots 3924a, 3924b can be disposed along a top surface of the respective first and second top compartments 3922a, 3922b proximate a first side 3920a of the box 3920. The handles of the threaders 3909a, 3909b can be accessible from the second side 3920b of the box 3020. The two suture limbs 3918a, 3918b can be retained in securing slots 3928a, 3928b disposed in the respective first and second top compartments 3924a, 3924b. The retaining button 3926 can be pushed inward to retain the patch 3910 in the box during the threading operation. For example, when the button 3926 is actuated, the button can be retained in the bottom portion 3924. In some embodiments, the retaining button 3936 can extend upward past the surfaces of the first and second top compartments in an unengaged configuration, as shown in phantom in FIG. 39A, and the top surface of the button 3926t can be flush with the top surfaces of the first and second compartments 3923a, 3923b, as shown in FIG. 39B. A person skilled in the art will recognize that many other configurations of a deconstructable box are possible, and thus although the present disclosure provides for a single base portion, two top compartments, and a push button, any number of base portions, top compartments, and push buttons can be used together to achieve the same results without departing from the spirit of the present disclosure.

Figure 39C:
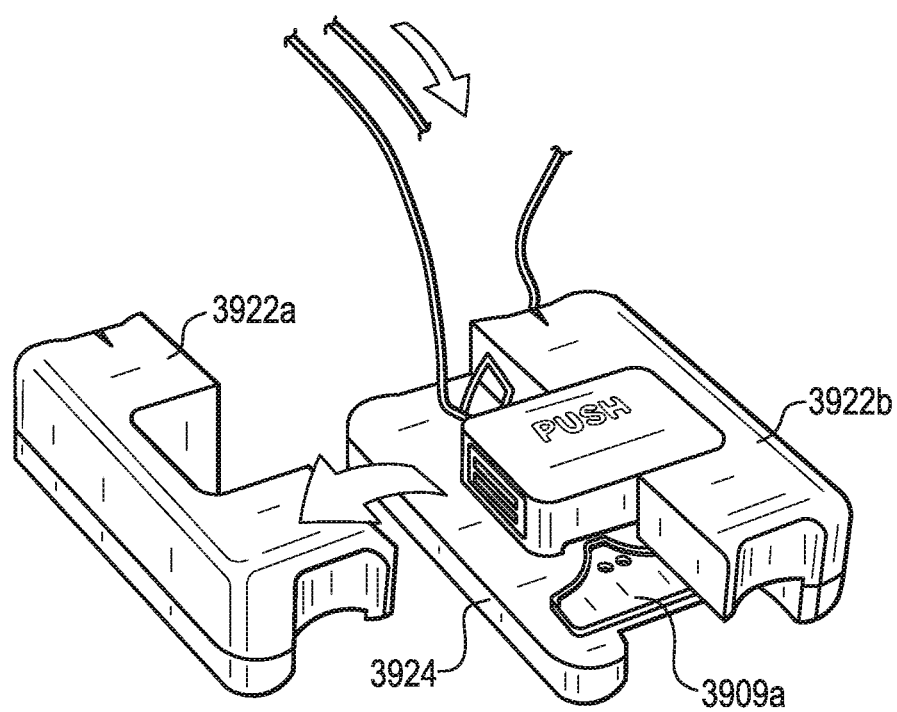
Figure 39D:
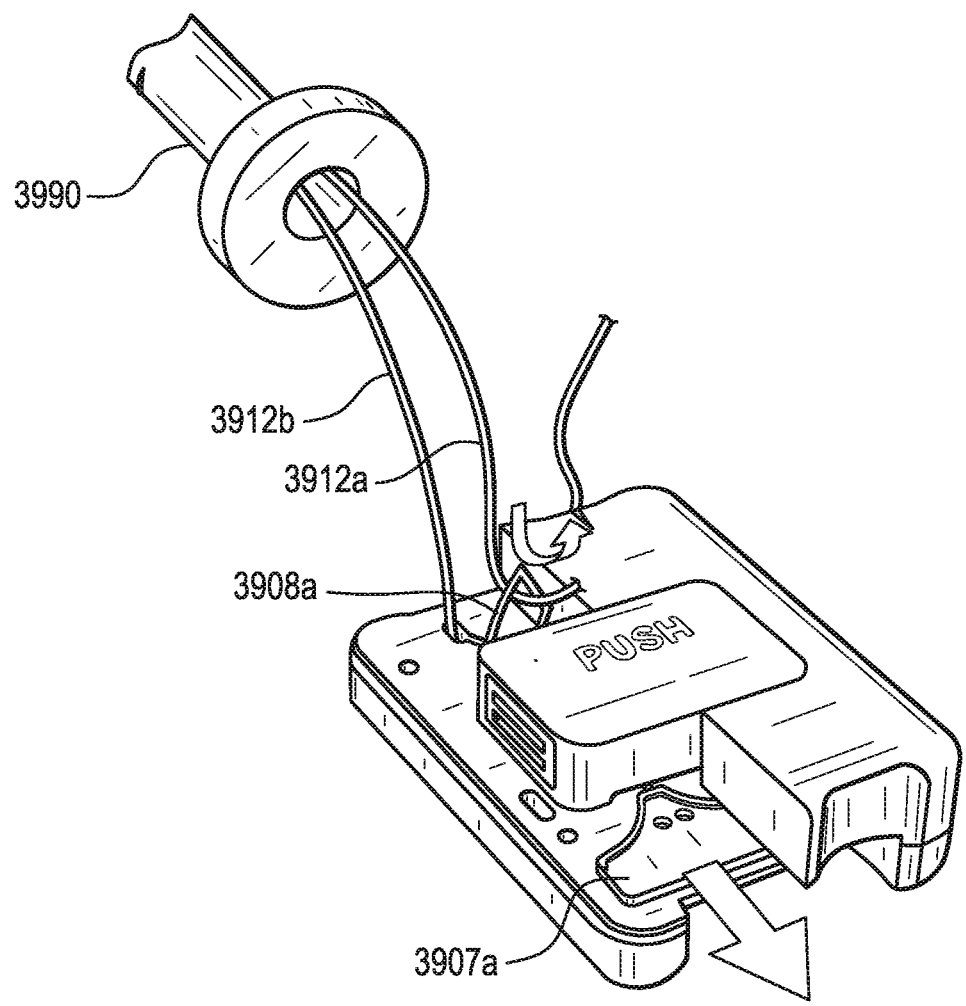
Figure 39E:
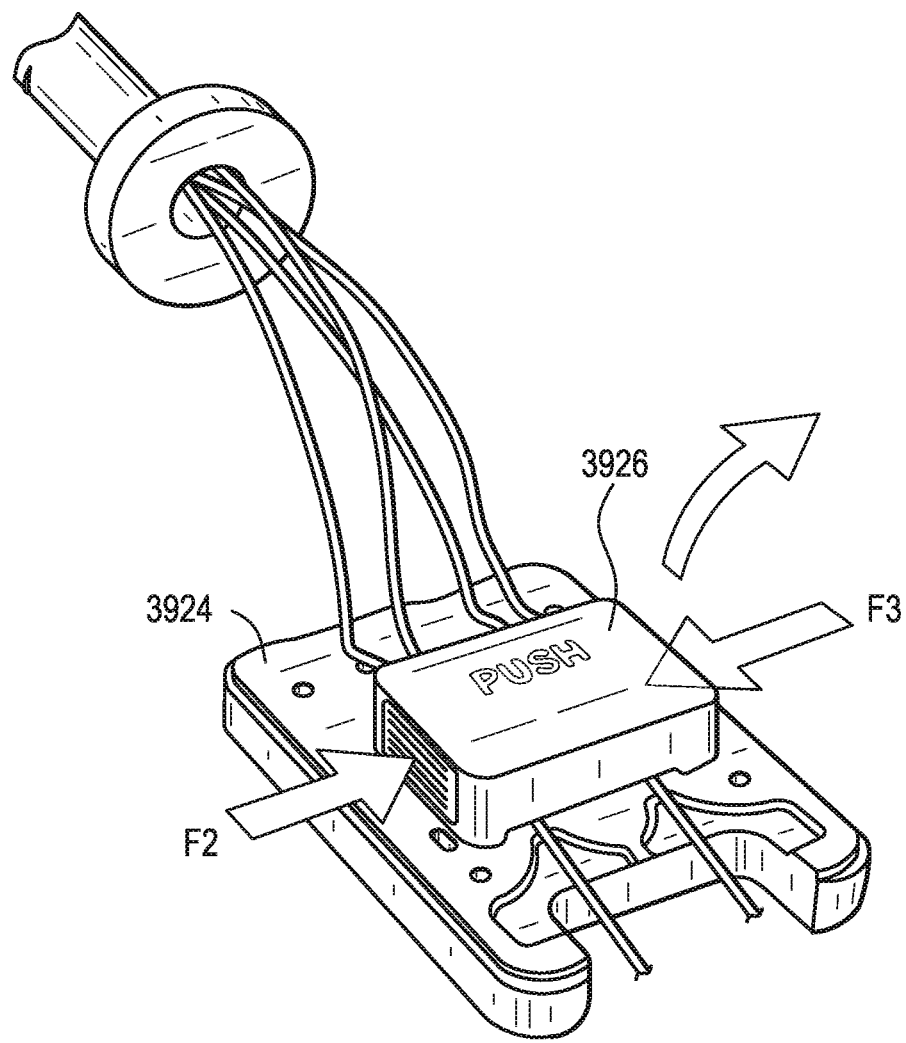
Figure 39F:
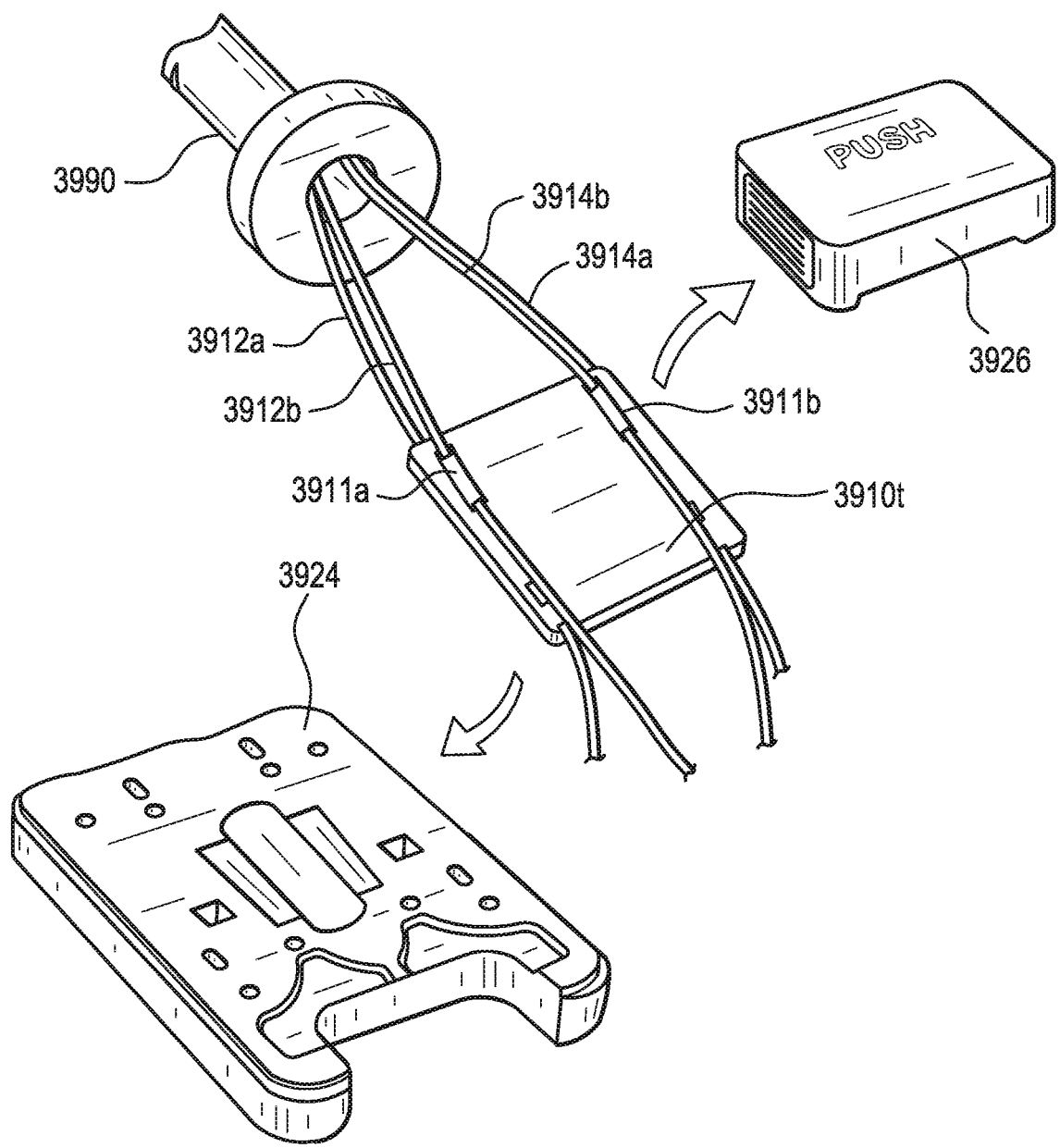

In use, as shown in FIGS. 39B-39F, four operative sutures 3912a, 3912b, 3914a, 3914b can exit through a cannula 3990 (FIG. 39D) from a surgical repair site. A first pre-threaded suture 3918a can be released from the first slot 3929a of the first top compartment 3922a and secured to a first operative suture 3912b, for instance using a knot 3913a. In one embodiment approximately 40.0 millimeters to 60.0 millimeters of slack can be left in the first pre-threaded suture 3918a after the knot 3913a is tied. The first top compartment 3922a can then be released from the base portion 3924, as shown in FIG. 39C. Next, for example, a leading side of the first operative suture can then be threaded through a cuff feature 3911a (FIG. 39F) with the first pre-threaded suture 3918a. The patch 3910 can include first and second cuffs 3911a, 3911b that are fixed to the top surface 3910t of the patch 3910 to retain operative sutures 3912b, 3914b for fixing the location of the patch 3910 once installed in the surgical site, as shown in FIG. 39F. The second operative suture 3912a can then be threaded into the patch 3910 with the threader 3909a using techniques provided for throughout the present disclosure, as shown in FIG. 39D. This process can then be completed with the third and fourth operative sutures 3914a, 3914b and the second top compartment 3922b removed, as shown in FIG. 39E, these components operating in a similar fashion as those described in conjunction with the removal of the first top compartment 3922a. Once the operative sutures 3912a, 3912b, 3914a, 3914b have been threaded onto the respective cuffs 3911a, 3911b and the patch 3910, the retaining button 3926 can be released from the base portion 3924 by application of opposing force F2, F3 to sides 3926a, 3926b of the button 3926. The patch 3910 is thus released from the box 3920, as shown in FIG. 39F. The patch 3910 and suture limbs 3912a, 3912b, 3914a, 3914b can then be advanced into the surgical site and the soft tissue repair can be completed using techniques provided for throughout the present disclosure.

In alternative embodiments, any number of threaders can be disposed through the constructs of the various construct management cards, cartridges, and boxes to achieve any of the disclosed construct embodiments provided for herein. In a further alternative embodiment, delivery tools like the construct management cards, cartridges, and boxes of FIGS. 37A-40, as well as other delivery tools provided for herein, can be mounted directly onto a cannula to free a hand of the operator during the suture threading of a construct. For example, FIG. 40 provides a construct cartridge 4022 having two construct retaining buttons 4026a, 4026b and two threaders 4009a, 4009b. The retaining buttons 4026a, 4026b can be depressed to retain a construct disposed therein during a threading operation. The illustrated construct cartridge 4022 can be directly mounted to the proximal end 4090p of the cannula 4090 such that the construct disposed therein, not shown, can be threaded by the operative suture limbs while fixed relative to the cannula 4090. The cartridge 4022 can be removably associated with the proximal end of the cannula 4090 with any known releasable interfaces. Alternatively, any of the delivery tools provided in the present disclosure, including the construct management cards, cartridges, and boxes of FIGS. 37A-40, can be removably mounted to the cannula 4090.

Additional tools for delivering constructs into a surgical site through a cannula, or other opening, are illustrated in FIGS. 41A-41E. As noted above, tissue augmentation constructs can include patches or scaffolds 4110. In some embodiments, a patch 4110 can include two suture limbs 4112a, 4114a associated with a proximal end 4110p of the patch and two suture limbs 4112b, 4114b associated with a distal end 4110d. Alternatively, the patch 4110 can include two suture limbs disposed through respective lumens in the patch, not shown, from the proximal end 4110p to the distal end 4110d. In some embodiments, the patch 4110 can include an opening 4120, the opening having a construction that includes but is not limited to a hole, slot, or slit disposed proximate the distal end 4110d of the patch. The opening can be configured to receive a delivery tool. For example, a tool 4130 having a shaft 4132 and a distal patch engaging end 4136 can be used in conjunction with the opening 4120. In the illustrated embodiment, the tool 4130 resembles a femoral aimer. As shown in FIG. 41B, the distal patch engaging end 4136 can include an offset extension 4137 and a shelf 4138 at the distal terminal end of the tool 4130. In an alternative embodiment shown in FIG. 41C, the tool 4130' can be similar to a Gryphon anchor inserter (available from DePuy Synthes of Raynham, MA), and can have an extension 4137' that is substantially axially aligned with a central longitudinal axis A1 of the shaft 4132'. In a further alternative embodiment, as shown in FIG. 41D, the tool 4130" can have a tapered end 4137" having a maximum diameter that is larger than the diameter of the hole 4120 in the patch 4110. A person skilled in the art will recognize many other configurations of tools that can be used in conjunction with patches in view of the present disclosure.

In use, the patch 4110 can be inserted into the surgical site using the tool 4130, or alternative embodiments of such tools provided for herein or otherwise derivable from the present disclosures. The patch 4110 can be inserted distal end 4110d first. The offset extension 4137 can be inserted into the hole 4120 of the patch 4110 until the shelf 4138 is in contact with a surface of the patch 4110 such that the tool 4130 cannot advance through the hole 4120. The tool 4130 can then be used to advance the patch 4110 through a cannula or incision site to push the patch 4110 into the surgical site. The tool 4130 can then be disengaged from the patch 4110 and removed from the patient by moving it in the proximal direction. An additional tool may be used to hold the patch in place while the delivery tool 4130 is removed, or alternatively, a location at the surgical site can be used to help hold the patch at the desired location. A person skilled in the art will recognize how a patch can be disconnected from the tool in conjunction with a surgical procedure in view of the present disclosures. The patch 4110 can then be installed according to techniques provided for herein.

A further alternative delivery tool, as described a delivery needle tool 4230, is illustrated in FIGS. 42A-42C. In contrast to the tools of FIGS. 41A-41E, the delivery needle 4230 can be actuated to unload, or release, an associated patch 4210. The delivery needle 4230 can include an outer sleeve 4232 and a retractable needle 4234 slidably disposed within the outer sleeve 4232. The outer sleeve 4232 can have a central lumen 4233 extending from a proximal most end 4232p to a distal most end 4232d of the sleeve 4232 through which the needle 4234 can be slidably disposed. A handle portion 4236 of the needle 4234 can be proximate the proximal end 4232p of the sleeve 4232 and an insertion end 4238 of the needle can be proximate the distal end 4232d of the sleeve 4232. The insertion end 4238 of the needle 4234 can have constant diameter, or, as illustrated, can be tapered. The needle 4234 can be slidably disposed within the sleeve 4232 so that the needle 4234 can be retracted proximally within the sleeve such that the insertion end 4238 is entirely received within the lumen 4233. The sleeve 4232 can have a diameter D1 that is larger than the diameter D2 of the needle 4234. The diameters D1, D2 of the sleeve 4232 and the needle 4234 can depend on a variety of factors, including but not limited to the size of an opening of a patch with which the tool is to be associated, the anatomy of the patient, and the type of procedure being performed.

In use, the patch 4210 can be inserted into the surgical site using the tool 4230. The patch 4210 can be substantially similar to the patch 4110 and include an opening 4220 at a distal end 4210d thereof. The patch 4210 can be inserted through the cannula or incision site distal end 4210d first. The insertion end 4238 of the needle 4234 can be inserted into the hole 4220 of the patch 4210 until the distal end 4232d of the outer sleeve 4232 is in contact with a surface of the patch 4210 such that the tool 4230 cannot advance through the hole 4220, as shown in FIG. 42B. The tool 4230 can be used to advance the patch 4210 through a cannula or incision site to push the patch 4210 into the surgical site. Once the patch 4210 is at the desired location, a user can grasp the handle 4236 of the needle 4232 to retract the insertion end 4238 of the needle 4232 relative to the sleeve 4232. Thus, the insertion end 4238 can be removed from the hole 4220 until the distal most end 4238d of the insertion end 4238 is disposed in the sleeve 4234 such that the tool can be disengaged from the patch 4210 and removed from the patient. The patch 4210 can then be installed according to techniques provided for herein.

Tissue Augmentation Construct—Suture Leader

FIG. 43 provides for another exemplary embodiment of a tissue augmentation construct, as shown a suture leader 2701. A suture leader 2701 can be placed on a distal end of a suture 2712. The suture leader can have a first section 2704 having a diameter $D_1$ and a second section 2706 having a diameter $D_2$. As shown, $D_1$ is larger than $D_2$. The smaller diameter of $D_2$ can allow for the second section 2706 to be folded in half and more easily pulled through a lumen of a tissue augmentation construct while allowing the operative first portion 2704 to have the necessary diameter and strength to complete the repair. The suture leader 2701 can be integral with the suture 2712, or can be an additional end-cap that is installed over a distal-most end or proximal-most end of the suture 2712. The suture leader 2701 can be used with any of the above mentioned embodiments of tissue augmentation constructs and related methods, other medical procedures, and in applications outside of the medical field.

One skilled in the art will appreciate further features and advantages of the present disclosure based on the above-described embodiments. Accordingly, the disclosure is not to be limited by what has been particularly shown and described, except as indicated by the appended claims. Further, although the systems, devices, and methods provided for herein are generally directed to surgical techniques, at least some of the systems, devices, and methods can be used in applications outside of the surgical field. All publications and references cited herein are expressly incorporated herein by reference in their entirety.

What is claimed is:

1. A surgical method, comprising:
   inserting an anchor into bone, the anchor being coupled to a first collapsible loop of a surgical filament and a second collapsible loop of the surgical filament, the first and second collapsible loops being defined by first and second self-locking mechanisms of the surgical filament, the first collapsible loop extending from a first side of the first self-locking mechanism, a first tail of the surgical filament and a first portion of the surgical filament extending separately from a second side of the first self-locking mechanism, the second collapsible loop extending from a first side of the second self-locking mechanism, and a second tail of the surgical filament and a second portion of the surgical filament extending separately from a second side of the second self-locking mechanism;
   disposing the first and second collapsible loops through soft tissue adjacent to the bone;
   applying tension to at least one of the first tail or the second tail of the surgical filament to collapse at least one of the first or second collapsible loops, thereby drawing a tissue augmentation tack coupled to the first and second portions of the surgical filament towards the soft tissue and bone such that a distal face of the tissue augmentation tack applies a force to the soft tissue to draw the soft tissue towards the bone, the tissue augmentation tack having a diameter that is at least two times greater than a diameter of the suture filament, wherein the first and second tails of the surgical filament are disposed through the tissue augmentation tack and applying tension to either or both of the first tail or the second tail moves the respective first or second tail through the tissue augmentation tack, and wherein the first and second portions of the surgical filament pass into the tissue augmentation tack; and
   locking a location of the tissue augmentation tack with respect to the bone to set the location of the soft tissue with respect to the bone,
   wherein a position of the first portion of the surgical filament and the second portion of the surgical filament remains fixed with respect to the tissue augmentation tack throughout application of tension to at least one of the first tail or the second tail of the surgical filament.

2. The surgical method of claim 1, further comprising:
   positioning a distal end of a guide adjacent to the soft tissue,
   wherein inserting an anchor coupled to first and second collapsible loops of a surgical filament into bone further comprises passing the anchor through the guide.

3. The surgical method of claim 2, further comprising:
   advancing a punch through the guide to form a hole in the soft tissue, wherein disposing the first and second collapsible loops through soft tissue adjacent to the bone further comprises passing the first and second collapsible loops through the hole in the tissue.

4. The surgical method of claim 3, further comprising:
advancing the punch through the guide to form a hole in the bone,
wherein inserting an anchor coupled to first and second collapsible loops of a surgical filament into bone further comprises inserting the anchor into the hole in the bone.

5. The surgical method of claim 2, wherein the guide is removed before applying tension to the at least one of the first or second tail of the surgical filament to collapse the at least one of the first or second collapsible loops.

6. The surgical method of claim 1, wherein applying tension to at least one of the first tail or the second tail of the surgical filament further comprises:
applying tension to the first tail and the second tail of the surgical filament to collapse the first collapsible loop and the second collapsible loop.

7. The surgical method of claim 1, further comprising toggling the anchor to set a location of the anchor with respect to the bone.

8. The surgical method of claim 1, wherein the anchor is a soft anchor formed of a flexible construct, the method further comprising:
actuating the anchor from an unstressed configuration to a stressed configuration to set a location of the anchor with respect to the bone.

9. The method of claim 1, wherein the diameter of the tissue augmentation tack is at least three times greater than a diameter of the surgical filament.

10. The surgical method of claim 1, wherein the tissue augmentation tack comprises at least one of: fabric, plastic, synthetic polymer, natural polymer, collagen, collagen scaffold, reconstituted collagen, biological autograft connective tissue, biological allograft connective tissue, biological xenograft connective tissue, human dermal matrix, porcine dermal matrix, bovine dermal matrix, periosteal tissue, pericardial tissue, and fascia.

11. The surgical method of claim 10, wherein the tack comprises collagen.

12. The surgical method of claim 1, wherein at least one of the first and second self-locking mechanisms is disposed between the tissue augmentation tack and the first and second collapsible loops.

13. The surgical method of claim 1, wherein at least one of the first and second self-locking mechanisms comprises a self-locking sliding knot.

14. The surgical method of claim 1, wherein inserting an anchor into bone comprises first passing the anchor through the soft tissue.

15. A surgical method, comprising:
inserting an anchor into bone, the anchor being coupled to a first collapsible loop of a surgical filament and a second collapsible loop of the surgical filament, the first and second collapsible loops being defined by first and second self-locking mechanisms of the surgical filament, the first and second self-locking mechanisms being disposed separate from a tissue augmentation tack such that the first and second self-locking mechanisms are disposed between a distal face of the tissue augmentation tack and the collapsible loop, the tissue augmentation tack being coupled to the surgical filament;
disposing the first and second collapsible loops through soft tissue adjacent to the bone;
applying tension to at least one of a first tail of the surgical filament extending from the first self-locking mechanism or a second tail extending from the second self-locking mechanism to collapse at least one of the first or second collapsible loops, thereby drawing the tissue augmentation tack towards the soft tissue and bone such that the distal face of the tissue augmentation tack applies a force to the soft tissue to draw the soft tissue towards the bone, the tissue augmentation tack having a diameter that is at least two times greater than a diameter of the suture filament, wherein the first and second tails of the surgical filament are disposed through the tissue augmentation tack and applying tension to either or both of the first or second tails moves the respective tail through the tissue augmentation tack, and wherein a first portion and a second portion of the surgical filament extending respectively from the first and second self-locking mechanisms— are coupled to the tissue augmentation tack; and
locking a location of the tissue augmentation tack with respect to the bone to set the location of the soft tissue with respect to the bone,
wherein a position of the first portion of the surgical filament and the second portion of the surgical filament remains fixed with respect to the tissue augmentation tack throughout application of tension to at least one of the first tail or the second tail of the surgical filament.

16. The surgical method of claim 15, further comprising:
positioning a distal end of a guide adjacent to the soft tissue,
wherein inserting an anchor coupled to first and second collapsible loops of a surgical filament into bone further comprises passing the anchor through the guide.

17. The surgical method of claim 15, wherein applying tension to at least one of a first tail of the surgical filament extending from the first self-locking mechanism or a second tail extending from the second self-locking mechanism further comprises:
applying tension to the first tail and the second tail of the surgical filament to collapse the first collapsible loop and the second collapsible loop.

18. The surgical method of claim 15, wherein the anchor is a soft anchor formed of a flexible construct, the method further comprising:
actuating the anchor from an unstressed configuration to a stressed configuration to set a location of the anchor with respect to the bone.

19. The method of claim 15, wherein the diameter of the tissue augmentation tack is at least three times greater than a diameter of the surgical filament.

20. The surgical method of claim 15, wherein the tissue augmentation tack comprises at least one of: fabric, plastic, synthetic polymer, natural polymer, collagen, collagen scaffold, reconstituted collagen, biological autograft connective tissue, biological allograft connective tissue, biological xenograft connective tissue, human dermal matrix, porcine dermal matrix, bovine dermal matrix, periosteal tissue, pericardial tissue, and fascia.

21. The surgical method of claim 20, wherein the tack comprises collagen.

22. The surgical method of claim 15, wherein at least one of the first or second self-locking mechanisms comprises a self-locking sliding knot.

23. The surgical method of claim 15, wherein inserting an anchor into bone comprises first passing the anchor through the soft tissue.

* * * * *